United States Patent
Dart et al.

(10) Patent No.: US 11,534,504 B2
(45) Date of Patent: Dec. 27, 2022

(54) COMPOSITIONS AND METHODS FOR STABILIZING COELENTERAZINE AND ANALOGS AND DERIVATIVES THEREOF

(71) Applicant: Promega Corporation, Madison, WI (US)

(72) Inventors: Melanie Dart, Madison, WI (US); Thomas Smith, Madison, WI (US); Thomas Kirkland, Atascadero, CA (US); Thomas Machleidt, Madison, WI (US); Keith Wood, Mount Horeb, WI (US)

(73) Assignee: Promega Corporation, Madison, WI (US)

( * ) Notice: Subject to any disclaimer, the term of this patent is extended or adjusted under 35 U.S.C. 154(b) by 120 days.

(21) Appl. No.: 16/592,310

(22) Filed: Oct. 3, 2019

(65) Prior Publication Data

US 2020/0109146 A1    Apr. 9, 2020

Related U.S. Application Data

(60) Provisional application No. 62/805,517, filed on Feb. 14, 2019, provisional application No. 62/740,622, filed on Oct. 3, 2018.

(51) Int. Cl.
    *A61K 49/00*    (2006.01)
    *C07D 487/04*   (2006.01)
    *G01N 33/58*    (2006.01)

(52) U.S. Cl.
    CPC ...... *A61K 49/0054* (2013.01); *A61K 49/0021* (2013.01); *C07D 487/04* (2013.01); *G01N 33/582* (2013.01)

(58) Field of Classification Search
    None
    See application file for complete search history.

(56) References Cited

U.S. PATENT DOCUMENTS

| | | |
|---|---|---|
| 7,268,229 B2 | 9/2007 | Wood et al. |
| 7,537,912 B2 | 5/2009 | Wood et al. |
| 7,659,078 B1 | 2/2010 | Daunert et al. |
| 8,557,970 B2 | 10/2013 | Encell et al. |
| 8,669,103 B2 | 3/2014 | Binkowski et al. |
| 8,809,529 B2 | 8/2014 | Klaubert et al. |
| 9,139,836 B2 | 9/2015 | Klaubert et al. |
| 9,487,520 B2 | 11/2016 | Klaubert et al. |
| 9,676,997 B2 | 6/2017 | Kirkland et al. |
| 9,840,730 B2 | 12/2017 | Binkowski et al. |
| 9,908,918 B2 | 3/2018 | Lin et al. |
| 9,924,073 B2 | 3/2018 | Shakhmin et al. |
| 9,927,430 B2 | 3/2018 | Zhou et al. |
| 9,938,564 B2 | 4/2018 | Klaubert et al. |
| 9,951,373 B2 | 4/2018 | Binkowski et al. |
| 10,000,500 B2 | 6/2018 | Hall et al. |
| 10,077,244 B2 | 9/2018 | Cali et al. |
| 10,280,447 B2 | 5/2019 | Hall et al. |
| 10,308,975 B2 | 6/2019 | Shakhmin et al. |
| 10,316,070 B2 | 6/2019 | Zhou et al. |
| 10,428,075 B2 | 10/2019 | Hall et al. |
| 2008/0248511 A1 | 10/2008 | Daily et al. |
| 2012/0107849 A1 | 5/2012 | Klaubert et al. |
| 2013/0272966 A1 | 10/2013 | Xiong et al. |
| 2014/0099654 A1 | 4/2014 | Cali et al. |
| 2014/0227759 A1 | 8/2014 | Binkowski et al. |
| 2015/0094219 A1 | 4/2015 | Trowell et al. |
| 2015/0225642 A1* | 8/2015 | Bryan ............... A61K 49/0045 435/188 |
| 2017/0108442 A1 | 4/2017 | Dragavon et al. |
| 2017/0233789 A1 | 8/2017 | Shakhmin et al. |
| 2018/0030059 A1 | 2/2018 | Hall et al. |
| 2018/0155350 A1 | 6/2018 | Hall et al. |
| 2019/0337939 A1 | 11/2019 | Binkowski et al. |
| 2020/0062766 A1 | 2/2020 | Walker et al. |

FOREIGN PATENT DOCUMENTS

| | | |
|---|---|---|
| JP | 2016082975 | 5/2016 |
| WO | WO 2003/040100 | 5/2003 |
| WO | WO 2012/061529 | 5/2012 |
| WO | WO 2014/036482 | 3/2014 |
| WO | WO 2014/151736 | 9/2014 |
| WO | WO 2015/007317 | 1/2015 |
| WO | WO 2016/131833 | 8/2016 |
| WO | WO 2018/219953 | 12/2018 |
| WO | WO 2019/028504 | 2/2019 |
| WO | WO 2019/038375 | 2/2019 |
| WO | WO 2020/006530 | 1/2020 |

OTHER PUBLICATIONS

Yeh et al. Red-shifted luciferase-luciferin pairs for enhanced bioluminescence imaging. 2017 Nat. Methods 14: 971-974 and 4 p of online methods. Epub Sep. 4, 2017. (Year: 2017).*
Hall et al. Engineered luciferase reporter from a deep sea shrimp utilizing a novel imidazopyrazinone substrate. 2012 ACS Chem. Biol. 7: 1848-1857. (Year: 2012).*
Ali, M. M. et al., "Detection of DNA using bioactive paper strips." *Chem Commun (Camb)* 2009, (43), 6640-6642.
Arts, R. et al., "Detection of Antibodies in Blood Plasma Using Bioluminescent Sensor Proteins and a Smartphone." *Anal Chem* 2016, 88 (8), 4525-4532.
Chen, Y. et al., "Double-Enzymes-Mediated Bioluminescent Sensor for Quantitative and Ultrasensitive Point-of-Care Testing." *Anal Chem* 2017, 89 (10), 5422-5427.

(Continued)

*Primary Examiner* — Jennifer Lamberski
(74) *Attorney, Agent, or Firm* — Anne M. Reynolds; Casimir Jones, S.C.

(57) ABSTRACT

Provided herein are compositions and methods for stabilizing coelenterazine and analogs or derivatives thereof, and for improving the solubility and reconstitution efficiency of coelenterazine and analogs and derivatives thereof.

17 Claims, 84 Drawing Sheets
(69 of 84 Drawing Sheet(s) Filed in Color)
Specification includes a Sequence Listing.

(56) References Cited

OTHER PUBLICATIONS

Chu et al., "A bright cyan-excitable orange fluorescent protein facilitates dualemission microscopy and enhances bioluminescence imaging in vivo," 2016, *Nature Biotechnology* 34:7, 760-767.

Hsieh, P. Y. et al., "RNA Protection is Effectively Achieved by Pullulan Film Formation." *Chembiochem* 2017, 18, 502-505.

Int'l Search Report and Written Opinion of PCT/US2019/054501, dated Jun. 23, 2020 (44 pages).

Jahanshahi-Anbuhi, S. et al., "Automating multi-step paper-based assays using integrated layering of reagents." *Lab Chip* 2017, 17 (5), 943-950.

Jahanshahi-Anbuhi, S. et al., "Pullulan encapsulation of labile biomolecules to give stable bioassay tablets." *Angew Chem Int Ed Engl* 2014, 53, 6155-6158.

Jahanshahi-Anbuhi, S. et al., "Simple and ultrastable all-inclusive pullulan tablets for challenging bioassays." *Chem. Sci.* 2016, 7, 2342-2346.

Le et al., "Real-time, continuous detection of maltose using bioluminescence resonance energy transfer (BRET) on a microfluidic system," 2014, *Biosensors and Bioelectronics* 177-183.

Leung, V. et al., "Long-Term Preservation of Bacteriophage Antimicrobials Using Sugar Glasses." *ACS Biomater. Sci. Eng.* 2018, 4, 3802-3808.

Liu, M. et al., "Target-Induced and Equipment-Free DNA Amplification with a Simple Paper Device." *Angew Chem Int Ed Engl* 2016, 55 (8), 2709-2713.

Nguyen, D. T. et al., "The development of paper discs immobilized with luciferase/D-luciferin for the detection of ATP from airborne bacteria." *Sens. Actuators B Chem.* 2018, 260, 274-281.

Oh et al., "An orange calcium-modulated bioluminescent indicator for non-invasive activity imaging," 2019, *Nature Chemical Biology* 15, 433-436.

Soni, S. R. and Ghosh, A., "Exploring pullulan-poly(vinyl alcohol) interpenetrating network microspheres as controlled release drug delivery device." *Carbohydr Polym* 2017, 174, 812-822.

Teekamp, N. et al., "Addition of Pullulan to Trehalose Glasses Improves the Stability of beta-Galactosidase at High Moisture Conditions." *Carbohydr Polym* 2017, 176, 374-380.

Tenda et al., "Paper-Based Antibody Detection Devices Using Bioluminescent BRET-Switching Sensor Proteins," 2018, *Angew. Chem. Int. Ed. 57*, 15369-15373.

Xue, L. et al., "Bioluminescent Antibodies for Point-of-Care Diagnostics." *Angew Chem Int Ed Engl 2017*, 56 (25), 7112-7116.

Yang, X. et al., "Homogeneous enzyme immunoassay modified for application to luminescence-based biosensors." *Anal Biochem 2005*, 336 (1), 102-107.

\* cited by examiner

FIG. 1
A.
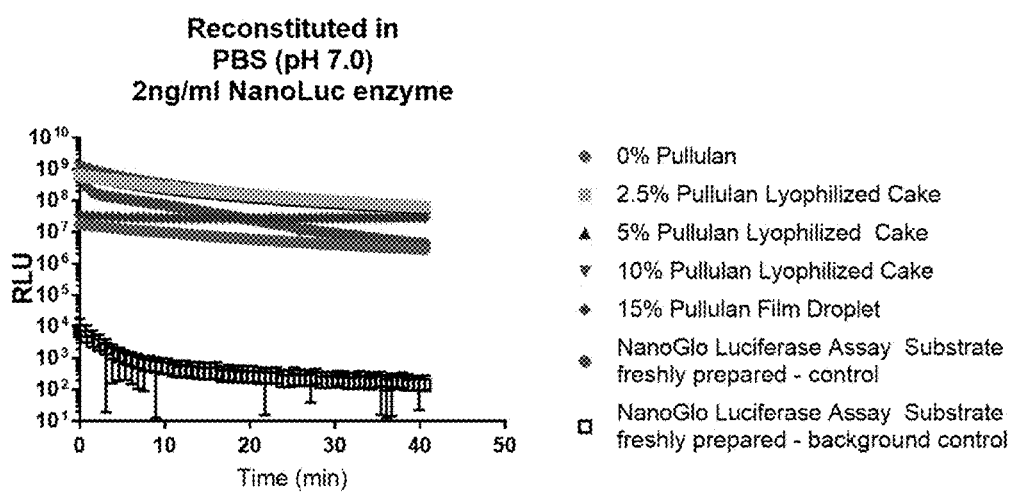
B.
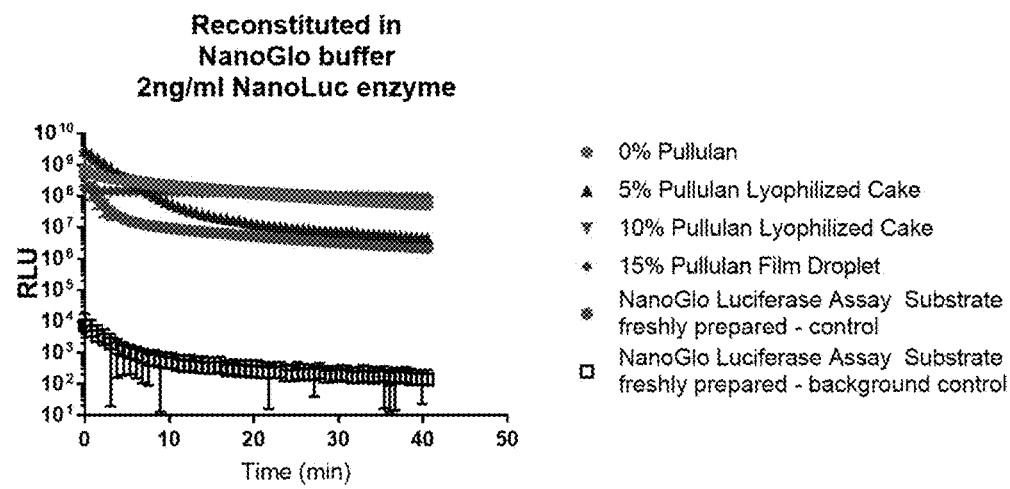
C.
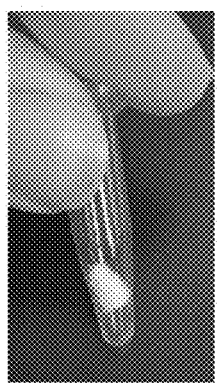
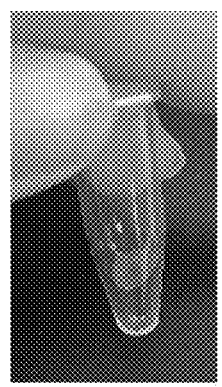

FIG. 3
A.
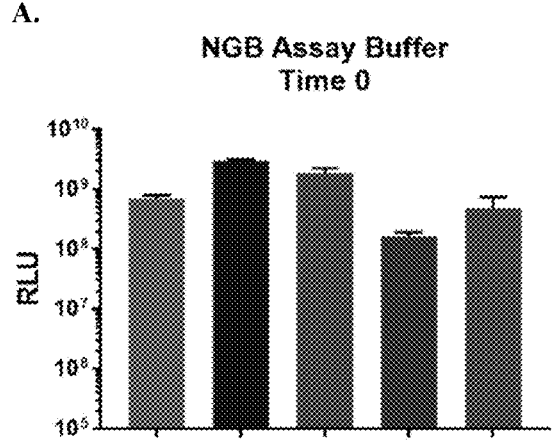
B.
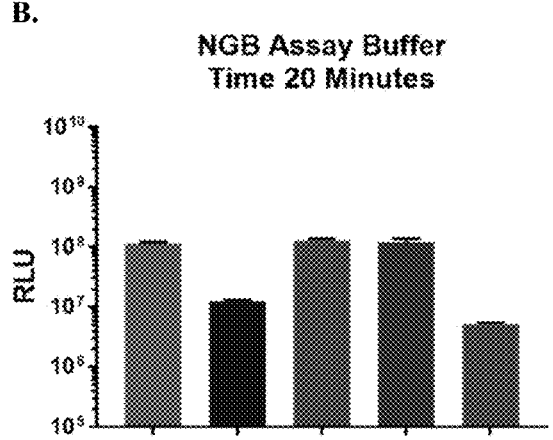
C.
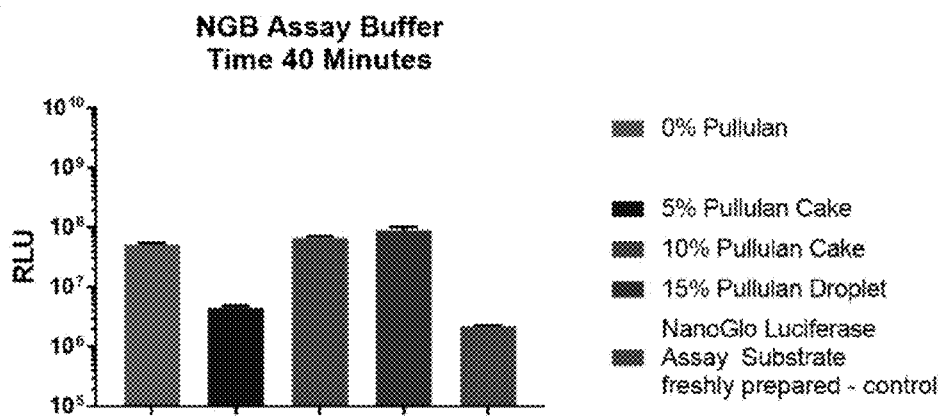

FIG. 4
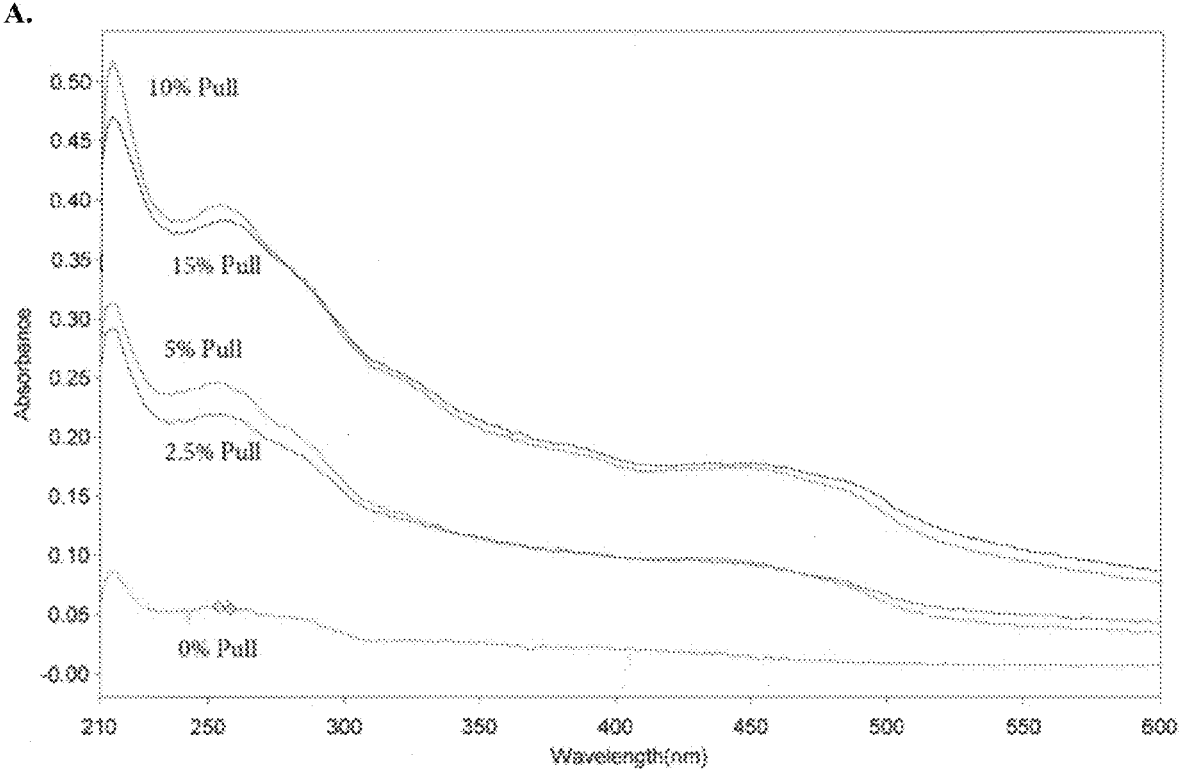
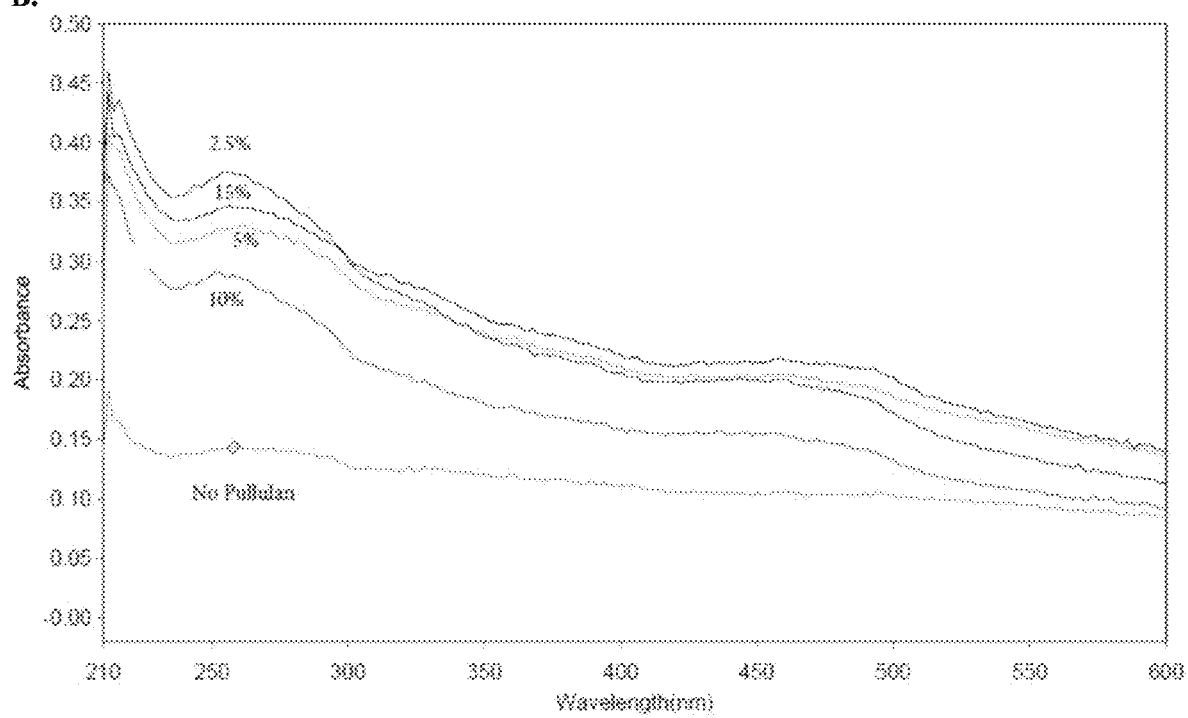

C.

FIG. 6
A.
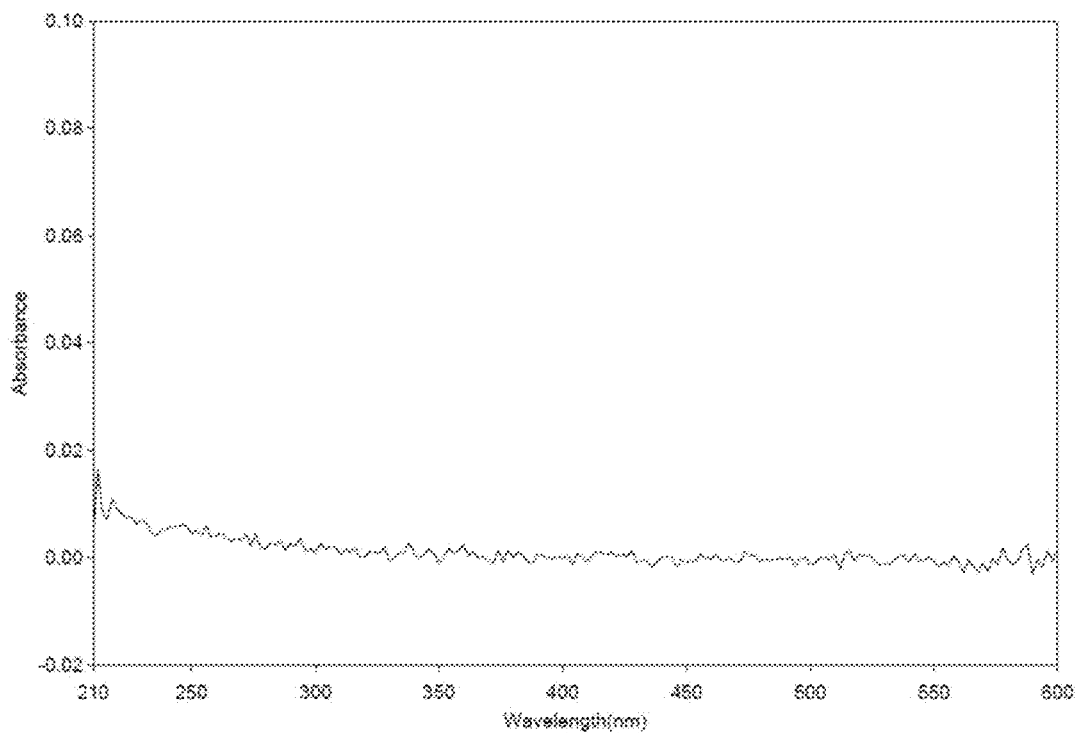
B.
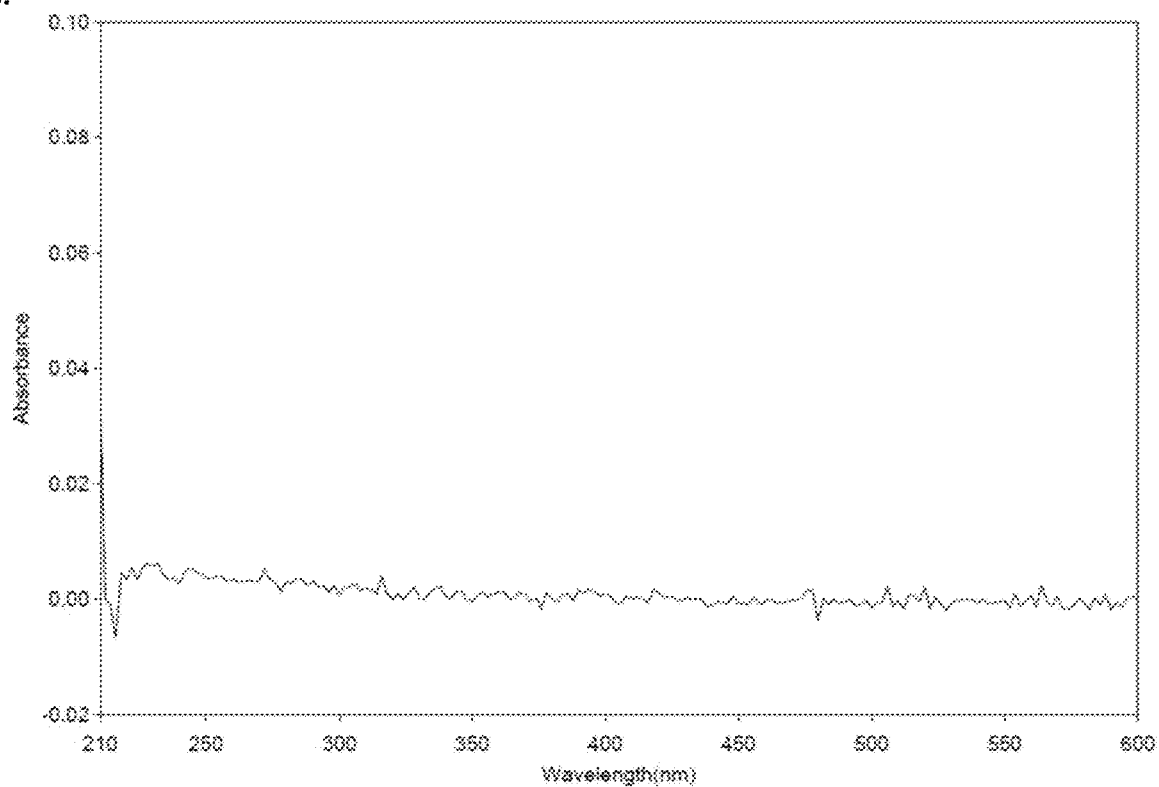

FIG. 7
A.
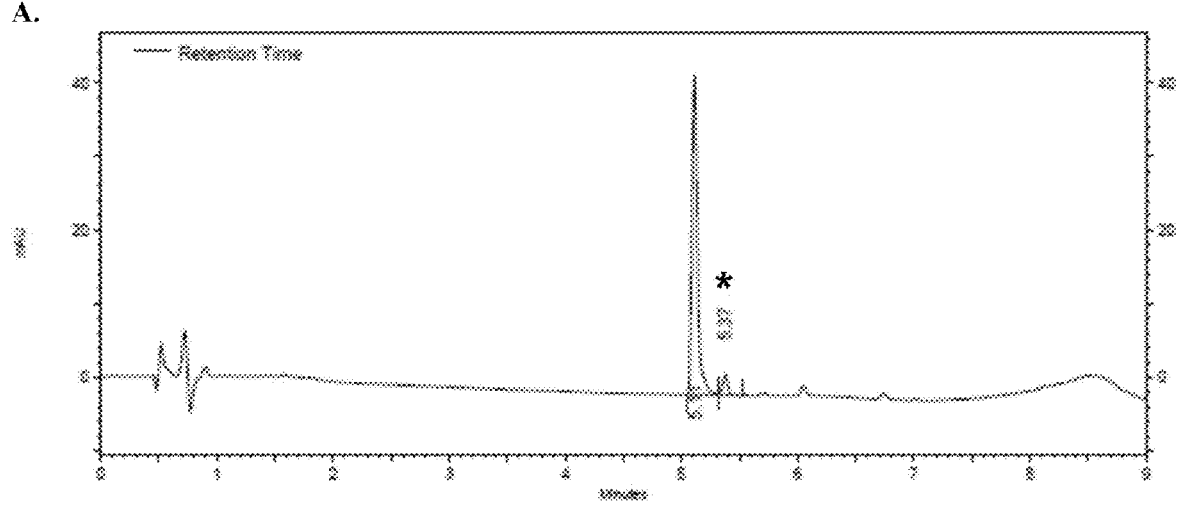
B.
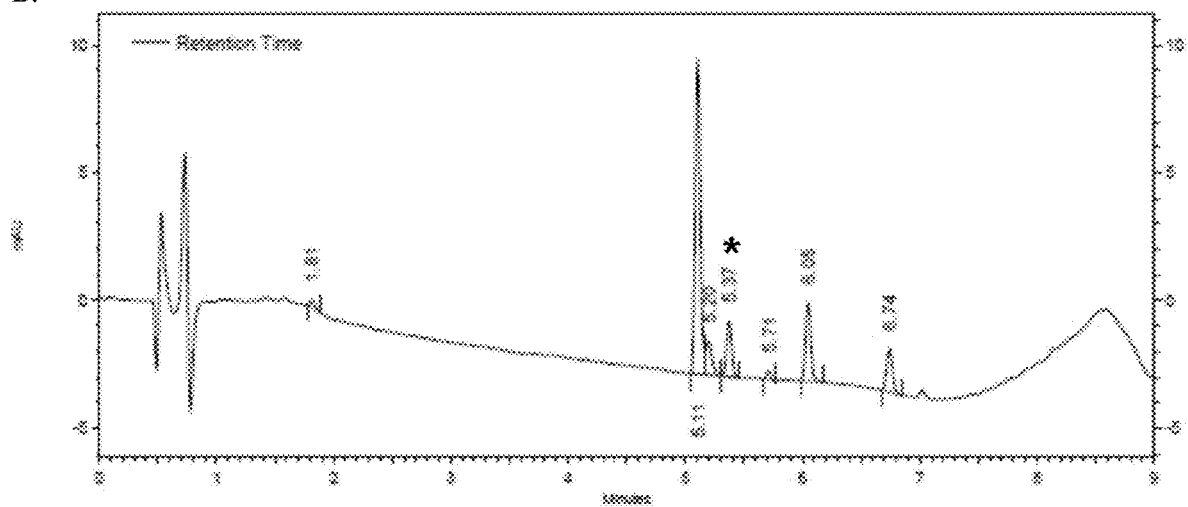

FIG. 8
A.
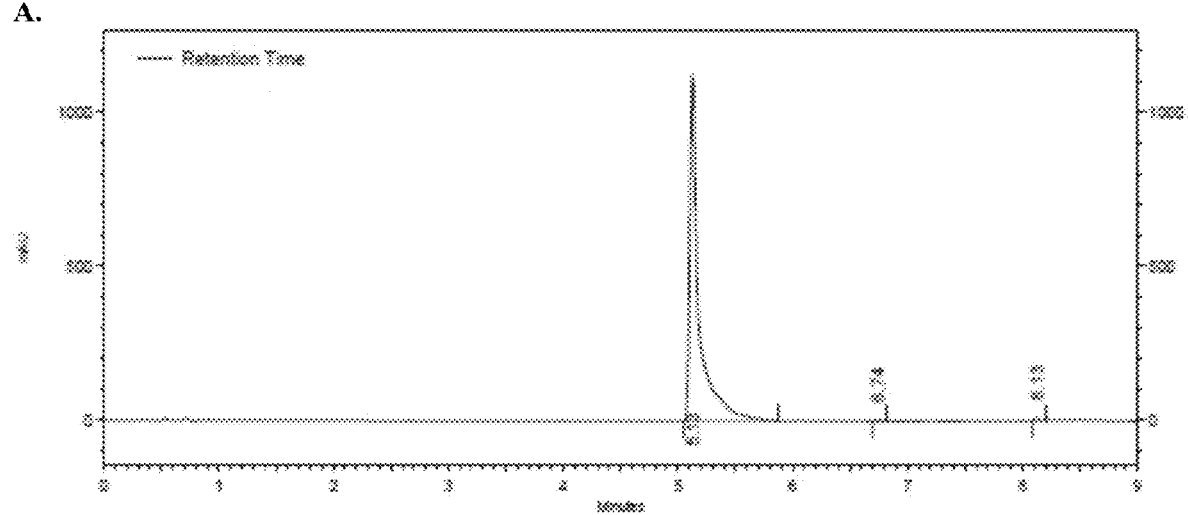
B.
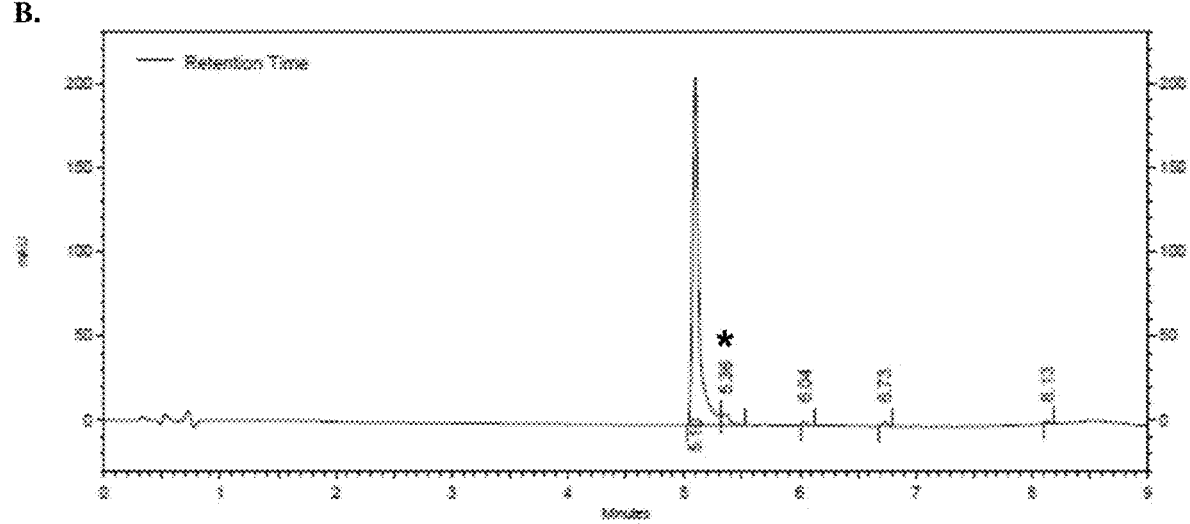

FIG. 9
A.
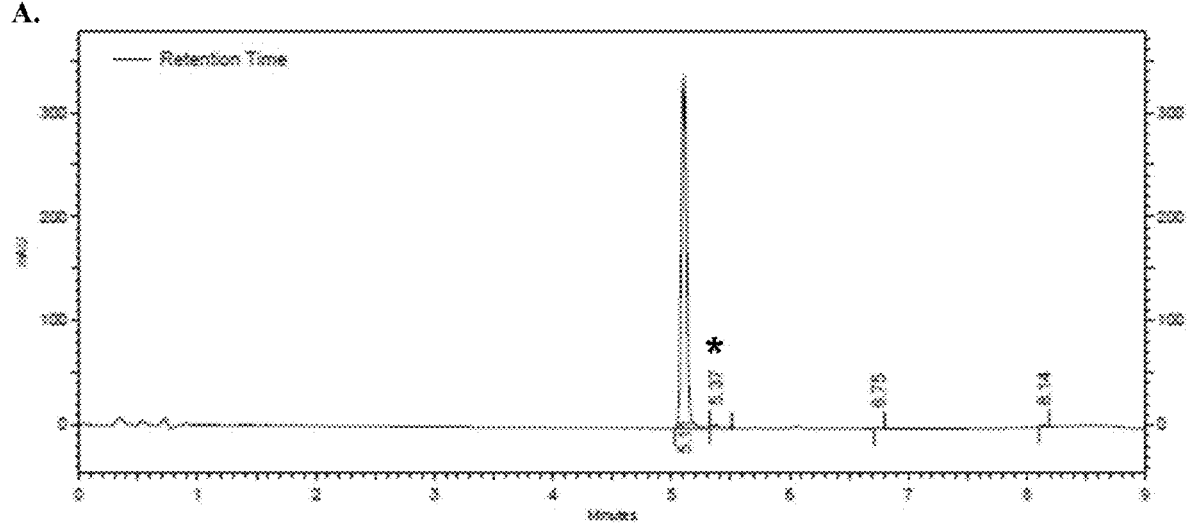
B.
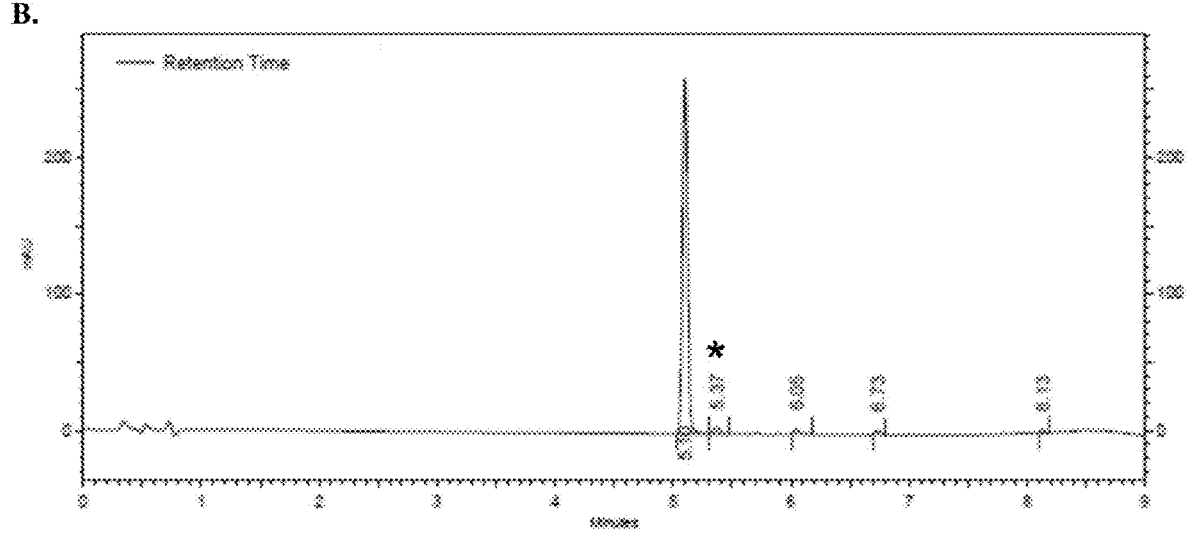

FIG. 10
A.
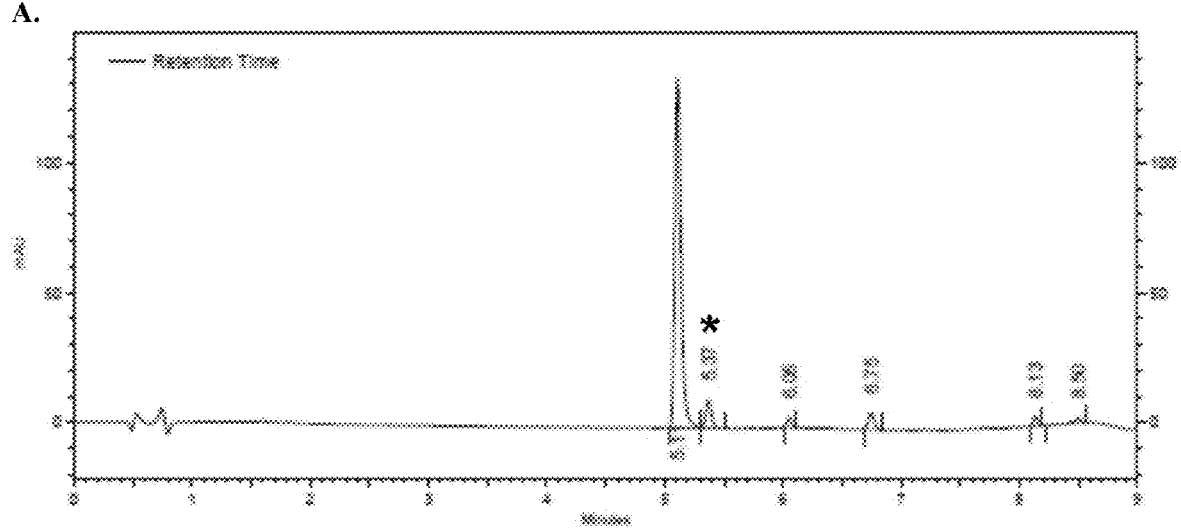
B.
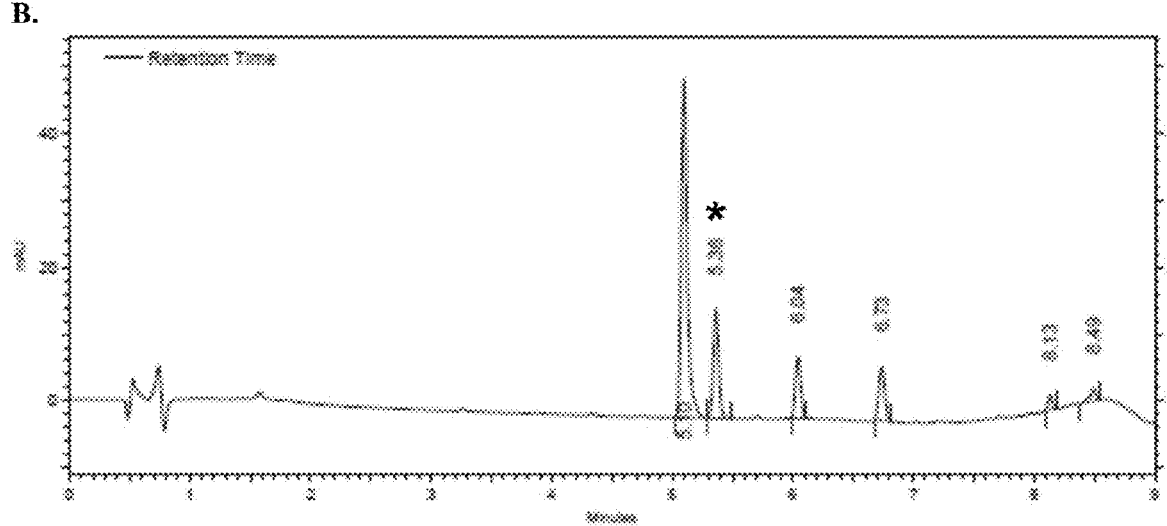

FIG. 11
A.
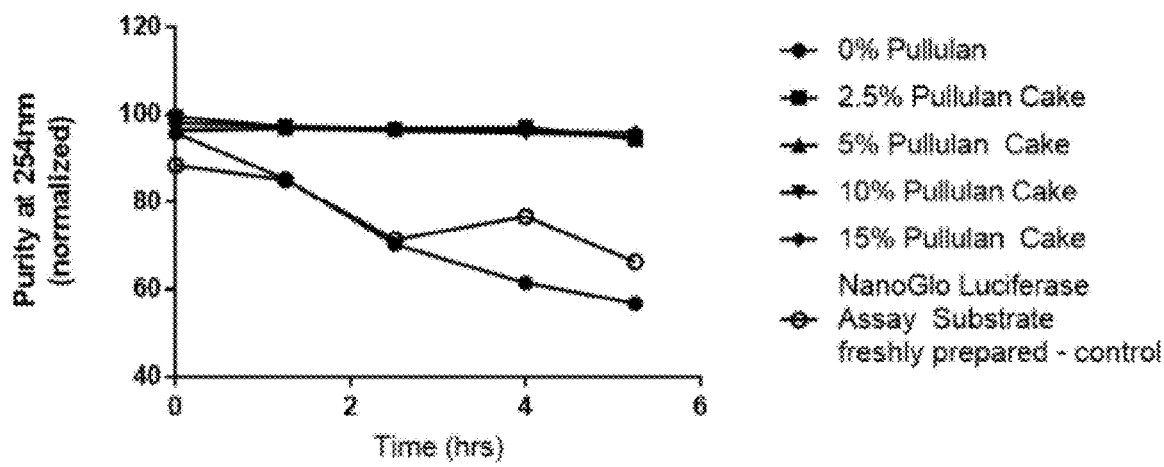
B.
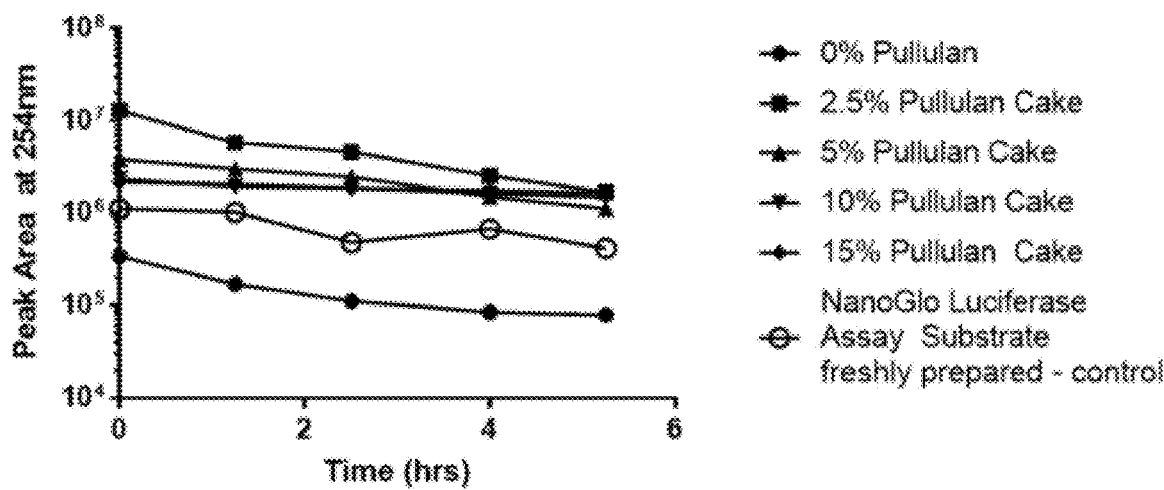

FIG. 13
A.
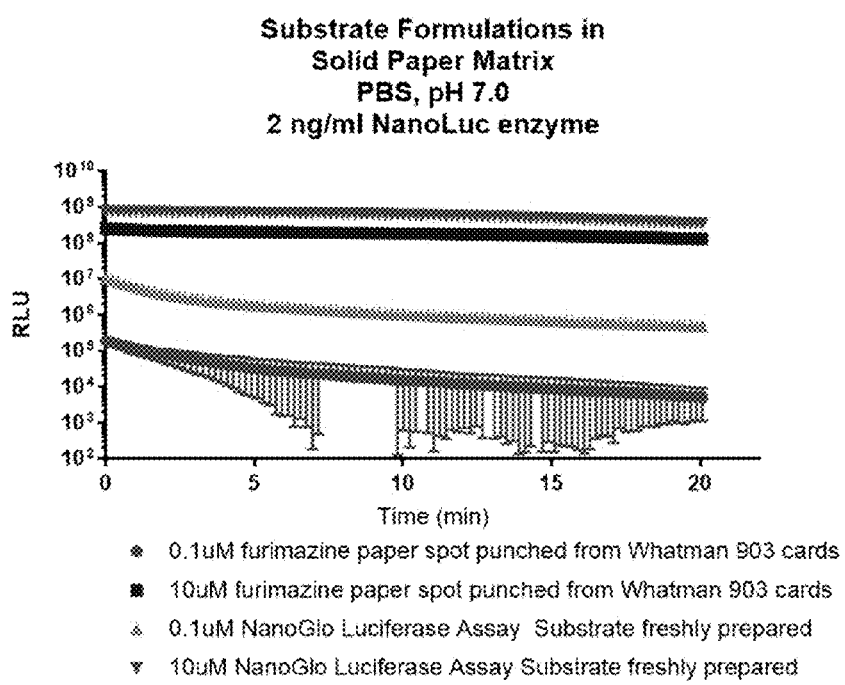
B.
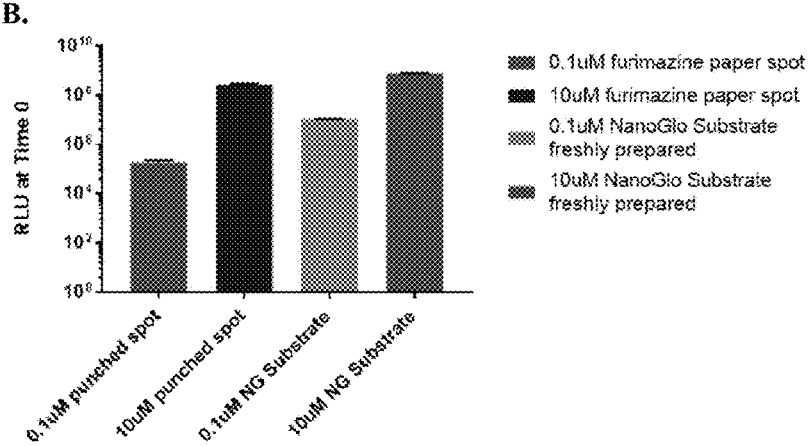
C.

FIG. 14
A.
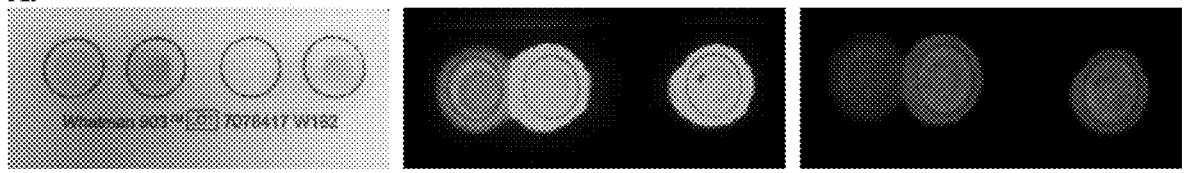
B.
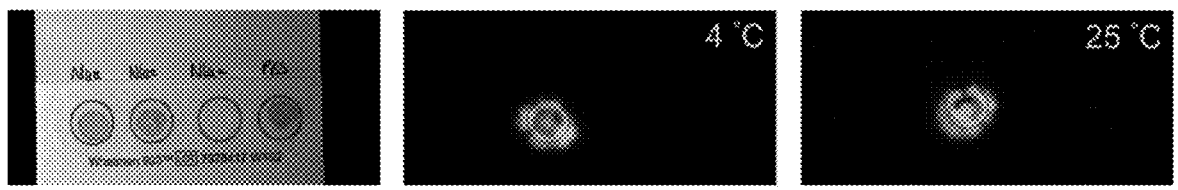

FIG. 15

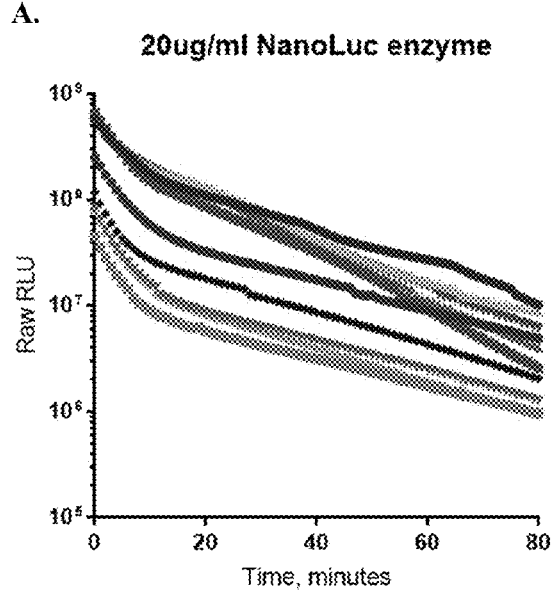

A. 20ug/ml NanoLuc enzyme

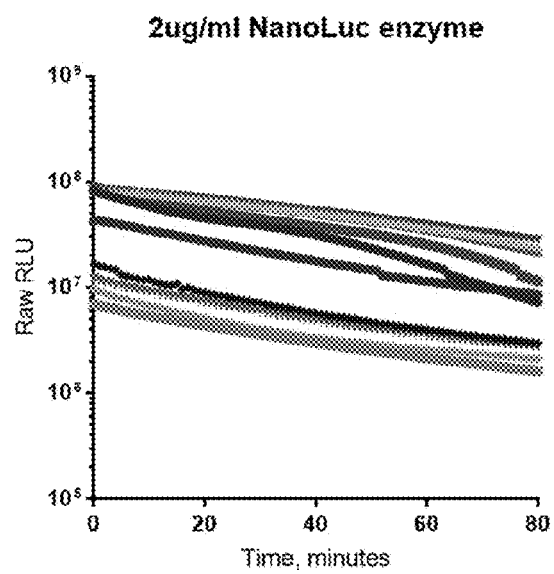

B. 2ug/ml NanoLuc enzyme

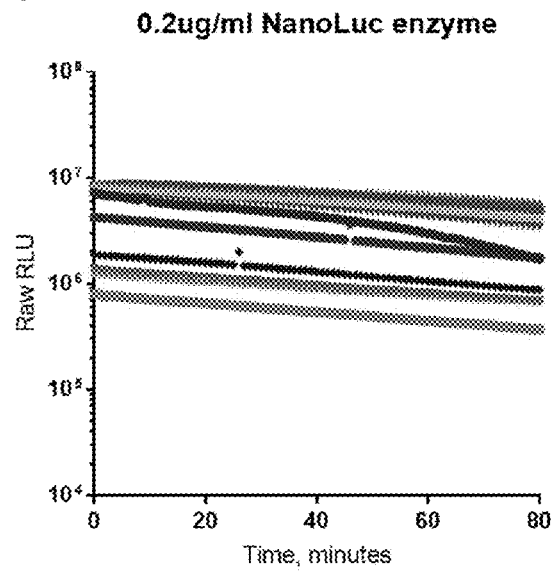

C. 0.2ug/ml NanoLuc enzyme

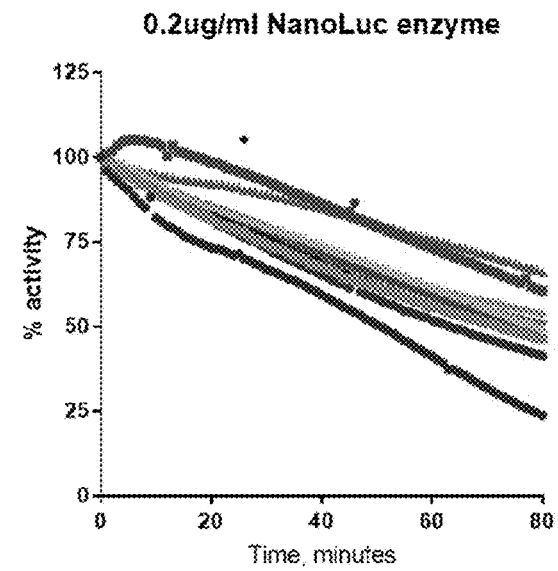

D. 0.2ug/ml NanoLuc enzyme

1. Furimazine in water
2. Furimazine + Sucrose protein buffer
3. Furimazine + ATT (20mM)
4. Furimazine + ATT (50mM)
5. Furimazine + ATT (20mM) + Sucrose protein buffer
6. Furimazine + ATT (50mM) + Sucrose protein buffer
7. Furimazine + Thiourea (20mM)
8. Furimazine + Thiourea (100mM)
9. Furimazine + Thiourea (20mM) + Sucrose protein buffer
10. Furimazine + Thiourea (100mM) + in Sucrose protein buffer FIG. 17
A.
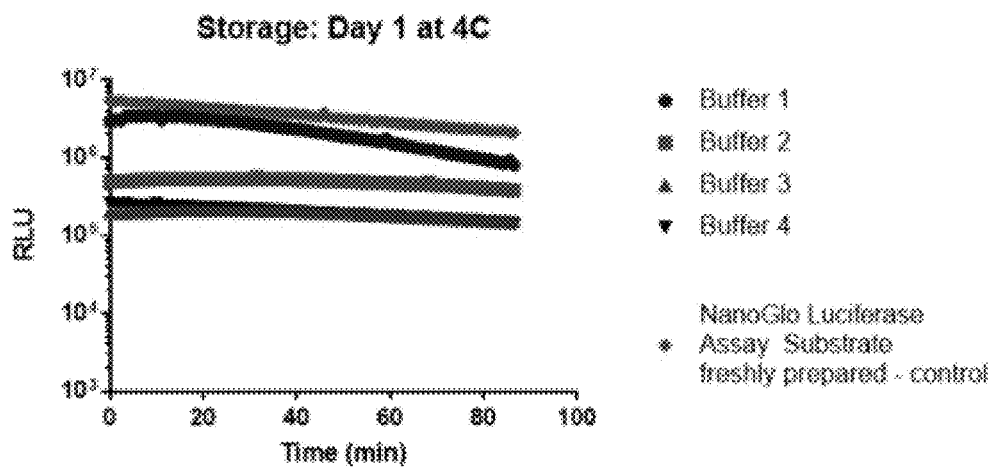
B.
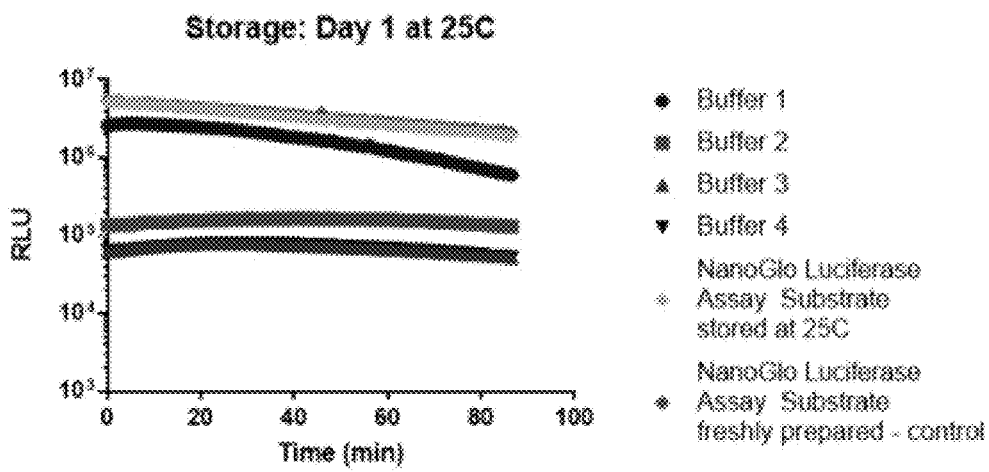
C.
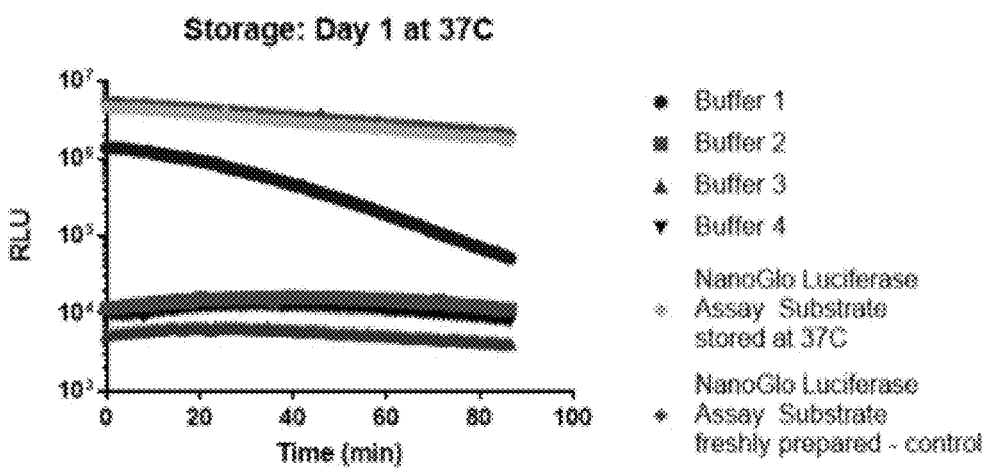

FIG. 18
A.
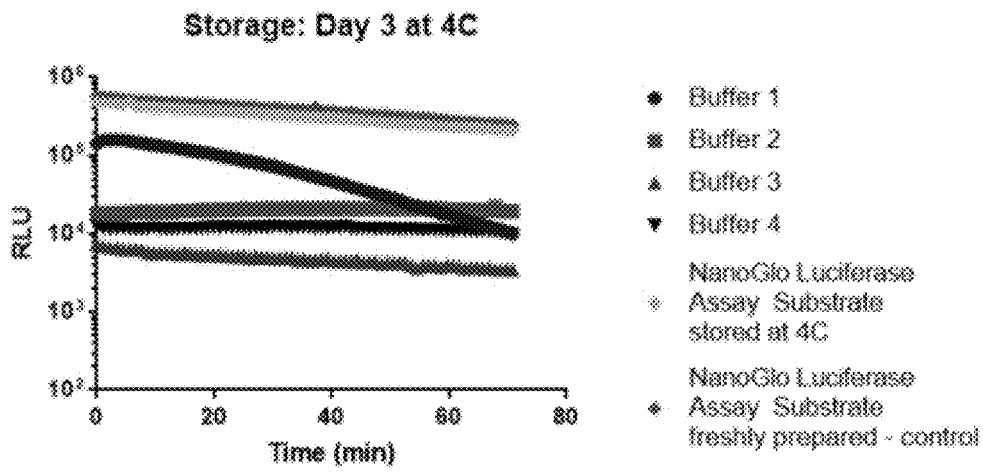
B.
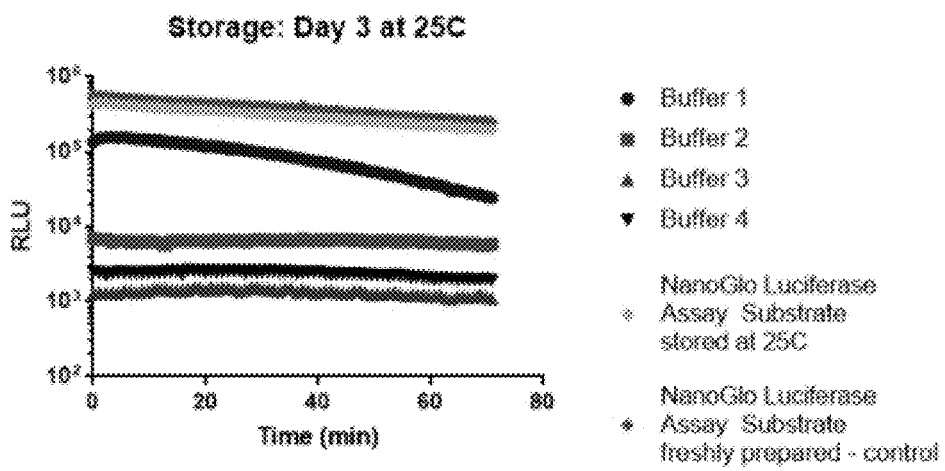
C.
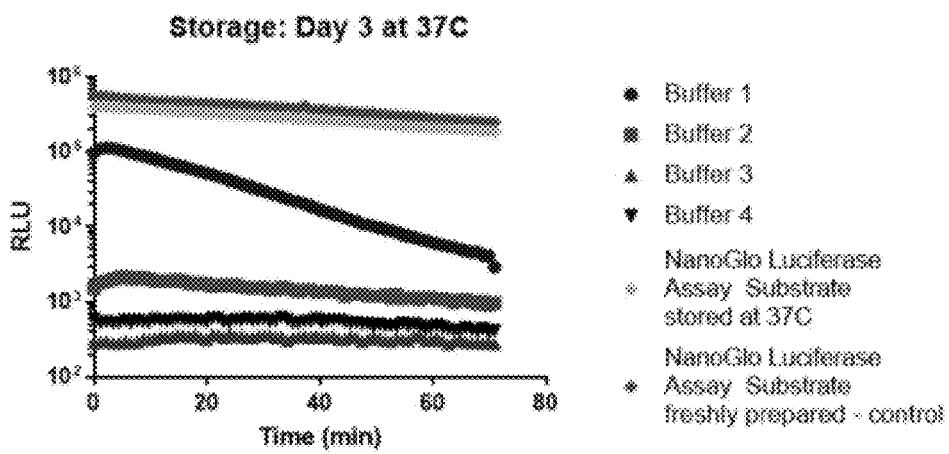

FIG. 19
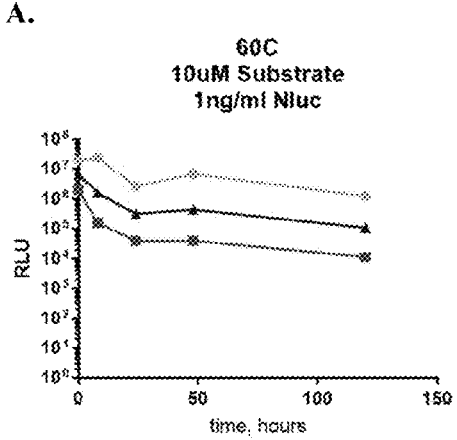
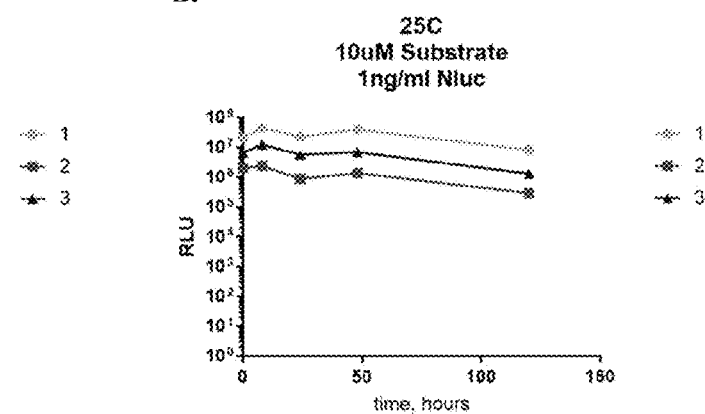
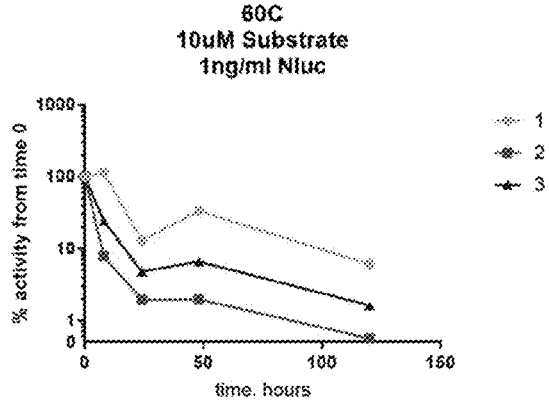
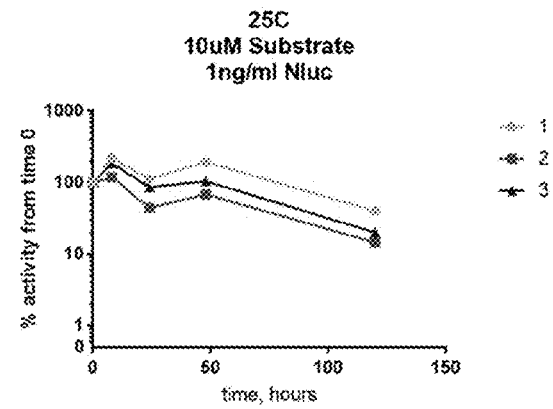

FIG. 20
A.
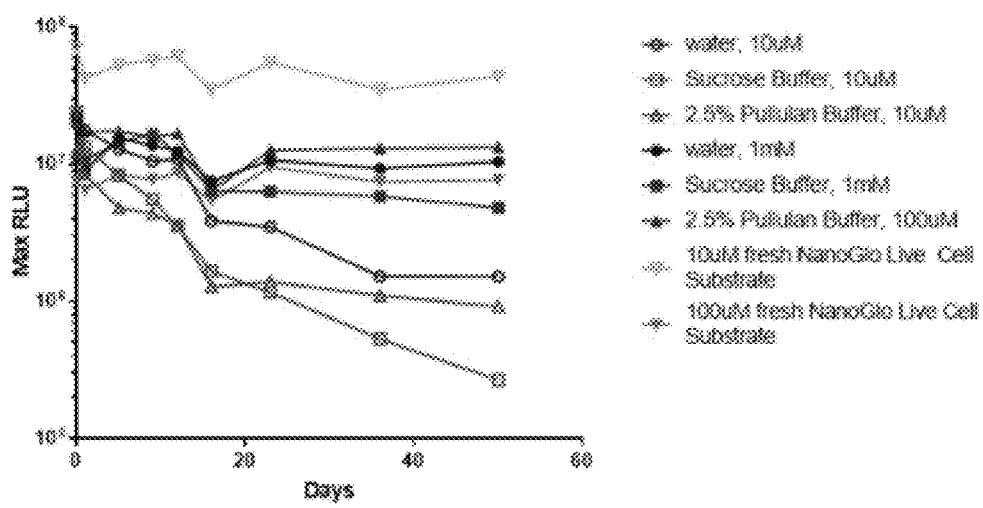
B.
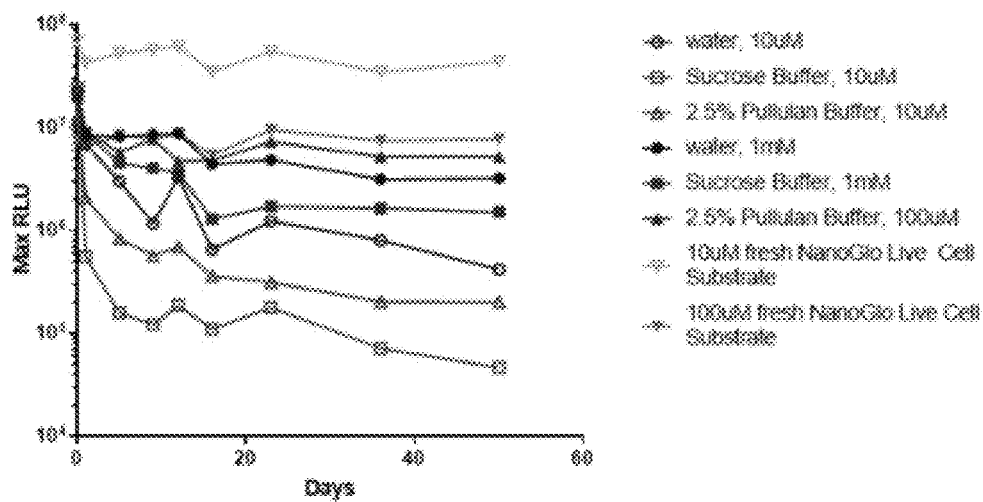

FIG. 20 (cont'd)
C.
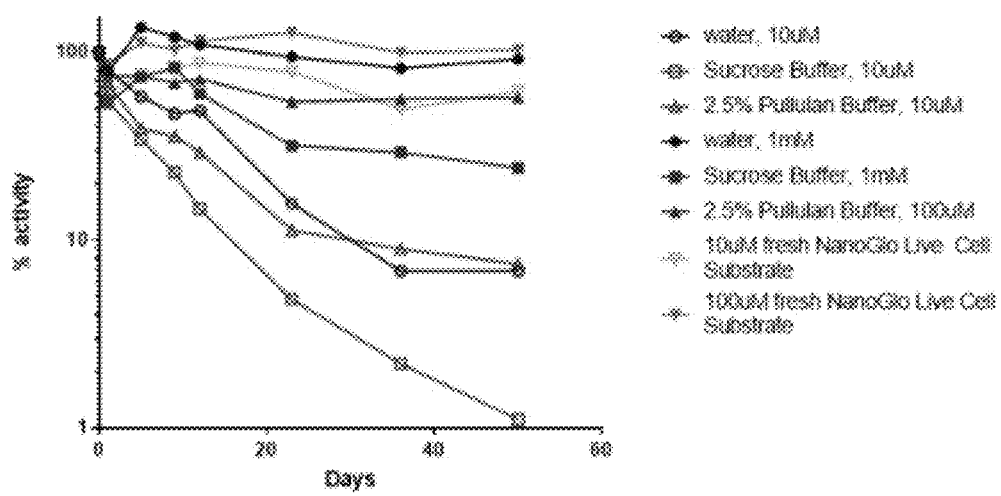
D.
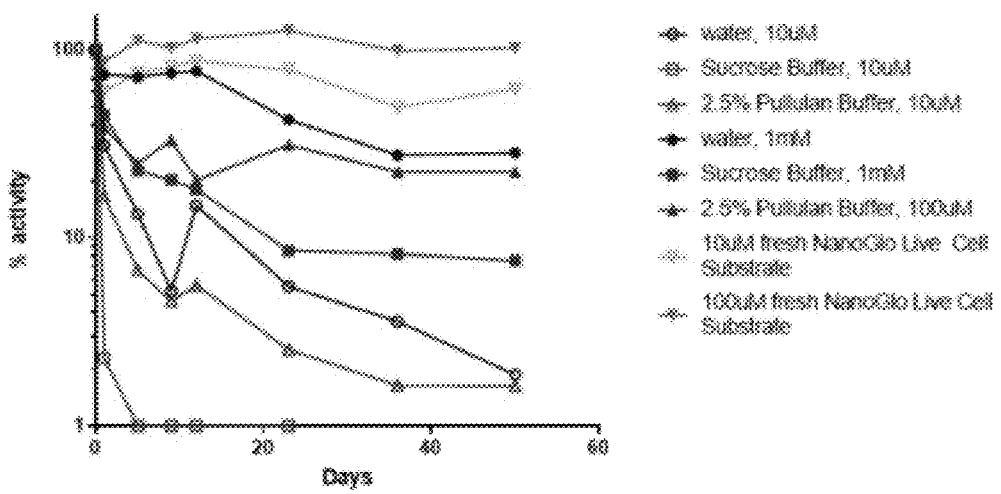

FIG. 21
A.
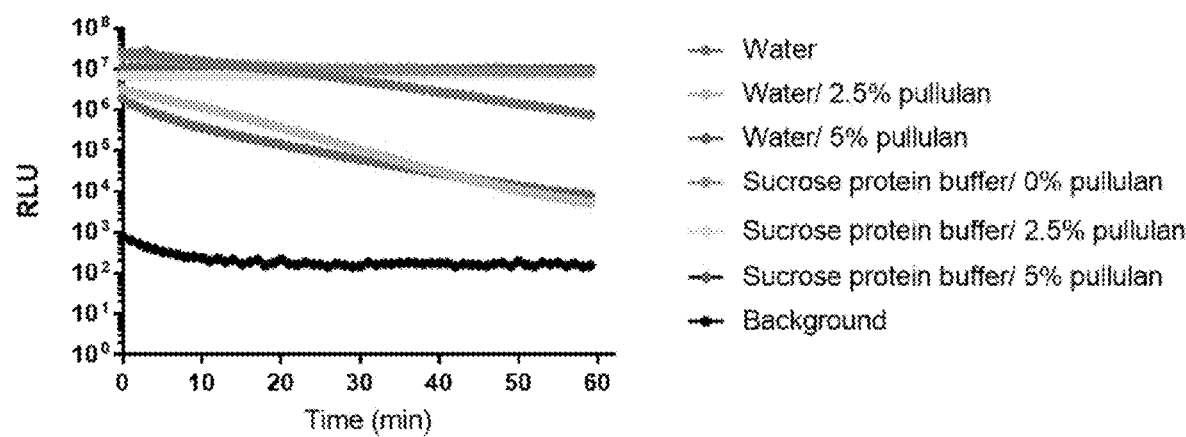
B.
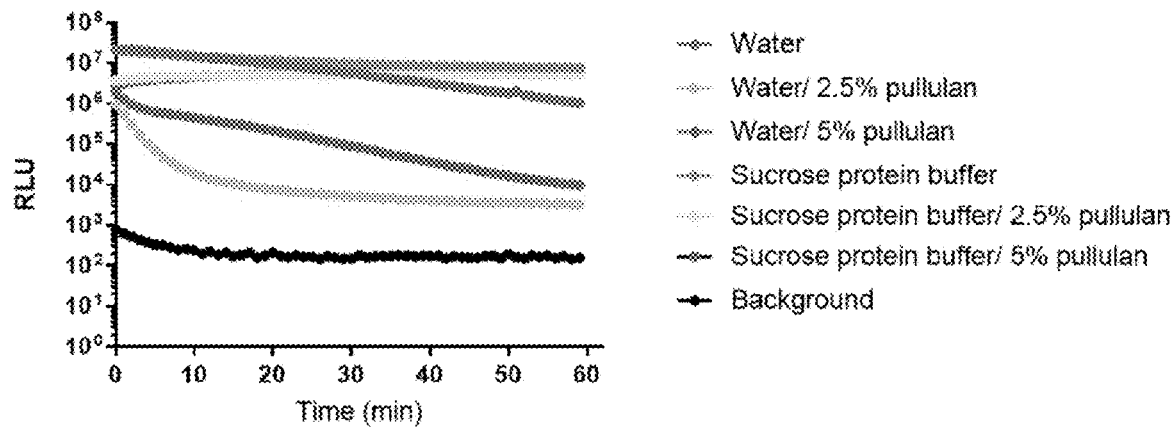

C.

FIG. 22
A.
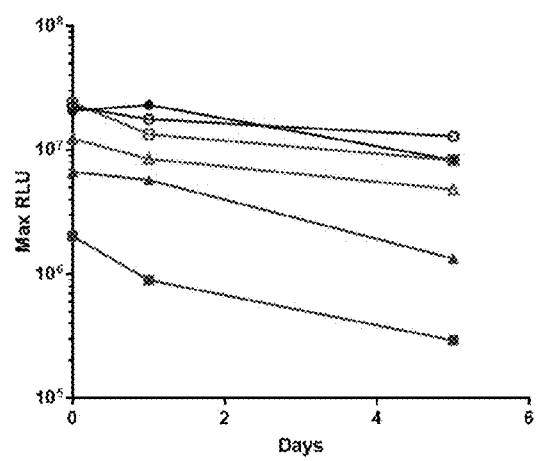
B.
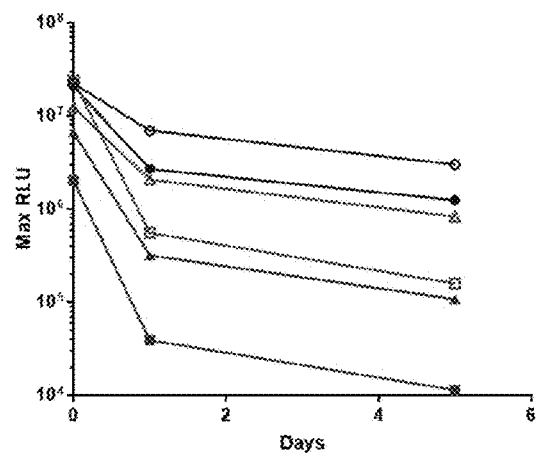
C.
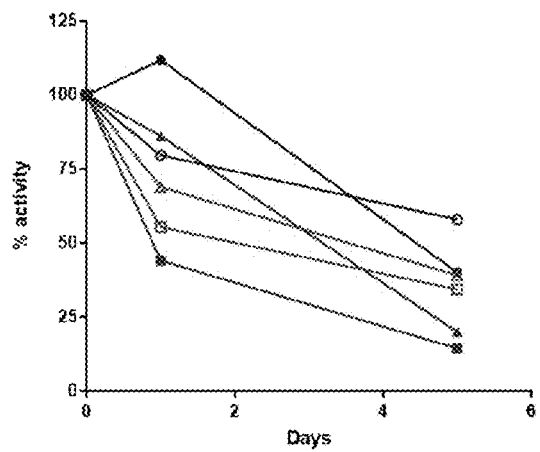
D.
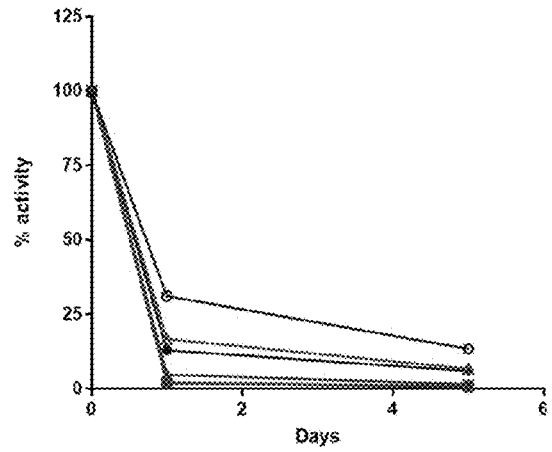
○ Water, baked  ● Water, vacuum
□ Sucrose protein buffer, baked  ▨ Sucrose protein buffer, vacuum
△ 2.5% pullulan protein buffer, baked  ▲ 2.5% pullulan protein buffer, vacuum FIG. 25
A.
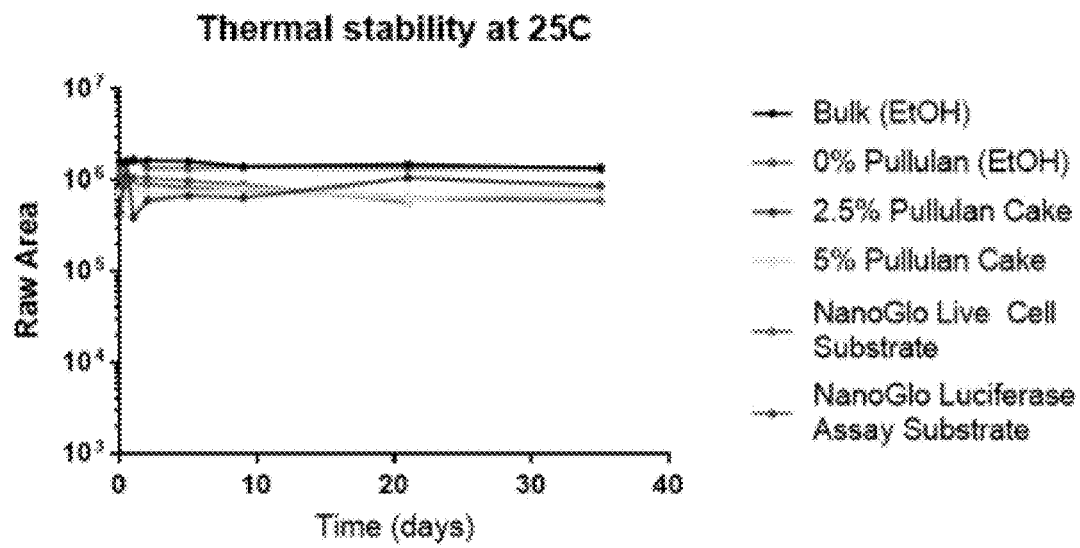
B.
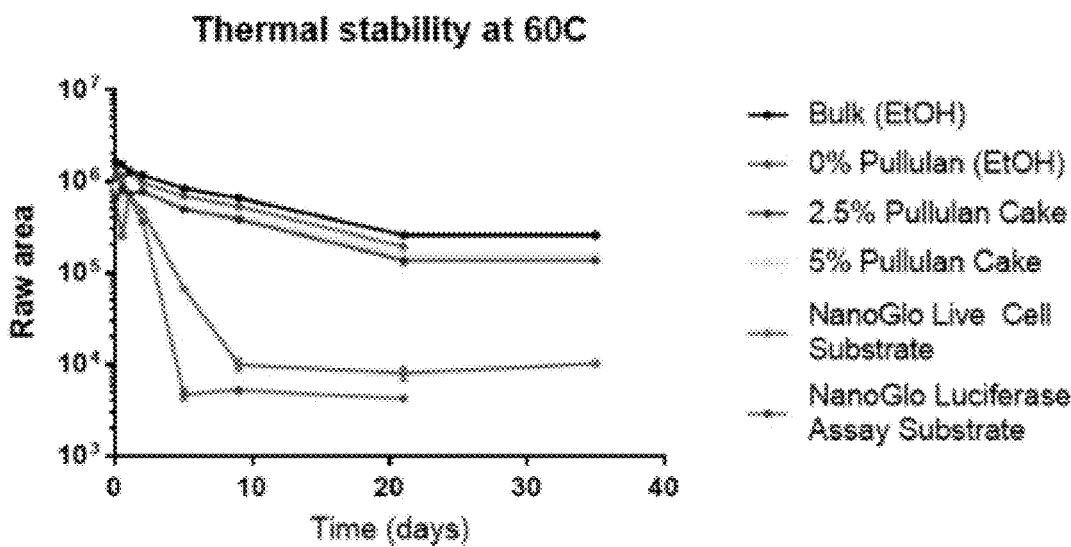

FIG. 25 (cont'd)
C.
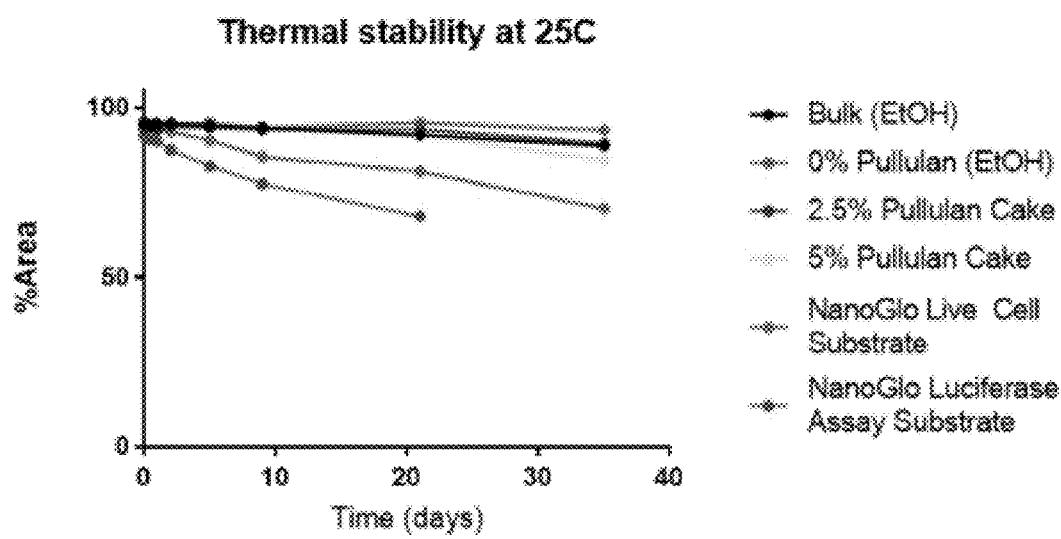
D.
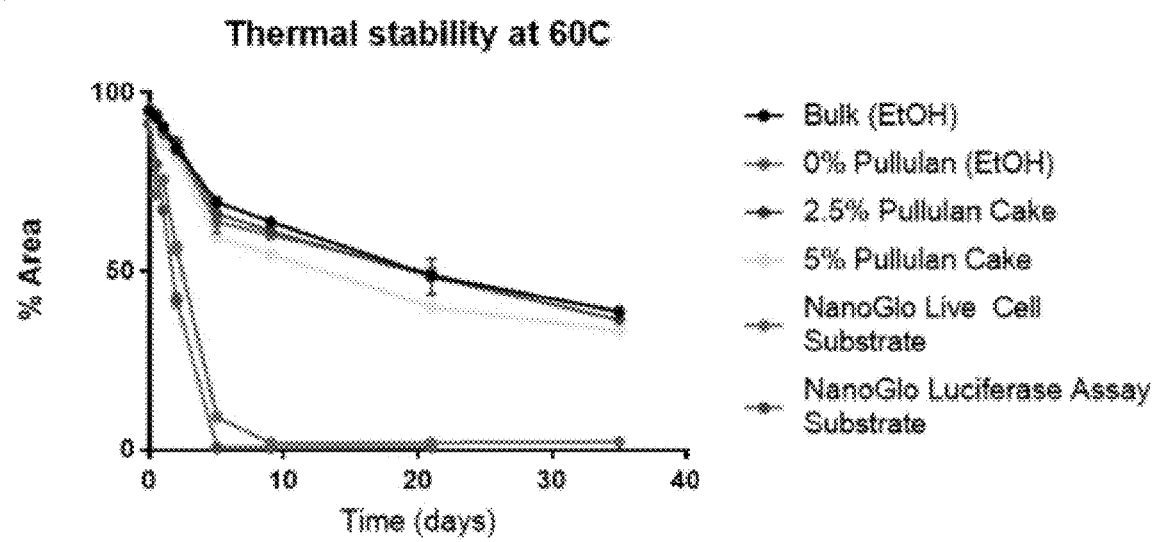

FIG. 26
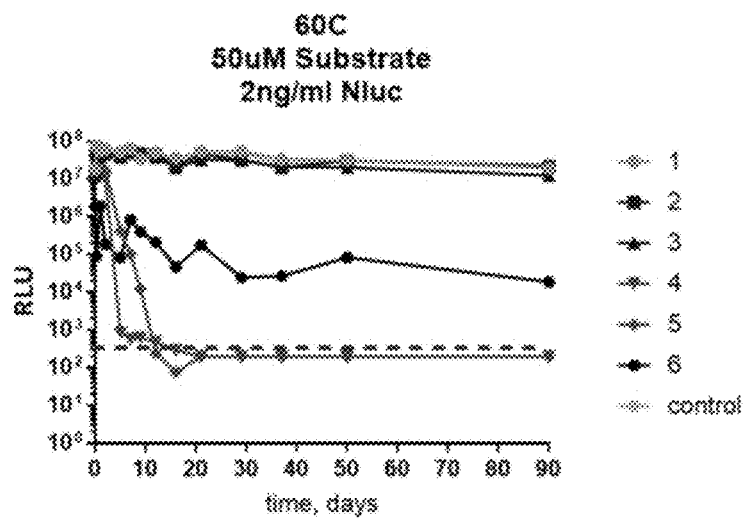
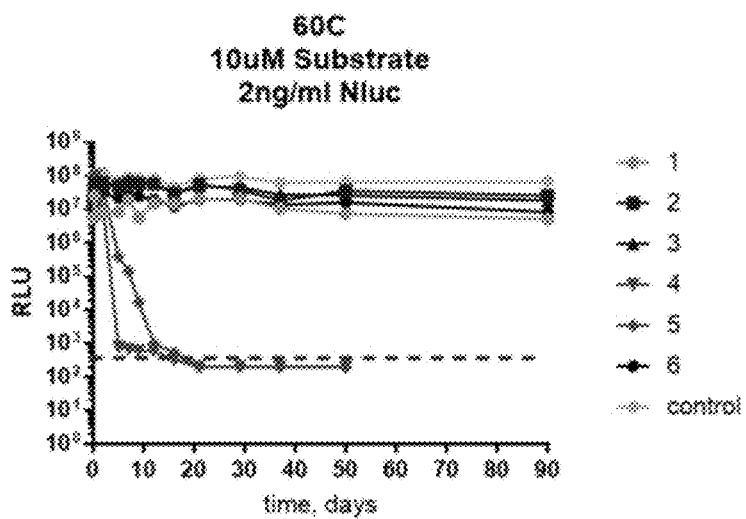
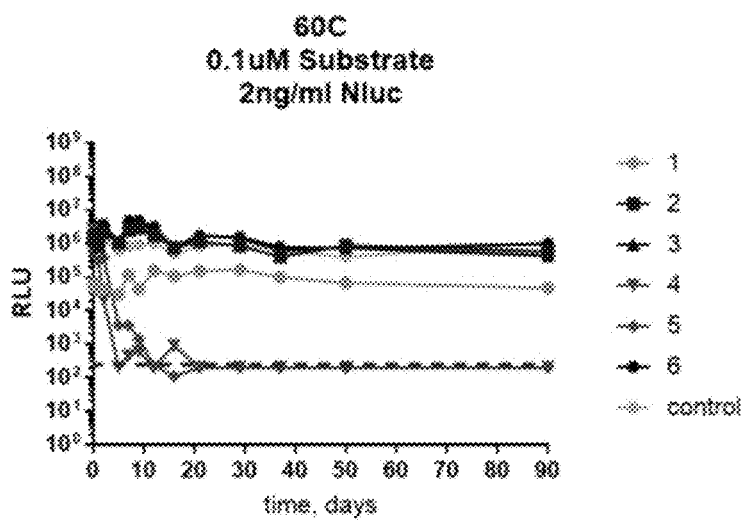

FIG. 26 (cont'd)
D.
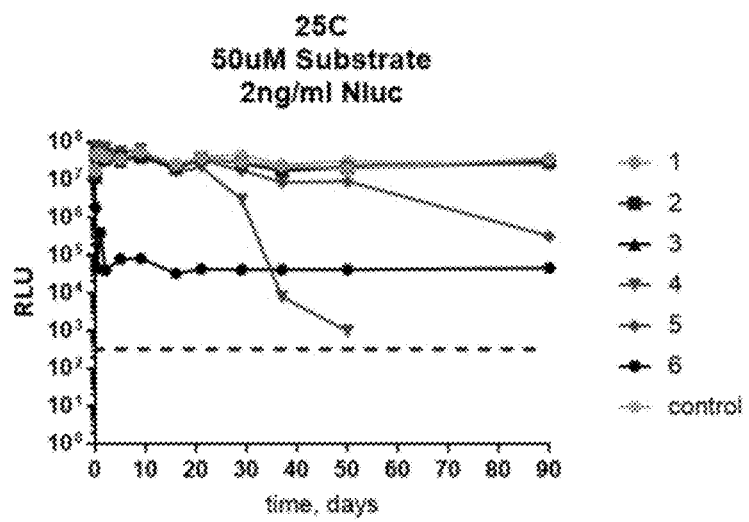
E.
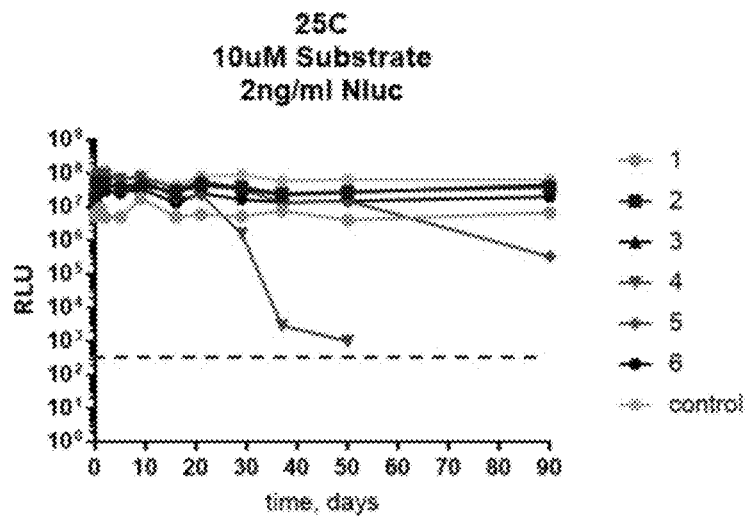
F.
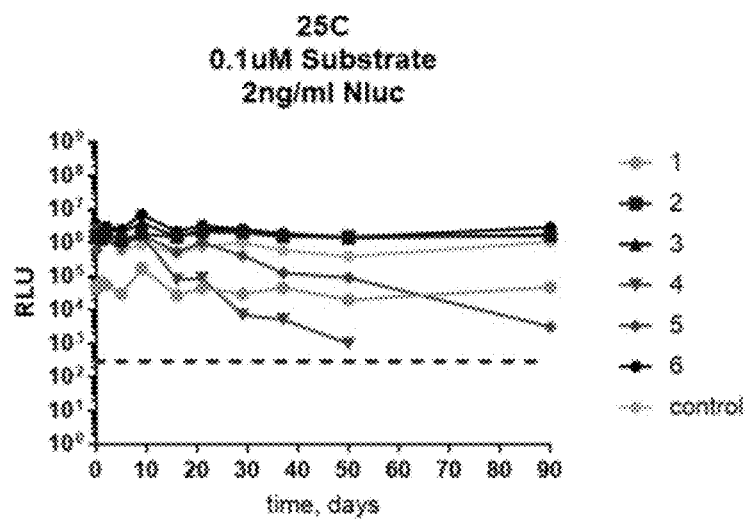

FIG. 27
A.
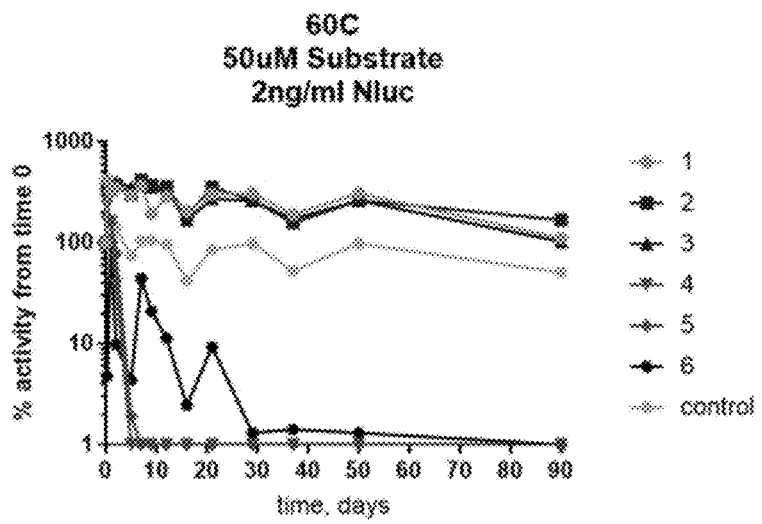
B.
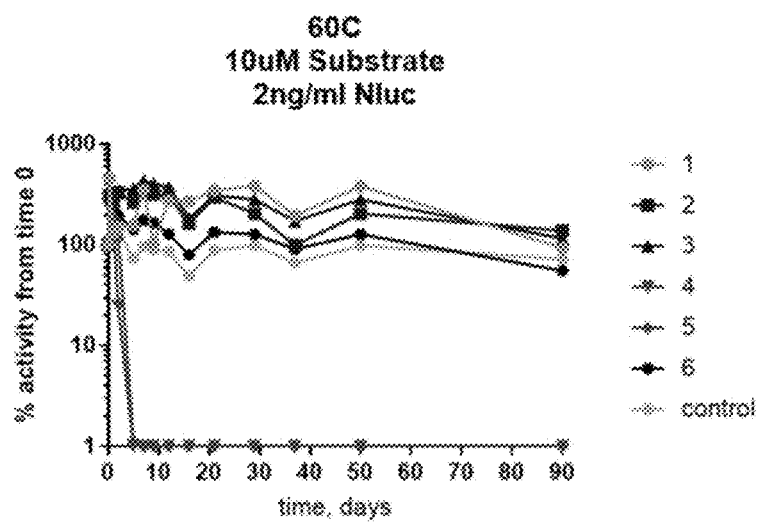
C.
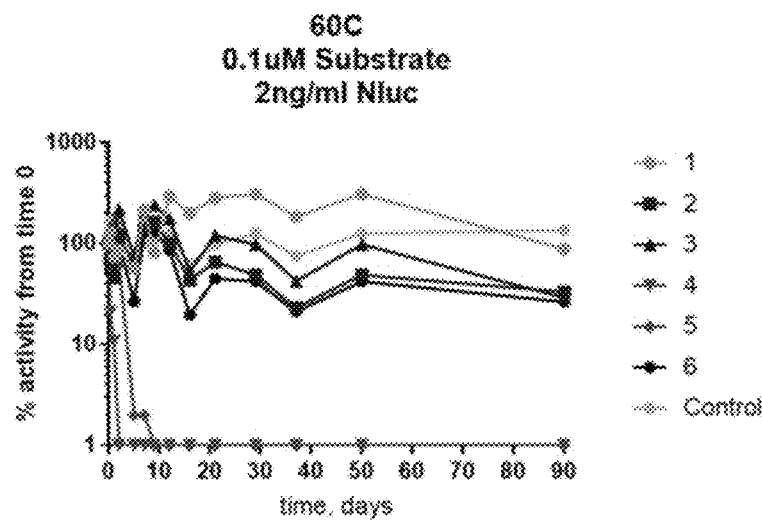

FIG. 27 (cont'd)
D.
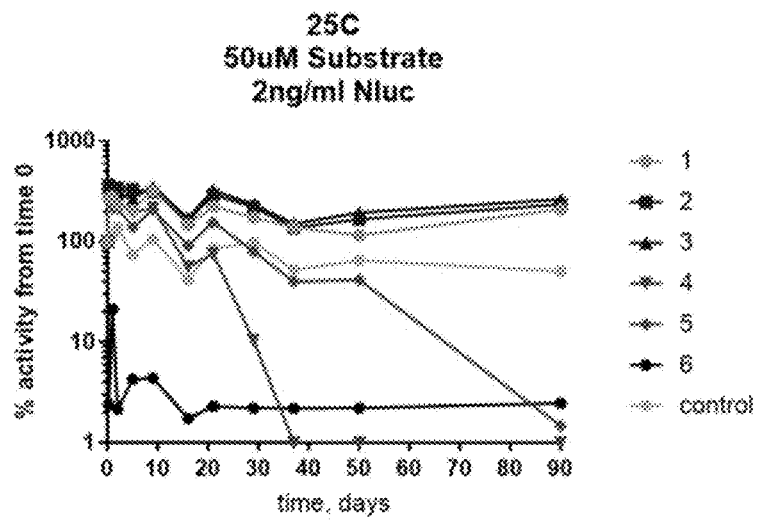
E.
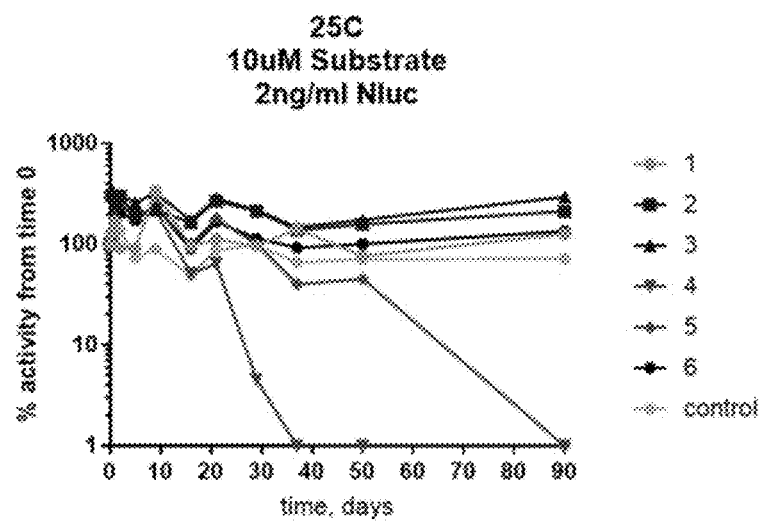
F.
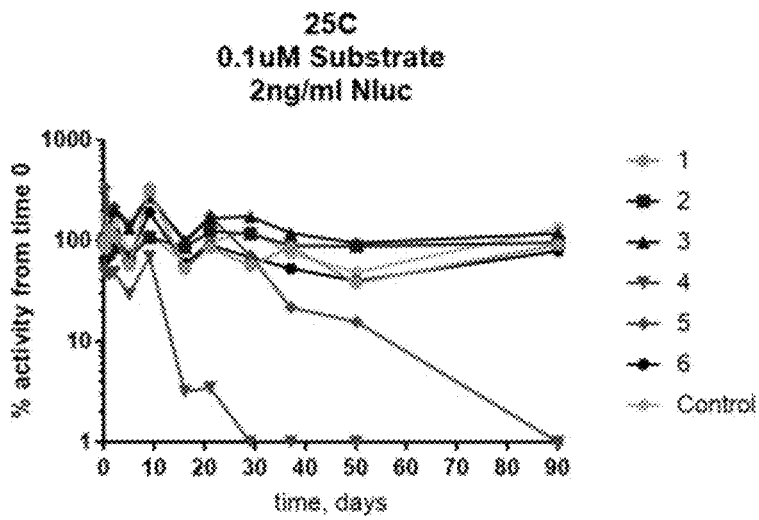

FIG. 28
A.
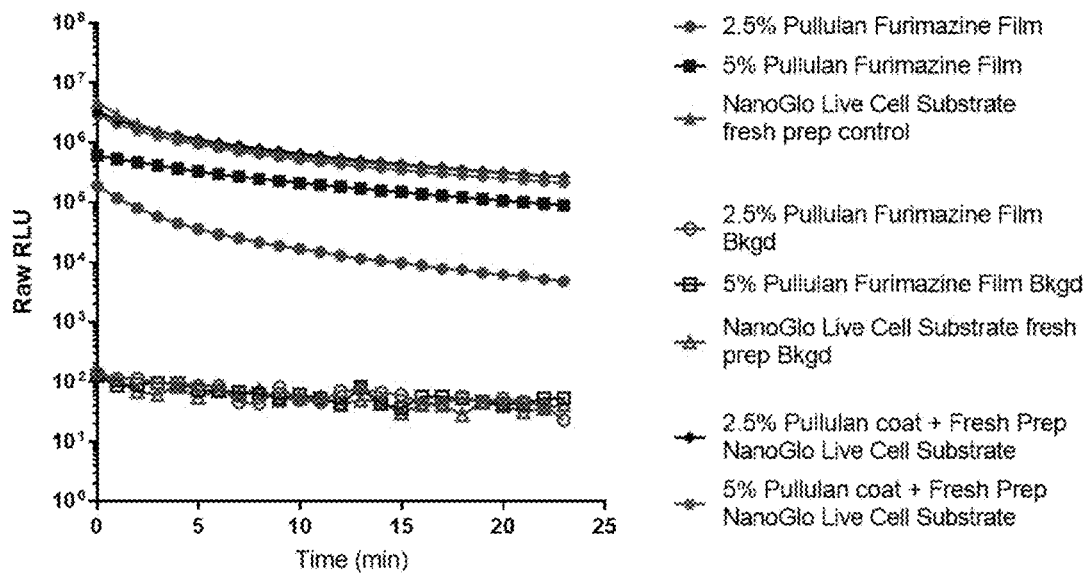
B.
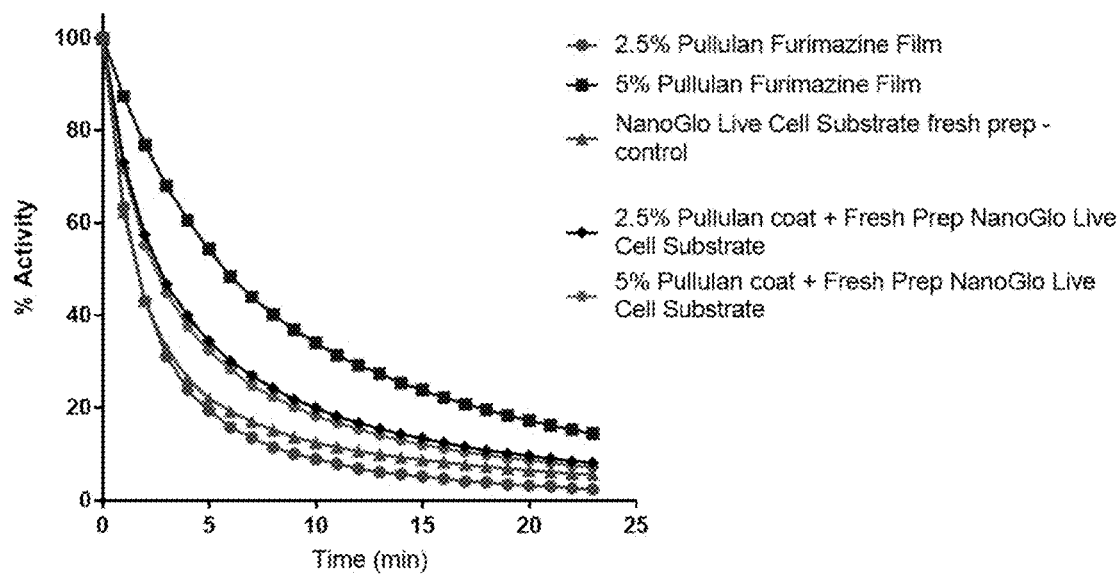

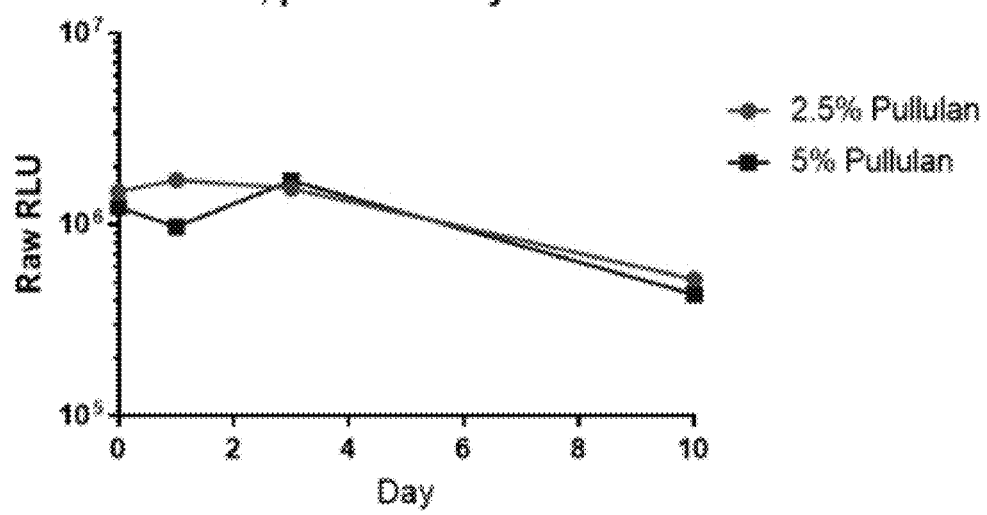

FIG. 31
A.
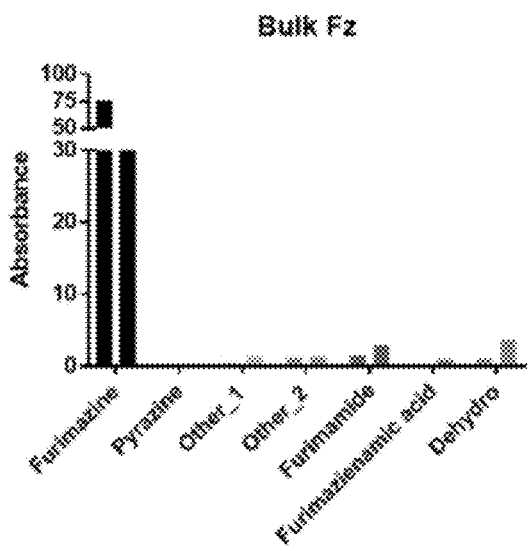
B.
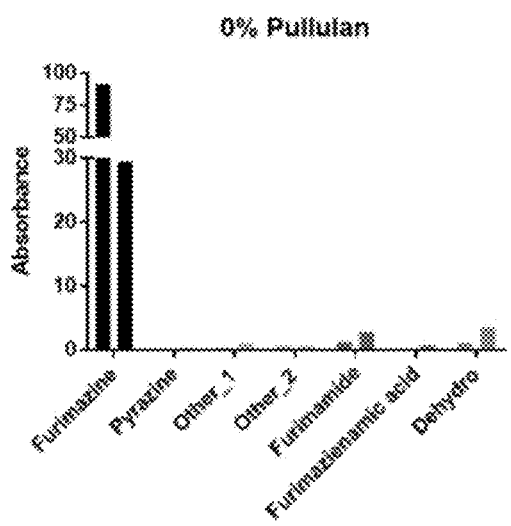
C.
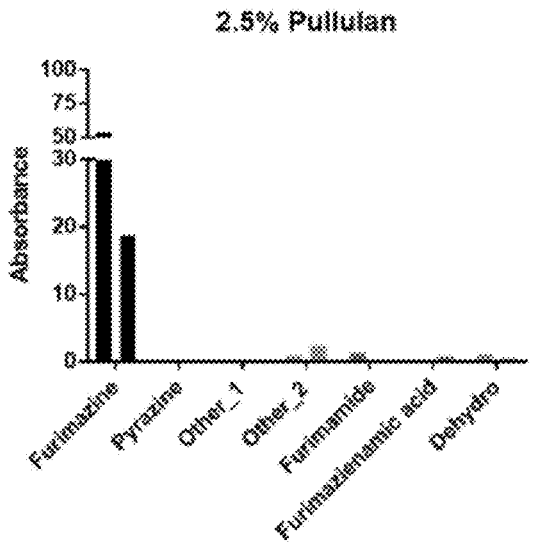
D.
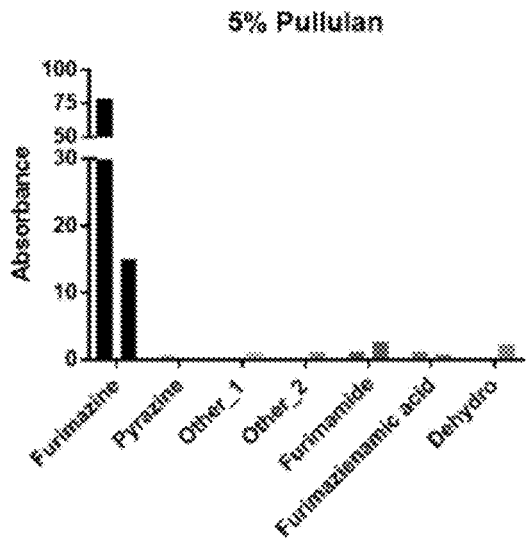

FIG. 31 (cont'd)
E.
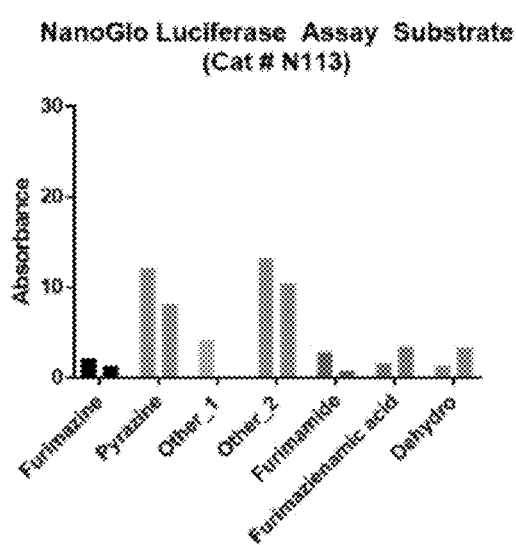
F.
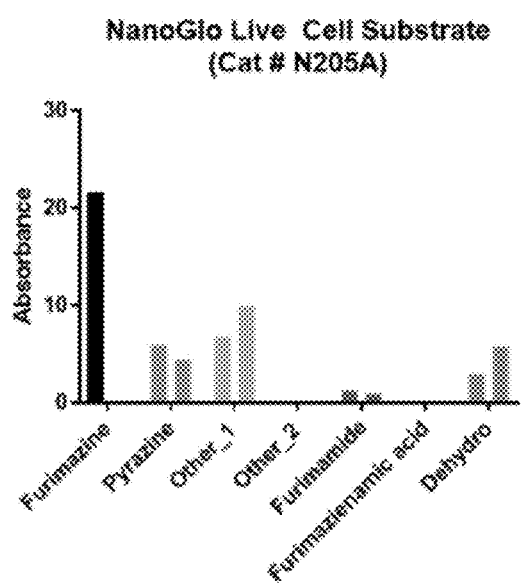

FIG. 32
A.
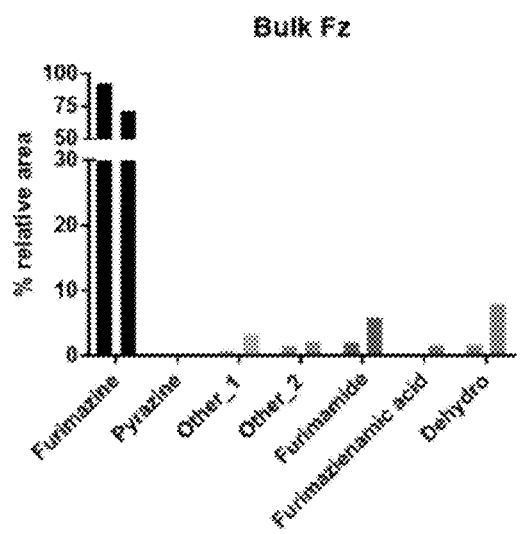
B.
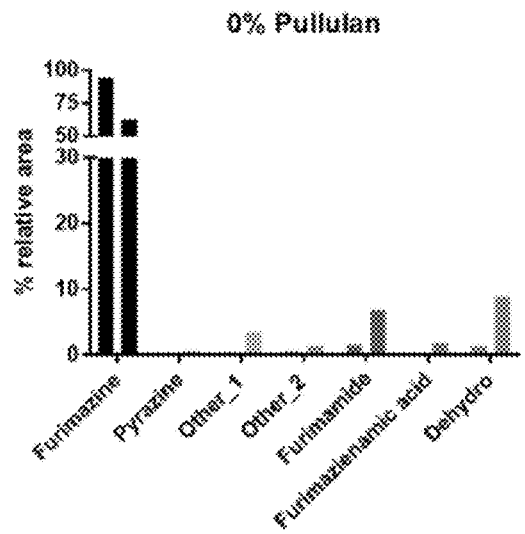
C.
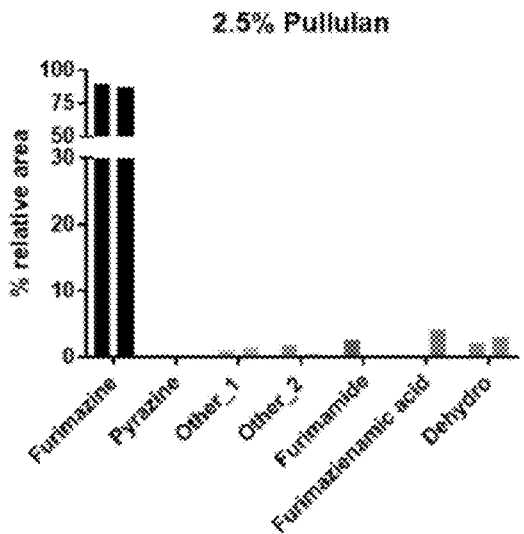
D.
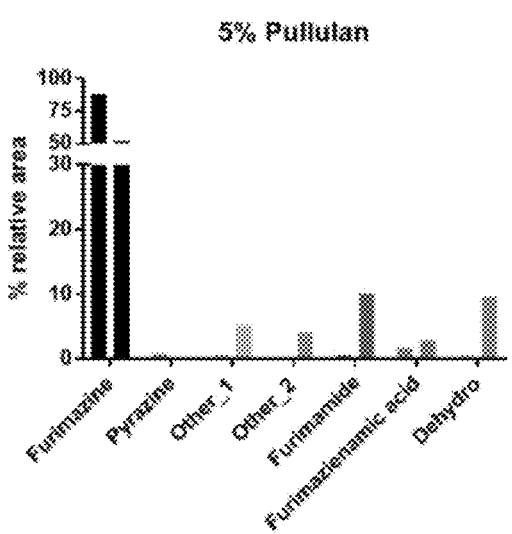

FIG. 32 (cont'd)
E.
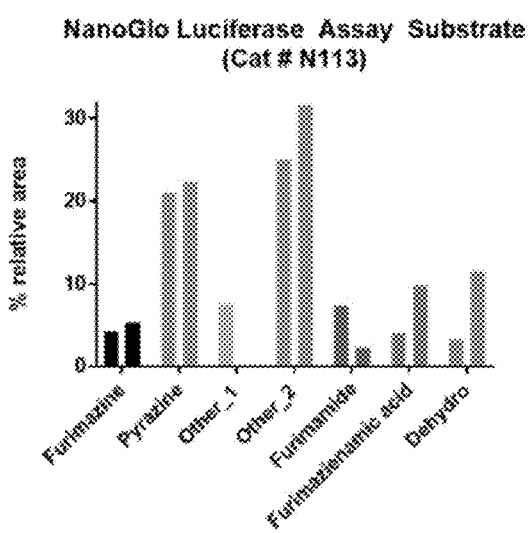
F.
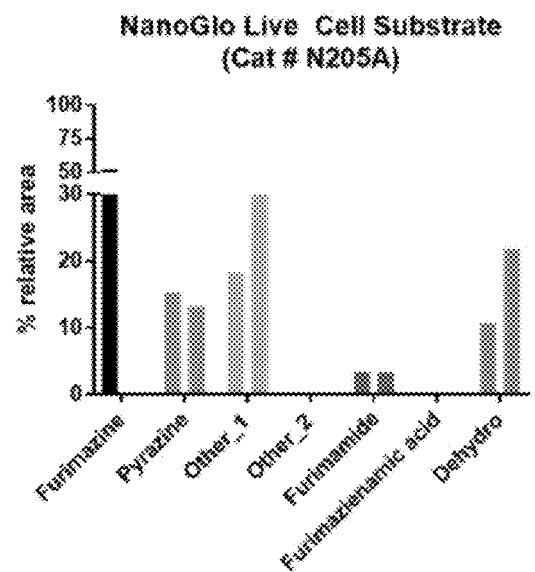

FIG. 34
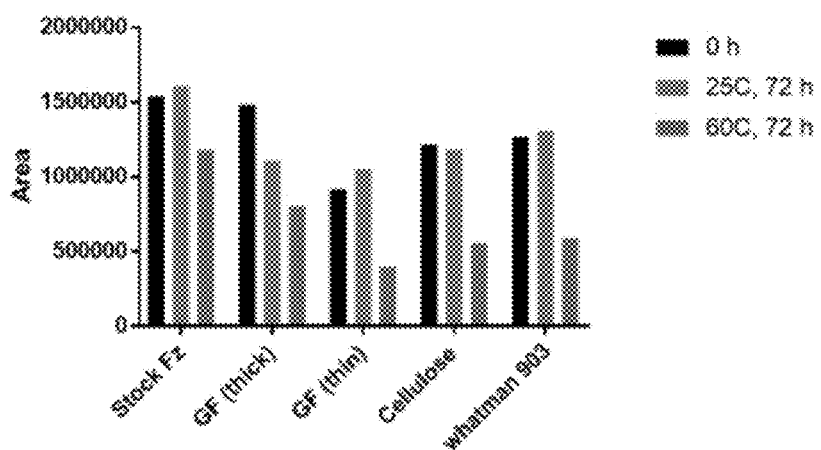
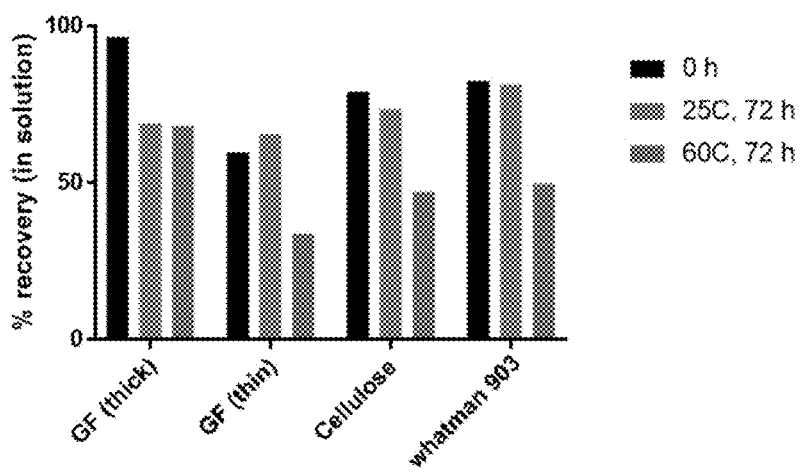
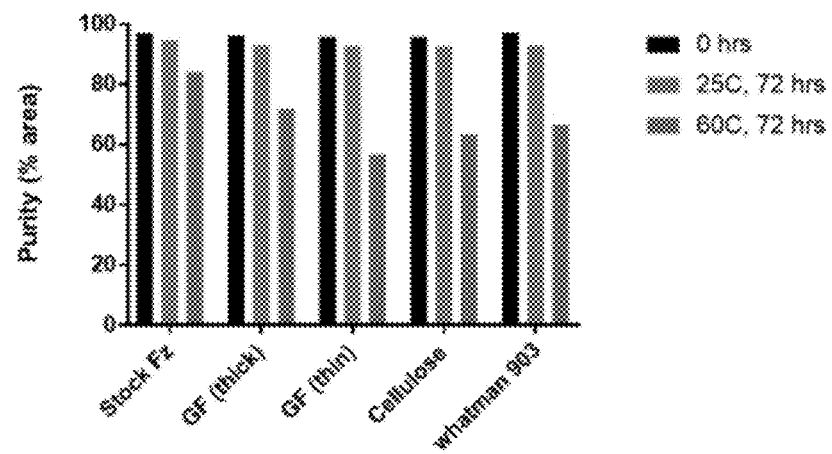

FIG. 35
A.
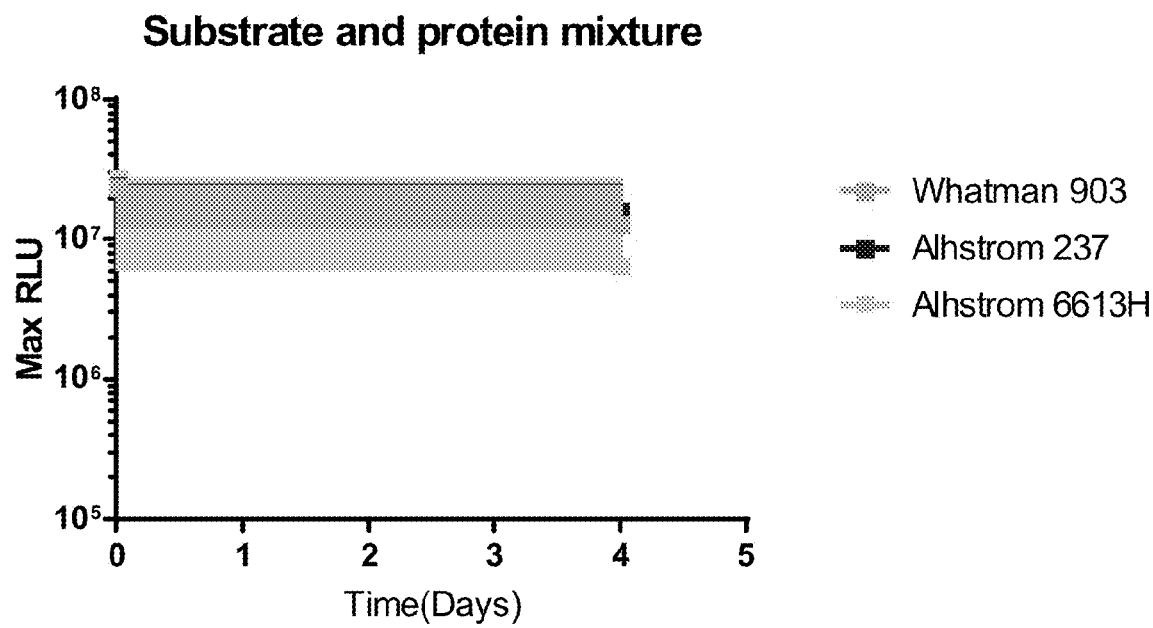
B.
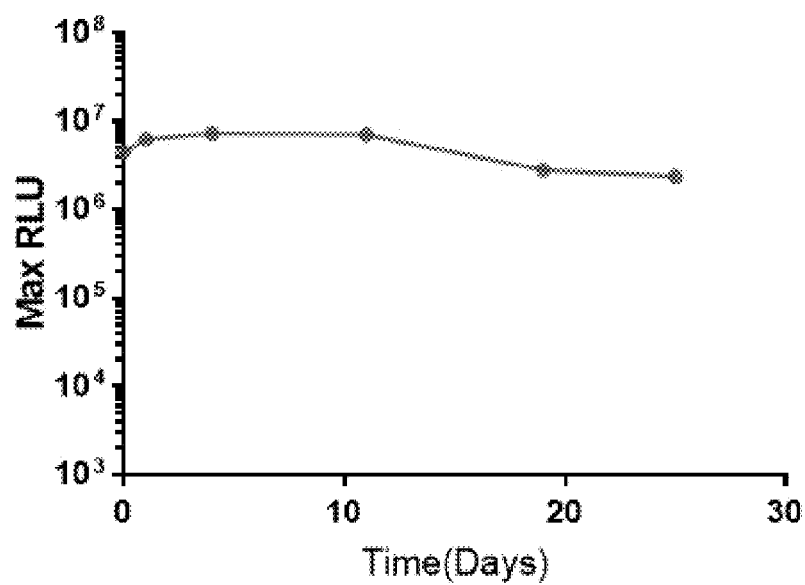

FIG. 36
A.
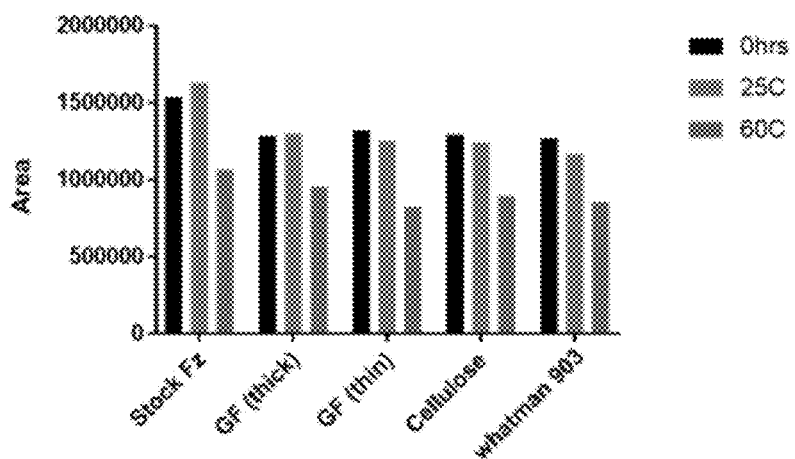
B.
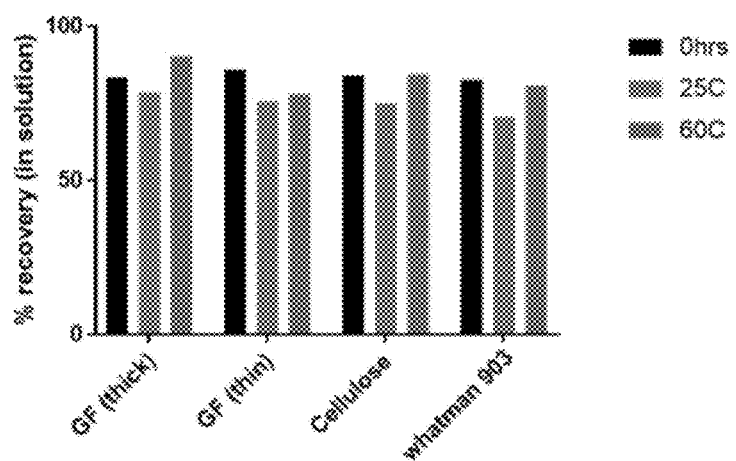
C.
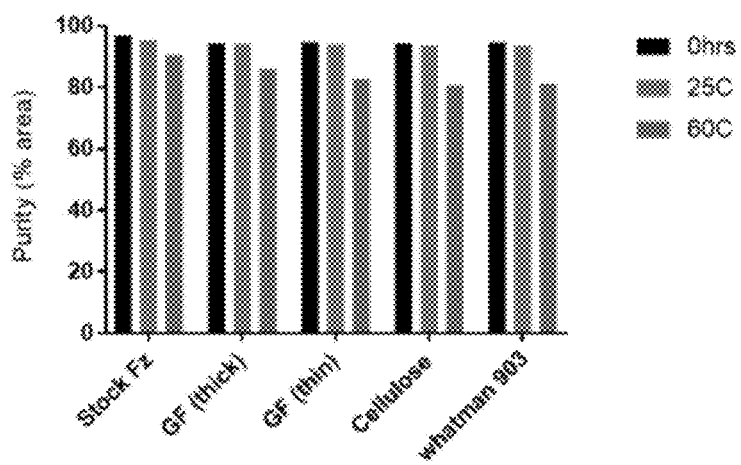

FIG. 37
A.
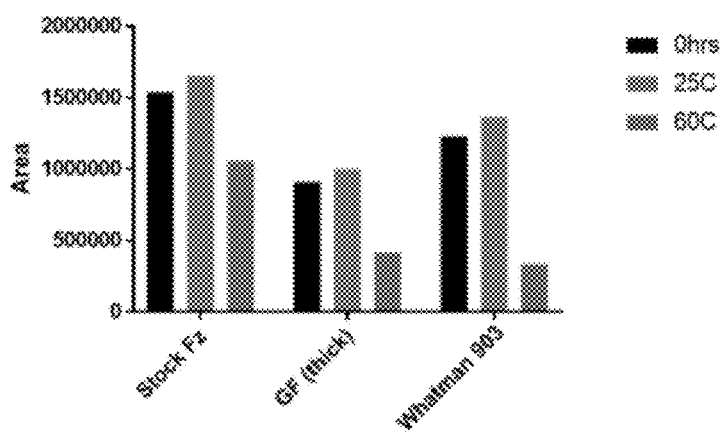
B.
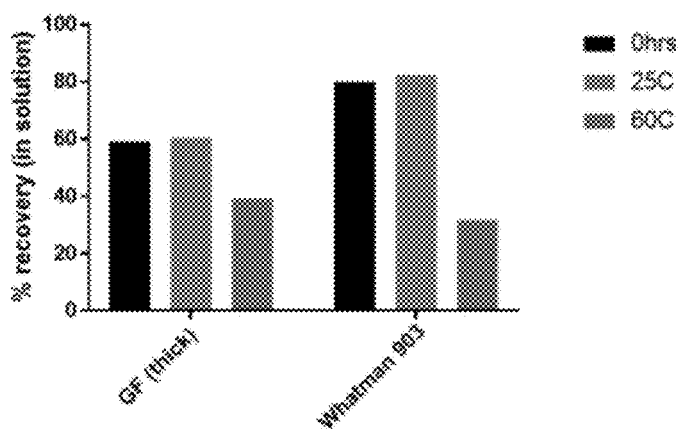
C.
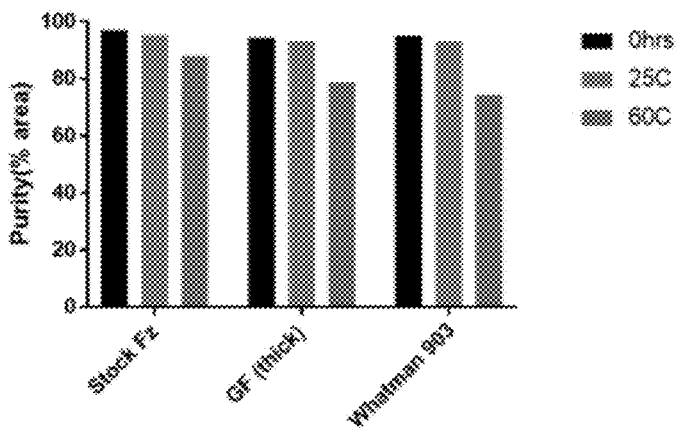

FIG. 38
A.
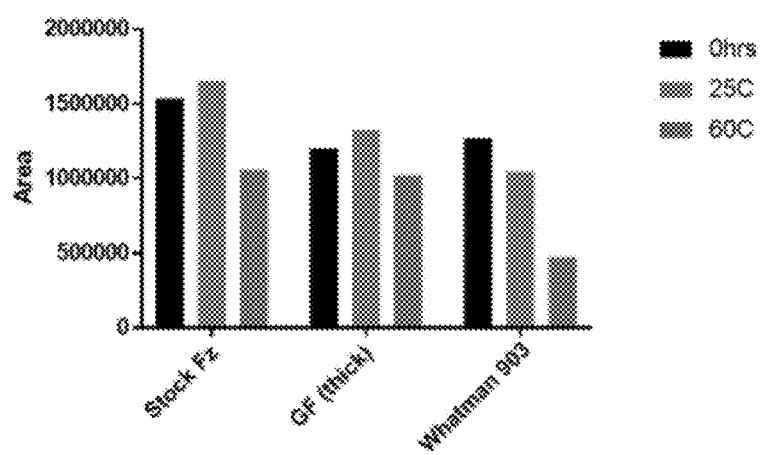
B.
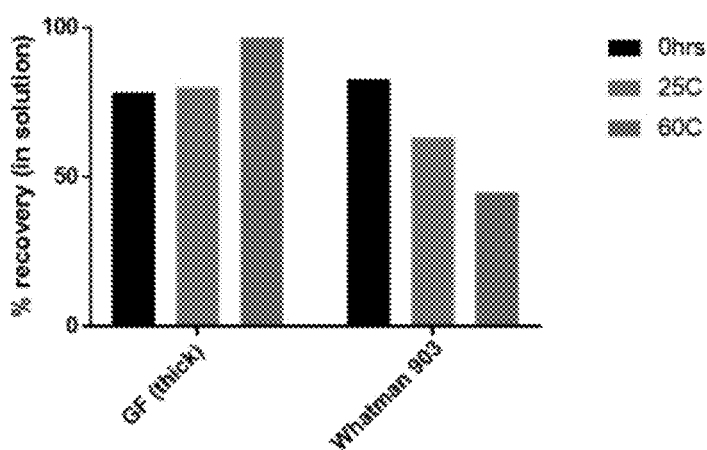
C.
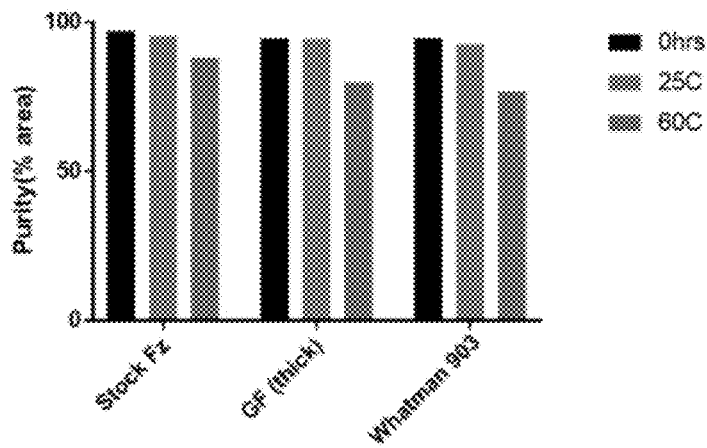

FIG. 39
A.
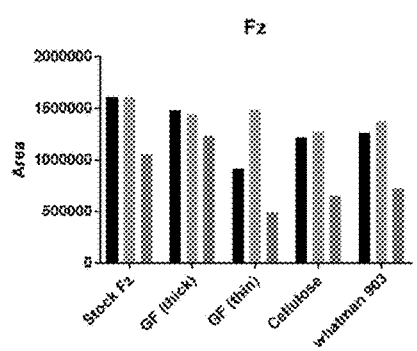
B.
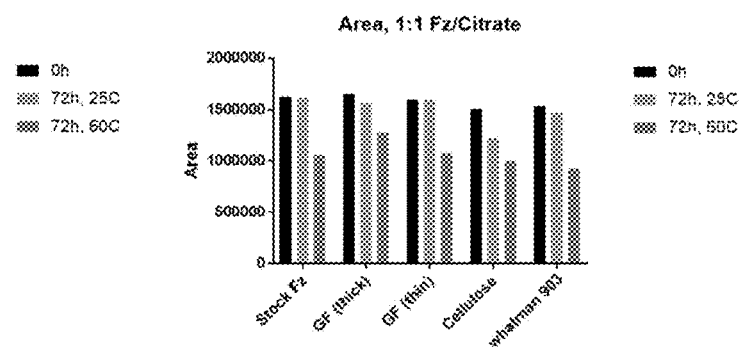
C.
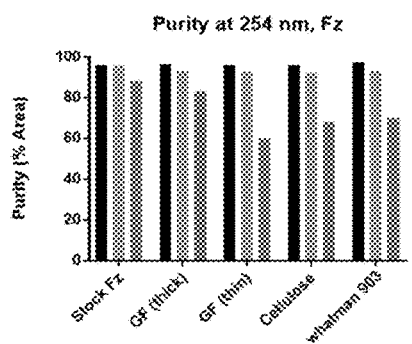
D.
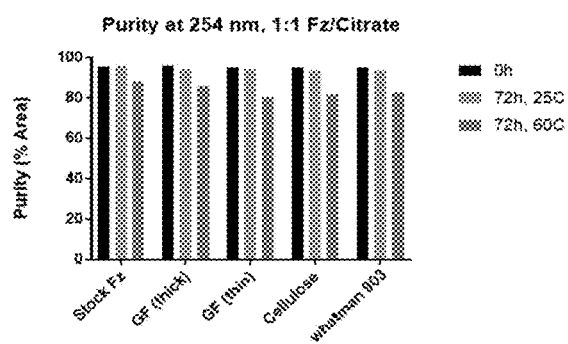

FIG. 40
A.
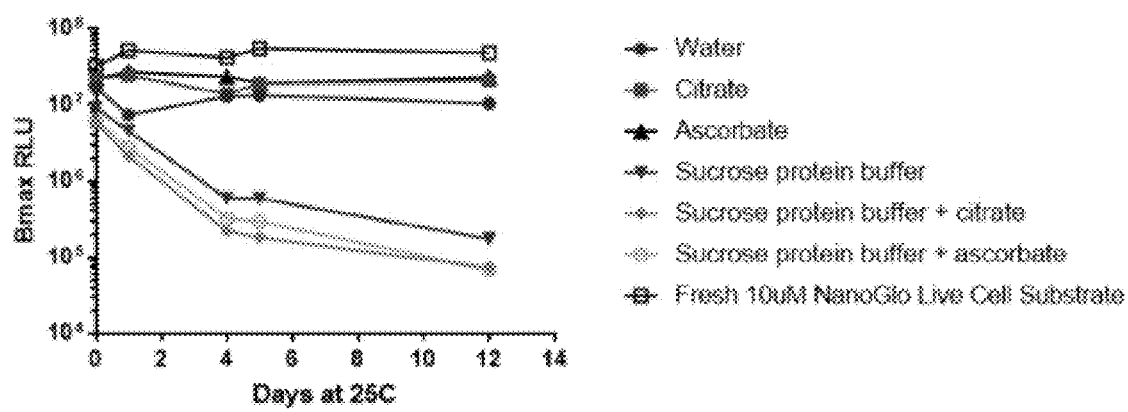
B.
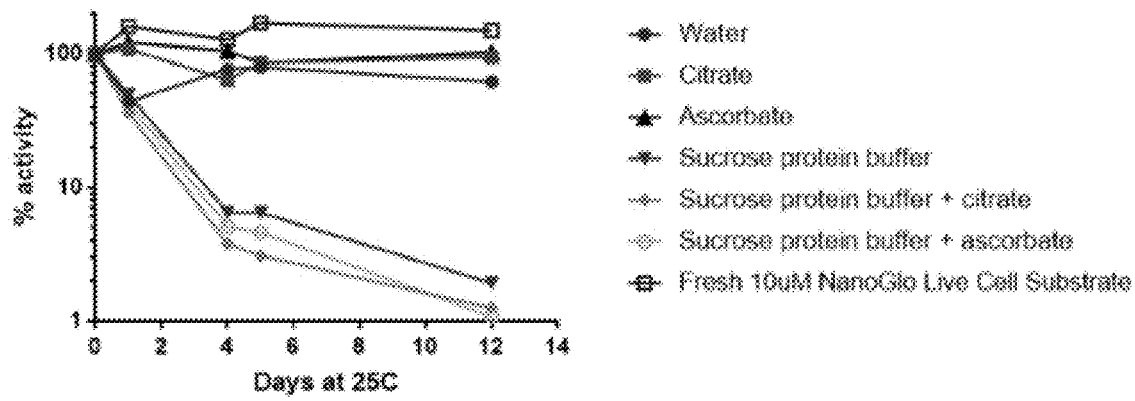

FIG. 41
A.
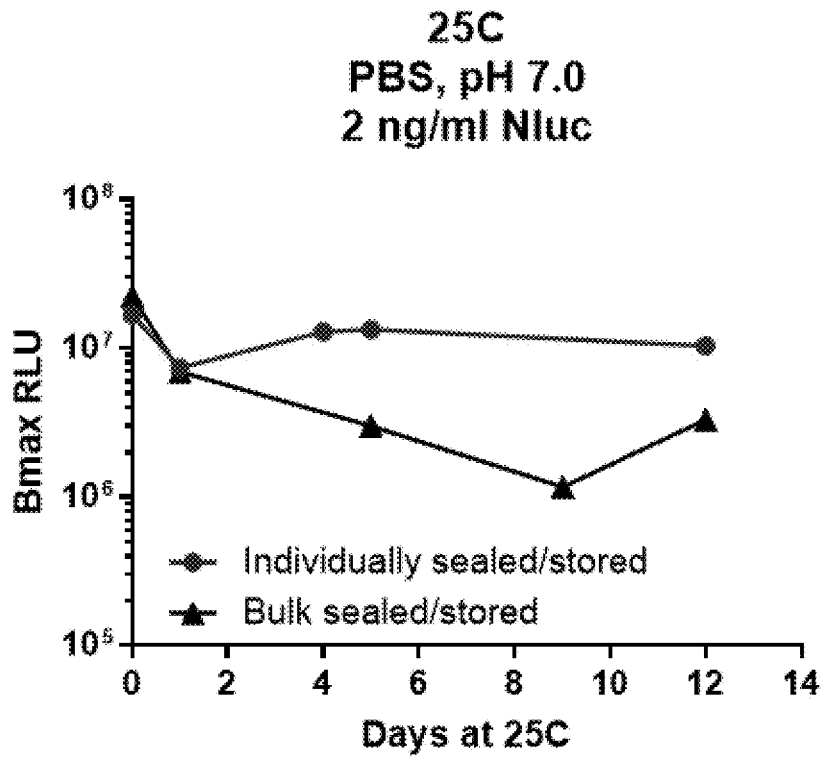
B.
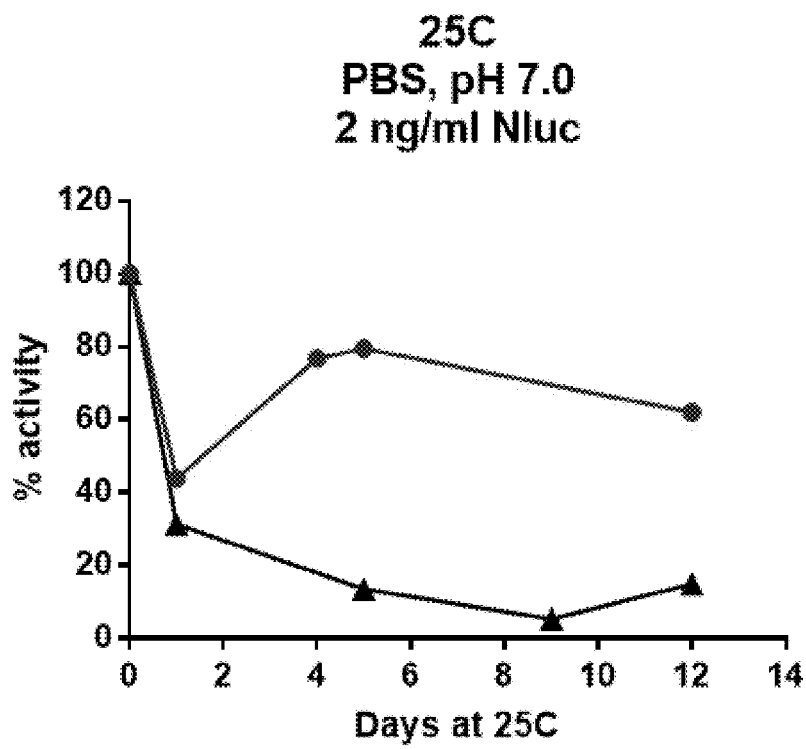

FIG. 42
A.
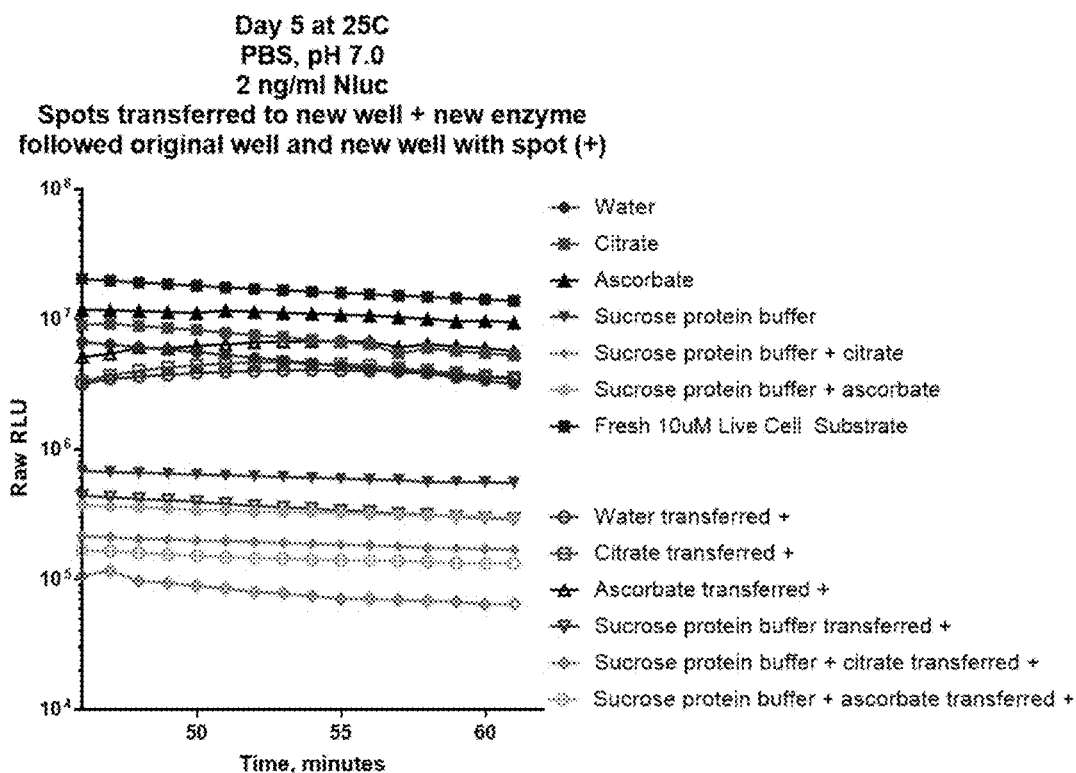
B.
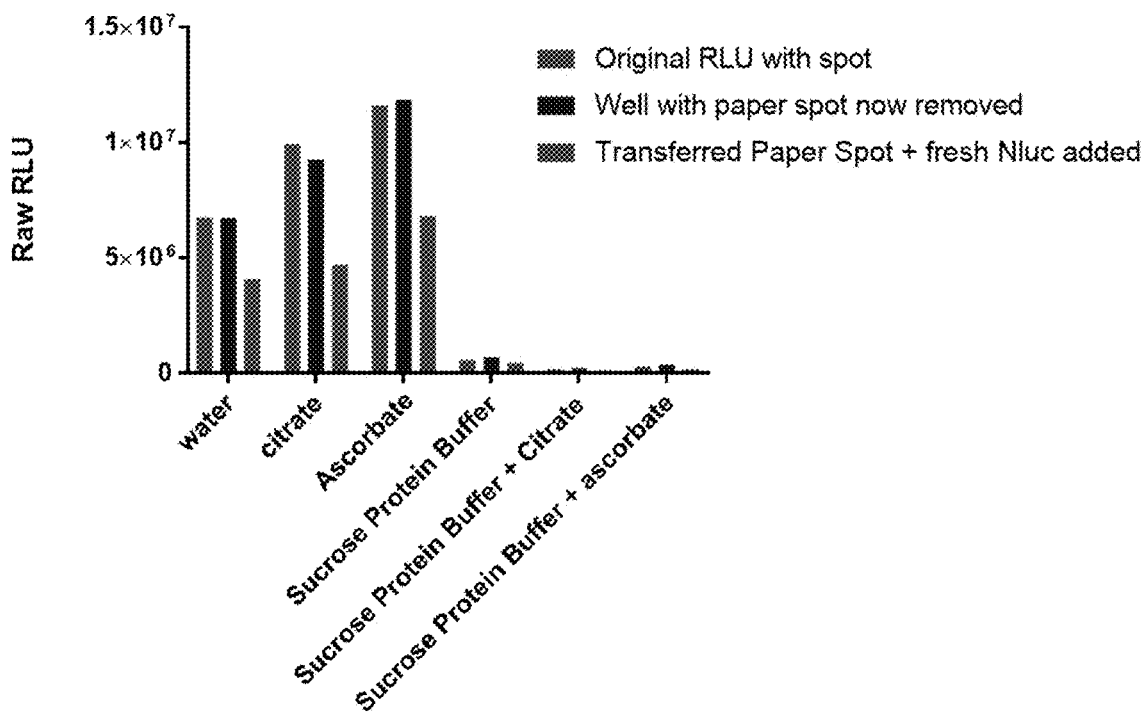

FIG. 43
A.
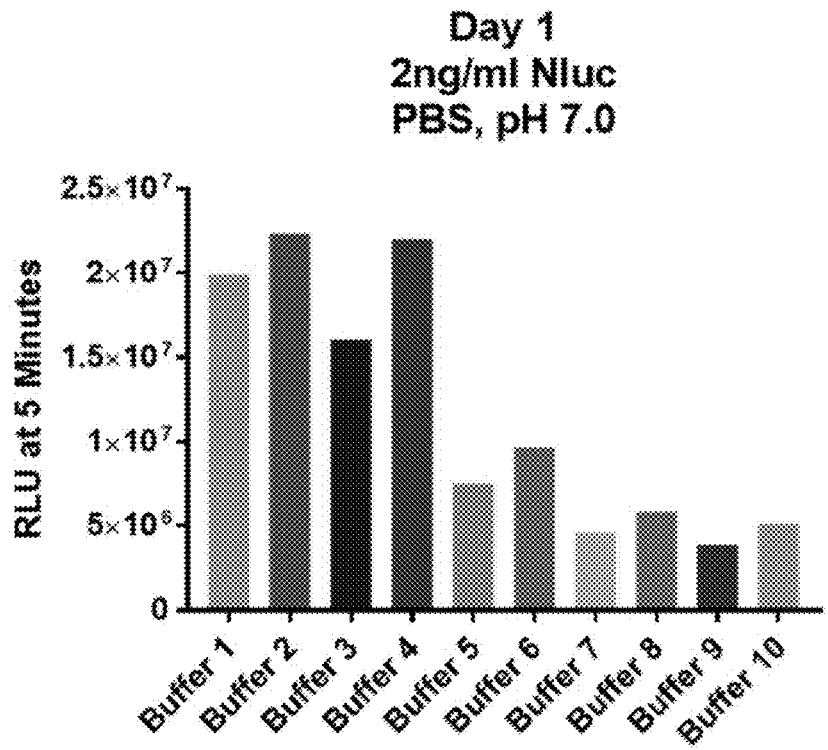
B.
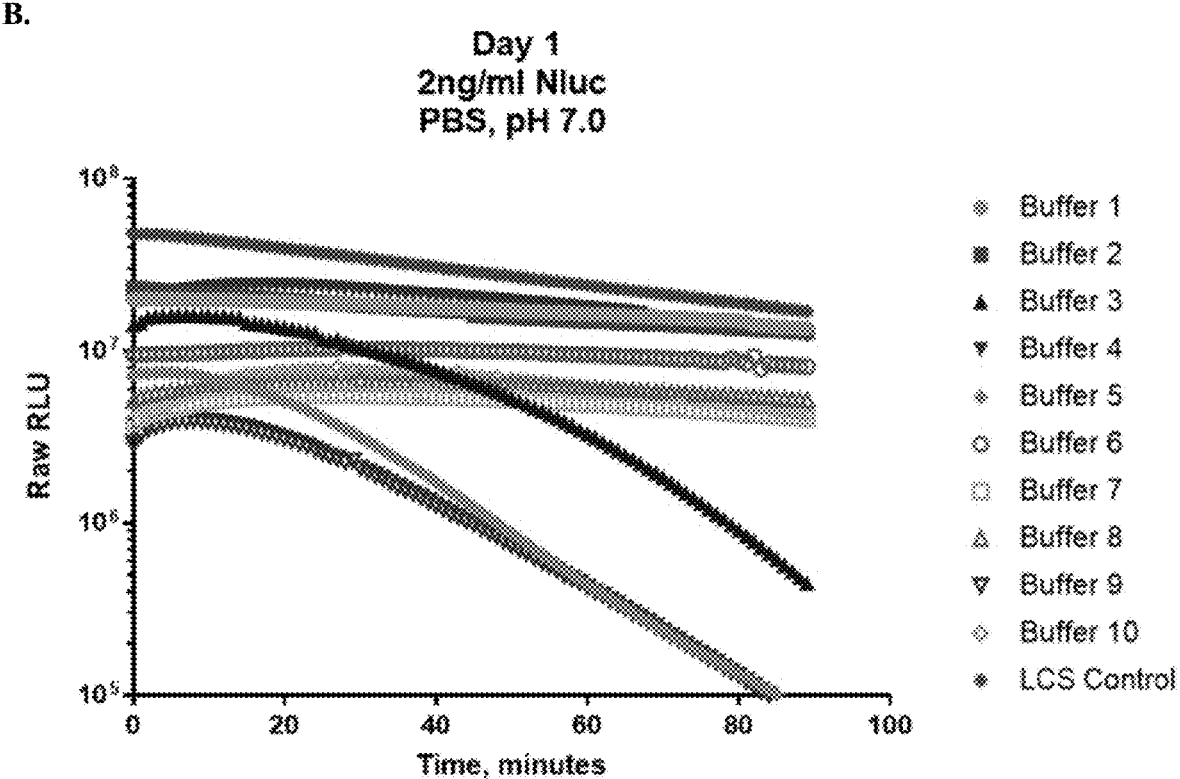

FIG. 44
A.
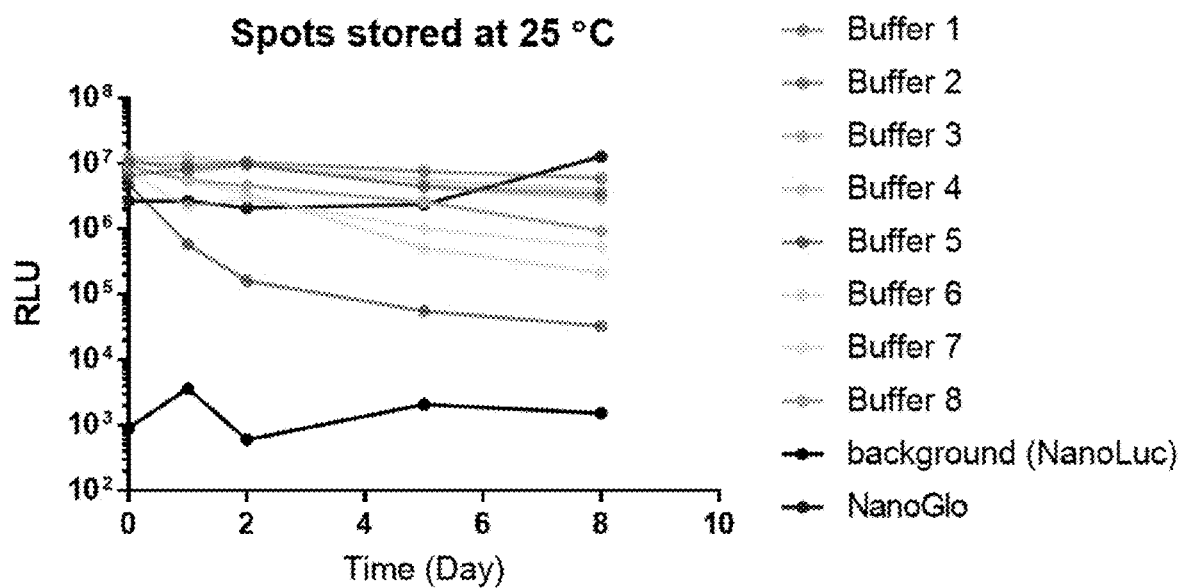
B.
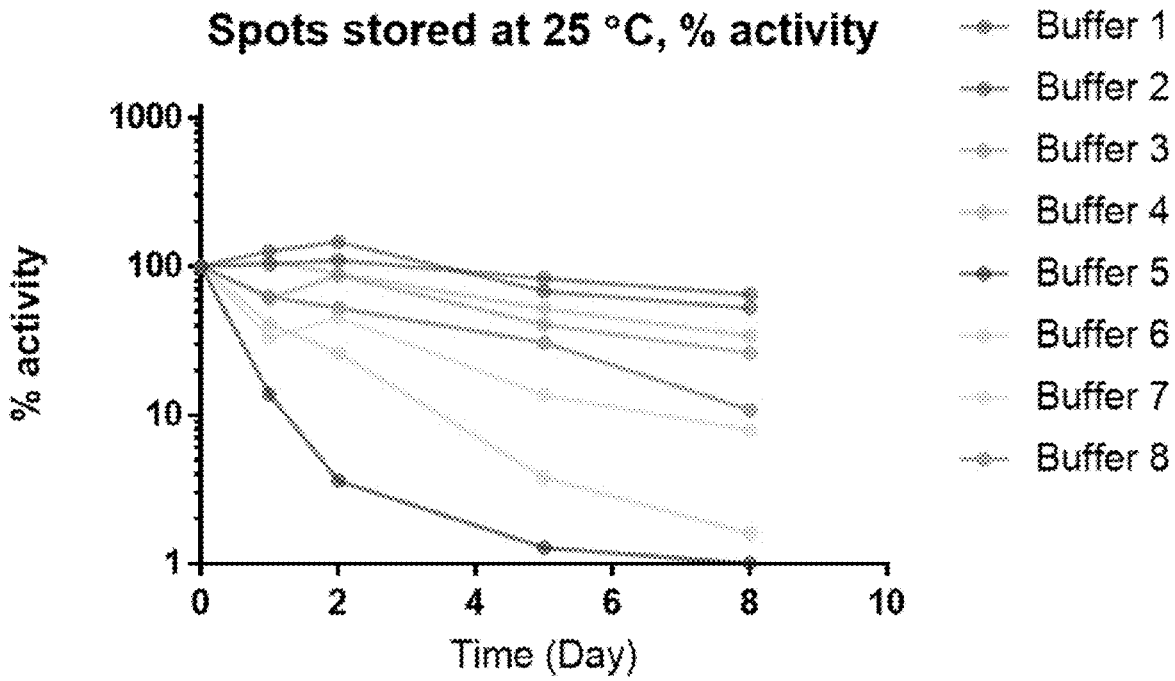

C.

FIG. 45
A.
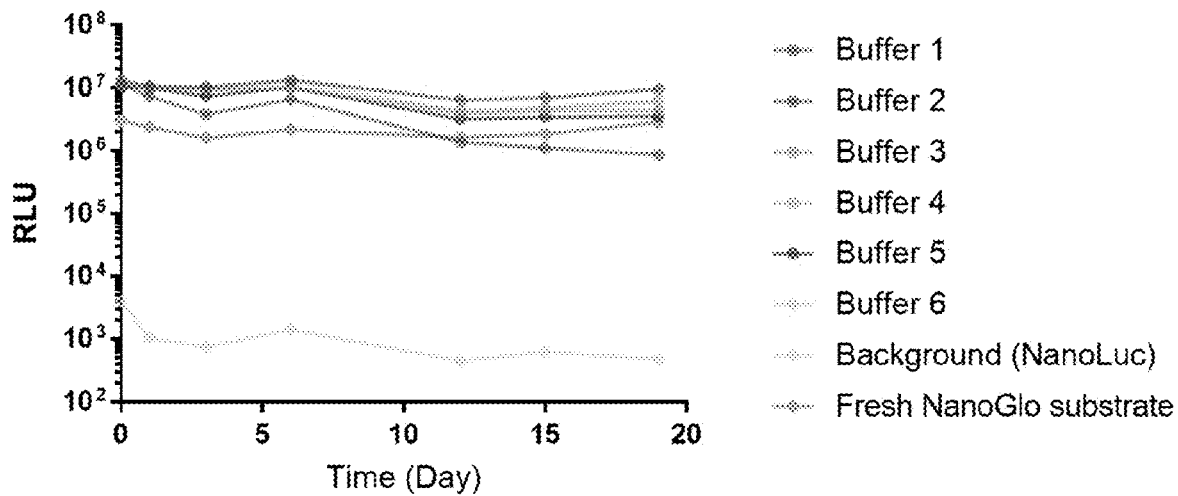
B.
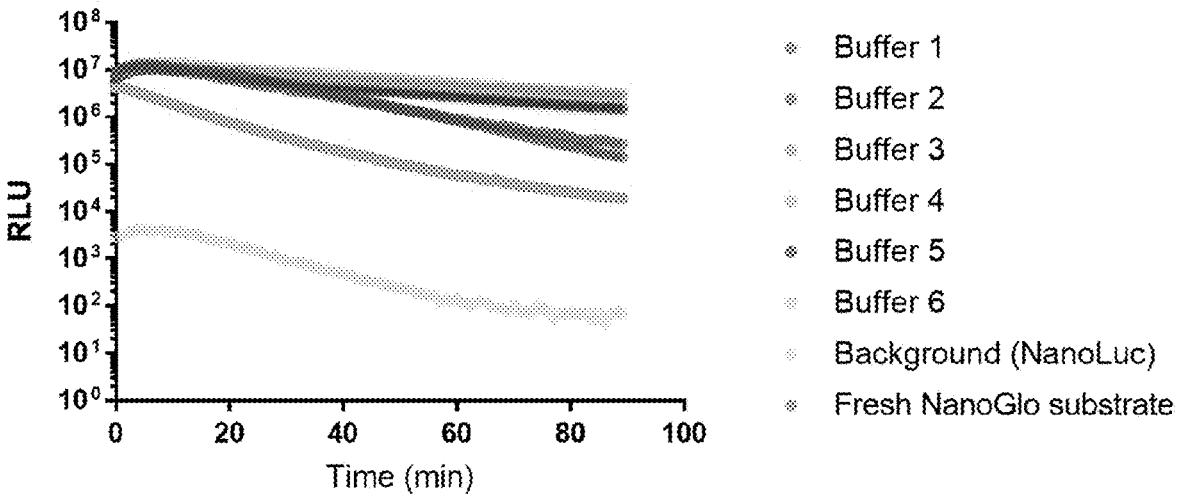

FIG. 46
A.
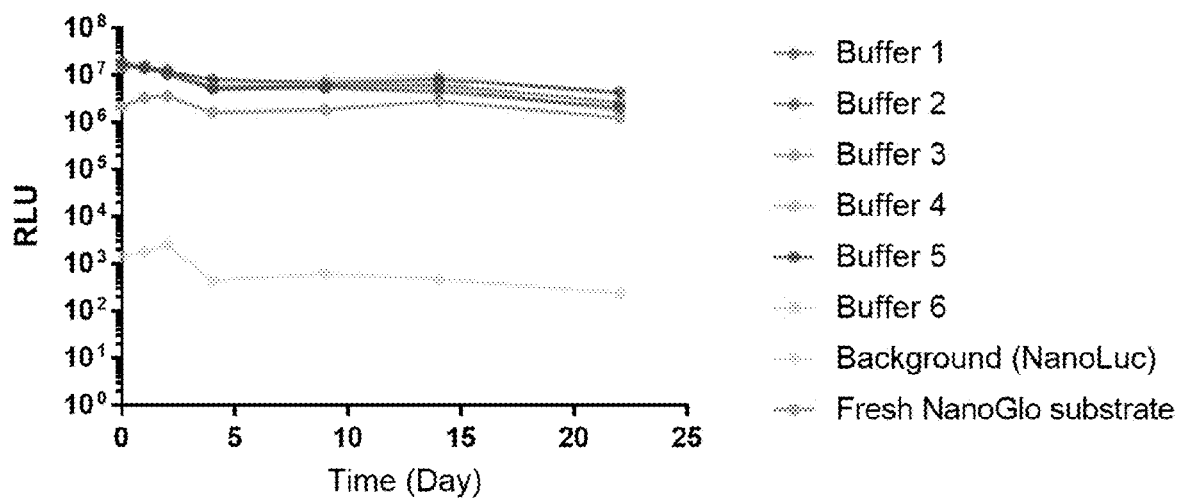
B.
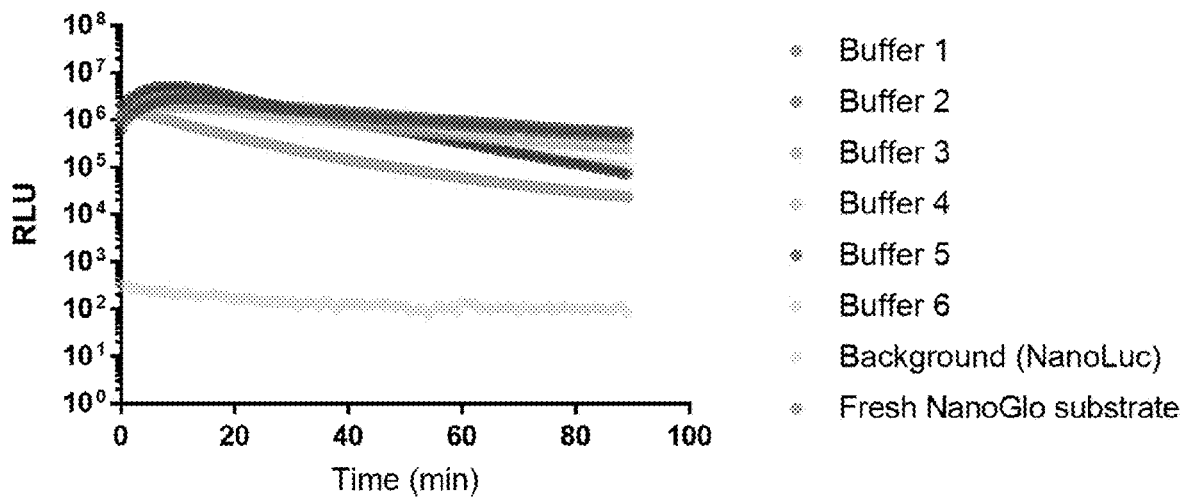

FIG. 47
A.
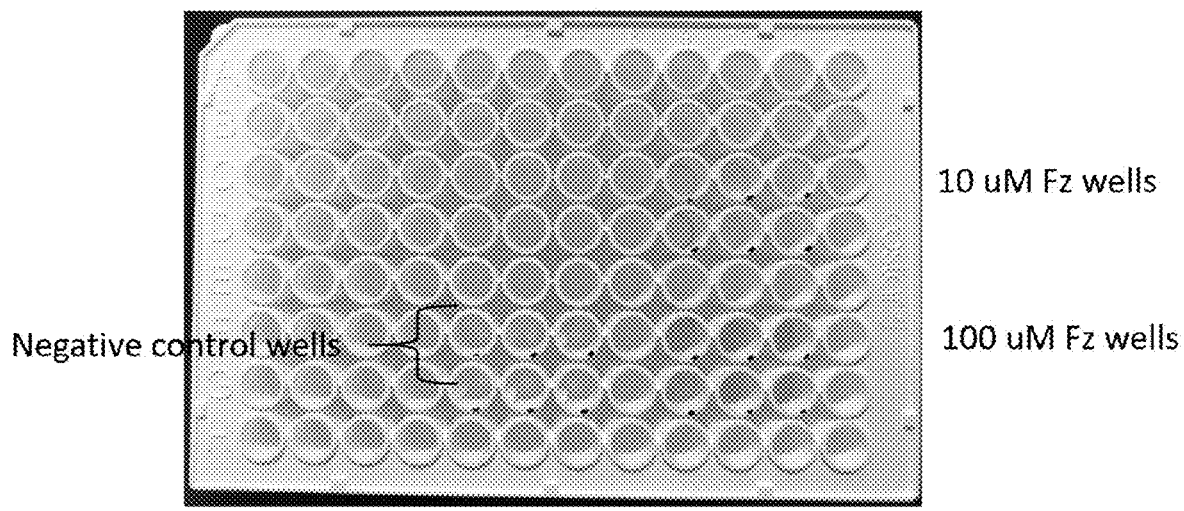
B.
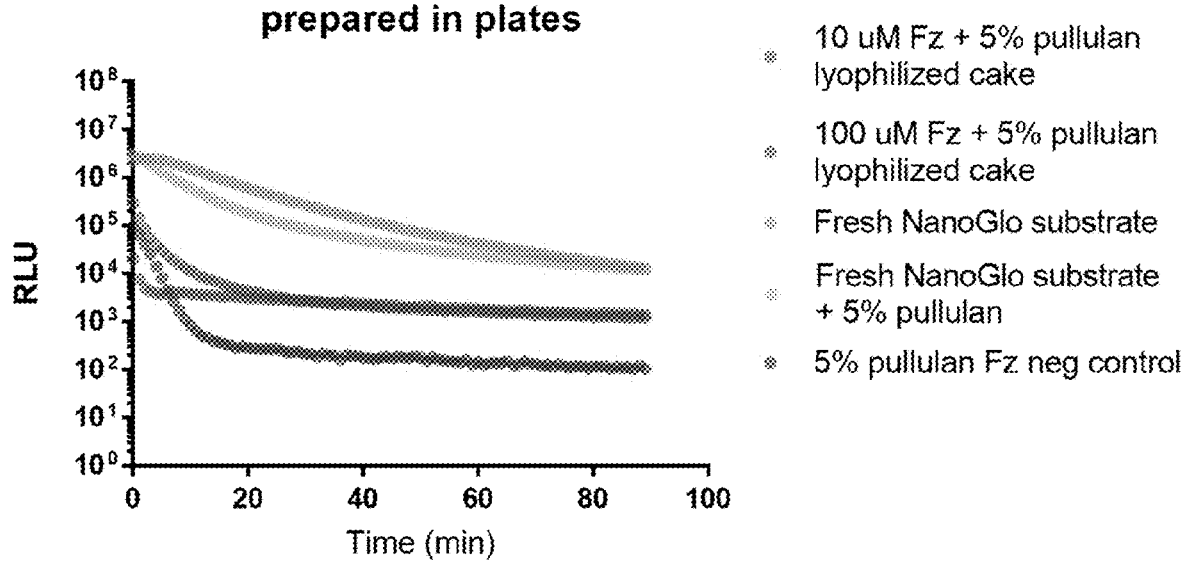

FIG. 51
A.
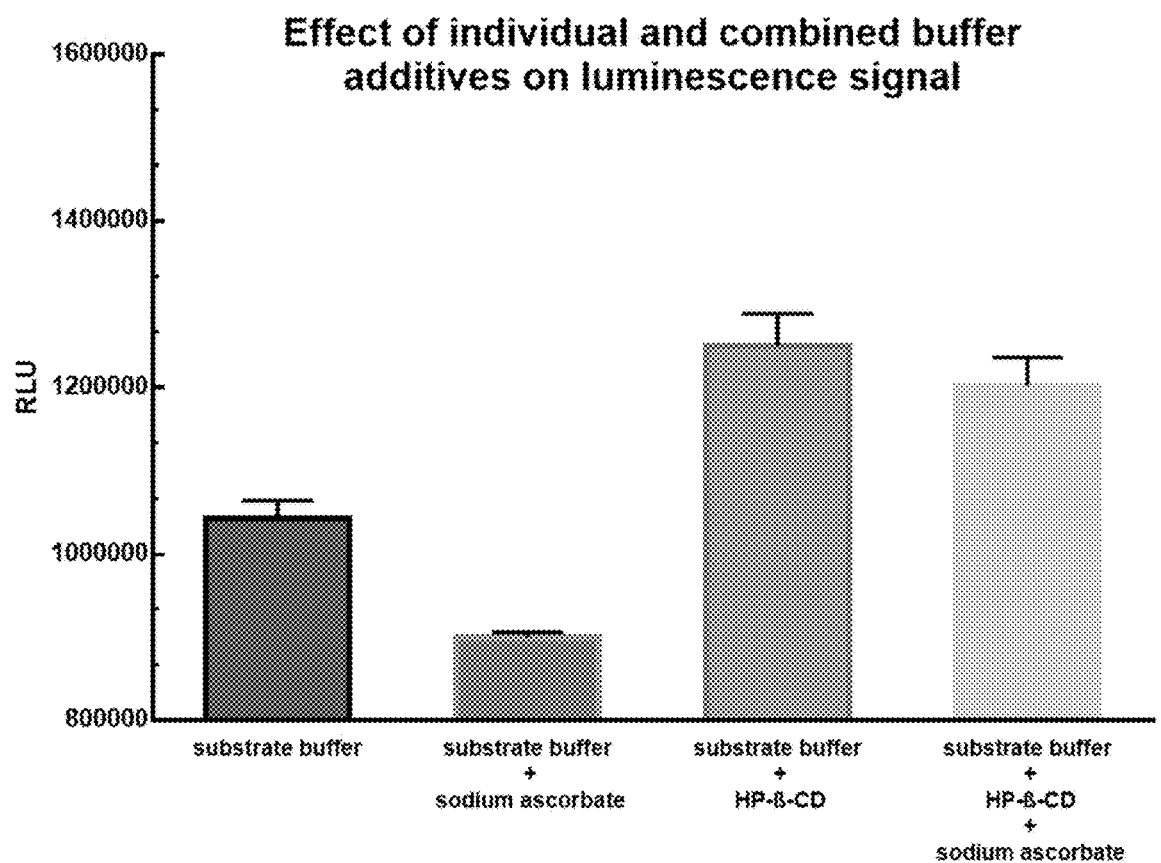
B.
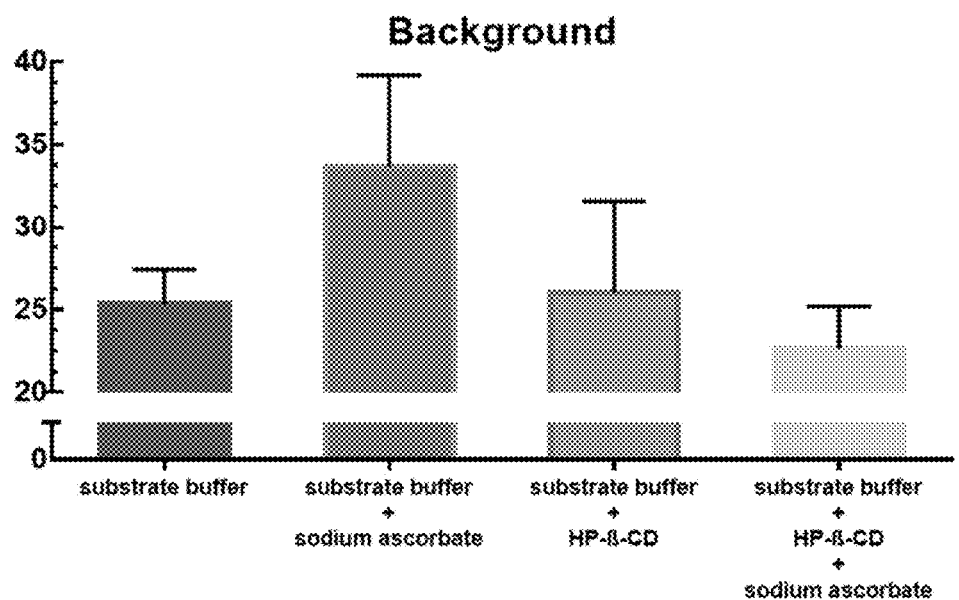

FIG. 54
A.
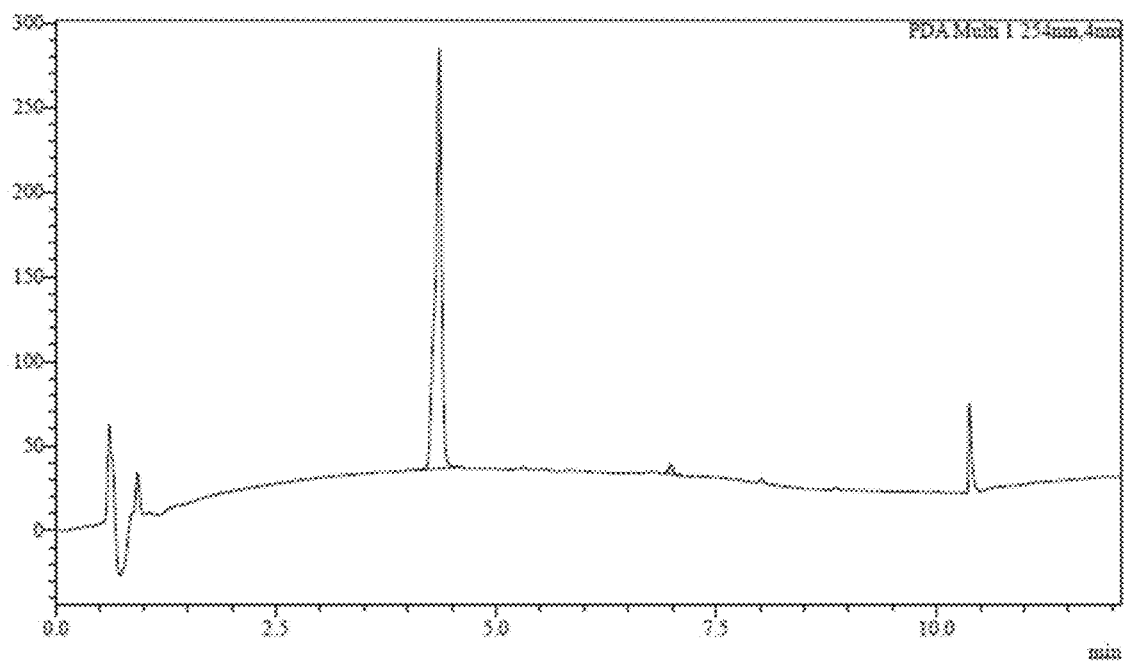
B.
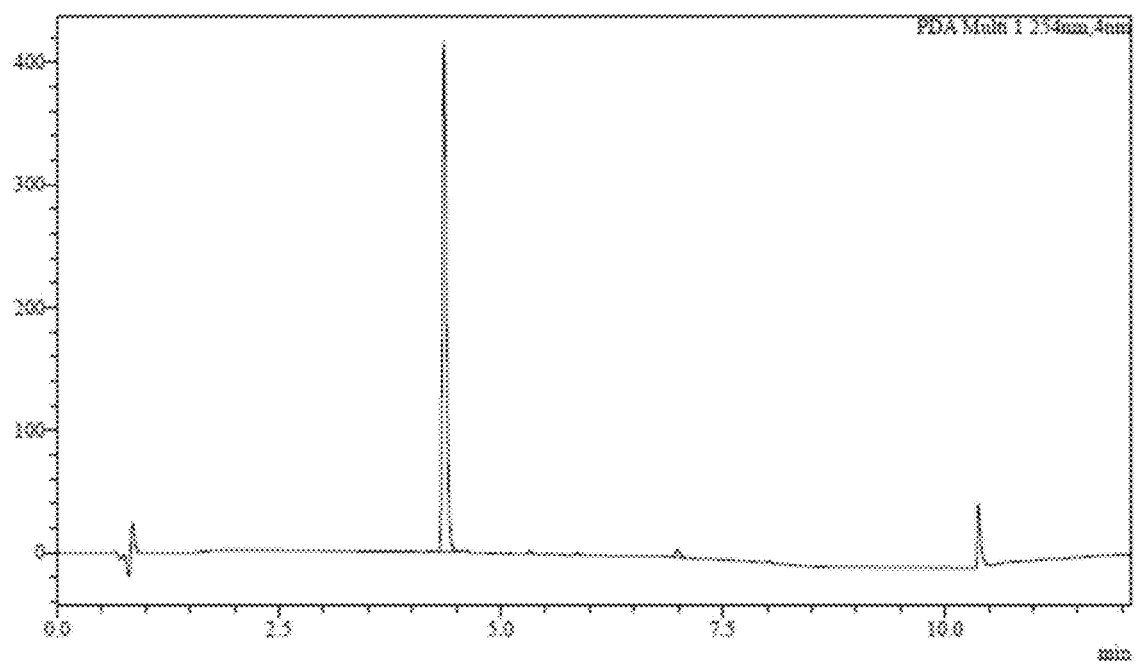

C.

FIG. 55
A.
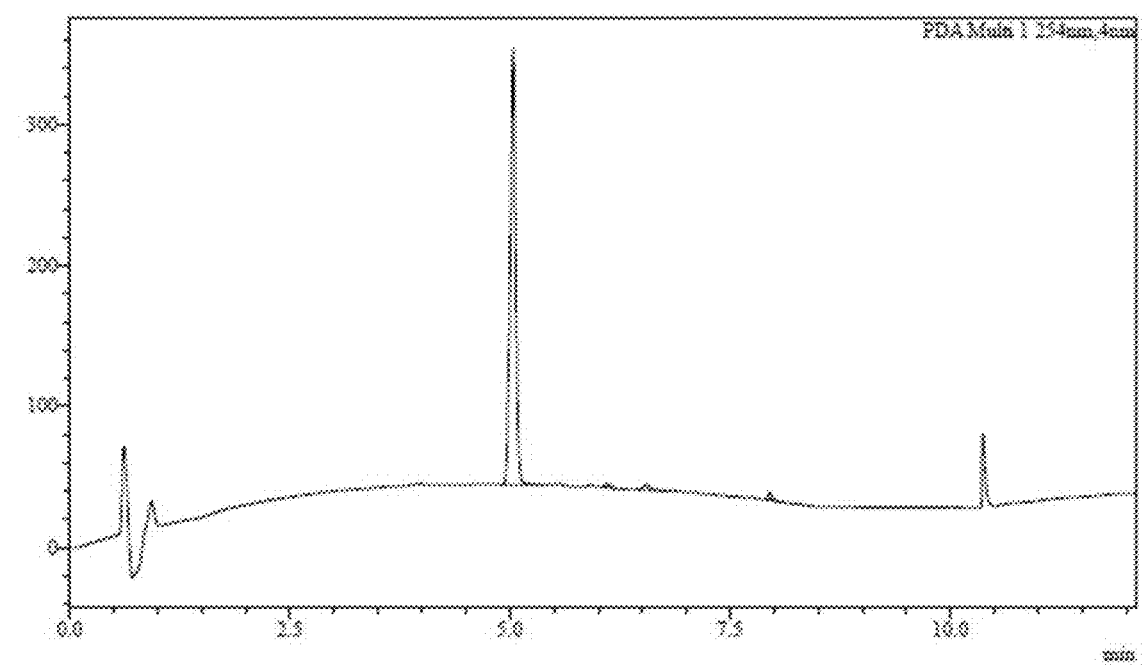
B.
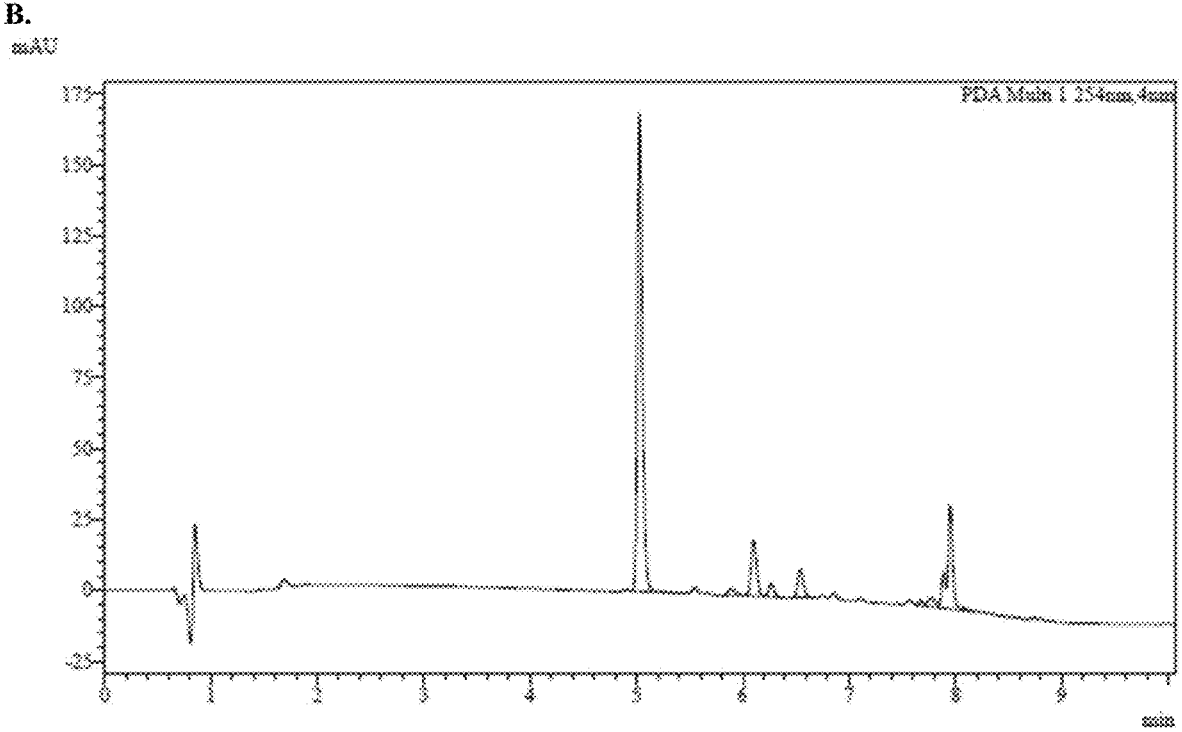

FIG. 56
1 2 3 4
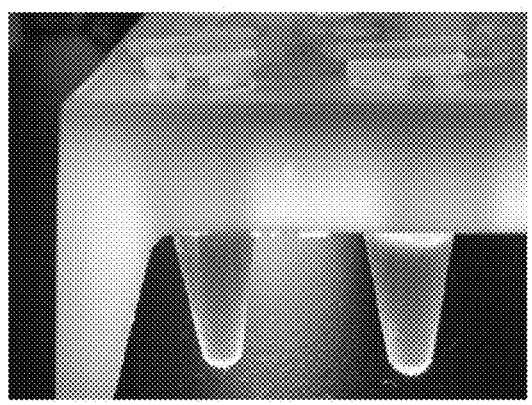 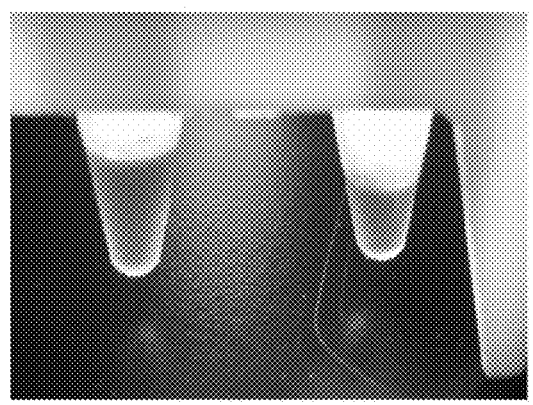

FIG. 58
A.
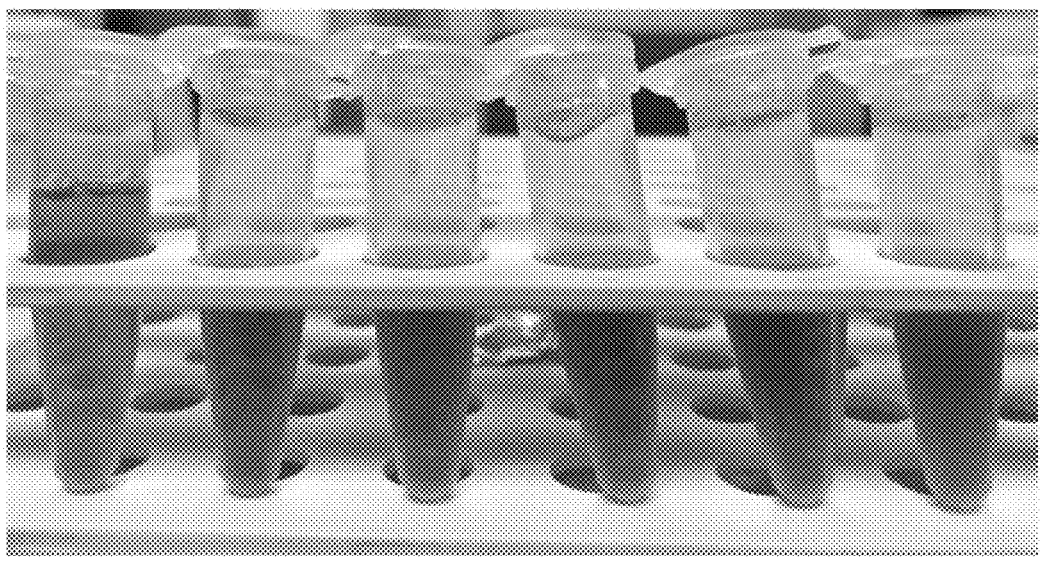
B.
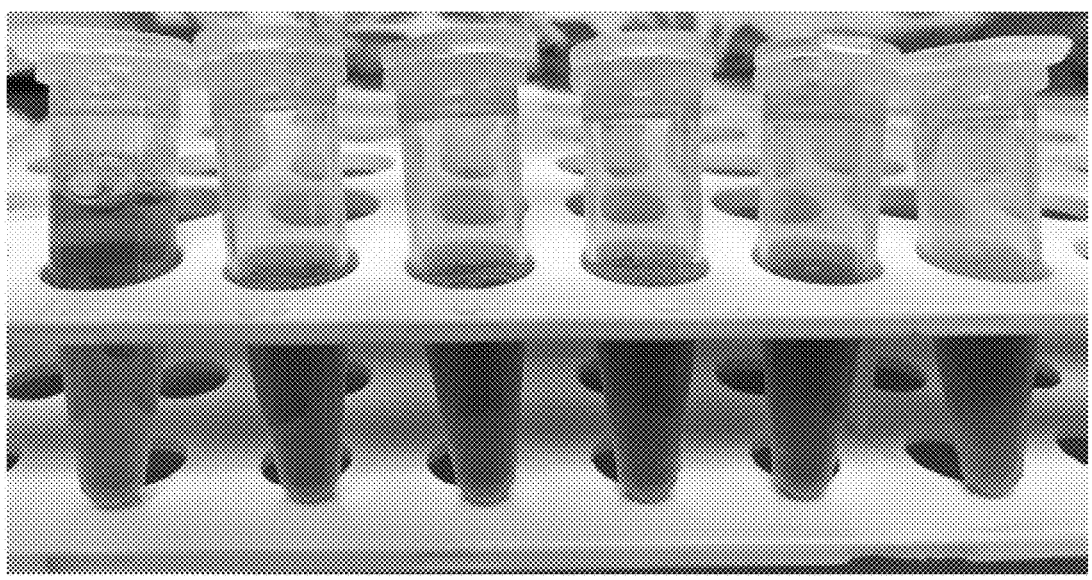

FIG. 59
A.
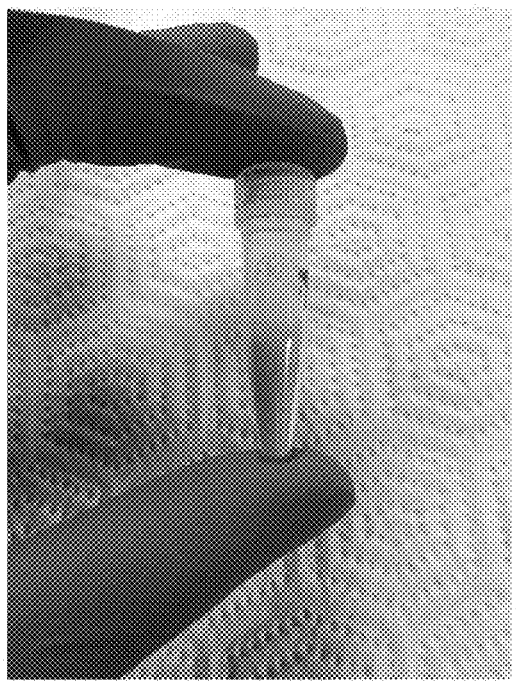
B.
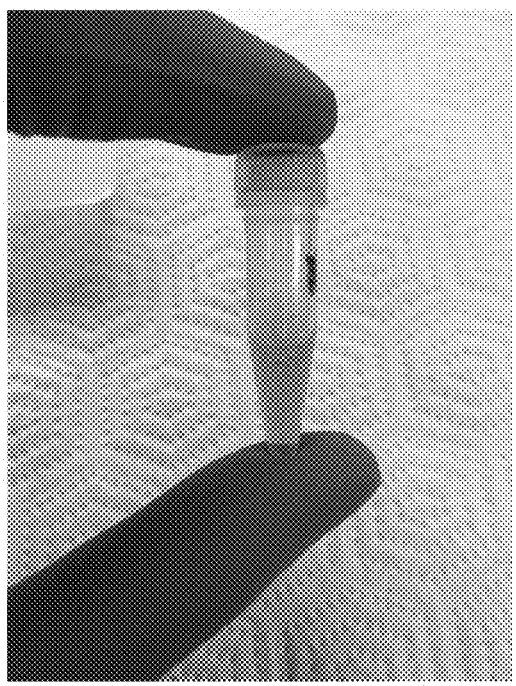

FIG. 60
A.
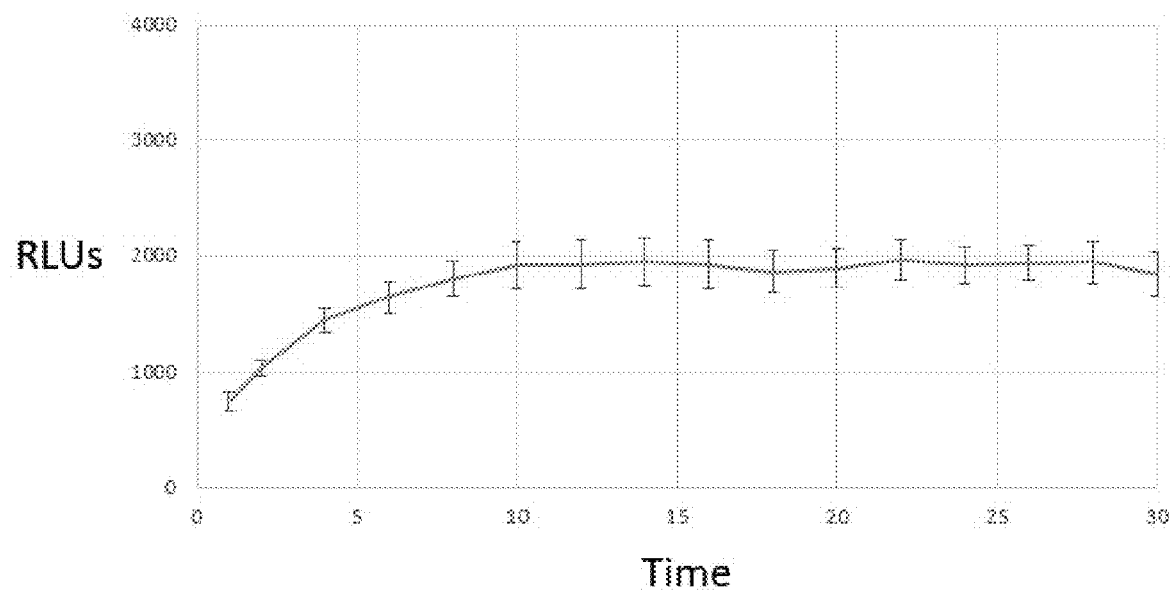
B.
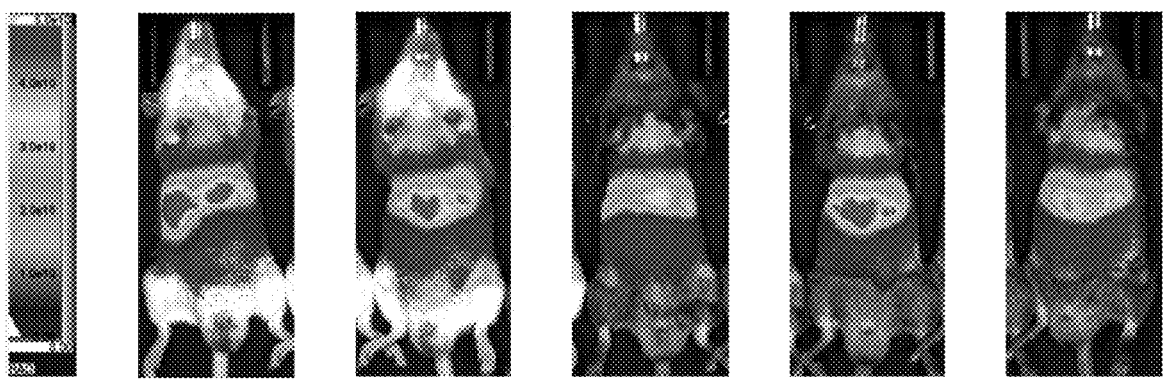

FIG. 61
A.
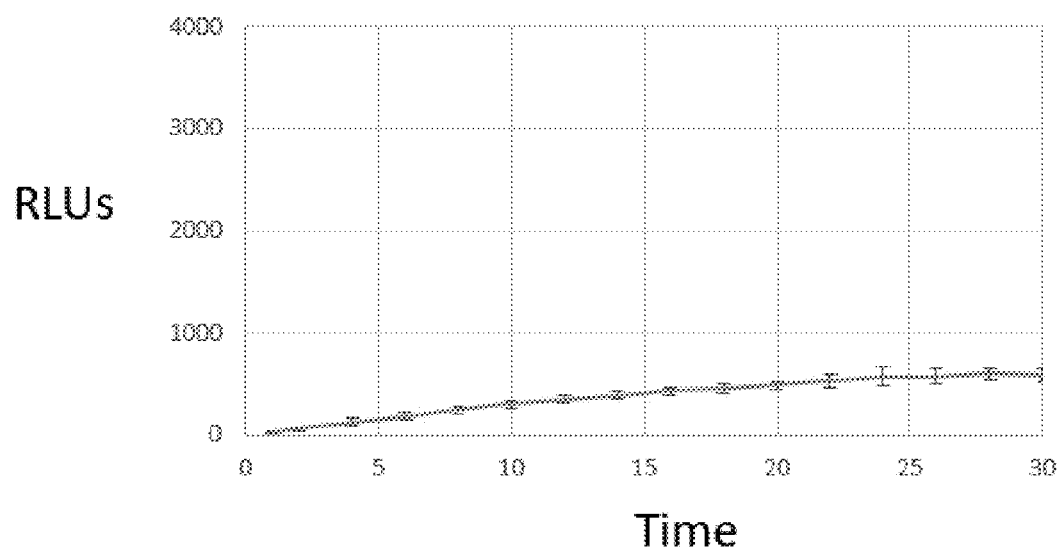
B.
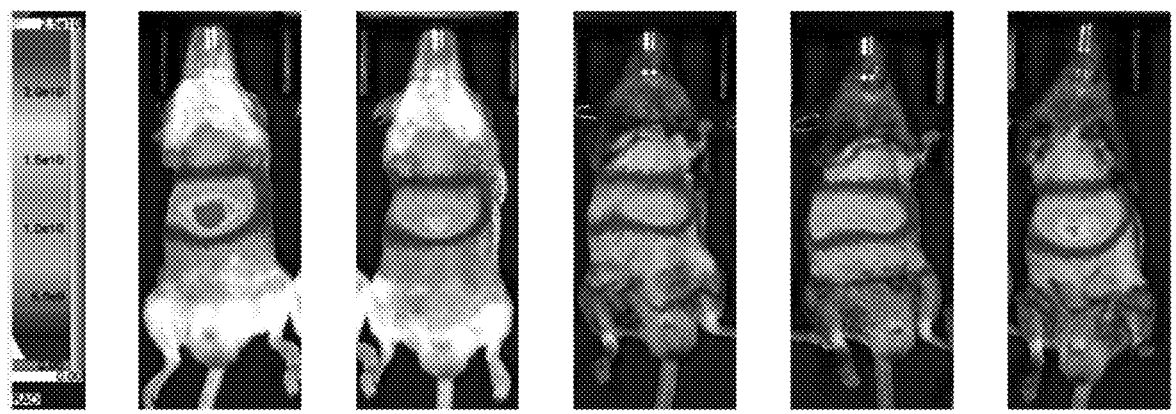

FIG. 62A-B

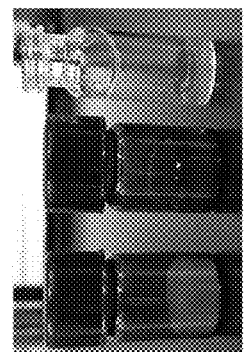
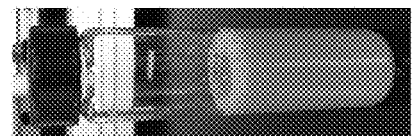
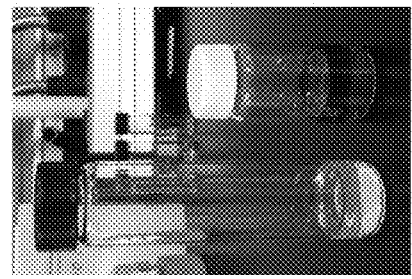
FIG. 64A-C

COMPOSITIONS AND METHODS FOR STABILIZING COELENTERAZINE AND ANALOGS AND DERIVATIVES THEREOF

CROSS REFERENCE TO RELATED APPLICATIONS

The present application claims priority to and the benefit of U.S. Provisional Patent Application No. 62/740,622, filed Oct. 3, 2018, and U.S. Provisional Patent Application No. 62/805,517, filed Feb. 14, 2019, each of which is incorporated herein by reference in its entirety and for all purposes.

FIELD

Provided herein are compositions and methods for stabilizing coelenterazine, and analogs and derivatives thereof, and for improving the solubility and reconstitution efficiency of coelenterazine and analogs and derivatives thereof.

BACKGROUND

Luminescence is used in biological assays as a measure of the activity of a reporter molecule. The reporter molecule, in turn, links the luminescent measurement to a biological process of interest such as transcription (gene expression), translation (protein expression), protein-protein interactions, and the like, thereby allowing for quantitative measurements of changes occurring in the biological process. The reporter molecule is typically a luminogenic enzyme (e.g., firefly luciferase, *Renilla* luciferase, Oplophorus luciferase, etc.) that, when provided with its luminogenic substrate, results in the production of light (i.e. luminescence).

SUMMARY

Luminogenic substrates, such as coelenterazine, and analogs and derivatives thereof, can decompose during storage (e.g., storage in organic solvent, storage at higher temperature, storage at incorrect pH, etc.) thereby resulting in loss of the substrate before addition to or use in a biological assay. Such decomposition can be the result of instability of the luminogenic substrate in solution over time in a temperature-dependent manner. This decomposition results in waste of the luminogenic substrate as well as reduced sensitivity and reproducibility of luminescent measurements derived from biological assays that employ the decomposed luminogenic substrate. The products of this decomposition also inhibit the luminescent reaction. Additionally, some coelenterazines have low solubility in different assay buffers or directly into test samples or may exhibit inconsistent reconstitution in different assay buffers. While coelenterazines can be dissolved in an organic solvent prior to dilution into an appropriate buffer solution, the organic solutions of coelenterazine compounds may suffer from instability in storage (both thermal instability and photo-instability). However, while solid coelenterazines and coelenterazine analogs and derivatives (e.g., furimazine) are considerably more stable than organic solutions thereof, they exhibit extremely poor reconstitution speed and efficiency, dissolve inconsistently, and are difficult to employ directly in assays and other methods, especially when non-organic solvents are required. These drawbacks have greatly limited the number and types of applications for which coelenterazine, and its analogs and derivatives, have been developed.

Accordingly, there is a need for new compositions and/or methods for stabilizing, improving the solubility of, and/or increasing the reconstitution efficiencies of luminogenic substrates. In particular, having substrates with improved physical characteristics and/or solubility is beneficial for long-term storage (e.g., >12 months at room temperature), assay format(s) compatibility, robustness, and user-friendliness.

Provided herein are compositions and methods for stabilizing and improving the solubility and/or the reconstitution efficiency of a luminogenic substrate such as coelenterazine or an analog or derivative thereof. Characterization of the substrate's chemical integrity and/or reconstitution efficiency within different solid compositions, formulations, and formats was performed using HPLC, absorbance, and mass spectroscopy. Additional functional characterization of the substrate under assay relevant conditions was performed by monitoring bioluminescence via relative light units (RLU) in the presence of the NanoLuc® enzyme. Provided herein are compositions comprising a compound selected from coelenterazine and an analog or derivative thereof, and a polymer. In some embodiments, the compound is selected from coelenterazine, coelenterazine-h, coelenterazine-h-h, furimazine, JRW-0238, JRW-1743, and JRW-1744. In some embodiments, the compound is furimazine. In some embodiments, the compound is JRW-0238. In some embodiments, the compound is JRW-1743. In some embodiments, the compound is JRW-1744.

In some embodiments, the polymer is a naturally-occurring biopolymer. In some embodiments, the naturally-occurring biopolymer is selected from pullulan, trehalose, maltose, cellulose, dextran, and a combination of any thereof. In some embodiments, the naturally-occurring biopolymer is pullulan. In some embodiments, the polymer is a cyclic saccharide polymer or a derivative thereof. In some embodiments, the polymer is hydroxypropyl β-cyclodextrin. In some embodiments, the polymer is a synthetic polymer. In some embodiments, the synthetic polymer is selected from polystyrene, poly(meth)acrylate, and a combination of any thereof. In some embodiments, the synthetic polymer is a block copolymer comprising at least one poly(propylene oxide) block and at least one poly(ethylene oxide) block. In some embodiments, the synthetic polymer is a poloxamer.

In some embodiments, the composition further comprises a buffer, a surfactant, a reducing agent, a salt, a radical scavenger, a chelating agent, a protein, or any combination thereof. In some embodiments, the composition further comprises a buffer selected from a phosphate buffer, tricine, and 2-(N-morpholino)ethanesulfonic acid. In some embodiments, the composition further comprises a surfactant selected from polysorbate 20, polysorbate 40, and polysorbate 80. In some embodiments, the composition comprises a reducing agent selected from thiourea and 6-aza-2-thiothymine. In some embodiments, the composition further comprises a salt selected from sodium chloride and sodium phosphate. In some embodiments, the composition further comprises a radical scavenger agent selected from ascorbic acid and sodium ascorbate. In some embodiments, the composition further comprises a chelating agent, and the chelating agent is selected from citric acid and trans-1,2-diaminocyclohexane-tetraacetic acid. In some embodiments, the composition further comprises a protein selected from bovine serum albumin, gelatin, and a polypeptide fraction of highly purified dermal collagen of porcine origin.

In some embodiments, the composition is in the form of a lyophilized powder or cake. In some embodiments, the composition is in the form of a malleable film. In some embodiments, the composition is a solution.

Provided herein are compositions comprising: a compound selected from coelenterazine and an analog or derivative thereof; and a surface selected from a paper or fiber matrix, a plastic, a glass, or a metal. In some embodiments, the compound is selected from coelenterazine, coelenterazine-h, coelenterazine-h-h, furimazine, JRW-0238, JRW-1743, and JRW-1744. In some embodiments, the compound is furimazine. In some embodiments, the compound is JRW-0238. In some embodiments, the compound is JRW-1743. In some embodiments, the compound is JRW-1744. In some embodiments, the composition further comprises a polymer. In some embodiments, the polymer is a naturally-occurring biopolymer. In some embodiments, the naturally-occurring biopolymer is selected from pullulan, trehalose, maltose, cellulose, dextran, and a combination of any thereof. In some embodiments, the naturally-occurring biopolymer is pullulan. In some embodiments, the polymer is a cyclic saccharide polymer or a derivative thereof. In some embodiments, the polymer is hydroxypropyl β-cyclodextrin. In some embodiments, the polymer is a synthetic polymer. In some embodiments, the synthetic polymer is selected from polystyrene, poly(meth)acrylate, and a combination of any thereof. In some embodiments, the synthetic polymer is a block copolymer comprising at least one poly(propylene oxide) block and at least one poly(ethylene oxide) block. In some embodiments, the synthetic polymer is a poloxamer.

In some embodiments, the composition further comprises a buffer, a surfactant, a reducing agent, a salt, a radical scavenger, a protein or any combination thereof. In some embodiments, the composition further comprises a buffer selected from a phosphate buffer, tricine, and 2-(N-morpholino)ethanesulfonic acid. In some embodiments, the composition further comprises a surfactant selected from polysorbate 20, polysorbate 40, and polysorbate 80. In some embodiments, the composition comprises a reducing agent selected from thiourea and 6-aza-2-thiothymine. In some embodiments, the composition further comprises a salt selected from sodium chloride and sodium phosphate. In some embodiments, the composition further comprises a radical scavenger agent selected from ascorbic acid and sodium ascorbate. In some embodiments, the composition further comprises a chelating agent, and the chelating agent is selected from citric acid and trans-1,2-diaminocyclohexane-tetraacetic acid. In some embodiments, the composition further comprises a protein selected from bovine serum albumin, gelatin, and a polypeptide fraction of highly purified dermal collagen of porcine origin. In some embodiments, the surface is selected from a cellulose paper, a nitrocellulose paper, a nylon paper, a cotton paper, a polyester paper, sodium carboxymethyl cellulose, a porous or polymeric membrane, a high purity cotton fiber, a cotton/rayon blended high purity cotton, and a glass microfiber.

Provided herein are methods of stabilizing a compound selected from coelenterazine and an analog or derivative thereof, comprising contacting the coelenterazine compound or the analog or derivative thereof with an effective amount of a polymer and/or a paper or fiber matrix to form a composition. In some embodiments, the compound is stabilized against thermal decomposition, chemical decomposition, light-induced decomposition, or any combination thereof.

Provided herein are methods of improving the solubility of a compound selected from coelenterazine and an analog or derivative thereof, comprising contacting the coelenterazine compound or the analog or derivative thereof with an effective amount of a polymer and/or a paper or fiber matrix to form a composition. In some embodiments, the solubility of the compound is improved in an aqueous solution compared to the compound that has not been contacted with the polymer and/or the paper or fiber matrix.

Provided herein are methods of improving the reconstitution rate of a compound selected from coelenterazine and an analog or derivative thereof comprising contacting the coelenterazine compound or the analog or derivative thereof with an effective amount of a polymer and/or a paper or fiber matrix to form a composition, wherein the reconstitution rate for the compound is improved compared to a compound that has not been contacted with the polymer or the paper or fiber matrix.

In some embodiments, the compound is selected from coelenterazine, coelenterazine-h, coelenterazine-h-h, furimazine, JRW-0238, JRW-1743, and JRW-1744. In some embodiments, the compound is furimazine. In some embodiments, the compound is JRW-0238. In some embodiments, the compound is JRW-1743. In some embodiments, the compound is JRW-1744.

In some embodiments, the polymer is a naturally-occurring biopolymer. In some embodiments, the naturally-occurring biopolymer is selected from pullulan, trehalose, maltose, cellulose, dextran, and a combination of any thereof. In some embodiments, the naturally-occurring biopolymer is pullulan. In some embodiments, the polymer is a cyclic saccharide polymer or a derivative thereof. In some embodiments, the polymer is hydroxypropyl β-cyclodextrin. In some embodiments, the polymer is a synthetic polymer. In some embodiments, the synthetic polymer is selected from polystyrene, poly(meth)acrylate, and a combination of any thereof. In some embodiments, the synthetic polymer is a block copolymer comprising at least one poly(propylene oxide) block and at least one poly(ethylene oxide) block. In some embodiments, the synthetic polymer is a poloxamer.

In some embodiments, the composition further comprises a buffer, a surfactant, a reducing agent, a salt, a radical scavenger, a protein or any combination thereof. In some embodiments, the composition further comprises a buffer selected from a phosphate buffer, tricine, and 2-(N-morpholino)ethanesulfonic acid. In some embodiments, the composition further comprises a surfactant selected from polysorbate 20, polysorbate 40, and polysorbate 80. In some embodiments, the composition comprises a reducing agent selected from thiourea and 6-aza-2-thiothymine. In some embodiments, the composition further comprises a salt selected from sodium chloride and sodium phosphate. In some embodiments, the composition further comprises a radical scavenger agent selected from ascorbic acid and sodium ascorbate. In some embodiments, the composition further comprises a chelating agent, and the chelating agent is citric acid. In some embodiments, the composition further comprises a protein selected from bovine serum albumin, gelatin, and a polypeptide fraction of highly purified dermal collagen of porcine origin. In some embodiments, the paper or fiber matrix is selected from a cellulose paper, a nitrocellulose paper, a nylon paper, a cotton paper, a polyester paper, sodium carboxymethyl cellulose, a porous or polymeric membrane, a high purity cotton fiber, a cotton/rayon blended high purity cotton, and a glass microfiber.

In some embodiments, the contacting step comprises: dissolving the compound in an organic solvent to form a first solution; mixing the first solution with the polymer and/or the paper or fiber matrix to form a mixture; and drying the mixture. In some embodiments, the mixing step comprises dissolving the polymer in a second solution and mixing the second solution with the first solution. In some embodiments, the mixing step comprises applying the first solution to the paper or fiber matrix. In some embodiments, the drying step comprises lyophilization. In some embodiments, the drying step comprises air-drying. In some embodiments, the drying is conducted at ambient temperature in an inert atmosphere. In some embodiments, the drying comprises vacuum drying. In some embodiments, the drying is conducted at a temperature from about 30° C. to about 70° C. In some embodiments, one or all of the solutions are deoxygenated.

In some embodiments, the method comprises contacting the compound with the polymer. In some embodiments, the method comprises contacting the polymer with the paper or fiber matrix. In some embodiments, the method comprises contacting the polymer with the polymer and the paper or fiber matrix.

Provided herein are kits comprising any one of the compositions disclosed herein. In some embodiments, the composition is included in one or more containers. In some embodiments, the composition is included in a plurality of tubes. In some embodiments, the composition is in the form of a plurality of paper spots, each spot having a diameter of about 2 mm to about 5 mm.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1, Panels A-C show signal kinetics when compositions according to the present disclosure were tested for luminescence output in (A) phosphate buffered saline (PBS), pH 7.0 and (B) Nano-Glo® Luciferase Assay Buffer as described in Example 1. FIG. 1(C) shows images of furimazine substrate samples in pullulan-based lyophilized cake and pullulan film-droplet formulations.

FIG. 3, Panels A-C show RLU values at various time points following addition of purified NanoLuc® enzyme when compositions according to the present disclosure were tested for luminescence output in Nano-Glo® Luciferase Assay Buffer as described in Example 1.

FIG. 6, Panels A-B show absorbance values over the range of 210-600 nm of pullulan in PBS, pH 6.8 as described in Example 4.

FIG. 7, Panels A-B show representative HPLC traces for 0% w/v pullulan-based lyophilized cake formulations containing furimazine at (A) 0 hours and (B) 5 hours after reconstitution as described in Example 5.

FIG. 8, Panels A-B show representative HPLC traces for 2.5% w/v pullulan-based lyophilized cake formulations containing furimazine at (A) 0 hours and (B) 5 hours after reconstitution as described in Example 5.

FIG. 9, Panels A-B show representative HPLC traces for 15% w/v pullulan-based lyophilized cake formulations containing furimazine at (A) 0 hours and (B) 5 hours after reconstitution as described in Example 5.

FIG. 10, Panels A-B show representative HPLC traces for Nano-Glo® Luciferase Assay substrate at (A) 0 hours and (B) 5 hours after reconstitution as described in Example 5.

FIG. 11, Panels A-B show analyses of HPLC traces for formulated furimazine samples with or without pullulan showing: (A) the absorbance at 254 nm over time and (B) peak areas over time as described in Example 5.

FIG. 13, Panels A-C show: (A) kinetic analysis of RLU values when compositions were tested for luminescence output as described in Example 6; (B) RLU values at time zero when compositions were tested for luminescence output as described in Example 6; and (C) an image of paper spots, created from hole punching Whatman® 903 protein saver cards, which were prepared as described in Example 6.

FIG. 14, Panels A-B show images of samples in which formulated furimazine samples were dried onto Whatman® 903 protein saver cards and maintained for (A) 2 weeks at 4° C. or (B) 3 months at 4° C. or 25° C. as further described in Example 7.

FIG. 15, Panels A-D show data demonstrating the effects of additives on assay performance of formulated furimazine samples dried into paper spots created from hole punching Whatman® 903 protein saver cards as described in in Example 8.

FIG. 17, Panels A-C show data demonstrating RLU output of furimazine samples in paper spots created from hole punching Whatman® 903 protein saver cards and tested after one day of storage at: (A) 4° C., (B) 25° C., and (C) 37° C. as described in Example 9.

FIG. 18, Panels A-C show data demonstrating RLU output of formulated furimazine samples in paper spots created from hole punching Whatman® 903 protein saver cards and tested after three days of storage at: (A) 4° C., (B) 25° C., and (C) 37° C. as described in Example 9.

FIG. 19, Panels A-D show data for formulated furimazine samples placed into paper spots created from hole punching Whatman® 903 protein saver cards and pre-treated with different protein buffers and tested for activity with purified NanoLuc® enzyme as described in Example 10 showing RLU output after spot storage at: (A) 60° C. and (B) 25° C. and % activity over time after spot storage at: (C) 60° C. and (D) 25° C.

FIG. 20, Panels A-D show accelerated stability data demonstrating RLU output of formulated furimazine samples in paper spots created from hole punching Whatman® 903 protein saver cards and tested for substrate activity over days stored at 25° C. or 60° C. as described in Example 10 showing RLU output after spot storage at: (A) 60° C. and (B) 25° C. and % activity over time after spot storage at: (C) 60° C. and (D) 25° C.

FIG. 22, Panels A-D show data demonstrating RLU output and percent activity over days of formulated furimazine samples in paper spots created from hole punching Whatman® 903 protein saver cards and prepared using different drying methods as described in Example 11.

FIG. 25, Panels A-D show analysis of HPLC data showing thermal stability of formulated furimazine samples as raw areas (FIG. 25A at 25° C. and FIG. 25B at 60° C.) and as percent areas (FIG. 25C at 25° C. and FIG. 25D at 60° C.) as described in Example 12.

FIG. 26, Panels A-F show RLU data for formulated furimazine samples tested with purified NanoLuc® enzyme following furimazine sample storage. FIGS. 26A-C show data for samples stored at 60° C. for varying periods of time prior to reconstitution and testing using 50 μM substrate (A), 10 μM substrate (B), and 0.1 μM substrate (C); FIGS. 26D-F show data for samples stored at 25° C. for varying periods of time prior to reconstitution and testing using 50 μM substrate (D), 10 μM substrate (E), and 0.1 μM substrate (F) as described in Example 12.

FIG. 27, Panels A-F show percent substrate activity at time zero when formulated furimazine samples were tested for activity with purified NanoLuc® enzyme following furimazine sample storage. FIGS. 27A-C show data for samples stored at 60° C. for varying periods of time prior to reconstitution and testing using 50 μM substrate (A), 10 μM substrate (B), and 0.1 μM substrate (C); FIGS. 27D-F show data for samples stored at 25° C. for varying periods of time prior to reconstitution and testing using 50 μM substrate (D), 10 μM substrate (E), or 0.1 μM substrate (F) as described in Example 12.

FIGS. 30A-C show data for a representative example of a pullulan-based film containing furimazine alone or also containing NanoLuc® enzyme adhered to the bottom of a standard 96-well microtiter plate following reaction with NanoLuc® enzyme or simple reconstitution with PBS for wells in which the NanoLuc® enzyme was placed at the same time as the furimazine formulation; FIG. 30A shows raw RLUs; FIG. 30B shows % activity; and FIG. 30C shows % activity over 10 days as described in Example 13.

FIG. 31, Panels A-F show the normalized absorbance of the degradation products for furimazine prepared as a pullulan-based lyophilized cake after storage at 25° C. (first bar) or 60° C. (second bar) for each condition compared to commercial furimazine products as described in Example 14.

FIG. 32, Panels A-F show the relative percent area of the degradation products for furimazine prepared as a pullulan-based lyophilized cake after storage at 25° C. (first bar) or 60° C. (second bar) for each condition compared to commercial furimazine products as described in Example 14.

FIG. 34, Panels A-C show representative examples of HPLC analyses of furimazine samples dried on different types of paper matrices as described in Example 16.

FIG. 35, Panels A-B show representative examples of bioluminescent signals from samples of furimazine formulated with the reporter protein, LgTrip, on three different solid phase materials following reconstitution.

FIG. 36, Panels A-C show representative examples of HPLC analyses of furimazine samples stored as 1:1 mixtures with ascorbic acid on different types of paper matrices as described in Example 17.

FIG. 37, Panels A-C show representative examples of HPLC analyses of furimazine samples that were stored on paper matrices that were pre-treated with 30% citric acid as described in Example 18.

FIG. 38, Panels A-C show representative examples of HPLC analyses of furimazine samples that were stored on paper matrices after the matrices were pretreated with water and dried under reduced pressure overnight as described Example 19.

FIG. 39, Panels A-D show representative examples of HPLC analyses of furimazine stored as a 1:1 mixture with citric acid on different paper matrices as described in Example 20.

FIG. 41, Panels A-B show data demonstrating RLU output and % activity over days of formulated furimazine samples in paper spots created from hole punching Whatman® 903 protein saver cards stored under different conditions and sampled over days of storage at 25° C. as described in Example 22.

FIG. 45, Panels A-B show data demonstrating RLU output of various formulated furimazine solutions in paper spots created from hole punching Whatman® 903 protein saver cards and sampled over days of storage at 25° C. as described in Example 26.

FIG. 46, Panels A-B show data demonstrating RLU output of various formulated furimazine solutions containing Prionex, ascorbate and/or ATT in paper spots created from hole punching Whatman® 903 protein saver cards and sampled over days of storage at 25° C. as described in Example 27.

FIG. 47, Panels A-B shows data demonstrating RLU output of furimazine formulations that have been lyophilized directly into a 96-well microtiter plate as described in Example 28.

FIG. 51, Panels A-B shows data demonstrating RLU output of Nano-Glo® substrate (Promega cat #N113) formulations containing specific individual or combined buffer additives as described in Example 32.

FIG. 56 shows representative images of solution samples of JRW-0238 formulated with Pluronic® F-127 as described in Example 36.

FIG. 58, Panels A-B show representative images of samples of JRW-0238 formulated with Pluronic® F-127 as described in Example 37.

FIG. 59, Panels A-B show representative images of samples of formulated JRW-0238 as described in Example 38.

FIG. 60, Panels A-B show traces and images from mice that were injected intraperitoneally with reconstituted formulated JRW-0238 as described in Example 38.

FIG. 61, Panels A-B show traces and images from mice that were injected subcutaneously with reconstituted formulated JRW-0238 as described in Example 38.

FIG. 64A-C. Images of JRW-1743 during various synthesis/formulation steps: (A) the vial on left contains melted Pluronic® F-127, while the vial on the right contains JRW-1743 dissolved in EtOH; (B) JRW-1743 after the EtOH was removed, and the substrate/polymer mixture was reconstituted in 2.6 mL of pure water to a final concertation of 8.5 mM; (C) representative examples of formulated JRW-1743 after lyophilization: JRW-1743 in dry Pluronic® F-127 matrix (left) and the same material after reconstitution in pure water (middle and right) are depicted.

DEFINITIONS

Figure 2:
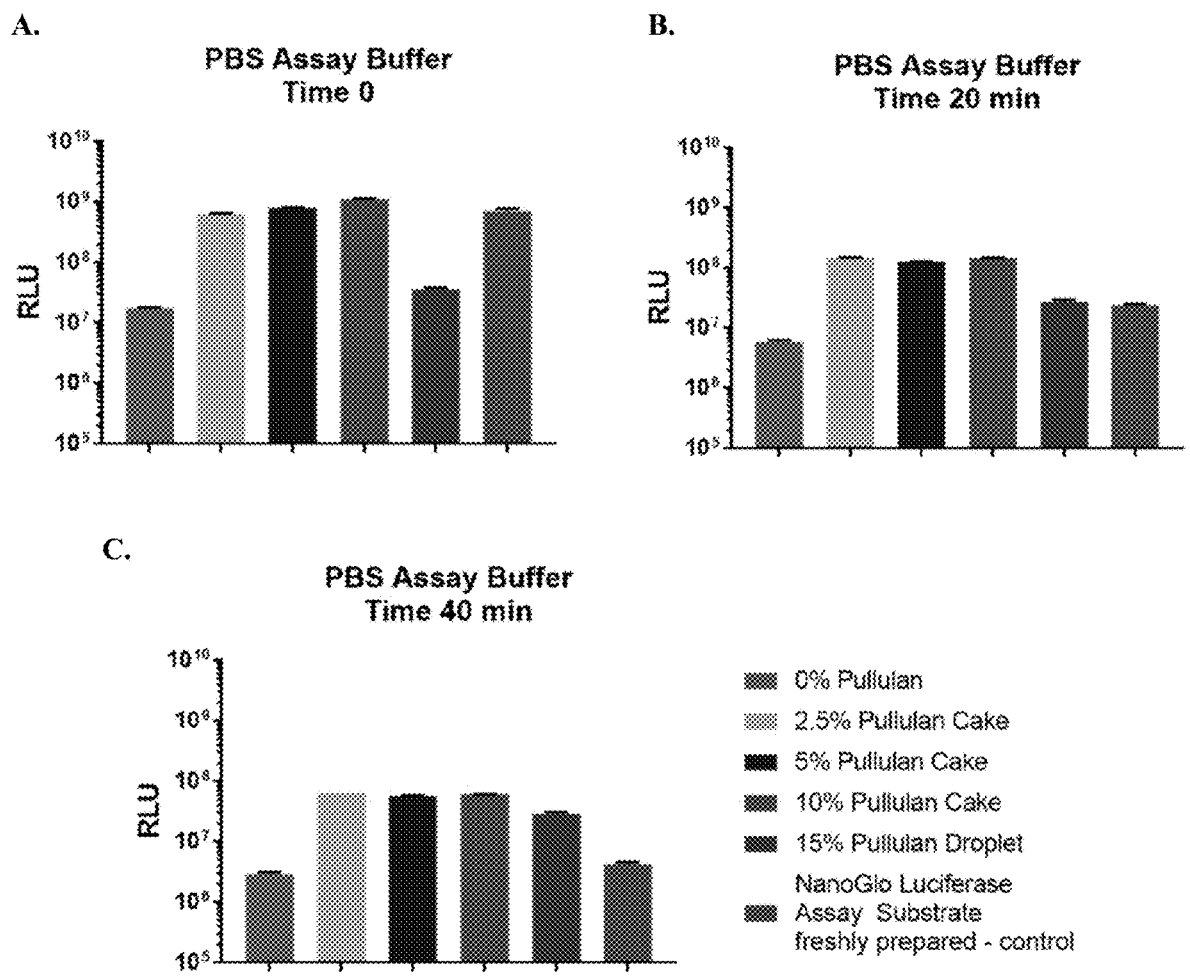
FIG. 2, Panels A-C show RLU values at various time points following addition of purified NanoLuc® enzyme when compositions according to the present disclosure were tested for luminescence output in PBS, pH 7.0 as described in Example 1.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described as these may vary in accordance with routine experimentation and optimization. It is also to be understood that the terminology used in the description is for describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein, the terms "Oplophorus luciferase" and "Oplophorus-derived luciferase" are used interchangeably and refer to a luciferase secreted from the deep-sea shrimp Oplophorus *gracilirostris* (e.g., SEQ ID NO: 1) including wild-type, variants, and mutants thereof. For example, suitable Oplophorus luciferase variants are described in U.S. Pat. Nos. 8,557,970 and 8,669,103, each of which is incorporated herein by reference in its entirety. Exemplary Oplophorus-derived luciferases include, for example, that of SEQ ID NO: 2 (also interchangeably referred to herein as "Nano-Luc," "Nluc," "Nluc luciferase," and "Nluc enzyme").

The term "polymer", as used herein, refers to an organic compound that includes two or more repeating units covalently bonded in a chain where the chain may be linear or branched. Typically, a polymer is composed of one or more repeating units that are joined together by covalent chemical bonds to form a linear backbone. The repeating units can be the same or different. Therefore, a structure of the type -A-A-A-A- wherein A is a repeating unit is a polymer, also known as a homopolymer. A structure of the type -A-B-A-B- or -A-A-A-B-A-A-A-B- wherein A and B are repeating units is also a polymer and is sometimes termed a copolymer. As used herein, the term "polymer" expressly includes chains of only two repeat units such as disaccharides and also includes chains of more repeating units such as oligosaccharides and polysaccharides. The term "polymer" also includes non-saccharide based polymers (and oligomers of as few as two monomer units) such as synthetic polymers. In some embodiments, polymers (e.g., polysaccharides) and oligomers (e.g., oligosaccharides) are limited to defined lengths (e.g., 2, 3, 4, 5, 6, 7, 8, 9, 10, 12, 14, 16, 18, 20, 25, 30, 35, 40, 45, 50, 60, 70, 80, 90, 100, 150, 200, 300, 400, 500, 750, 1000, or more, or ranges there between, e.g., 2-10, 5-25, 10-50, over 100, etc.).

As used herein and in the appended claims, the singular forms "a", "an", and "the" include plural reference unless the context clearly dictates otherwise. Thus, for example, reference to "a polymer" is a reference to one or more polymers and equivalents thereof known to those skilled in the art, and so forth.

As used herein, the term "comprise" and linguistic variations thereof denote the presence of recited feature(s), element(s), method step(s), etc., without the exclusion of the presence of additional feature(s), element(s), method step(s), etc. Conversely, the term "consisting of" and linguistic variations thereof, denotes the presence of recited feature(s), element(s), method step(s), etc., and excludes any unrecited feature(s), element(s), method step(s), etc., except for ordinarily-associated impurities. The phrase "consisting essentially of" denotes the recited feature(s), element(s), method step(s), etc., and any additional feature(s), element(s), method step(s), etc., that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

DETAILED DESCRIPTION

Provided herein are compositions comprising a compound selected from coelenterazine and an analog or derivative thereof and a polymer and/or a paper or fiber matrix or other surface such as plastic or glass. In some embodiments, the composition stabilizes the compound against decomposition (e.g., thermal decomposition, chemical decomposition, light-induced decomposition, etc.). In some embodiments, the composition stabilizes the compound against decomposition as compared to a composition that does not contain the polymer and/or the paper or fiber matrix or other surface. In some embodiments, the composition reduces or suppresses the formation of one or more decomposition products from the compound (e.g., as compared to a composition that does not contain the polymer or the paper or fiber matrix or other surface). In some embodiments, the composition enhances the reconstitution efficiency of the coelenterazine or analog or derivative thereof. In some embodiments, the composition enhances the kinetic solubility (e.g., as compared to a composition that does not contain the polymer and/or the paper or fiber matrix or other surface).

The compositions comprise a compound that is selected from coelenterazine and an analog or derivative thereof. When incorporated in to the composition, the compound may be protected against decomposition (e.g., thermal decomposition, chemical decomposition, light-induced decomposition, etc.).

In some embodiments, the compound is coelenterazine, which has the following structure:

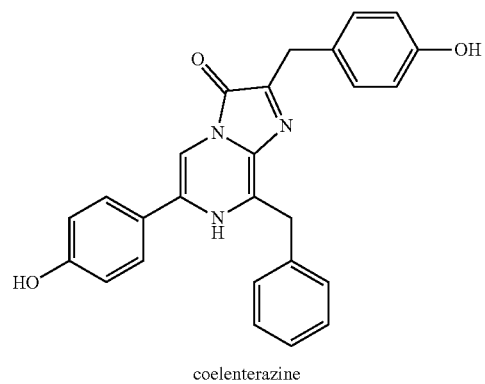 [SMILES: O=c1c(Cc2ccc(O)cc2)nc2c(Cc3ccccc3)[nH]c(-c3ccc(O)cc3)cn1-2]

coelenterazine

In some embodiments, the compound is a coelenterazine analog or derivative. Exemplary coelenterazine analogs include coelenterazine-h (2-deoxycoelenterazine or 2,8-dibenzyl-6-(4-hydroxyphenyl)imidazo[1,2-a]pyrazin-3(7H)-one), coelenterazine-h-h (dideoxycoelenterazine or 2,8-dibenzyl-6-phenylimidazo[1,2-a]pyrazin-3(7H)-one), furimazine (8-benzyl-2-(furan-2-ylmethyl)-6-phenylimidazo[1,2-a]pyrazin-3(7H)-one), JRW-0238 (8-benzyl-2-(furan-2-ylmethyl)-6-(3-hydroxyphenyl)imidazo[1,2-a]pyrazin-3(7H)-one), JRW-1744 (6-(3-amino-2-fluorophenyl)-8-benzyl-2-(furan-2-ylmethyl)imidazo[1,2-c]pyrazin-3(7H)-one, and JRW-1743 (6-(3-amino-2-fluorophenyl)-8-(2-fluorobenzyl)-2-(furan-2-ylmethyl)imidazo[1,2-c]pyrazin-3(7H)-one), which have the following structures:

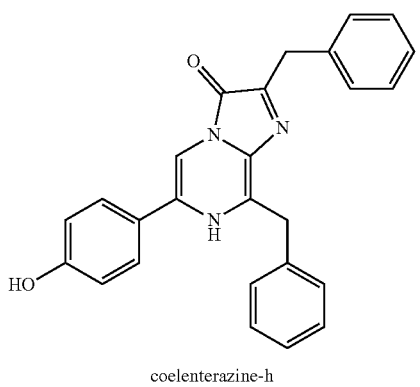

coelenterazine-h

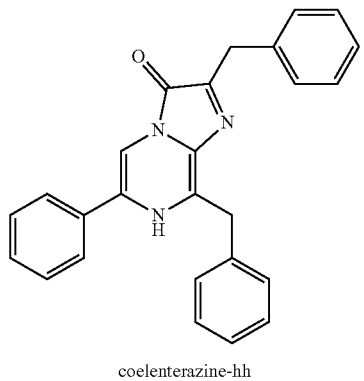

coelenterazine-hh

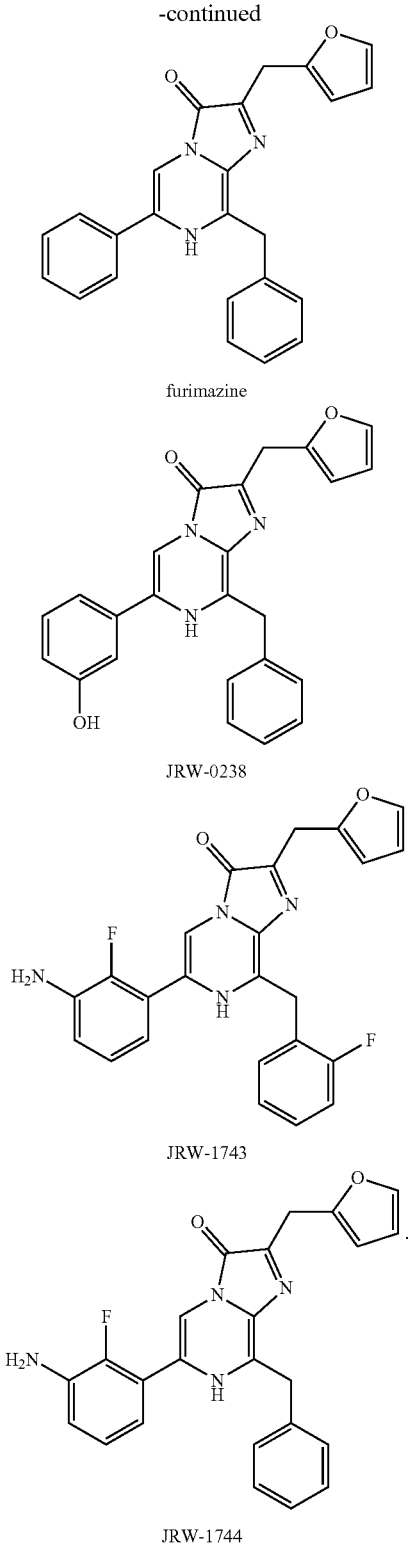

furimazine

JRW-0238

JRW-1743

JRW-1744

Additional exemplary coelenterazine analogs include coelenterazine-n, coelenterazine-f, coelenterazine-hcp, coelenterazine-cp, coelenterazine-c, coelenterazine-e, coelenterazine-fcp, coelenterazine-I, coelenterazine-icp, coelenterazine-v, 2-methyl coelenterazine, and the like. In some embodiments, the compound may be a coelenterazine analog described in WO 2003/040100; U.S. Pat. Pub. 2008/ 0248511 (e.g., paragraph [0086]); U.S. Pat. No. 8,669,103; WO 2012/061529; U.S. Pat. Pub. 2017/0233789; U.S. Pat. No. 9,924,073; U.S. Pat. Pub. 2018/0030059; U.S. Pat. No. 10,000,500; U.S. Pat. Pub. 2018/0155350; U.S. Provisional Pat. App. No. 62/665,346; U.S. application Ser. No. 16/399,410; U.S. Provisional Pat. App. No. 62/721,708; U.S. application Ser. No. 16/548,214; U.S. Pat. Pub. 2014/0227759; U.S. Pat. Nos. 9,840,730; 7,268,229; 7,537,912; 8,809,529; 9,139,836; 10,077,244; 9,487,520; 9,924,073; 9,938,564; 9,951,373; 10,280,447; 10,308,975; 10,428,075; the disclosures of which are incorporated by reference herein in their entireties. In some embodiments, coelenterazine analogs include pro-substrates such as, for example, those described in U.S. Pat. Pub. 2008/0248511; U.S. Pat. Pub. 2012/0707849; U.S. Pat. Pub. 2014/0099654; U.S. Pat. Nos. 9,927,430; 10,316,070; herein incorporated by reference in their entireties. In some embodiments, the compound is furimazine. In some embodiments, the compound is JRW-0238. In some embodiments, the compound is JRW-1743. In some embodiments, the compound is JRW-1744.

Coelenterazine and analogs and derivatives thereof may suffer from challenges associated with their reconstitution into buffer systems used in many assays such as the bioluminogenic assays and methods described herein. For example, coelenterazines or analogs or derivatives thereof, such as furimazine, may dissolve slowly and/or inconsistently in non-organic buffer solutions (e.g., due to the heterogeneous microcrystalline nature of the solid material). While dissolution in organic solvent prior to dilution with buffer may provide faster and more consistent results, coelenterazine compounds may suffer from instability in organic solutions during storage including both thermal instability and photo-instability. See, for example, U.S. Pat. No. 9,676,997, which is incorporated herein by reference. In some embodiments, incorporation of the coelenterazine or analog or derivative thereof into compositions described herein provides more reliable and consistent dissolution without such instability problems.

In some embodiments, the composition further comprises a polymer. As further described herein, in certain embodiments, the presence of the polymer stabilizes the compound against decomposition, and the presence of the polymer improves the solubility of the compound in water or in aqueous solutions. In some embodiments, by stabilizing the coelenterazine or coelenterazine analog or derivative (e.g., in comparison to coelenterazine or coelenterazine analog in organic solvent), improving the aqueous solubility of the coelenterazine or coelenterazine analog or derivative, and/or improving the reconstitution efficiency of the coelenterazine or coelenterazine analog in non-organic buffers (e.g., in comparison to the coelenterazine or coelenterazine analog or derivative in the absence of the polymer). The compositions and systems herein allow for the use of coelenterazine or coelenterazine analogs or derivatives in point-of-care, pre-packaged, and/or solid phase systems, methods, and assays for which unformulated and/or organic-phase coelenterazine or coelenterazine analogs are less suitable (e.g., not temperature or photo stable).

The polymer may be a naturally-occurring biopolymer or a synthetic polymer. In some embodiments, the polymer is a naturally-occurring biopolymer. Suitable naturally-occurring biopolymers are carbohydrates, including disaccharides (e.g., trehalose, maltose, and sucrose), polysaccharides (e.g., pullulan, dextran, and cellulose), and non-sulfated glycosaminoglycans (e.g., hyaluronic acid). Mixtures of naturally-occurring biopolymers may also be used. The polymer may be a derivative of a naturally-occurring polymer, such as a functionalized cellulose (e.g., hydroxypropyl cellulose, hydroxypropyl methylcellulose, or the like).

In some embodiments, the polymer is pullulan, which is a polysaccharide that includes maltotriose-repeating units. Maltotriose is a trisaccharide that includes three glucose units that are linked via α-1,4 glycosidic bonds. The maltotriose units within the pullulan polymer are linked to each other via α-1,6 glycosidic bonds. Pullulan is naturally produced from starch by the fungus Aureobasidum *pullulans*, and generally has a mass range of about $4.5 \times 10^4$ to about $6 \times 10^5$ Da, and is commercially available from a variety of suppliers (CAS No. 9057-02-7).

In some embodiments, the polymer is dextran, which is a complex branched polysaccharide that includes glucose repeating units. Straight chains linkages are generally formed by α-1,6 glycosidic bonds while branches typically begin from α-1,3 linkages. Naturally-occurring dextran can have a molecular weight ranging from about 9 kDa to about 2000 kDa. Dextran can be synthesized from sucrose by certain bacteria including *Leuconostoc mesenteroides* and *Streptococcus mutans*. Commercially available dextran (CAS No. 9004-54-0) produced by *Leuconostoc mesenteroides* can be purchased from a variety of suppliers including Sigma Aldrich, and may have a variety of molecular weight ranges ranging from about 1 kDa to about 670 kDa.

In some embodiments, the polymer is a cyclic saccharide polymer such as a cyclodextrin. Typical cyclodextrins are α-cyclodextrins, β-cyclodextrins, and γ-cyclodextrins, which have six, seven, and eight glucopyranose units respectively. The glucopyranose units can be functionalized. An exemplary cyclodextrin is hydroxypropyl-β-cyclodextrin.

In some embodiments, the polymer is a non-sulfated glycosaminoglycan. Glycosaminoglycans are linear polysaccharides having repeating disaccharide units, each repeating unit including one amino sugar (N-acetylglucosamine or N-acetylgalactosamine) and either an uronic sugar (glucuronic acid or iduronic acid) or galactose. An exemplary non-sulfated glycosaminoglycan is hyaluronic acid in which the repeating disaccharides include N-acetylglucosamine and glucuronic acid linked via alternating β-(1→4) and β-(1→3) glycosidic bonds. Polymers of hyaluronic acid can range in size from 5 to 20000 kDa.

In some embodiments, the polymer is cellulose, which is a polysaccharide of linear, repeating β-1,4 linked D-glucose units. Natural fibers can exist with up to 10,000 glucose units, with molecular weights of greater than 1000 Da.

In some embodiments, the polymer is a synthetic polymer. A synthetic polymer may be a homopolymer, copolymer, block copolymer (e.g., diblock copolymer, triblock copolymer, etc.). Non-limiting examples of suitable polymers include, but are not limited to, polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes (e.g., polyethylene and polypropylene), polyalkylene glycols (e.g., poly(ethylene glycol) (PEG) and poly (propylene glycol) (PPG)) and copolymers thereof (e.g., poloxamers), polyalkylene terephthalates (e.g., poly(ethylene terephthalate), etc.), polyvinyl alcohols (PVA), polyvinyl ethers, polyvinyl esters (e.g., poly(vinyl acetate), etc.), polyvinyl halides (e.g., poly(vinyl chloride) (PVC), etc.), polyvinylpyrrolidone, polysiloxanes, polystyrene (PS), polyurethanes, derivatized celluloses (e.g., alkyl celluloses, hydroxyalkyl celluloses, cellulose ethers, cellulose esters, nitro celluloses, hydroxypropylcellulose, carboxymethylcellulose, etc.), polymers of acrylic acids ("polyacrylic acids") (e.g., poly(methyl(meth)acrylate) (PMMA), poly(ethyl (meth)acrylate), poly(butyl(meth)acrylate), poly(isobutyl (meth)acrylate), poly(hexyl(meth)acrylate), poly(isodecyl (meth)acrylate), poly(lauryl(meth)acrylate), poly(phenyl (meth)acrylate), poly(methyl acrylate), poly(isopropyl acrylate), poly(isobutyl acrylate), poly(octadecyl acrylate), polydioxanone and its copolymers (e.g., polyhydroxyalkanoates, polypropylene fumarate), polyoxymethylene, poly (ortho)esters, poly(butyric acid), poly(valeric acid), poly (lactide-co-caprolactone), trimethylene carbonate, polyvinylpyrrolidone (PVP), poly(1-vinylpyrrolidone-co-vinyl acetate) (PVP-VA), poly(4-vinylpyridine), poly(4-vinylpyridine-co-butyl methacrylate), poly(4-vinylpyridine-co-styrene), poly[4-vinylpyridinium poly(hydrogen fluoride), methylacrylate (p(MAA-co-MMA)) copolymers, poly(1-vinylpyrrolidone-co-2-dimethylaminoethyl methacrylate), poly(1-vinylpyrrolidone-co-styrene), poly(4-vinylpyridinium p-toluenesulfonate), hydroxypropyl acetate succinate (HPMC), hydroxypropyl methylcellulose acetate succinate (HPMCAS), poly(ethylene-alt-propylene) (PEP), 2-methyl acrylamido glucopyranose (MAG), dimethyl adipimidate (DMA), polyvinyl caprolactam-polyvinyl acetate, and mixtures and copolymers of any thereof.

In some embodiments, the synthetic polymer is a polyalkylene glycol. In some embodiments, the synthetic polymer is a polyalkylene glycol copolymer. In some embodiments, the synthetic polymer is a block copolymer comprising at least one poly(propylene oxide) block and at least one poly(ethylene oxide) block, such as a poloxamer. Poloxamers are non-ionic, triblock copolymers having a central poly(propylene oxide) block flanked by two poly(ethylene oxide) blocks. Poloxamers are also known by certain trade names, including Pluronic® and Kolliphor®. Exemplary poloxamers include poloxamer 188 (Pluronic® F-68) and poloxamer 407 (Pluronic® F-127).

In some embodiments, the compound (i.e. coelenterazine or an analog or derivative thereof) and the polymer may be present in the composition in a weight ratio of about 0.001:1 to about 0.50:1, or about 0.0025:1 to about 0.40:1.

In some embodiments, the composition further comprises a paper or fiber matrix or other material, and the composition is placed into or onto the paper or fiber matrix or other material. In some embodiments, this material can allow for the coelenterazine (or analog or derivative thereof) to be used in a wide variety of environments such as field testing. In some embodiments, the paper or fiber matrix may be manufactured from high-quality cotton linters such as 100% pure cotton linters. In some embodiments, the paper or fiber matrix may be ashless. In some embodiments, the paper or fiber matrix may include up to 0.06% ash by weight. In some embodiments, the paper or fiber matrix may have a thickness of about 0.1 μm to about 1 mm. In some embodiments, the paper or fiber matrix may have a pore size range from about 0.02 µm to about 12 µm. Paper or fiber matrices may have a variety of characteristics including binding affinity, porosity, functionalization (e.g., with highly acidic or basic functional groups), etc.

Exemplary paper or fiber matrices include, but are not limited to, Whatman® brand papers, (e.g., W-903 paper, FTA paper, FTA Elute paper, FTA DMPK paper, etc.), Ahlstrom papers (e.g., A-226 paper, etc.), M-TFN paper, FTA paper, FP705 paper, Bode DNA collection paper, nitrocellulose paper, nylon paper, cellulose paper and sample pads (e.g. EMD Millipore CFSP20300M), Dacron paper, cotton paper, polyester papers (e.g. Ahlstrom polyester fibers grade 6613, Ahlstrom treated polyester fibers grade 6613H), sodium carboxymethyl cellulose, Noviplex™ plasma prep cards, Ahlstrom CytoSep®, Cobas® plasma separation card, porous and polymeric membranes, high purity cotton fibers (e.g. Ahlstrom grade 237), cotton/rayon blended high purity cotton (e.g. Ahlstrom grade 1218), glass microfibers (e.g. Ahlstrom 934-AH, EMD Millipore GFDX103000), and combinations thereof.

Other potential materials that could be used in place of the paper or fiber matrix include synthetic and/or polymeric membranes made from organic or inorganic materials (e.g., metal or ceramic materials), homogeneous or heterogeneous solids, liquids, or dissolvable tableting materials. Exemplary additional materials include, for example, cellulose acetate, cellulose esters, cellulose ethers, polysulfones, polyether sulfones, polyacrylonitrile, polyethylene, polypropylene, polyvinylidene fluoride, polyethylene glycol, polyvinyl alcohol, starch, and the like. Additional materials that could be used in place of the paper or fiber matrix include plastic or glass. In some embodiments the material can be a cuvette, a slide, a plate, or any other suitable surface made of plastic or glass. In some embodiments, the material can be a metal surface wherein the metal is a single metal or a metal alloy, for example steel, copper, brass, bronze, or silver.

In some embodiments, a composition comprises (i) a coelenterazine or a coelenterazine derivative or analog, (ii) a suitable polymer, and (iii) a paper or fiber matrix or other surface such as glass, plastic, or metal.

In addition to the compound and the polymer and/or the paper or fiber matrix or other surface, the composition may include additional components such as buffers, surfactants, reducing agents, salts, radical scavengers, chelating agents, proteins, or any combination thereof.

In some embodiments, compositions include a buffer such as a phosphate buffer, a borate buffer, an acetate buffer, or a citrate buffer, or other common buffers such as bicine, tricine, tris(hydroxymethyl)aminomethane (tris), N-[tris(hydroxymethyl)methyl]-3-aminopropanesulfonic acid (TAPS), 3-[N-tris(hydroxymethyl)methylamino]-2-hydroxypropanesulfonic acid (TAPSO), 2-[4-(2-hydroxyethyl)piperazin-1-yl]ethanesulfonic acid (HEPES), N-[tris(hydroxymethyl)methyl]-2-aminoethanesulfonic acid (TES), piperazine-N,N'-bis(2-ethanesulfonic acid) (PIPES), 2-(N-morpholino)ethanesulfonic acid (MES), or the like. In some embodiments, the composition includes a phosphate buffer. In some embodiments, the composition includes tricine. In some embodiments, the composition includes 2-(N-morpholino)ethanesulfonic acid. Compositions can also include any combination of buffers.

In some embodiments, the composition comprises a detergent or surfactant. In some embodiments, a detergent or surfactant is present at about 0.01 mol % to 5 mol % (e.g., 0.01%, 0.02%, 0.05%, 0.1%, 0.2%, 0.5%, 1%, 2%, 5%, or any ranges therebetween (e.g., 0.1 to 0.5%). Exemplary surfactants include non-ionic surfactants, anionic surfactants, cationic surfactants, and zwitterionic surfactants. Examples of nonionic detergents include Brij 35, Triton™ surfactants, such as the Triton™ X series (octylphenol ethoxylates such as Triton™ X-100, Triton™ X-100R, Triton™ X-114, etc.), octyl glucoside, polyoxyethylene(9)dodecyl ether, digitonin, octylphenyl polyethylene glycol (IGEPAL CA630), n-octyl-beta-D-glucopyranoside (betaOG), n-dodecyl-beta-D-maltoside, Tween® 20 (polysorbate 20 or polyethylene glycol(20) sorbitan monolaurate), Tween® 40 (polysorbate 40 or polyethylene glycol(20) sorbitan monopalmitate), Tween® 80 (polysorbate 80 or polyethylene glycol(20) sorbitan monooleate), polidocanol, n-dodecyl beta-D-maltoside (DDM), Nonidet P40-substitute, NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Pluronic® F-68 (poloxamer 188), Pluronic® F-127 (poloxamer 407), saponin, Emulgen, polyethylene glycol trimethylnonyl ether, and polyoxyethylene 10 lauryl ether (C12E10). Examples of ionic detergents (anionic or cationic) include deoxycholate, sodium cholate, sodium dodecyl sulfate (SDS), N-lauroylsarcosine, and cetyltrimethylammoniumbromide (CTAB). Examples of zwitterionic reagents include Chaps, zwitterion 3-14, and 3-[(3-cholamidopropyl)dimethylammonio]-1-propanesulfonate. In some embodiments, the surfactant is polysorbate 20. Compositions can also include any combination of surfactants.

In some embodiments, the composition may include a reducing agent such as dithiothreitol (DTT), 2-mercaptoethanol (BME), cysteamine, (2S)-2-amino-1,4-dimercaptobutane (DTBA), thiourea, 6-aza-2-thiothymine (ATT), or the like. In some embodiments, the reducing agent is thiourea. In some embodiments, the reducing agent is ATT. Compositions can also include any combination of reducing agents.

In some embodiments, the composition may include a salt such as sodium chloride, potassium chloride, magnesium chloride, sodium phosphate, or the like. In some embodiments, the salt is sodium chloride. In some embodiments, the salt is sodium phosphate. Compositions can also include any combination of salts.

In some embodiments, the composition may include radical scavengers such as ascorbic acid, sodium ascorbate, or the like. In some embodiments, the composition may include a metal chelator such as citric acid, ethylenediamine tetraacetic acid, trans-1,2-diaminocyclohexane-tetraacetic acid, or the like. In some embodiments, the composition includes ascorbic acid. In some embodiments, the composition includes sodium ascorbate. In some embodiments, the composition includes citric acid. In some embodiments, the composition includes trans-1,2-diaminocyclohexane-tetraacetic acid. Compositions can include any combination of radical scavengers and/or chelators.

In some embodiments, the composition may include a complete buffer composition, such as Nano-Glo® Luciferase Assay Buffer (Promega Catalog No. N112), Nano-Glo® Live Cell Substrate (LCS) Dilution Buffer (Promega Catalog No. N206), or the like. A complete buffer composition may include a combination of components that are disclosed herein, including the buffer itself and one or more of a salt, a metal chelator, a reducing agent, and a non-ionic surfactant.

In some embodiments, the composition may include a protein. For example, the composition can include a carrier protein to prevent surface adsorption of luminogenic enzymes that may be added in downstream assays. In some embodiments, the protein may be bovine serum albumin (BSA). In some embodiments, the protein may be a polypeptide fraction of highly purified dermal collagen of porcine origin (e.g., Prionex). In some embodiments, the protein may be gelatin. Compositions can also include any combination of proteins.

In some embodiments, the composition may include a solvent. Some compositions are fully dried such that any solvents may be removed, while other compositions may include solvents or some amount of residual solvents. In some embodiments, the composition may include an organic solvent, such as methanol, ethanol, iso-propanol, ethylene glycol, propylene glycol, or the like, or any combination thereof. For example, the composition may include a combination of ethanol and propylene glycol.

As described above, the composition can include any combination of the above-described components. For example, in some embodiments the composition can include a protein, a buffer, and a reducing agent. In some embodiments the composition can include a protein, a buffer, and a metal chelator.

The composition may be in the form of a lyophilized powder or cake. Such a composition can be prepared by freeze-drying a mixture of the components of the composition as further described below. The powdered product may be provided in a container such as a bottle, a vial, a snap tube, microtiter plate, on a paper or fiber matrix or other solid material support, in a lab-on-chip, or the like. The powdered product may be included in a plurality of snap tubes with each tube containing a pre-determined amount of the composition that be dissolved into an appropriate amount of a solution and directly used in an assay of interest.

The composition may also be in the form of a hard but malleable material such as a "drop" cast or a film. Such a composition can be prepared by applying a solution containing the components of the composition to a surface and drying the composition, e.g., by air-drying, drying at ambient temperature, drying at an elevated temperature (e.g., at a temperature of about 30° C. to about 70° C., or about 30° C. to about 40° C., for example at about 30° C., about 35° C., about 40° C., about 45° C., about 50° C., about 55° C., about 60° C., about 65° C., or about 70° C.), drying under an inert atmosphere, or by drying under vacuum. The drop cast or film may be provided in a container, such as a bottle, a vial, a snap tube, a microtiter plate, microtiter plate, on a paper or fiber matrix or other solid material support, in a lab-on-chip, or the like.

In some embodiments, the composition is in the form of a solution (e.g., an aqueous solution). When the composition is a solution, the composition may have a pH of about 5.5 to about 8.0, e.g., about 6.5 to about 7.5. In some embodiments, the composition has a pH of about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 77.3, 7.4, 7.5, 7.6, 7.7, 7.8, 7.9, or 8.0.

The composition may also be provided in other forms such as tablets or capsules including dissolvable tablets or capsules that can be dropped into a sample such as a buffer or a biological sample. The compositions could also be included as pre-formed films on surfaces such as the wells of 96-well plates, such that the compositions can be dissolved straight into an appropriate amount of a solution, and used directly in an assay of interest.

When the composition is provided on a paper or fiber matrix, the paper or fiber matrix may be in the form of a card with spots that can be punched such that the spots can be reconstituted and used directly in an assay of interest. Alternatively, the paper or fiber matrix can be provided in the form of pre-punched spots (e.g., of about 1-5 mm in diameter) that can be reconstituted for use in an assay of interest. The paper or fiber matrix with the composition can be dried, e.g., by air-drying, drying at ambient temperature, drying at an elevated temperature (e.g., at a temperature of about 30° C. to about 70° C., or about 30° C. to about 40° C., for example at about 30° C., about 35° C., about 40° C., about 45° C., about 50° C., about 55° C., about 60° C., about 65° C., or about 70° C.), drying under an inert atmosphere, or by drying under vacuum.

The compositions of the disclosure may be used in any way that luciferase substrates, e.g., coelenterazine and analogs and derivatives thereof, have been used. For example, they may be used in a bioluminogenic method that employs coelenterazine, or an analog or derivative thereof, to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution including multiphasic solutions (e.g., emulsions or suspensions) or on solid supports (e.g., particles, capillaries, or assay vessels).

In certain embodiments, the compositions may be used to quantify a molecule of interest. In some embodiments, the composition can be used as a probe of a specific biochemical activity, e.g., apoptosis or drug metabolism.

In certain embodiments, the compositions can be used for detecting luminescence in live cells or animals, e.g., in vivo. In some embodiments, a luciferase can be expressed in cells (as a reporter or otherwise), and the cells treated with the composition. The coelenterazine, or analog or derivative thereof, will permeate cells in culture, react with the luciferase, and generate luminescence. In some embodiments, the compositions can be used for more robust, live cell luciferase-based reporter assays. In still other embodiments, a sample (including cells, tissues, animals, etc.) containing a luciferase and a composition of the present disclosure may be assayed using various microscopy and imaging techniques, e.g., in vivo imaging. In still other embodiments, a secretable luciferase is expressed in cells as part of a live-cell reporter system.

Also provided herein is a method of stabilizing a compound selected from coelenterazine, or an analog or derivative thereof, comprising contacting the compound with an effective amount of a polymer and/or a paper or fiber matrix to form a composition. The compound may be stabilized against thermal decomposition, chemical decomposition, light-induced decomposition, or any combination thereof.

In some embodiments, compositions herein stabilize the compound (i.e. coelenterazine or an analog or derivative thereof) against decomposition (e.g., compared to the coelenterazine compound or an analog or derivative thereof that has not been contacted with the polymer and/or the paper or fiber matrix) at temperatures from about −80° C. to about 80° C., about −75° C. to about 80° C., about −70° C. to about 80° C., about −65° C. to about 80° C., about −60° C. to about 80° C., about −55° C. to about 80° C., about −50° C. to about 80° C., about −45° C. to about 80° C., about −40° C. to about 80° C., about −35° C. to about 80° C., about −30° C. to about 80° C., about −25° C. to about 80° C., about −20° C. to about 80° C., about −15° C. to about 80° C., about −10° C. to about 80° C., about −5° C. to about 80° C., about 0° C. to about 80° C., about −80° C. to about 75° C., about −80° C. to about 70° C., about −80° C. to about 65° C., about −80° C. to about 60° C., about −80° C. to about 55° C., about −80° C. to about 50° C., about −80° C. to about 45° C., about −80° C. to about 40° C., about −80° C. to about 35° C., about −80° C. to about 30° C., about −80° C. to about 25° C., about −20° C. to about 60° C., about −20° C. to about 55° C., about −20 to about 50° C., about −20° C. to about 45° C., about −20° C. to about 40° C., about −20° C. to about 35° C., about −20° C. to about 30° C., or about −20° C. to about 25° C.

In some embodiments, compositions herein stabilize the compound (i.e. coelenterazine or an analog or derivative thereof) against decomposition (e.g., compared to the coelenterazine compound or an analog or derivative thereof that has not been contacted with the polymer and/or the paper or fiber matrix) at about −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 75° C., or 80° C. The composition may stabilize the compound against decomposition at about −80° C., about −20° C., about 4° C., about 20° C., about 25° C., or about 37° C.

In some embodiments, compositions herein stabilize the compound (i.e. coelenterazine or an analog or derivative thereof) against decomposition (e.g., compared to the coelenterazine compound or an analog or derivative thereof that has not been contacted with the polymer and/or the paper or fiber matrix) in the presence of light. The composition may increase a half-life of the compound in the presence of light as compared to a composition that does not contain the polymer or paper or fiber matrix. The composition may increase the half-life of the compound in the presence of light about 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, or 5.0-fold or more, as compared to the composition that does not contain the polymer or paper or fiber matrix.

In some embodiments, compositions herein stabilize the compound (i.e., coelenterazine or an analog or derivative thereof) against decomposition (e.g., compared to the coelenterazine compound or an analog or derivative thereof that has not been contacted with the polymer and/or the paper or fiber matrix) for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, 65 days, 70 days, 75 days, 80 days, 85 days, 90 days, 100 days, 110 days, 120 days, 130 days, 140 days, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350 days, 360 days, 1 year, 2 years, 3 years, 4 years, or 5 years, as compared to the composition that does not contain the polymer or the paper or fiber matrix.

In some embodiments, compositions increase the half-life of the compound (i.e., coelenterazine or an analog or derivative thereof) against decomposition (e.g., compared to the coelenterazine compound or an analog or derivative thereof that has not been contacted with the polymer and/or the paper or fiber matrix) by at least about 1.25-fold, 1.5-fold, 1.75-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, or 25-fold as compared to the composition that does not include the polymer or the paper or fiber matrix.

Also provided herein is a method of improving the solubility of a compound selected from coelenterazine and an analog or derivative thereof comprising contacting the compound with an effective amount of a polymer and/or a paper or fiber matrix wherein the solubility of the coelenterazine compound or analog or derivative thereof is improved compared to a compound that has not been contacted with the polymer. The solubility of the compound may be improved in an aqueous solution compared to a corresponding compound that has not been contacted with the polymer and/or the paper or fiber matrix. The solubility of the compound may be improved when in the presence of the polymer after reconstitution of the lyophilized powder, drop case film or "droplet," or from rehydration of the paper or fiber matrix or other solid support material to which the compound has been placed onto or into.

The composition may increase the solubility of the compound (i.e. coelenterazine or an analog or derivative thereof) in, e.g., pure water or in aqueous solutions such as those that further include a buffer, a salt, a protein, a reducing agent, a radical scavenger, a surfactant, or the like, or any combination of such components. The composition may increase the solubility of the compound in, e.g., an aqueous buffer such as phosphate-buffered saline (PBS) S) at a pH of about 6.5 to about 7.5 (e.g., at a pH of about 6.5, 6.6, 6.7, 6.8, 6.9, 7.0, 7.1, 7.2, 7.3, 7.4, or 7.5, or any range therebetween) or in another suitable buffer such as Nano-Glo® Luciferase Assay Buffer. The composition may increase the solubility of the compound in, e.g., biological or environmental fluids such as a biological sample from a subject, culture media (e.g., tissue culture media), or the like.

For example, the composition may increase the solubility of the compound in the presence of light about 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, or 5.0-fold or more, as compared to the composition that does not contain the polymer and/or the paper or fiber matrix.

Also provided herein is a method of improving the reconstitution rate of a compound selected from coelenterazine and an analog or derivative thereof, comprising contacting the compound with an effective amount of a polymer and/or a paper or fiber matrix, wherein the reconstitution rate for the compound is improved compared to a compound that has not been contacted with the polymer and/or the paper or fiber matrix.

The composition may increase the reconstitution rate of the compound in, e.g., pure water or in aqueous solutions such as those that further include a buffer, a salt, a protein, a reducing agent, a surfactant, or the like, or any combination of such components. The composition may increase the reconstitution rate of the compound in, e.g., an aqueous buffer such as phosphate-buffered saline (PBS) at a pH of about 6.5 to about 7.5 (e.g., at a pH of about 6.5, 6.6, 6.7, 6.8, 6.9, 7.0, 7.1, 7.2, 7.3, 7.4, or 7.5, or any range therebetween) or in another suitable buffer such as Nano-Glo® Luciferase Assay Buffer. The composition may increase the solubility of the compound in, e.g., biological or environmental fluids such as a biological sample from a subject, culture media (e.g., tissue culture media), or the like.

For example, the composition may increase the reconstitution rate of the compound (e.g., coelenterazine compound or an analog or derivative thereof) in the presence of light about 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, or 5.0-fold or more, as compared to the composition that does not contain the polymer.

The compositions can have any combination of the properties disclosed herein. For example, a composition may have increased solubility as described herein, an improved reconstitution rate as described herein, increased stability as described herein, and/or an increased half-life as disclosed herein. A composition may have one of the disclosed characteristics or any combination of the disclosed characteristics, and may further have other improved properties.

In embodiments of the methods described herein, the contacting step may comprise the steps of: dissolving the compound (i.e. coelenterazine or an analog or derivative thereof) in a first solvent to form a first solution; mixing the first solution with a polymer and/or a paper or fiber matrix to form a mixture; and drying the mixture. In some embodiments, the contacting step comprises the steps of: dissolving the compound in a first solvent to form a first solution; dissolving the polymer in a second solvent to form a second solution; mixing the first solution and the second solution to form a mixture; and drying the mixture. In some embodiments, the contacting step comprises the steps of: dissolving the compound in a solvent to form a first solution; applying the first solution to the paper or fiber matrix; and drying the paper or fiber matrix. In some embodiments, the contacting step comprises the steps of: dissolving the compound in a first solvent to form a first solution; dissolving the polymer in a second solvent to form a second solution; combining the first solution and the second solution to form a third solution; applying the third solution to a paper or fiber matrix; and drying the paper or fiber matrix.

In some embodiments, the drying step comprises lyophilization. In some embodiments, the drying step comprises air-drying. In some embodiments, the drying step comprises drying at ambient temperature under an inert atmosphere (e.g., under nitrogen or argon). In some embodiments, the drying step comprises drying at elevated temperatures (e.g., 30° C.). In some embodiments, the drying step comprises vacuum drying. In some embodiments, one or all of the solutions used in the methods may be deoxygenated. Deoxygenation can be achieved by degassing the solution under vacuum, by bubbling an inert gas (e.g., nitrogen or argon) through the solution, or the like.

Compositions may be tested by using them as substrates for luciferases to produce luminescence and analyzing the luminescence from the compositions after reconstitution. "Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate.

The luminescence reaction in various embodiments is carried out in a solution. The solution may contain a lysate, for example, from the cells in a prokaryotic or eukaryotic expression system. The solution may contain purified proteins, peptides, or small molecules tagged with the luminogenic enzyme components. In other embodiments, expression occurs in a cell-free system, or the luciferase protein is secreted into an extracellular medium such that, in the latter case, it is not necessary to produce a lysate. In some embodiments, the reaction is started by adding appropriate materials, e.g., a composition of the present disclosure, a buffer, etc., into a reaction chamber (e.g., a well of a multi-well plate such as a 96-well plate, a test tube or vial, a cuvette, or the like) containing the luminescent protein. The reaction chamber may be situated in a reading device, which can measure the light output, e.g., using a luminometer, a photomultiplier, or a camera (e.g., a smartphone camera, a CCD camera, or any other hand-held device that can record an image). The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs). In certain embodiments, the compositions may be tested by using them as substrates for an Oplophorus luciferase.

In still other embodiments, the luciferase and/or the composition are introduced into a host, and measurements of luminescence are made on the host or a portion thereof, which can include a whole organism or cells, tissues, explants, or extracts thereof.

In other embodiments, the luminescence reaction is carried out on a solid support. The solid support could be, for example, a bead, a resin, a magnetic particle, a membrane, or a surface such as the surface of a vial, microtiter plate, a cassette, a cuvette, a swab, or the like. This reaction may then be situated in a reading device that can measure the light output from the specific solid support format.

In other embodiments, the luminescence reaction is carried out in vivo for whole animal imaging. Vehicles for injection of substrates into animals must be non-toxic and highly compatible with mammalian biology, significantly restricting the options available. Pullulan and many other polymers described herein are non-toxic, even being approved as food additives, which makes them particularly suited to be components of an injectable solution. In addition, the improved solubility and reconstitution of coelenterazine analogs such as furimazine into simple buffers like PBS is ideal for administration into animals such as by intravenous injection, intraperitoneal injection, intracranial administration, etc. The composition components could be combined just prior to injection, and the superior reconstitution allows the sample to be homogenous quickly, which is important for animal work where the presence of undissolved microcrystals can be fatal. Once the substrate formulation is introduced into the animal (e.g. intravenous or intraperitoneal injection), sedated animals will be placed into an imaging chamber and analyzed for the in vivo production of bioluminescence.

In certain embodiments, the compositions disclosed herein are provided as part of a kit. The composition may be contained within a single container. In some embodiments, the kit may further include one or more luciferases (in the form of a polypeptide, a polynucleotide, or both), along with suitable reagents and instructions to enable a user to perform assays such as those disclosed herein. The kit may also include one or more buffers such as those disclosed herein. The kit may include instructions for storing the composition and/or the single container containing the composition. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides instructions.

EXPERIMENTAL

Experiments conducted during development of embodiments herein demonstrate the utility of the compositions and methods described herein. Unless otherwise indicated, pullulan was obtained from Sigma-Aldrich (CAS No. 9057-02-7).

Abbreviations used in the Examples include the following: ATT is 6-aza-2-thiothymine; EtOH is ethanol; Fz is furimazine; HPLC is high performance liquid chromatography; NGB is Nano-Glo® Luciferase Assay Buffer (Promega catalog #N112); PBS is phosphate-buffered saline; and TFA is trifluoroacetic acid.

Example 1

Furimazine-Pullulan Compositions

Samples were prepared as follows. For each of the following conditions, all substrates and additives were combined at the listed concentrations in a solution of varying percent w/v of pullulan in water. In each case, the substrate was added from a stock solution in ethanol such that the total amount of ethanol (v/v) in the final solution containing the polymer does not exceed 10% v/v.

Condition 1: Solutions were prepared with 0, 2.5, 5, or 10% (w/v) pullulan in water. A stock solution of 30 mM furimazine in ethanol was prepared. 4 µL of the furimazine stock was added to 46 µL of the solution containing pullulan where the final concentration of furimazine was 2 mM. The total concentration of ethanol was <10% v/v in the final solution for all cases. The samples were frozen and then lyophilized overnight to form powdered products.

Condition 2: A solution of 15% (w/v) pullulan, 200 mM Tricine, and 2 mM furimazine in <10% v/v ethanol/water was prepared as described above. A series of 60 µL aliquots were pipetted onto parafilm and allowed to dry at 25° C., in the dark, for at least 3 hours to form hard malleable "drops."

Condition 3: A solution of 15% (w/v) pullulan and 2 mM furimazine in <10% v/v ethanol/water was prepared as described above. A series of 60 µL aliquots were pipetted onto parafilm and allowed to dry at 25° C., in the dark, for at least 3 hours.

Samples were tested by dissolving the formulated furimazine into NGB or PBS, pH 7.0 with vortexing as needed. In each case, the sample was diluted in 5 mL of the buffer to a final working concentration of 10 µM furimazine.

Empirical results are as follows. The sample according to Condition 1 with 2.5% (w/v) pullulan easily went into solution in NGB and PBS, pH 7.0 in less than one minute. The samples according to Condition 1 with 5% (w/v) and 10% (w/v) fully dissolved in PBS, pH 7.0 within a few minutes. The sample according to Condition 2 needed further vortexing and required about 10-15 minutes to fully dissolve in PBS, pH 7.0. The sample according to Condition 1 with no pullulan required approximately 10 minutes to fully dissolve in PBS (determined empirically), pH 7.0.

After storage of the samples at 4° C. for five weeks, the samples were diluted with 1×NGB to 6 mL for a 20 µM stock or with 1×PBS, pH 7.0 to 6 mL for a 20 µM stock. Purified NanoLuc® (Nluc) luciferase enzyme was added at a final 1× concentration (where 2× stock solutions had been prepared in either PBS or NGB starting from a 1000× stock of NanoLuc® enzyme, Promega #E499). Control samples included Nluc in assay buffers with 10 µM final Nano-Glo® substrate. Assays were performed on a solid white nonbinding surface (NBS) plate with a total assay volume of 100 µL using a kinetic read on luminometer (specifically a GloMax® Discover Multimode Microplate reader—Promega Cat. #GM3000) collecting total luminescence. Kinetic traces for samples reconstituted in PBS are shown in FIG. 1A, and kinetic traces for samples reconstituted in NGB are shown in FIG. 1B. FIG. 1C shows images of lyophilized cake and film droplet formulations. Data from FIG. 1A at specified time points are presented in the bar graphs in FIGS. 2A-C, and data from FIG. 1B at specified time points are presented in the bar graphs in FIGS. 3A-C.

The results illustrated in FIGS. 1-3 demonstrate increased solubility of the furimazine compositions in neutral buffer with no need for organic solvents or special buffer conditions. Luminescence from the furimazine compositions is strong relative to a commercial furimazine formulation.

Example 2

Absorbance of Reconstituted Furimazine Compositions

Bulk solid furimazine was diluted in ethanol to a final concentration of 10 mM (solution 1). Dry pullulan was dissolved in pure water to final concentrations of 0%, 2.5%, 5%, 10%, 15% w/v (solutions 2a, 2b, 2c, 2d, and 2e respectively). 45 µL of solutions 2a-e were pipetted into separate 1.5 mL snap-tube vials. 5 µL of solution 1 was then added to each vial and pipetted vigorously to mix, to form solutions 3a-e, each of which contained a final concentration of 1 mM (19.08 µg) furimazine in 50 µL of solution. After mixing, vials containing solutions 3a-e were placed in dry ice to freeze for 1 hour. These frozen stocks where then lyophilized overnight for form dry pullulan matrices containing furimazine.

Figure 4:
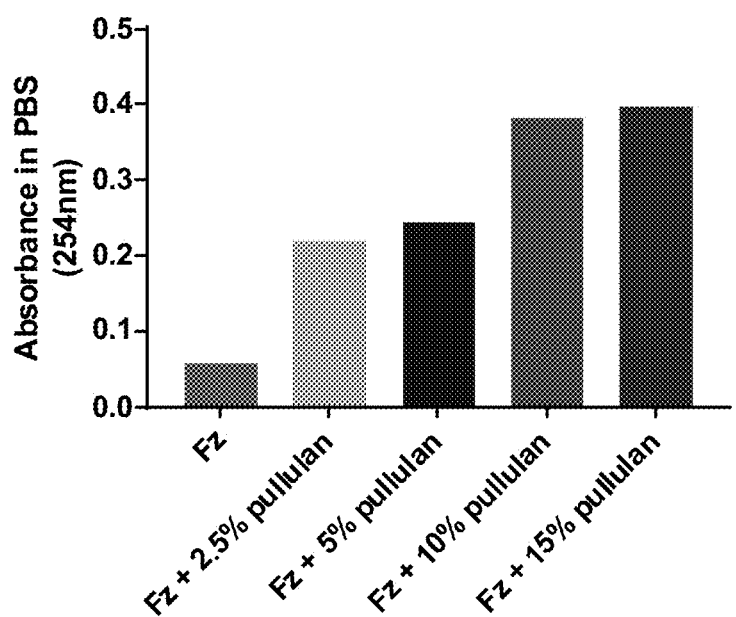
FIG. 4, Panels A-C show absorbance values in aqueous solution when compositions according to the present disclosure were tested for absorbance over the range of 210-600 nm in PBS, pH 6.8 as described in Example 2.

Powder formulations of furimazine (19.08 µg) in the pullulan matrix (0%-15% w/v) were diluted in 0.5 mL of PBS buffer, pH 6.8, equilibrated for 30 minutes at room temperature, and the absorbance was read at 254 nm. Absorbance spectra of the formulated dry furimazine (50 nmols) with increasing amounts of pullulan after reconstitution in the PBS buffer are shown in FIG. 4A. Formulated furimazine with pullulan led to an increase in furimazine absorbance in aqueous solution. Concentration of furimazine was determined by Beer's law using the extinction coefficient of furimazine in methanol ($21000\ M^{-1}cm^{-1}$) with absorbance measured at 254 nm. Bulk furimazine had an absorbance of 0.0571 corresponding to a calculated concentration of 0.0082 mM. Furimazine formulation with 2.5%-5% pullulan w/v led to an absorbance of 0.2204 and 0.2467 giving calculated concentrations of 0.032 mM and 0.035 mM respectively. Formulated furimazine with 10-15% pullulan w/v led to an absorbance of 0.3964 and 0.3836 giving calculated concentrations of 0.055 mM and 0.052 mM, respectively, in PBS. A summary of the absorbance data displayed in FIG. 4A can be found in FIG. 4C showing an increase in furimazine (Fz) concentrations in solution when furimazine is formulated with pullulan compared to the sample containing no pullulan.

Separately, dried formulations of furimazine (95.4 µg) in pullulan matrices (0%-15% w/v), which were prepared similarly to the samples described above, were diluted in 0.5 mL of PBS buffer, pH 6.8, equilibrated for 30 minutes at room temperature, and the absorbance was read at 254 nm. Absorbance of the formulated furimazine (95 µg) with increasing amounts of pullulan after reconstitution in the PBS buffer are shown in FIG. 4B. The solid furimazine formulated with increasing concentrations of pullulan matrix led to an increased in absorbance, and thus furimazine concentration in PBS buffer, compared to the conditions that contained only furimazine without pullulan.

Example 3

Reconstitution of Stored Samples

Figure 5:
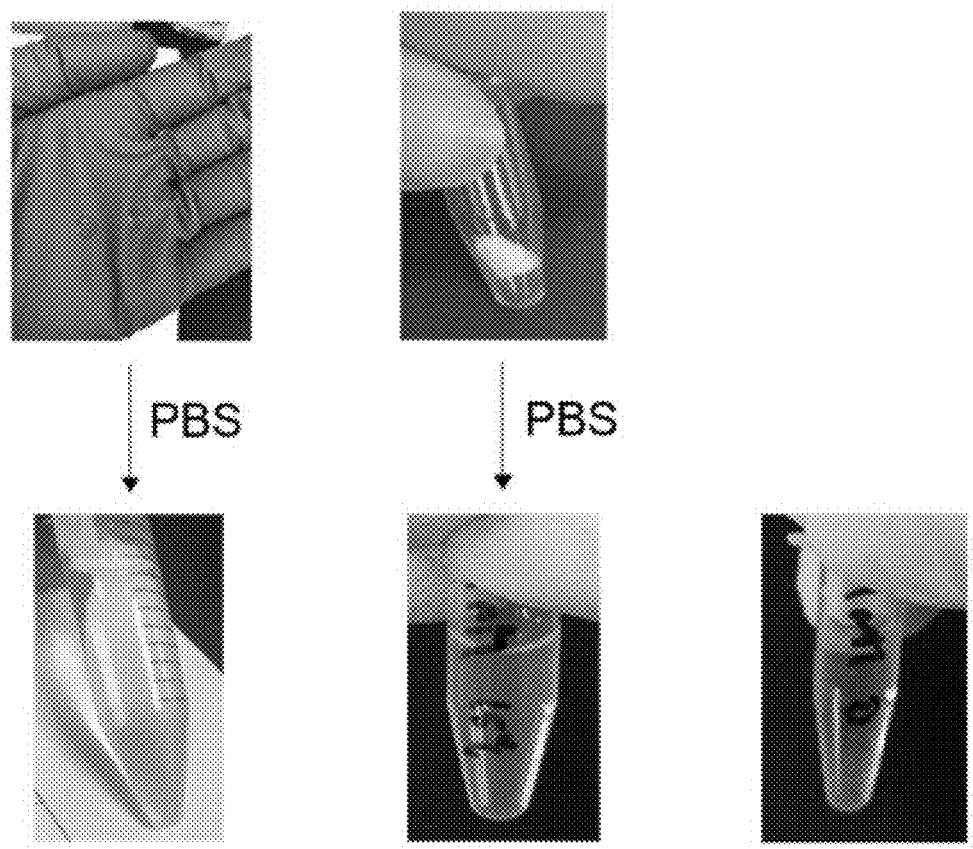
FIG. 5 shows images demonstrating the ability of the compositions according to the present disclosure to reconstitute into PBS, pH 7.0 as described in Example 3.

Solid furimazine was dissolved in ethanol, and the dissolved solution was added to an aqueous solution of pullulan (0 or 15% w/v) for a total concentration of 1 mM furimazine in 50 µL of solution containing <10% v/v ethanol. The samples were freeze-dried or were dried under ambient temperature. FIG. 5 shows images demonstrating the ability of these compositions to reconstitute into PBS, pH 7.0. The "droplet" formulation dried under ambient temperature with 15% w/v pullulan went in to solution after brief pipetting. The freeze-dried sample with 15% w/v pullulan dissolved immediately after addition of PBS. The sample with no pullulan did not fully dissolve in PBS even after 15 minutes of vortexing, demonstrating lower solubility in PBS.

Example 4

Absorbance of Pullulan Samples

Samples of neat 2.5% w/v pullulan and neat 10% w/v pullulan in PBS, pH 6.8 were tested for their absorbance. Absorbance spectra over the range of 210-600 nm are illustrated in FIG. 6A (2.5%) and 6B (10%). These spectra demonstrate that pullulan does not absorb in the same wavelength range as furimazine and does not artificially boost absorbance signals in samples containing furimazine.

Example 5

HPLC Analysis of Furimazine Samples

Bulk solid furimazine was diluted in ethanol to a final concentration of 10 mM (solution 1). Dry pullulan was dissolved in pure water to final concentrations of 0%, 2.5%, 5%, 10%, or 15% w/v (solutions 2a, 2b, 2c, 2d, and 2e respectively). 45 µL of solutions 2a-2e was pipetted into separate 1.5 mL snap-tube vials. 5 µL of solution 1 was then added to each vial and pipetted vigorously to mix to form solutions 3a-e, each of which contains a final concentration of 1 mM furimazine. After mixing, vials containing solutions 3a-e were placed in dry-ice to freeze for 1 hour. These frozen stocks where then lyophilized overnight to form dry pullulan matrices containing furimazine.

General method for all HPLC traces: Furimazine samples described above (containing 19.08 m furimazine) were diluted with 0.5 mL PBS, pH 6.8 to 38.16 m/mL in the small snap cap tubes. 15 µL of this solution was injected neat on HPLC (vials with inserts) over 5 hours to assess stability and solubility over time. Instrument: Synergi Max-RP 50×4.6 mm, 2.54u. Solvent: 0.1% TFA/Aq, acetonitrile. Commercial furimazine (5 mM, Promega cat. #N113) was diluted in PBS to 38.16 m/mL and was also run for comparison.

HPLC traces of samples immediately after dilution with 0.5 mL PBS, pH 6.8, and 5 hours after dilution were obtained and are shown in FIG. 7 (0% pullulan— (A) 0 hours, (B) 5 hours), FIG. 8 (2.5% pullulan— (A) 0 hours, (B) 5 hours), FIG. 9 (15% pullulan— (A) 0 hours, (A) 5 hours), and FIG. 10 (Nano-Glo® Luciferase Assay Substrate— (A) 0 hours, (B) 5 hours) respectively. (Traces for 5% pullulan and 10% pullulan formulations and the commercial furimazine sample were similarly obtained, data not shown.) Peaks at retention time 5-10-5.13 min (the predominant peak in each spectrum) represent furimazine. Peaks at a retention time of 5.36-5.37 min (marked with an asterisk) represent aminopyrazine, a known degradation product of furimazine (confirmed spectroscopically). Specific peaks and area percents are summarized in Table 1.

TABLE 1

| Sample | FIG. | Retention Time (min) | Area Percent |
|---|---|---|---|
| 0% pullulan, 0 hours | 7(a) | 5.11 | 94.15 |
|  |  | 5.37 | 5.85 |
| 0% pullulan, 5 hours | 7(b) | 1.81 | 1.07 |
|  |  | 5.11 | 56.80 |
|  |  | 5.20 | 7.26 |
|  |  | 5.37 | 10.11 |
|  |  | 5.71 | 1.30 |
|  |  | 6.05 | 144.44 |
|  |  | 6.74 | 9.01 |
| 2.5% pullulan, 0 hours | 8(a) | 5.13 | 99.51 |
|  |  | 6.74 | 0.16 |
|  |  | 8.13 | 0.33 |
| 2.5% pullulan, 5 hours | 8(b) | 5.10 | 94.53 |
|  |  | 5.36 | 3.55 |
|  |  | 6.04 | 0.71 |
|  |  | 6.73 | 0.82 |
|  |  | 8.13 | 0.39 |
| 15% pullulan, 0 hours | 9(a) | 5.11 | 98.11 |
|  |  | 5.37 | 1.11 |
|  |  | 6.75 | 0.29 |
|  |  | 8.14 | 0.49 |

TABLE 1-continued

| Sample | FIG. | Retention Time (min) | Area Percent |
|---|---|---|---|
| 15% pullulan, 5 hours | 9(b) | 5.10 | 95.85 |
| | | 5.37 | 1.72 |
| | | 6.05 | 1.10 |
| | | 6.73 | 0.87 |
| | | 8.13 | 0.41 |
| Nano-Glo ® Luciferase Assay Substrate, 0 hours | 10(a) | 5.11 | 85.05 |
| | | 5.37 | 6.07 |
| | | 6.05 | 1.80 |
| | | 6.75 | 3.87 |
| | | 8.13 | 1.57 |
| | | 8.50 | 1.65 |
| Nano-Glo ® Luciferase Assay Substrate, 5 hours | 10(b) | 5.10 | 60.05 |
| | | 5.36 | 17.18 |
| | | 6.04 | 9.45 |
| | | 6.73 | 9.14 |
| | | 8.13 | 1.92 |
| | | 8.49 | 2.25 |

Figure 12:
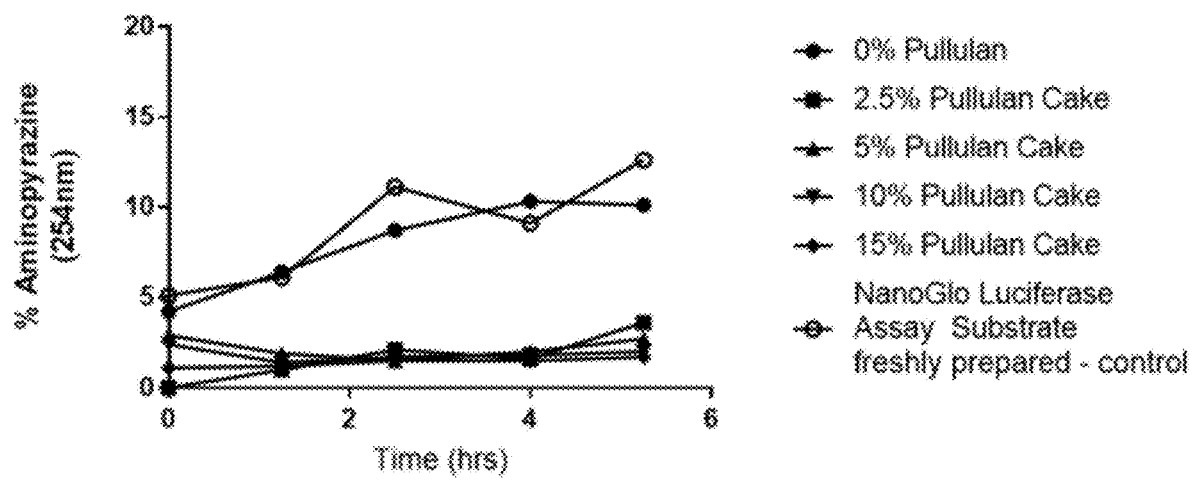
FIG. 12 shows data from HPLC traces for formulated furimazine samples with or without pullulan showing the production of an aminopyrazine degradation product over time as described in Example 5.

FIGS. 11 and 12 show analysis of compiled and processed data from the HPLC traces shown in FIGS. 7-10, along with traces obtained via the same methods at additional time points.

FIG. 11A shows analyses of the purity of each sample as measured by absorbance at 254 nm with each trace normalized to time 0. All conditions that were prepared as a dry formulation with pullulan showed a high level of purity in aqueous solution and with no significant loss of absorbance. Conditions that lacked pullulan (0% condition as well as commercial furimazine solution, Promega cat. #N113), showed considerable loss of absorbance over approximately 6 hours due to chemical degradation.

FIG. 11B shows analyses of the peak areas of formulated furimazine samples (50 nmols) in PBS with increasing amounts of pullulan (0%-15% w/v). (The analyses are for the same traces analyzed in FIG. 11A). The loss of purity for the commercial furimazine and the 0% conditions in the graph in FIG. 11a corresponds to a decrease in peak area as well, indicating that the loss of signal is not due to a change in solubility over time, but rather to product degradation in the Nano-Glo® Luciferase Assay Substrate and the 0% pullulan conditions over the course of the experiment. Accordingly, the presence of pullulan not only helps improve aqueous solubility of furimazine, but also helps prevent its degradation in solution.

FIG. 12 shows the formation of the aminopyrazine byproduct of furimazine in the samples as described above. This data suggests that the presence of pullulan helped prevent the formation of aminopyrazine in solution. Formulations of furimazine that contained pullulan showed minimal aminopyrazine formation over 5.5 hours after reconstitution in PBS. In contrast, both bulk furimazine lacking pullulan (0% condition), as well as the commercial Nano-Glo® Luciferase Assay substrate formulation, showed approximately a 12% increase in aminopyrazine over the course of the experiment. This data is consistent with the change in purity shown in FIG. 11B being due to furimazine degradation in the Nano-Glo® Luciferase Assay substrate and 0% pullulan samples.

Example 6

Furimazine Compositions on Paper Matrices

Paper spots were generated by pressing out 3.2 mm diameter circle "spots" from Whatman® 903 Protein Saver cards using a standard 3.2 mm hand-held hold punch (Dance® brand). 200 μM and 2 μM stock solutions of furimazine were prepared in ethanol. 5 μL of these solutions were applied to each paper spot and dried under vacuum for 60 minutes. These spots were then stored in the dark at 4° C. until testing.

At the time of testing, each spot was placed in an individual well of a standard 96-well plate, and reconstituted with 100 μL of PBS buffer, pH 7.0 that contained purified NanoLuc® (Nluc) enzyme at a final concentration of 2 ng/mL. The final working concentration of furimazine was 10 μM and 0.1 μM respectively. Freshly prepared commercial Nano-Glo® Luciferase Assay substrate was prepared at 10 μM and 0.1 μM for comparison.

Results are illustrated in FIG. 13. FIG. 13A shows change in RLU over time for the paper spot samples and the freshly prepared commercial Nano-Glo® Luciferase Assay substrate samples. FIG. 13B shows the initial RLU at time 0 for each sample. FIG. 13C shows an image of the punched spots in a tube. These results demonstrate that formulated furimazine can be dried down into solid matrix/paper and reconstituted at a later point with non-organic, aqueous buffer conditions.

Example 7

Furimazine Compositions on Paper Matrices

This experiment is based on a structural complementation assay disclosed in International Patent Pub. No. WO 2014/151736. Whatman® 903 protein saver cards containing assay components were prepared by first diluting 5 μL goat anti-mouse IgG3-SmBiT (0.4 mg/mL) in 495 μL sucrose protein buffer containing 20 mM Na$_3$PO$_4$, 5% w/v BSA, 0.25% v/v Tween20, 10% w/v sucrose. 5 μL of this stock solution was then added to positions 2 and 4 on the Whatman® 903 card and allowed to dry at 35° C. for 1 hour. 5 μL goat anti-mouse IgG3-LgBiT (0.4 mg/mL) was diluted in 495 μL of the same sucrose protein buffer, and 5 μL of this solution was added directly to the Whatman® 903 protein card as positions 2 and 4. The Whatman® 903 cards were then dried at again at 35° C. for 1 hour.

A 5 mM stock of furimazine was prepared in ethanol, and 5 μL of this stock was added to card positions to conditions 1, 2, and 4. The card was then placed under high vacuum for 15 minutes.

The cards were maintained at 4° C. or 25° C. and tested at several time points for activity by addition of NanoLuc® enzyme conjugated IgG. 10 pg of fresh NanoLuc®-labeled antibodies in PBS were added position 1 to test for substrate activity. Images were recorded and are illustrated in FIG. 14A: left—image taken with a standard camera; center—image taken using a LAS300 imager; right—image taken with an iPhone camera. Spots 1, 2, and 4 all produced bioluminescence at this time point upon addition of the NanoLuc® enzyme indicating that the substrate has maintained activity.

Additional sets of samples were prepared similarly and stored for 3 months at 4° C. or 25° C. Images were recorded and are illustrated in FIG. 14B: left—image taken with a standard camera; center—image of card stored at 4° C. following addition of 10 pg NanoLuc®-labeled antibody in PBS to determine substrate activity to spots 1, 2, and 3, with spot 4 receiving PBS only as a negative control; right—image of card stored at 25° C. following addition of 10 pg NanoLuc®-labeled antibody in PBS. Only spot 2 produced light whereas spot 1 did not. This example shows that all or some of the components of the sucrose protein-loading buffer (20 mM $Na_3PO_4$, 5% w/v BSA, 0.25% v/v Tween20, 10% w/v sucrose) are necessary for substrate activity at this time point and temperature and that furimazine can be dried down together on a solid paper matrix and reconstituted after storage at either 4° C. or 25° C. for an extended period of time.

Example 8

Furimazine Compositions on Paper Matrices with Buffers and Additives

A goal of this example was to demonstrate the effects of additives on overall reconstitution efficiency and assay performance. Samples were stored at different temperatures to simulate a range of thermal stressors and to test overall performance and stability under these conditions.

Whatman® 903 protein saver spot cards (3.2 mm punches), sucrose protein buffer (20 mM $Na_3PO_4$, 5% w/v BSA, 0.25% v/v Tween20, 10% w/v sucrose (prepared the night before use)); 200 µM furimazine solution in ethanol; 20 mM and 50 mM stocks of 6-aza-2-thiothymine (ATT) in water; and 20 mM and 100 mM stocks of thiourea in water.

To the 3.2 mm Whatman® 903 protein saver card spots were added 5 µL of 200 µM furimazine in ethanol with various additional components, as follows:
Sample 1: Furimazine
Sample 2: Furimazine+sucrose protein buffer
Sample 3: Furimazine+ATT (20 mM)
Sample 4: Furimazine+ATT (50 mM)
Sample 5: Furimazine+ATT (20 mM)+sucrose protein buffer
Sample 6: Furimazine+ATT (50 mM)+sucrose protein buffer
Sample 7: Furimazine+Thiourea (20 mM)
Sample 8: Furimazine+Thiourea (100 mM)
Sample 9: Furimazine+Thiourea (20 mM)+sucrose protein buffer
Sample 10: Furimazine+Thiourea (100 mM)+sucrose protein buffer Spots that contain protein buffer were dried at 35° C. for 1 hour before the addition of other components (furimazine, ATT, and/or thiourea). When ATT was used, 5 µL of the appropriate solution was added to the spot, followed by drying under vacuum for 30 minutes (providing final concentrations of 1 mM ATT when using the 20 mM solution and 2.5 mM ATT when using the 50 mM solution). When thiourea was used, 5 µL of the appropriate solution was added to the spot, followed by drying under vacuum for 30 minutes (providing final concentrations of 1 mM when using the 20 mM solution and 5 mM when using the 100 mM solution). Spots were made and stored at 4° C. for 5 days prior to testing.

RLU Experimental conditions—assay buffer: PBS, pH 7.0; Plate: NB S solid white plate (Corning® 3600). Varying final concentrations of Nluc enzyme were used (20 m/mL, 2 m/mL, or 0.2 m/mL).

Data is presented in FIGS. 15A-D, with FIGS. 15A-C showing the raw RLU from the luminescence reaction at varying concentrations of Nluc enzyme (20 m/mL, 2 m/mL, and 0.2 µg/mL respectively), and FIG. 15D the % activity of the Nluc enzyme at one concentration (0.2 µg/mL). This data suggests that the addition of additives such as ATT or thiourea may help improve overall RLUs and signal stability once reconstituted in PBS compared to other formulations.

Example 9

Furimazine Compositions on Paper Matrices with Different Polymers

Materials and methods: Whatman® 903 protein saver spot cards (3.2 mm punches); furimazine. Protein buffers were prepared the day before testing with the components described below.
Protein buffer 1: purified water
Protein buffer 2: 20 mM $Na_3PO_4$, 5% w/v BSA, 0.25% v/v Tween20, 10% w/v sucrose
Protein buffer 3: 20 mM $Na_3PO_4$, 5% w/v BSA, 0.25% v/v Tween20, 2.5% w/v pullulan
Protein buffer 4: 20 mM $Na_3PO_4$, 5% w/v BSA, 0.25% v/v Tween20, 2.5% w/v trehalose 5 µL of one of protein buffers 1-4 was applied to each spot, and the spots were allowed to dry at 35° C. for one hour. Then, 5 µL of a freshly prepared 200 µM solution of furimazine in ethanol was applied to each spot, and the spots were dried under vacuum for 30 minutes. Spots were stored in the dark at 4° C., 25° C., and 35° C.

For luminescent measurements, at the time of testing, each spot was placed in an individual well of a standard 96-well plate and reconstituted with 100 µL of PBS buffer, pH 7.0 that contained purified NanoLuc® (Nluc) enzyme at a final concentration of 8 ng/mL. Kinetic reads were started immediately.

Figure 16:
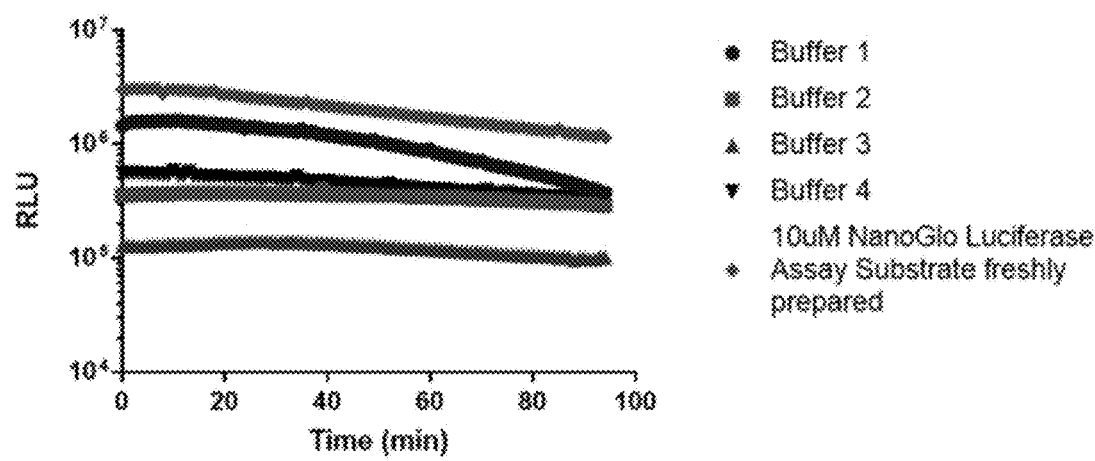
FIG. 16 shows data demonstrating RLU output of formulated furimazine samples in paper spots created from hole punching Whatman® 903 protein saver cards prepared as described in Example 9.

Results from spots tested immediately following preparation are shown in FIG. 16 with a trace of freshly prepared Nano-Glo® substrate shown for comparison. Results from spots tested after storage for one day at 4° C., 25° C., and 37° C. are shown in FIGS. 17A, 17B, and 17C respectively. Results from spots tested after storage for three days at 4° C., 25° C., and 37° C. are shown in FIGS. 18A, 18B, and 18C respectively. These data indicate that signals are more stable for furimazine compositions on paper matrices, but overall signals are lower. Addition of protein buffer with additives prior to addition of furimazine to the spots may have prevented sufficient furimazine from fully entering the paper, though the samples still produced useful and stable signals.

Example 10

Accelerated Stability Studies on Formulated Furimazine Substrate in Paper Matrix Paper furimazine samples were tested to determine the effects of formulations on the thermal stability and functional integrity of furimazine as measured by RLU with comparisons to known furimazine formulations (Nano-Glo® substrate, Promega cat. #N113, and Nano-Glo® Live Cell Substrate, Promega cat. #N205).

Whatman® 903 protein saver spot cards (3.2 mm punches) were treated as follows.

For conditions 1 and 2, the paper spots pretreated with 5 µL of either water (condition 1) or protein buffer (20 mM $Na_3PO_4$, 5% w/v BSA, 0.25% v/v Tween20, 10% w/v sucrose —condition 2). Condition 3 was prepared with a pretreatment of 5 µL protein buffer that lacked the sucrose component (20 mM $Na_3PO_4$, 5% w/v BSA, 0.25% v/v Tween20). All conditions were then dried at 35° C. for 60 minutes. 200 µM stock solution of furimazine was prepared in ethanol, and 5 μL of this stock was added to conditions 1 and 2 as described above. For condition 3, a 200 μM stock of furimazine was prepared in a mixture of 2.5% pullulan in water with <10% v/v ethanol. 5 μL of this solution was then added to condition 3, and all spots were then dried at under reduced pressure for an additional 30 minutes. The spots were then stored at in the dark at either 25° C. of 60° C. At time of measurement, one spot from each condition was placed into an individual well and diluted with PBS containing Nluc. The final theoretical concentration of furimazine is 10 μM and the final concentration of Nluc is 1 ng/mL.

Complied RLU data are shown in FIG. 19, with data for samples stored at: (A) 60° C. and (B) 25° C. for varying periods of time prior to reconstitution and testing. FIG. 19 also shows data for the percent enzyme activity at time 0 after samples were stored at: (C) 60° C. and (D) 25° C. for varying periods of time prior to reconstitution and testing.

The above experiment was expanded to include high concentrations (1 mM and 100 μM final) and a low concentration (10 μM final) of furimazine (FIG. 20). Each condition was prepared as described above: Spots were pretreated with water, protein buffer, or protein buffer that lacked sucrose. In the first two conditions, 5 μL of either a 2 mM or 200 μM solution of furimazine in ethanol was added to each spot and then dried at 35° C. for an additional 30 minutes. In the third condition, either a 20 mM stock or a 200 μM stock of furimazine was prepared in a mixture of 2.5% pullulan in water with <10% v/v ethanol. 5 μL of this solution was then added to condition 3 and all spots were dried at 35° C. for an additional 30 minutes. The spots were then stored at in the dark at either 25° C. of 60° C.

FIG. 20 shows compiled RLU data for samples stored at: (A) 60° C. and (B) 25° C. for varying periods of time prior to reconstitution and testing. FIG. 20 also shows data for the percent enzyme activity at time 0 after samples were stored at: (C) 60° C. and (D) 25° C. for varying periods of time prior to reconstitution and testing By increasing the loading concentration of furimazine, there is an overall improvement in both max RLU as well as percent activity. The spots that did not receive a pretreatment (water), however, still performed better overall compared to both pretreatments that contained protein buffer or protein buffer with pullulan at a comparable concentration.

Example 11

Effect of Drying Method of Furimazine Formulations in Paper Samples 3.2 mm punched Whatman® 903 protein saver card spots were treated with either water or protein buffer (20 mM $Na_3PO_4$, 5% w/v BSA, 0.25% v/v Tween20, 10% w/v sucrose) and dried for 1 hour at 35° C. A 10 mM stock solution of furimazine in ethanol was prepared, and 20 μL of this solution was added to 980 μL of a solution of either 2.5% (w/v) pullulan or 5% (w/v) pullulan in water. After mixing well, 5 μL of this solution was added to each spot. The spots were dried under vacuum or under ambient temperature in the dark for 2 hours. After drying, the spots were stored at 4° C. in the dark overnight.

For testing, spots were added to individual wells of a 96-well NBS plate. 100 μL of a 1.068 nM Nluc solution in PBS buffer, pH 7.4 was added to each well. The plate was placed in a luminometer and read for up to 60 minutes. Each spot was run in triplicate.

Figure 21:
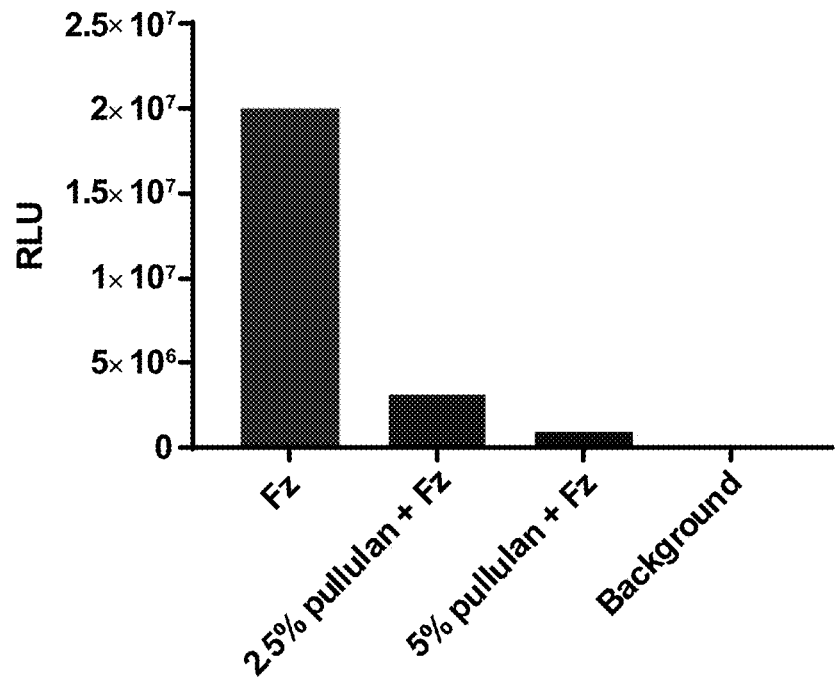
FIG. 21, Panels A-C show data demonstrating RLU output of formulated furimazine samples in paper spots created from hole punching Whatman® 903 protein saver cards and prepared using different drying methods as described in Example 11.

Results are shown in FIG. 21, with FIG. 21A showing data for samples dried under vacuum and FIG. 21B showing data for samples dried under ambient air. The substrate performance does not seem to be significantly affected whether the spots were dried under vacuum or ambient temperature.

FIG. 21C shows summary data of FIG. 21A indicating that the presence of pullulan reduces overall RLU output. Empirical observation indicated that presence of pullulan made the surface of the paper matrix hard and waxy. This may have prevented the accessibility of the substrate to the protein, leading to lower light output. This observation also indicates that the order in which the different components are added to the paper matrix may play a role in overall function.

An additional set of spots were compared that were dried for a second time after substrate addition, either under ambient temperature or dried at 35° C. Each spot was pretreated with either water, sucrose protein buffer (20 mM $Na_3PO_4$, 5% w/v BSA, 0.25% v/v Tween20, 10% w/v sucrose), or pullulan protein buffer (20 mM $Na_3PO_4$, 5% w/v BSA, 0.25% v/v Tween20, 2.5% w/v pullulan) and allowed to dry at 35° C. for 1 hour. 200 μM stock of furimazine was prepared in ethanol, and 5 μL of this furimazine stock was added to each spot. The spots where then allowed to sit in the dark under ambient temperature or at 35° C. for 30 minutes. The spots were then stored at 25° C. or at 60° C., in the dark, for up to 5 days. At time of testing, a spot corresponding to each condition was placed into a well of a standard 96-well plate, and was rehydrated with 100 μL PBS solution, pH 7.0, and 2 ng/mL Nluc in each well for a final concentration of 10 μM furimazine in the solution.

Results are shown in FIG. 22. Spots that had been dried for a second time at 35° C. showed higher RLU output then spots that had been dried a second time at ambient temperature. These results were consistent across the condition (protein buffer pretreatment or water control) or whether or not the spots were stored at 25° C. or 60° C. for up to 5 days (with max RLU values shown in FIGS. 22A and 22B, and % activity shown in FIGS. 22C and 22D). These results suggest that a difference in drying method had an effect on overall substrate performance and that drying the spots for a second time at 35° C. was favorable for substrate performance.

Example 12

Accelerated Substrate Test for Powdered Pullulan Formulations

Powdered furimazine samples were tested to determine the effects of pullulan formulations on the thermal stability and functional integrity of furimazine as measured by both RLU and HPLC with comparisons to known furimazine formulations (Nano-Glo® substrate, Promega cat. #N113, and Nano-Glo® Live Cell Substrate, Promega cat. #N205).

Materials and methods: bulk solid furimazine was diluted in ethanol to a final concentration of 10 mM (solution 1); dry pullulan was dissolved in pure water to final concentrations of 0%, 2.5%, 5%, 10%, and 15% w/v (solutions 2a, 2b, 2c, 2d, and 2e respectively). 45 μL of solutions 2a-e were pipetted into separate 1.5 mL snap-tube vials. 5 μL of solution 1 was then added to each vial, pipetted vigorously to mix, to form solutions 3a-e, each of which contained a final concentration of 1 mM furimazine.

After mixing, vials containing solutions 3a-e were placed in dry-ice to freeze for 1 hour. These frozen stocks where then lyophilized overnight to form a dry pullulan matrix containing furimazine.

Specific powdered furimazine samples for testing were prepared as follows:

1) 1 mM (50 nmols total) furimazine stocks prepared as powdered formulation with 0% pullulan 2) 1 mM (50 nmols total) furimazine stocks prepared as powdered formulation with 2.5% pullulan 3) 1 mM (50 nmols total) furimazine stocks prepared as powdered formulation with 5% pullulan 4) 1 mM (50 nmols total) furimazine stocks prepared as a N113 solution (Promega cat. #N113)

5) 1 mM (50 nmols total) furimazine stocks prepared as a N205 solution (Promega cat. #N205) (Note: the N205 solution was made— 15 hours after the N113 solution)

6) Bulk furimazine (50 nmols, aliquoted out from a stock solution in ethanol)

Figure 23A:
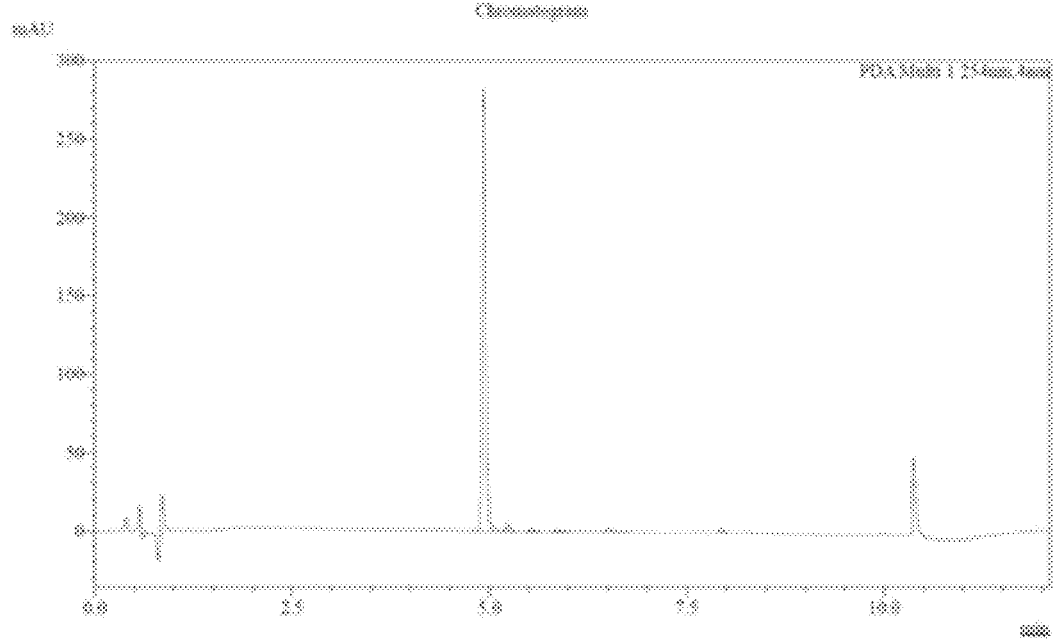
FIGS. 23A-B show HPLC traces for a representative pullulan-based lyophilized furimazine sample after storage for: A—0 hours, and B—48 hours at 60° C. as described in Example 12.
Figure 23B:
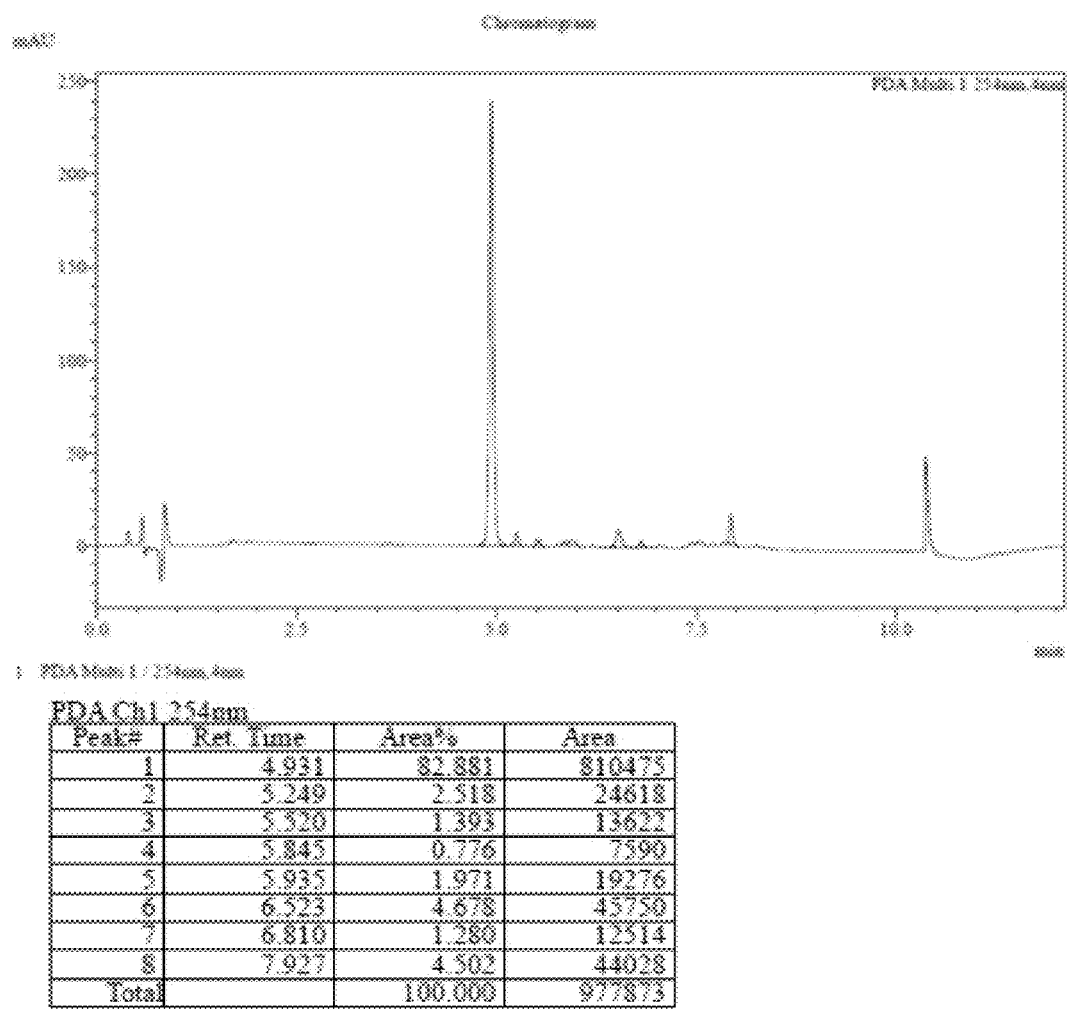
Figure 24A:
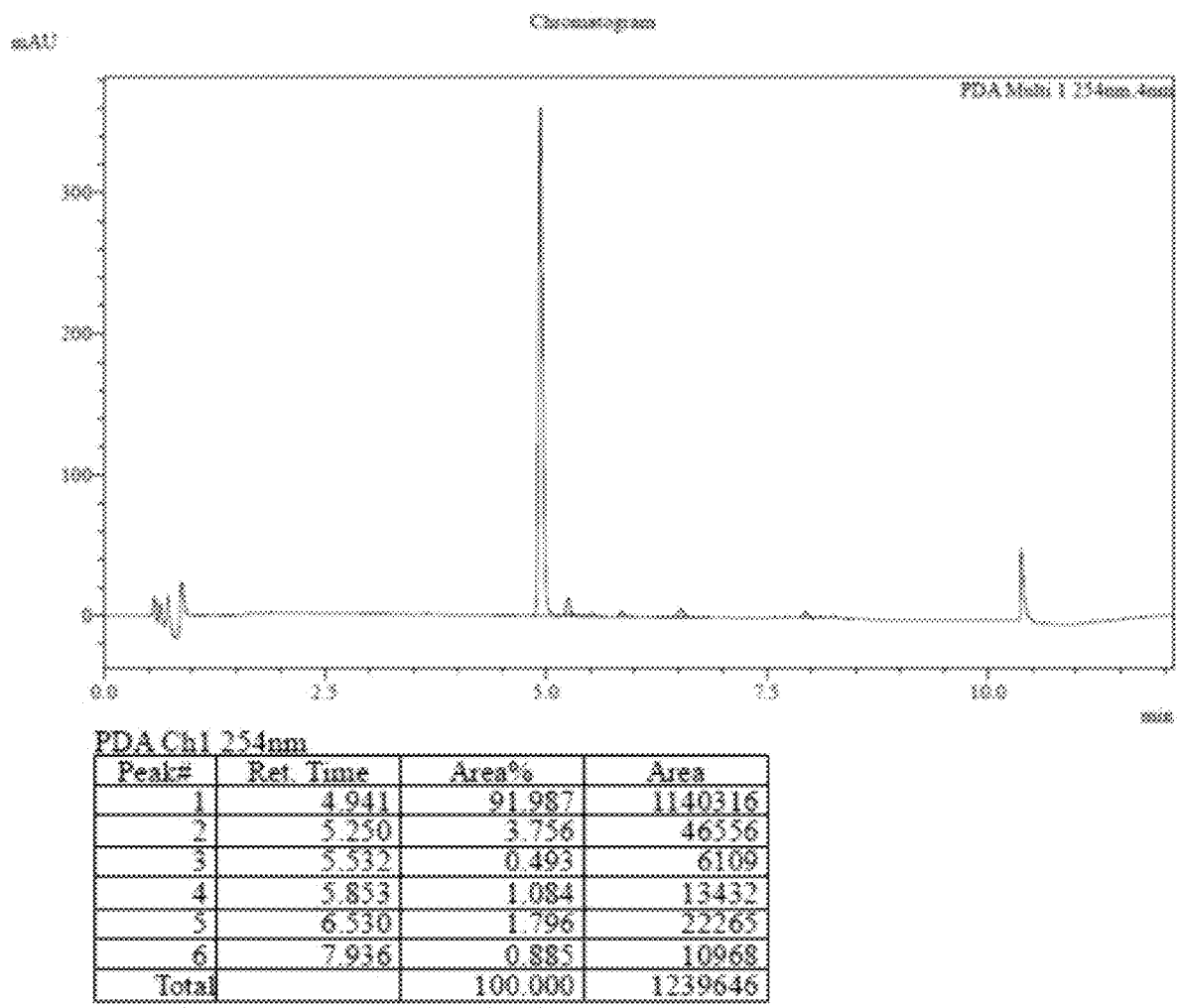
FIGS. 24A-B show HPLC traces for a commercial Nano-Glo® Luciferase Assay Substrate sample after storage (FIG. 24A for 0 hours and FIG. 24B for 48 hours at 60° C.) as described in Example 12.
Figure 24B:
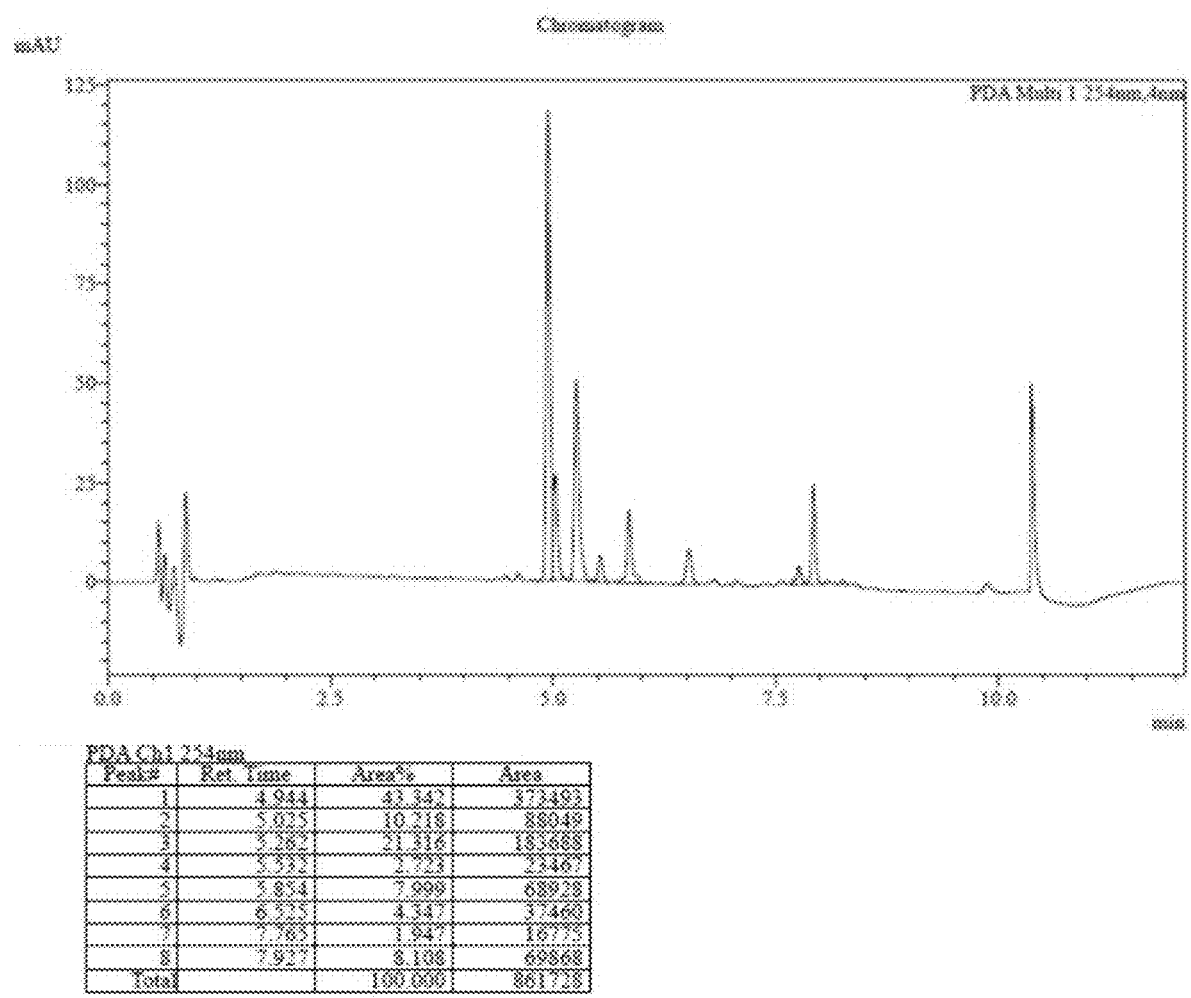

Prior to HPLC testing, half of the samples were stored at 25° C. and half were stored at 60° C. for extended periods of time prior to testing. For HPLC testing, formulated furimazine (19.08 μg) was diluted with 0.5 mL PBS buffer, pH 6.8 in small snap cap tubes. Tubes were vortexed for ~15 seconds and then allowed to equilibrate for 30 minutes at room temperature in the dark. 15 μL sample was injected neat on HPLC (vials without inserts), 0.1% TFA/Aq, acetonitrile, Synergi Max-RP 50×4.6 mm, 2.54u. HPLC traces for samples including 5% w/v pullulan at 0 hours (FIG. 23A) or after 48 hours of storage at 60° C. (FIG. 23B) show only minimal degradation. HPLC traces for the N113 sample at 0 hours (FIG. 24A) or after 48 hours of storage at 60° C. (FIG. 24B) show significantly more degradation.

HPLC data were obtained for other samples (not shown), and the data were processed to show the thermal stability traces in FIG. 25. Areas underneath the curves were measured and plotted over 35 days. "Bulk" refers to manufactured, solid furimazine. "0% pullulan" refers to furimazine that was dissolved into a stock solution of ethanol, added to water (without pullulan), and lyophilized. FIGS. 25A and 25B show thermal stability at 25° C. and 60° C. as raw peak areas while FIGS. 25C and 25D show thermal stability at 25° C. and 60° C. as percent peak areas. Formulations consisting solid furimazine showed a high level and consistent chemical integrity when stored at room temperature or at 60° C. In contrast, furimazine formulated in the Nano-Glo® Luciferase Assay Substrate (Promega cat. #N113) and Nano-Glo® Live Cell Substrate (Promega cat. #N205) solutions showed considerable loss of peak height and area over the measured time when stored at elevated temperatures.

For luminescent measurements, powder furimazine samples #1-5 were reconstituted in PBS while sample #6 was reconstituted in ethanol (500 μL for all). Samples equilibrated for 30 minutes at room temperature. The samples were then further diluted 1:5 (from 100 μM to 20 μM) and then 1:100 (from 20 μM to 0.2 μM). 50 μL of this solution was added to a well of a 96-well plate, background was read, and then NanoLuc® (Nluc) enzyme was added. (Prior to addition, stock commercial Nluc sample was diluted in PBS to a concentration of 2 ng/mL, and 50 μL was added to each well.) With the dilution, the final concentrations were 0.1 μM furimazine and 1 ng/mL Nluc. RLUs were then determined. (Background is the reading of the 2× substrate solution without the addition of Nluc.)

Complied RLU data are shown in FIG. 26. The numbers in each graph legend correspond to the following formulations: 1-0% pullulan (note—this sample experienced solubility problems and may not have fully reconstituted); 2-2.5% pullulan lyophilized cake formulation; 3-5% pullulan lyophilized cake formulation; 4—Nano-Glo® Luciferase Assay Substrate (Promega cat. #N113); 5—Nano-Glo® Live Cell Substrate (N205); 6—bulk furimazine (which was reconstituted in ethanol). Shown in FIGS. 26A-C are data after samples were stored at 60° C. for varying periods of time prior to reconstitution and testing, as described above, using 50 μM substrate (FIG. 26A), 10 μM substrate (FIG. 26B), or 0.1 μM substrate (FIG. 26C). Shown in FIGS. 26D-F are data after samples were stored at 25° C. for varying periods of time prior to reconstitution and testing as described above, using 50 μM substrate (FIG. 26D), 10 μM substrate (FIG. 26E), or 0.1 μM substrate (FIG. 26F).

FIG. 27 shows data for the percent enzyme activity. The numbers in each graph legend correspond to the following formulations: 1-0% pullulan (note—this sample experienced solubility problems and may not have fully reconstituted); 2-2.5% pullulan lyophilized cake formulation; 3-5% pullulan lyophilized cake formulation; 4—Nano-Glo® Luciferase Assay Substrate (Promega cat. #N113); 5—Nano-Glo® Live Cell Substrate (N205); 6—bulk furimazine (which was reconstituted in ethanol). FIGS. 27A-C show enzyme activity at time 0 after samples were stored at 60° C. for varying periods of time prior to reconstitution and testing, as described above, using 50 μM substrate (FIG. 27A), 10 μM substrate (FIG. 27B), or 0.1 μM substrate (FIG. 27C), and FIGS. 27D-F show enzyme activity at time 0 after samples were stored at 25° C. for varying periods of time prior to reconstitution and testing, as described above, using 50 μM substrate (FIG. 27D), 10 μM substrate (FIG. 27E), or 0.1 μM substrate (FIG. 27F).

Solid furimazine samples showed consistent chemical integrity as shown by RLU output in a luciferase assay after exposed to elevated temperatures. In contrast, furimazine formulated in the commercial N113 and N205 solutions showed loss of luminescent signal over time after being stored at elevated temperatures. (Note: sample 6 was dissolved in ethanol, which inhibits Nluc enzyme activity at the higher concentrations.)

Example 13

Formulated Furimazine Film-Coated Microtiter Plates

Figure 29:
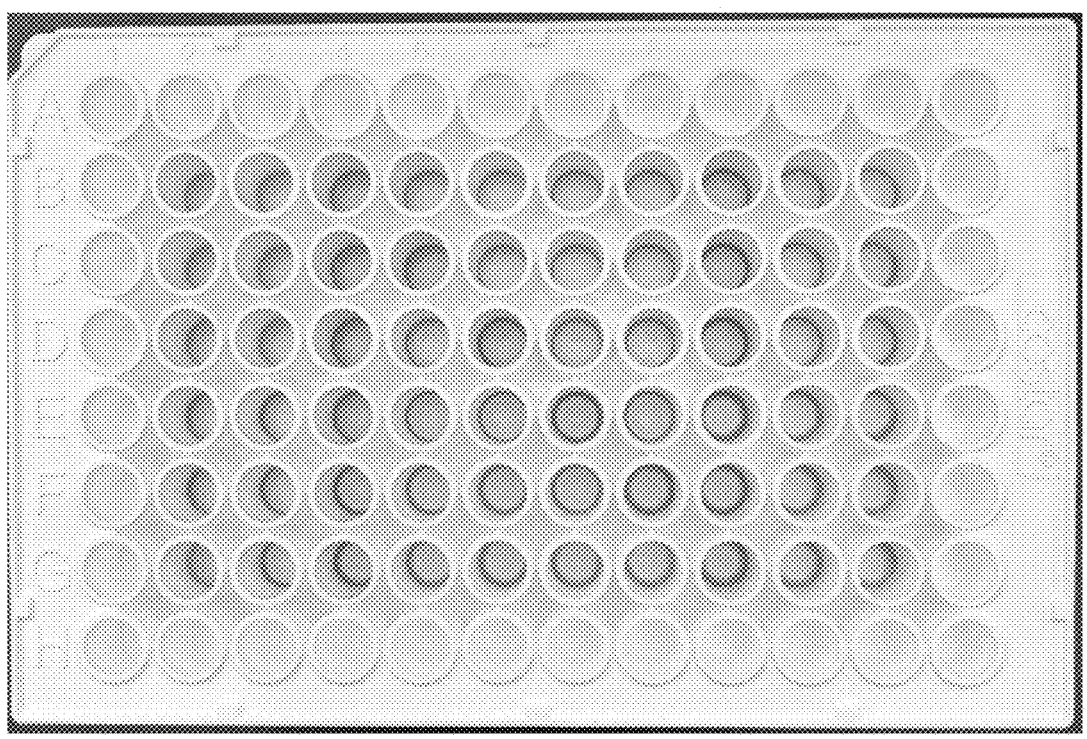
FIG. 29 shows representative example of pullulan-based film format containing furimazine coating the bottom of a standard 96-well microtiter plate within a pullulan film matrix as described in Example 13.

Formulated furimazine films were formed directly onto microtiter plates. A film containing 200 mM furimazine in either 2.5% (w/v) pullulan or 5% (w/v) pullulan were prepared directly in wells of a microtiter plate. A representative image of this format is seen in FIG. 29 (artificially colored for clarity and presentation purposes). Well coatings were prepared as follows: 2 mM furimazine stock in ethanol was prepared (solution 1). Separately, solutions of 2.5% and 5% w/v pullulan were prepared in water (solution 2 and solution 3 respectively). 45 μL of either solution 2 or solution 3 were added to individual wells of a standard 96-well plate. 5 μL of solution 1 was then added to each of the wells containing either solution 2 or solution 3 and pipetted thoroughly to mix. The concentration of ethanol in the final solution must be less than 5% v/v. Higher concentrations of ethanol will cause pullulan to crash out of solution.

Figure 28:
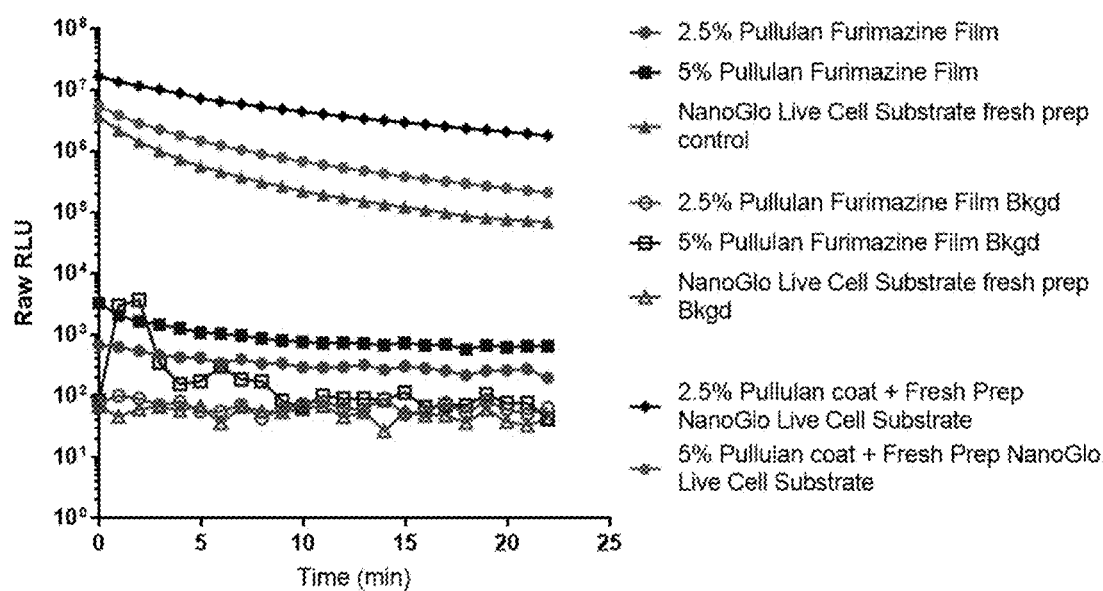
FIG. 28, Panels A-C show RLU data for formulated pullulan film coated 96-well microtiter plates containing furimazine substrate when tested with purified NanoLuc® enzyme as described in Example 13.

The plates were then allowed to dry in the dark under ambient conditions for 3 hours. Films in the wells were rehydrated with 100 μL PBS, pH 7.0, and 2 ng/mL Nluc was added to each well either right away or after a 30-minute pre-equilibration period in 50 μL/well of PBS on a shaker with a final concentration of 10 μM furimazine in the solution for all conditions. RLUs were read and were compared to freshly prepared commercial furimazine substrate (Nano-Glo® Live Cell Substrate, Promega cat. #N205). Data is shown in FIG. 28, with (a) showing data as raw RLU with no pre-equilibration, (b) showing data as activity with no pre-equilibration, and (c) showing data as raw RLU with pre-equilibration This example highlights that furimazine can be dried down in a pullulan-based film on a hard surface and be reconstituted at a designated time. Based on visual observation, the films also reconstituted more rapidly and more completely than the bulk solid furimazine. This data also shows that pre-equilibration of the furimazine-pullulan based films in PBS microtiter plates resulted in significantly decreased light output.

FIG. 29 shows an image of the furimazine filmed plates which were created using the same method as described above, but with the addition of food coloring to be able to visualize the film coating.

Figure 30A:
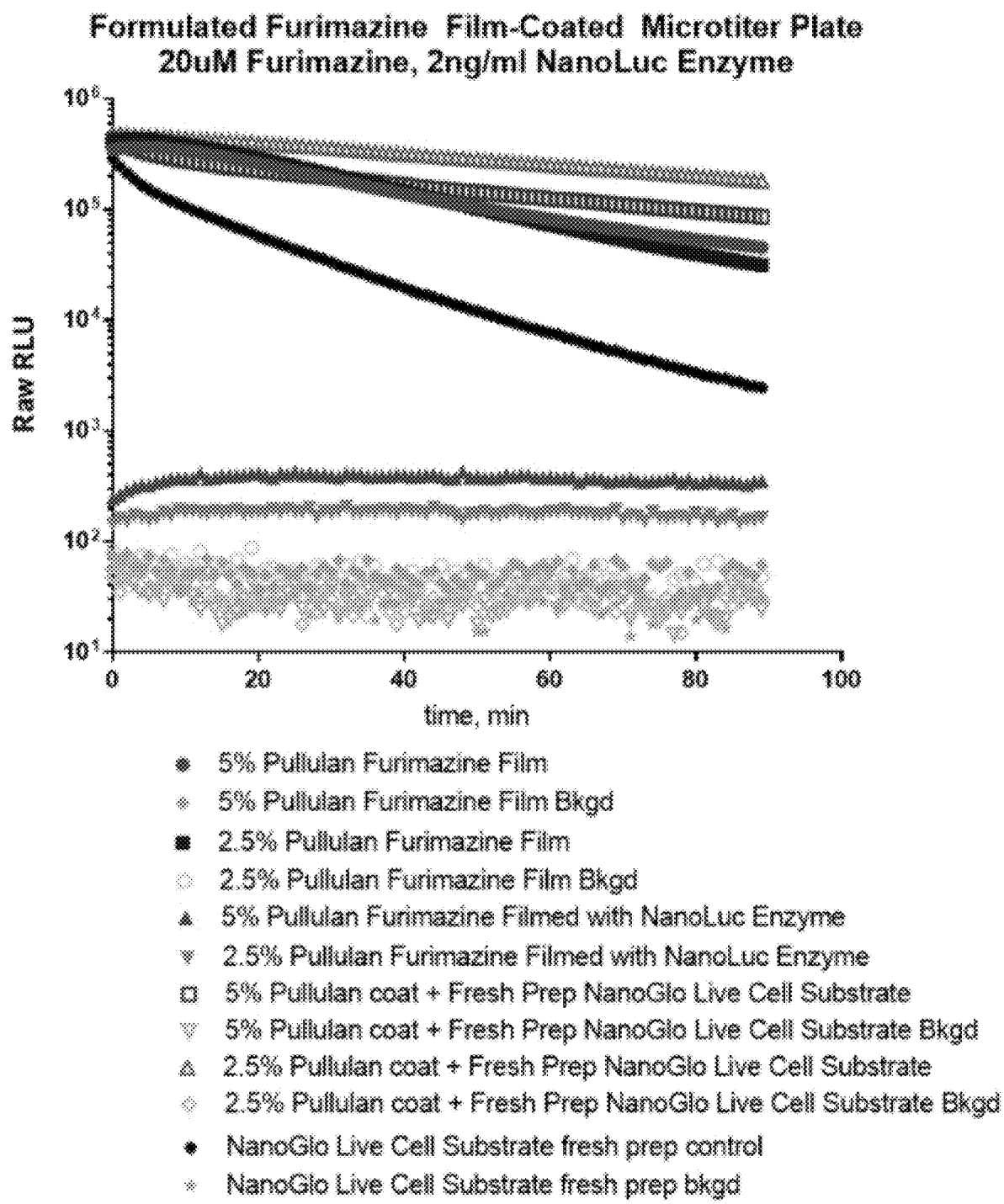
Figure 30B:
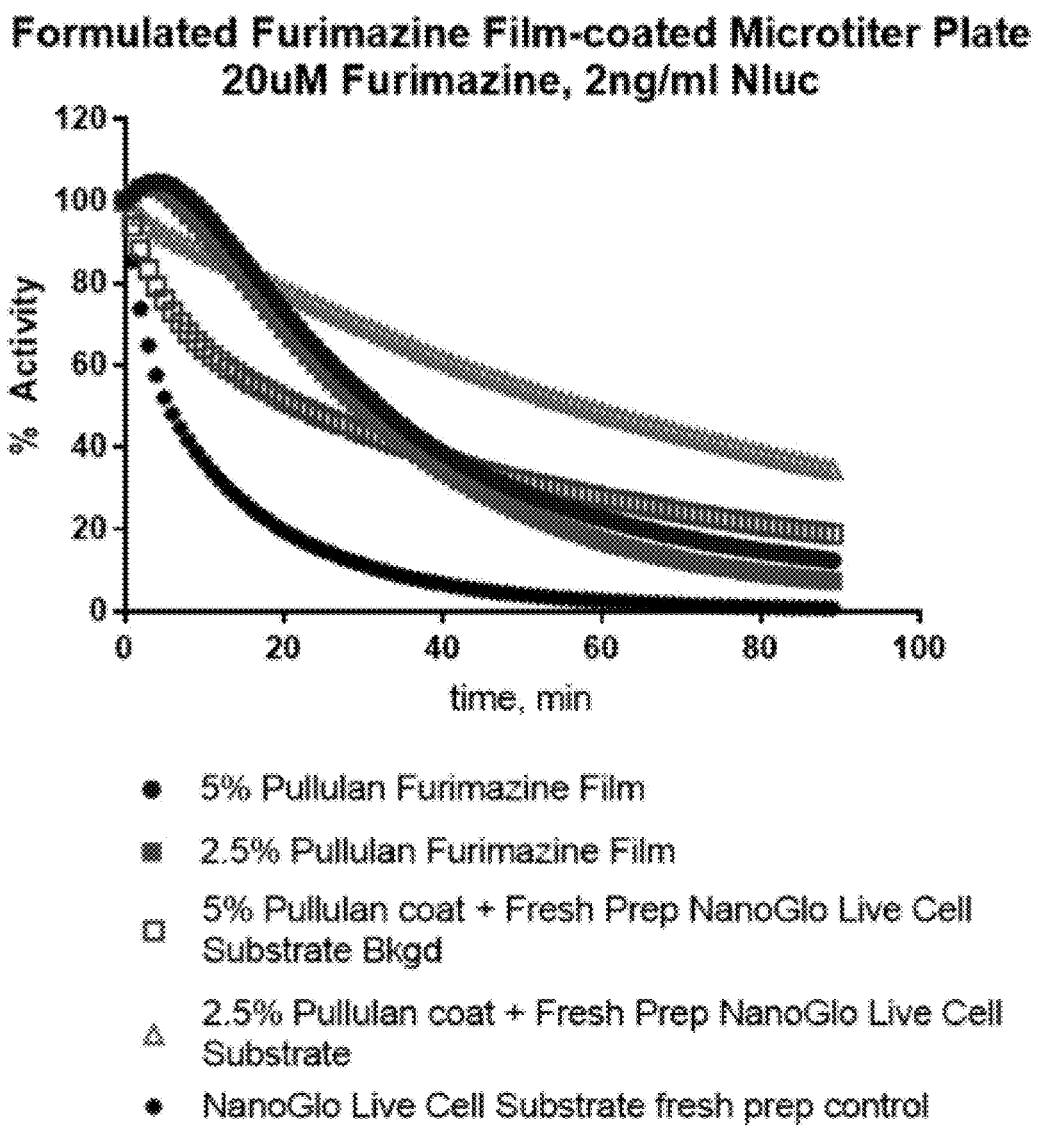

FIG. 30A shows a kinetic read of the same format preparation described for data presented in FIG. 28, but with a higher loading concentration of furimazine (20 μM in 100 μL final) and in some cases the furimazine formulation contained NanoLuc® enzyme that was filmed together as a complete solution. FIG. 30B shows the percent activity for the same experiment described in FIG. 30A. FIG. 30C shows the results of a stability study of the filmed microtiter plates after a period of storage, with about 35% activity remaining at day 10.

Example 14

HPLC and Mass Spectrometry Analysis on Purity, Stability and Byproducts Formation of Formulated Furimazines Formulated furimazine in lyophilized pullulan matrix were prepared as described in Example 12 with 19.07 μg of furimazine in 0%, 2.5%, and 5% w/v pullulan. Samples, including bulk furimazine, Nano-Glo® Luciferase Assay Substrate (Promega Cat #N113), and Nano-Glo® Live Cell Substrate (Promega Cat #N205), were stored at either 25° C. or 60° C. for 35 days. Samples were reconstituted in PBS buffer, or ethanol in the case of the bulk furimazine sample and the 0% pullulan sample, allowed to equilibrate for 30 minutes at room temperature, and then analyzed on HPLC for known byproducts of the furimazine degradation pathway. Absorbance data are shown in FIG. 31: A—bulk furimazine; B—0% pullulan; C—2.5% pullulan; D—5% pullulan; E—Nano-Glo® Luciferase Assay Substrate; and F—Nano-Glo® Live Cell Substrate. In every case, formulated furimazine in the solid form showed significantly less degradation products relative to the commercial solution-based storage formulations (Promega Cat #N113 and Cat #N205).

FIG. 32 shows the percent area of the individual byproducts relative to the furimazine peak: A—bulk furimazine; B—0% pullulan; C—2.5% pullulan; D—5% pullulan; E—Nano-Glo® Luciferase Assay Substrate; and F— Nano-Glo® Live Cell Substrate. In the solid pullulan formulations, furimazine is the major peak with a minimal amount of byproduct formation, especially when stored at room temperature (left bar for each condition). In contrast, after 35 days, there was an almost total loss of furimazine when stored in the commercial formulations when stored at either 25° C. (left bar) of 60° C. (right bar).

Example 15

Figure 33:
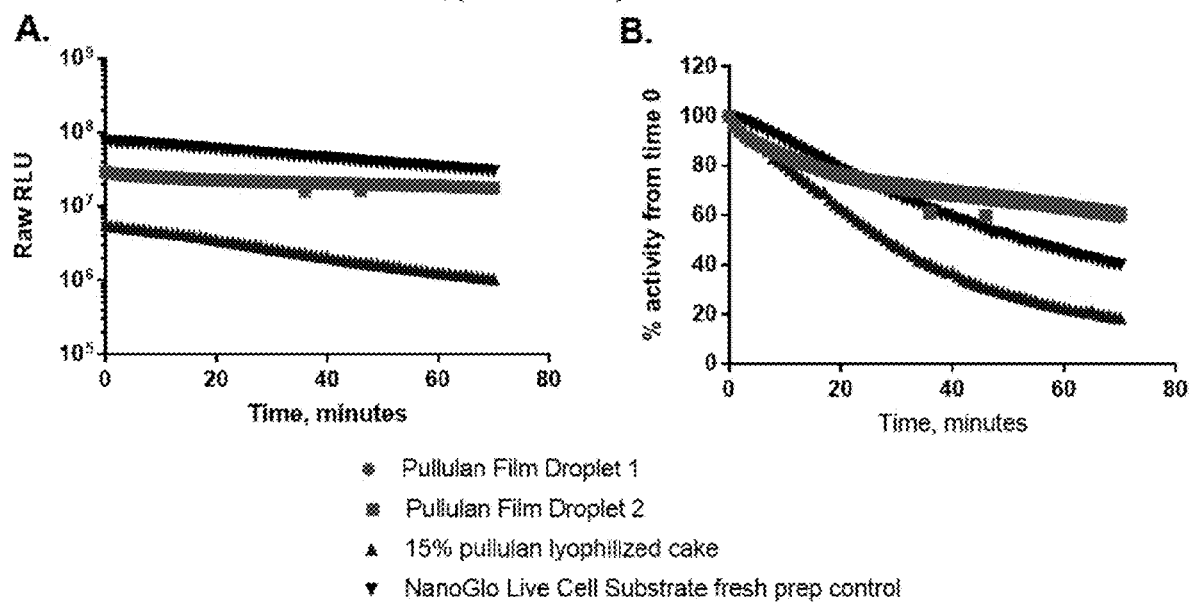
FIG. 33, Panels A-B show data for representative examples of pullulan-based formats that contain furimazine that were stored at room temperature for 6 months as described in Example 15.

Formulated Furimazine Compositions Substrate Activity at 6 Months Storage at Room Temperature 19 μg of furimazine was formulated either as a lyophilized cake or a film droplet were prepared in 15% w/v pullulan as described in Example 1, Conditions 1 and 3. The samples were stored at 25° C. in the presence of ambient light for six months. Both formulations were reconstituted with 100 μL PBS, pH 7.0 and 1 ng/mL NanoLuc (Nluc) for a final concentration of 10 μM furimazine in the solution. RLUs were read and were compared to freshly prepared commercial furimazine substrate (Nano-Glo® Live Cell Substrate, Promega cat. #N205). The results of this experiment are shown in FIG. 33 (A— raw RLU, B— percent activity from time 0). After 6 months stored at ambient temperature and light, the formulated solid furimazine in a pullulan matrix was still viable when exposed to luciferase.

Example 16

Formulated Furimazine Activity and Stability on Different Solid Support Matrices Four different paper types were tested for different properties including substrate retention and effects on substrate integrity. The paper types included:
1. Glass fiber thick: Glass Microfiber 934-AH (Ahlstrom, particle retention: 1.5 μM, thickness: 435 μm);
2. Glass fiber thin: Glass fiber diagnostic pad (EMD Millipore), GFDX103000, Lot #495362;
3. Cellulose: Cellulose Sample Pad (EMD Millipore), CFSP20300M Lot #11065; and
4. Whatman® 903 Protein saver card Each paper sample was cut to a 7×7 mm square. 10 mM stocks of furimazine were prepared, and 10 μL of this stock was added to each paper matrix. The samples were dried for 30 minutes at 35° C. The cards were stored at either 25° C. or 60° C., in the dark, for 72 hours. The samples were then placed into a glass vial, and 1 mL of ethanol added. The vials were sonicated for 10 seconds, and the solvent extracted, filtered, and analyzed by analytical HPLC. The results from these experiments are shown in FIG. 34. FIG. 34A shows the raw area of the furimazine peak after extraction from the paper or fiber matrix. The amount of furimazine extracted from the paper, and analyzed from solution, is also affected by paper type (FIG. 34B). For substrate that was extracted back into solution, the rate of furimazine degradation is slightly faster when furimazine is dried onto a paper or fiber matrix compared to bulk furimazine. In addition, the furimazine substrate can be effectively dried down and reconstituted from a variety of solid surfaces (FIG. 34C).

Additional experiments were conducted to determine substrate stability on paper in combination with the reporter protein, LgTrip. To prepare the paper surfaces, a vial containing 200 μL of 5 uM LgTrip (3546) (SEQ ID NO: 3; see, e.g., U.S. patent application No. 62/684,014, incorporated herein by reference in its entirety), 5 mM ATT, and 5 mM ascorbic acid was prepared. About 5 μL of this solution was added to each spot, and the spots were then allowed to dry at 35° C. for 1 hour. After drying, 1 mM stock of furimazine in ethanol was prepared. About 5 μL of this solution was added to each spot and allowed to dry at 35° C. for an additional 30 minutes.

Different materials were tested with substrate and LgTrip input. At the time of testing, fresh Nluc was added to isolate the substrate. FIG. 35A shows bioluminescent signal in three different solid phase materials (Whatman 903, Ahlstrom 237, and Ahlstrom 6613H) resulting from reconstitution of the surface when fresh NanoLuc was added to dried LgTrip and substrate. Alhstrom6613H seems to be detrimental to signal output over time. Overall, the stability of the assay components can be affected by the composition of the solid matrix materials in which they are imbedded.

FIG. 35B shows bioluminescent signal from Whatman 903 paper that contains both LgTrip as well as substrate and stored under ambient conditions for over 25 days. Spots were exposed to 1 nM dipeptide in PBS at the time of testing. Overall, this experiment shows that there is no significant loss of signal from the materials after extended storage times under ambient temperature.

Example 17

Effects of Additives on Formulated Furimazine Activity and Stability on Different Solid Support Matrices Different additives were combined in solution with furimazine and dried onto the paper surface. These experiments were aimed to improve overall substrate integrity while dried within the paper matrix. A 10 mM ascorbic acid solution was prepared in ethanol. This solution was then added to bulk furimazine to make a solution containing 1:1 ascorbic acid and furimazine in ethanol. 10 µL of this solution was then added to the same paper matrices described in the previous example. The samples dried for 30 minutes at 35° C. The cards were stored at either 25° C., or 60° C., in the dark, for 72 hours. The samples were placed into a glass vial, and 1 mL of ethanol was added. The vials were sonicated for 10 seconds and the solvent was extracted, filtered, and analyzed by analytical HPLC.

The results of these experiments are described in FIG. 36. The raw area of the furimazine peak is plotted in FIG. 36A, which shows better absorbance for furimazine than samples that did not contain the ascorbic acid additive. This effect was also observed in overall percent recovery of furimazine into solution (FIG. 36B), as well as furimazine purity (FIG. 36C). There was an ~15-20% increase in purity, suggesting that the presence of ascorbic acid helps limit the thermal or chemical degradation of the furimazine substrate when stored on paper.

Example 18

Effects of Chemical Pre-Treatment of Different Solid Support Matrices on Formulated Furimazine Activity and Stability Paper matrices (Ahlstrom Glass Microfiber 934-AH and Whatman® 903 Protein saver card) were soaked in a solution of 30% w/v citric acid for 30 minutes and then allowed to dry overnight at 35° C. 10 mM stocks of furimazine in EtOH were prepared, and 10 µL of stock was added to 7×7 mm paper cards and dried at 35° C. for 30 minutes. The cards were then stored at RT or 60° C., in the dark, for 72 hours. At the time of reading, the cards were extracted with 1 mL of ethanol and sonicated for 15 seconds. The extracted solvent was then filtered and injected on an analytical HPLC.

The results are shown in FIG. 37. The raw area of the furimazine peak is shown in FIG. 37A. Pretreatment of the paper matrix with 30% citric acid solution prior to applying furimazine substrate had a minimal impact on overall purity of the substrate after extraction into ethanol compared to the paper matrix that did not have the citric acid pretreatment (FIG. 37C). There was also limited improvement in the amount of substrate that was recovered into solution after extraction with ethanol (FIG. 37B).

Example 19

Effects of Mechanical Pre-Treatment of Different Solid Support Matrices on Formulated Furimazine Activity and Stability Paper matrices (Ahlstrom Glass Microfiber 934-AH and Whatman® 903 Protein saver cards) were soaked in water for 30 minutes and then dried under reduced pressure overnight in order to collapse or shrink the pores present within the paper matrix. 10 mM stocks of furimazine in ethanol were prepared, and 10 µL of the stock solution was added to 7×7 mm paper cards and dried at 35° C. for 30 minutes. The cards were then stored at RT or 60° C., in the dark, for 72 hours. At time of reading, the cards were extracted with 1 mL of ethanol and sonicated for 15 seconds. The extracted solution was filtered and injected on an analytical HPLC for analysis.

The results of this experiment are shown in FIG. 38 with the raw area of the furimazine peak shown in FIG. 38A, the percent recovery shown in FIG. 38B, and the purity shown in FIG. 38C. There is no significant improvement in terms of substrate purity, or recovery into solution, between substrate that was added and dried to paper that was previously dried under pressure versus non-pretreated paper.

Example 20

Effects of Additives on Formulated Furimazine Activity and Stability on Different Solid Support Matrices Different additives were combined in solution with furimazine and dried onto the paper surface. This series of experiments were aimed to help improve overall substrate integrity while dried within the solid matrix. A 10 mM citric acid solution was prepared in ethanol. This solution was added to bulk furimazine to make a solution containing 1:1 citric acid and furimazine in ethanol. 10 µL of this solution was then added to the same paper matrixes described in the previous example. The samples were dried for 30 minutes at 35° C. The cards were stored at either 25° C. or 60° C., in the dark, for 72 hours. The samples were placed into a glass vial, and 1 mL of ethanol was added. The vials were sonicated for 10 seconds, and the solvent was filtered and analyzed by analytical HPLC.

The results of these experiments are described in FIG. 39. The raw area of the furimazine peaks are plotted in FIGS. 39A and 39B, for furimazine that was dried in paper in the presence (A) and absence (B) of citric acid. The purity at 254 nm is plotted in FIGS. 39C and 39D for furimazine that was dried in paper in the presence (C) and absence (D) of citric acid. The plots show better absorbance for furimazine when dried in a mixture with citric acid. This increase in absorbance corresponds to ~10-20% increase in purity, suggesting that the presence of citric acid helps limit the thermal chemical degradation of the furimazine substrate over the course of this experiment.

Example 21

Effects of Citric Acid and Ascorbic Acid on Formulated Furimazine Activity and Stability in the Presence of Sucrose Protein Loading Buffer The effects citric acid and ascorbate acid on furimazine activity and stability were tested in the presence or absence of sucrose protein buffer (20 mM $Na_3PO_4$, 5% w/v BSA, 0.25% v/v Tween20, 10% w/v sucrose). Spots were prepared from Whatman® 903 protein saver cards, as described above. Each spot was pretreated with either sucrose protein buffer or water and allowed to dry at 35° C. for 1 hour. 200 µM stock of furimazine was prepared in ethanol or in an ethanoic solution with either 200 µM citric acid or 200 µM ascorbate. 5 µL of furimazine or furimazine solution containing citric acid or ascorbic acid in an equal molar concentration, was added to each spot. The spots where then dried again at 35° C. for 1 hour. These spots were then stored at 25° C., in the dark, for up to 12 days.

Figure 40:
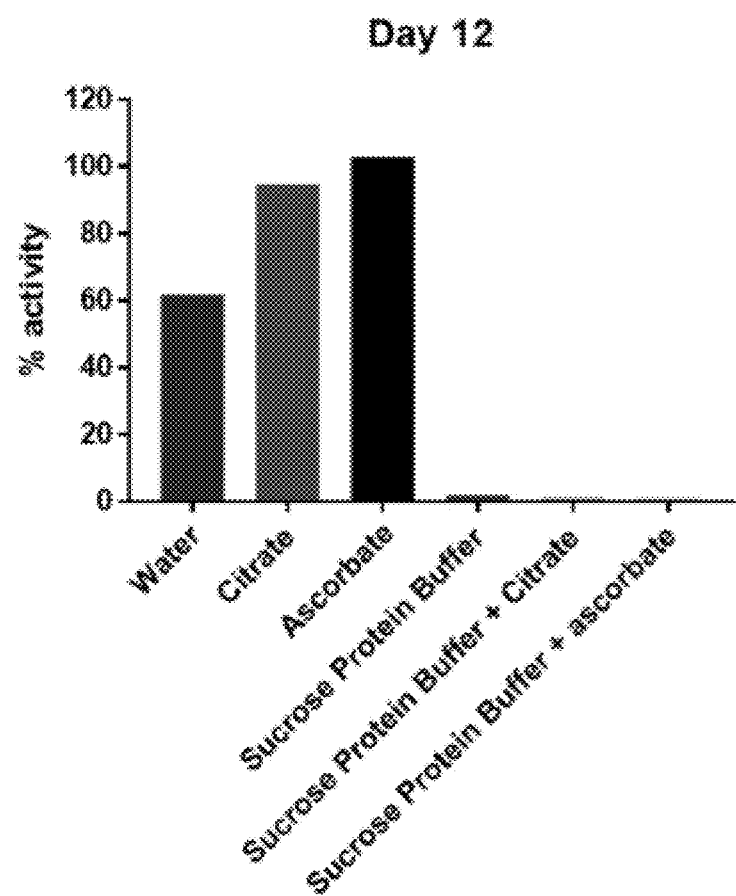
FIG. 40, Panels A-C show representative examples of max RLU (top) and % activity of formulated furimazine samples in (bottom) of Whatman® 903 paper spots created from hole punching Whatman® 903 protein saver cards and prepared using different drying methods that were treated with furimazine in a 1:1 molar ratio with either citrate or ascorbate, as described in Example 21, in the presence or absence of protein buffer.

At time of testing, a spot corresponding to each condition was placed into a well of a standard 96-well plate, and was rehydrated with 100 µL PBS solution, pH 7.0, and 2 ng/mL Nluc in each well for a final concentration of 10 µM furimazine in the solution. RLUs were read and were compared to freshly prepared commercial furimazine substrate (Nano-Glo® Live Cell Substrate, Promega cat. #N205). The results of these experiments are shown in FIG. 40.

In the paper spots pretreated with sucrose protein buffer showed considerable loss of signal over a period of 12 days (FIG. 40A). These results correspond to an almost complete loss of percent activity of the substrate compared to the conditions that were pretreated with water, or water in the presence of ascorbic acid or citric acid, which showed considerable stability and signal output over 12 days (FIG. 40B). A summary of these results is shown in FIG. 40C. Ascorbic acid and citric acid may help maintain substrate integrity when dried and stored on a paper surface, especially compared to a water pretreatment alone. However, one or more components within the sucrose protein buffer may have negative effects on substrate viability for long-term storage and reconstitution.

Example 22

Storage of Spots, in Isolation or in Bulk, on Furimazine Activity and Stability

The effects of specific storage procedures were tested on paper spots prepared from Whatman® 903 protein saver cards, as described above. Each spot was pretreated with water and then dried at 35° C. for 1 hour. 200 µM stock of furimazine was prepared in ethanol and 5 µL of this solution was added to each spot. The spots were then dried at 35° C. for an additional 30-60 minutes. The spots were then separated and stored individually in capped tubes, or together in one vial (bulk storage), at 25° C. in the dark, for up to 12 days. At time of testing, a spot corresponding to each condition was placed into a well of a standard 96-well plate, and was rehydrated with 100 µL PBS solution, pH 7.0, and 2 ng/mL Nluc in each well for a final concentration of 10 µM furimazine in the solution. Results of these experiments are described in FIG. 40.

The spots that were stored individually showed higher max RLU than spots that were stored in bulk (FIG. 41A). These results are consistent with observed percent activity (FIG. 41B). These results suggest that the method of storage can also have an effect on overall substrate performance. Storage in individual containers may help limit environmental exposure to detrimental factors such as light, air, and moisture compared to spots stored in bulk, which are exposed to these environmental factors each time a spot was taken out to be tested.

Example 23

Signal Generation after Removal of Spot from the Reaction Well

Spots were prepared from Whatman® 903 protein saver cards as described in Example 6. Each spot was pretreated with either sucrose protein buffer (20 mM $Na_3PO_4$, 5% w/v BSA, 0.25% v/v Tween20, 10% w/v sucrose) or with water, and allowed to dry at 35° C. for 1 hour. 200 µM stock of furimazine was prepared in ethanol or in an ethanoic solution with either 200 µM citrate or 200 µM ascorbate. 5 µL of furimazine or furimazine solution containing an equal molar ratio of citrate or ascorbate was added to the spots. The spots were then dried at 35 C for an additional hour. The spots were then stored at 25° C., in the dark, for up to 5 days.

Figure 42:
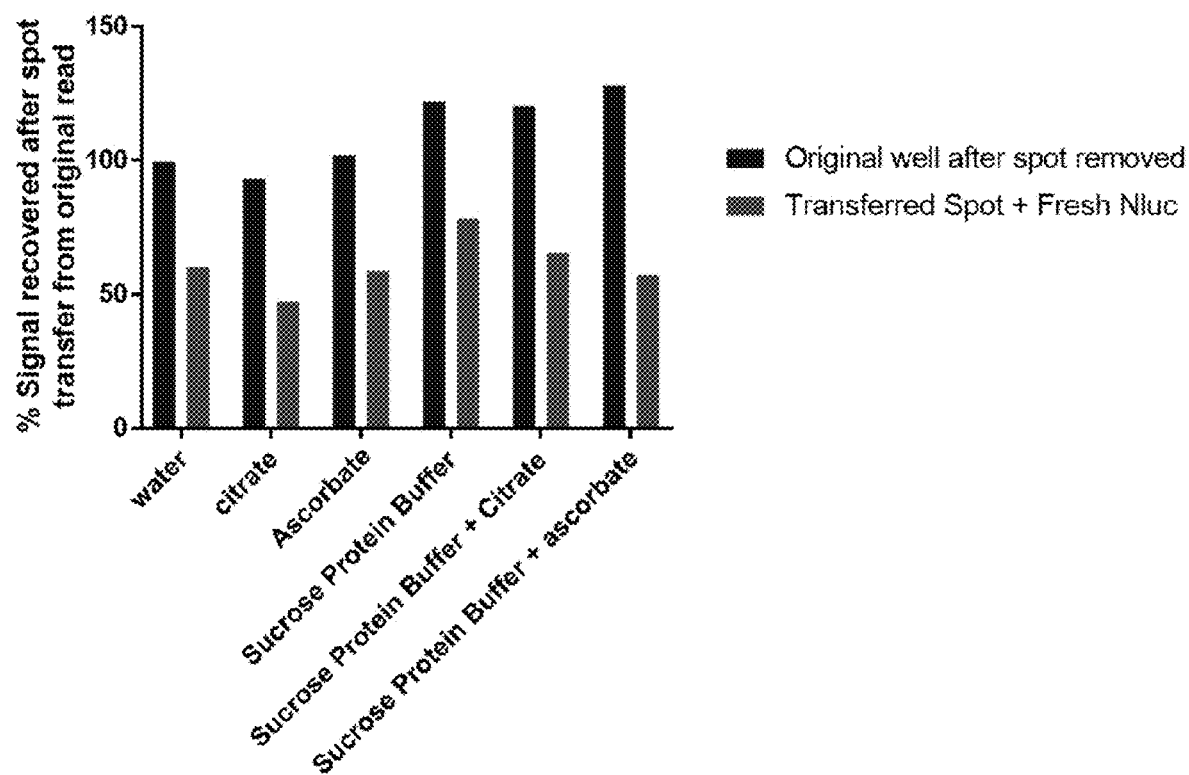
FIG. 42, Panels A-C show data demonstrating RLU output and % signal recovery of formulated furimazine samples in paper spots created from hole punching Whatman® 903 protein saver cards before and after removal of the spot from the original well to determine if substrate is released from the solid matrix support as described in Example 23.

At time of testing, the spots were reconstituted with PBS, pH 7.0, containing 2 ng/mL Nluc enzyme, and RLUs were read kinetically. After 45 minutes, the spot was physically removed from the well and placed into a new well containing fresh PBS solution, pH 7.0 and 2 ng/mL Nluc, and the kinetic RLU signal continued to be read on the wells that previously contained the spot and the new wells containing the transferred paper spot. FIG. 42A displays kinetic RLU values of the wells that had previously contained the spot and the new wells in which the spots were transferred to (indicated by the +after the substrate formulation). Summary RLU results are displayed in FIG. 42B comparing the RLU results from the original read RLUs at 45 minutes, the now empty well immediately following removal, and the RLU value taken immediately after transfer of the spot to a new well containing fresh enzyme. There was no change in RLU value from the original spot read to the well in which the spot was removed from indicating that substrate is released from the paper matrix and equilibrates into the surrounding solution. A lower signal is recovered in the well containing the transferred spot indicating some retainment of substrate formulation within the paper matrix itself. Percent signal recovery was calculated for each condition by comparing to the RLU signal that was present prior to the transfer of the spot out of the well to the signal remaining after the spot was removed or placed into a new well (FIG. 42C). After transfer of the spot to a new well containing fresh PBS solution, pH 7.0 and 2 ng/mL Nluc, about half of the percent signal was observed in the new well. This indicates that residual substrate remained in the paper itself, while most of the substrate was released into solution of the original well.

Example 24

Effects of BSA and Saccharide on Furimazine Activity and Stability 10 different versions of the protein-loading buffer were prepared in order to determine if the BSA and saccharide component had an effect on furimazine activity and stability after being dried down on a solid surface and reconstituted. The buffers that were prepared and tested are as follows:
1. Protein buffer 1: 20 mM $Na_3PO_4$, 5% w/v BSA, 0.25% v/v Tween20, 10% w/v sucrose
2. Protein buffer 2: 20 mM $Na_3PO_4$, 5% w/v BSA, 0.25% v/v Tween20, 10% w/v sucrose, 5 mM ascorbate
3. Protein buffer 3: 20 mM $Na_3PO_4$, 0.25% v/v Tween20, 10% w/v sucrose
4. Protein buffer 4: 20 mM $Na_3PO_4$, 0.25% v/v Tween20, 10% w/v sucrose, 5 mM ascorbate 5. Protein buffer 5: 20 mM $Na_3PO_4$, 5% w/v BSA, 0.25% v/v Tween20
6. Protein buffer 6: 20 mM $Na_3PO_4$, 5% w/v BSA, 0.25% v/v Tween20, 5 mM ascorbate
7. Protein buffer 7: 20 mM $Na_3PO_4$, 5% w/v BSA, 0.25% v/v Tween20, 2.5% pullulan
8. Protein buffer 8: 20 mM $Na_3PO_4$, 5% w/v BSA, 0.25% v/v Tween20, 2.5% pullulan, 5 mM ascorbate
9. Protein buffer 9: 20 mM $Na_3PO_4$, 0.25% v/v Tween20, 2.5% pullulan
10. Protein buffer 10: 20 mM $Na_3PO_4$, 0.25% v/v Tween20, 2.5% pullulan, 5 mM ascorbate The pH of each buffer was determined and are listed in Table 2.

TABLE 2

| Buffer | pH |
|---|---|
| 1 | 9.93 |
| 2 | 9.04 |
| 3 | 11.11 |
| 4 | 10.53 |
| 5 | 11.69 |
| 6 | 9.00 |
| 7 | 9.89 |
| 8 | 9.00 |
| 9 | 11.45 |
| 10 | 10.45 |

Spots were prepared from Whatman® 903 protein saver cards as described in Example 6. Each spot was treated with either buffer 1-10 and then dried at 35° C. for 1 hour. 200 µM stock of furimazine was prepared in ethanol, and 5 µL of this solution was added to each spot. The spots were then dried at 35° C. for an additional hour. At time of testing, a spot corresponding to each condition was placed into a well of a standard 96-well plate, and was rehydrated with 100 µL PBS solution, pH 7.0, and 2 ng/mL Nluc in each well for a final concentration of 10 µM furimazine in the solution. RLUs were read and were compared to freshly prepared commercial furimazine substrate (Nano-Glo® Live Cell Substrate, Promega cat. #N205).

Figure 43:
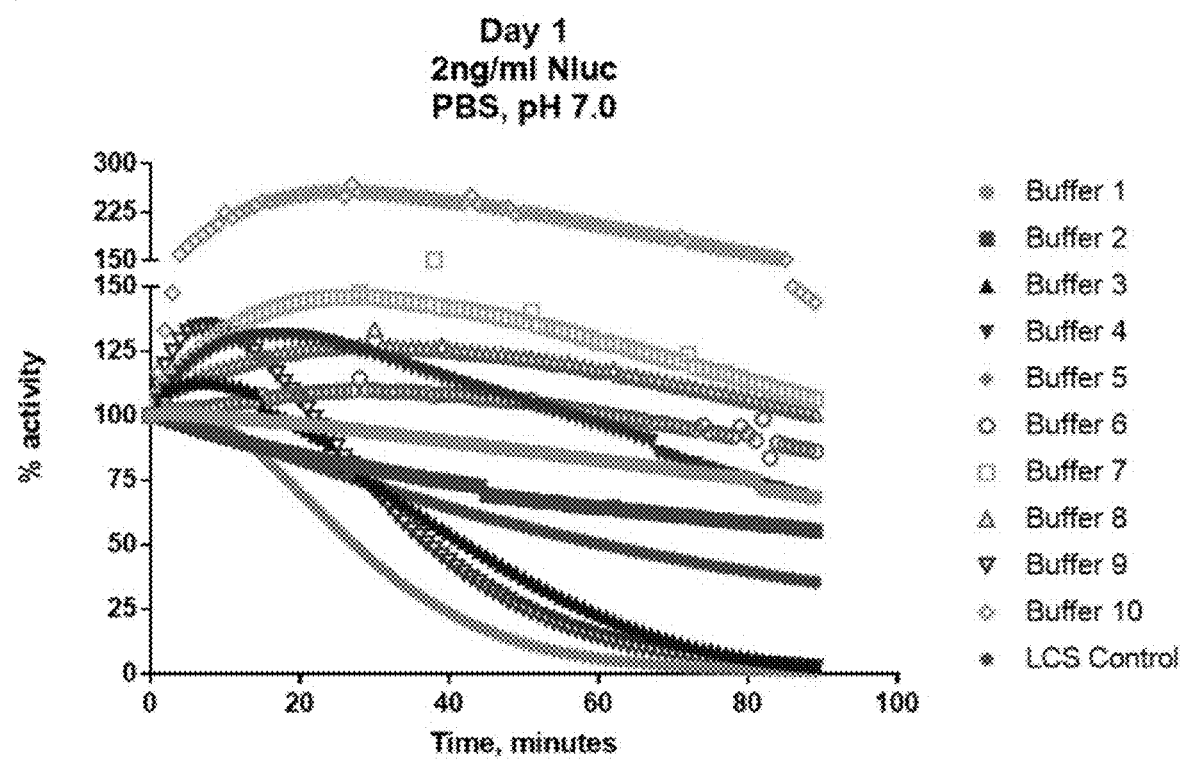
FIG. 43, Panels A-C show data demonstrating RLU output and % activity of various formulated furimazine solutions that contain different saccharide or polymer components as well as the presence or absence of ascorbate at varying pH in paper spots created from hole punching Whatman® 903 protein saver cards as described in Example 24.

These results are described in FIG. 43. By removing BSA, there was a small decrease in signal, which was returned in the presence of ascorbate (buffer 3 and buffer 4, FIG. 43A). A significant decrease in signal, however, was observed when the sucrose component was removed (buffer 5 and buffer 6). This signal was not returned in the presence of ascorbate, or if the sucrose component was replaced with 2.5% w/v pullulan (buffer 7 and buffer 8). The lowest signal was observed when neither BSA nor sucrose was present in the loading buffer.

Kinetic results are shown in FIG. 43B. In the conditions that lacked either sucrose, BSA, or both, there was a sharp decline in signal over the course of the experiment, which was not observed in the other conditions. The presence of ascorbate limited the rate of signal decay in these conditions (buffer 3 vs buffer 4, buffer 5 vs. buffer 6, or buffer 9 vs buffer 10). These differences correspond to a distinct change in percent activity (FIG. 43C). Buffers 3, 5, and 9 faired the worse in the solution kinetic RLU reads. These buffers also had the highest pH values (Table 2) indicating that pH could also play a role in substrate performance on Whatman® 903 papers.

Example 25

Effects of Individual Buffer Components on Furimazine Activity and Stability

Eight different protein-loading buffers were prepared in order to determine if specific buffer components had an effect on Furimazine activity and stability while being stored on a solid paper surface. The buffers that were prepared and tested are as follows:
1. Buffer 1: Water
2. Buffer 2: Water+5 mM ascorbate
3. Buffer 3: BSA
4. Buffer 4: BSA+5 mM ascorbate
5. Buffer 5: $Na_3PO_4$+Tween 20
6. Buffer 6: $Na_3PO_4$+Tween 20+5 mM ascorbate
7. Buffer 7: BSA+$Na_3PO_4$+Tween 20
8. Buffer 8: BSA+$Na_3PO_4$+Tween 20+5 mM ascorbate The pH of all the buffers was fixed at 7 prior to being added to the paper spots.

Spots were prepared from Whatman® 903 protein saver cards as described in Example 6. Each spot was treated with either buffer 1-8 and then dried at 35° C. for 1 hour. 200 µM stock of furimazine was prepared in ethanol, and 5 µL of this solution was added to each spot. The spots were then dried at 35° C. for an additional hour. At time of testing, a spot corresponding to each condition was placed into a separate well of a standard 96-well plate, and was rehydrated with 100 µL PBS solution, pH 7.0 and 2 ng/mL Nluc in each well for a final concentration of 10 µM furimazine in the solution. RLUs were read and were compared to freshly prepared commercial furimazine substrate (Nano-Glo® Live Cell Substrate, Promega cat. #N205).

Figure 44:
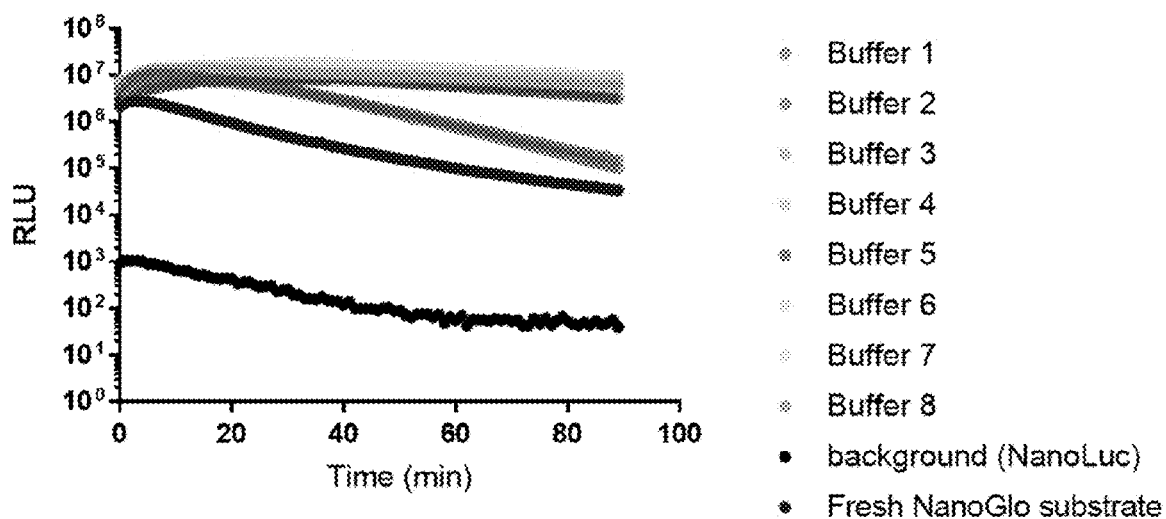
FIG. 44, Panels A-C show data demonstrating RLU output and % activity of various formulated furimazine solution components at a fixed pH=7.0 in paper spots created from hole punching Whatman® 903 protein saver cards as described in Example 25.

These results are shown in FIG. 44. Spots that were pretreated with buffers that contained either ascorbate, BSA, or a combination of the two, showed good stability over 8 days while being stored at 25° C. in the dark (FIG. 44A). Conditions that lacked either BSA or ascorbate and contained Tween 20 with a high level of salt showed a considerable loss of raw signal. There was also a noticeable loss of percent activity over the first few days (FIG. 44B). These results suggest that the presence of Tween 20 and/or high salt may have a negative effect on substrate integrity while being dried and stored on solid surfaces as seen by decrease in overall RLU output. The presence of ascorbic acid helps counteract this effect. A representative kinetic trace from day 0 is shown in FIG. 44C. The rate of signal loss is greater in conditions that lack components of the protein buffer (Buffer 1 or Buffer 2).

Example 26

Effects of Prionex on Furimazine Activity and Stability

Six different protein-loading buffers were prepared in order to determine if replacing BSA with Prionex had an effect on Furimazine activity and stability while stored on a solid surface. The buffers tested are as follows:
1. Buffer 1: Water
2. Buffer 2: Water+5 mM ascorbate
3. Buffer 3: 1% v/v Prionex
4. Buffer 4: 1% v/v Prionex+5 mM ascorbate 5. Buffer 5: 0.5% v/v Prionex
6. Buffer 6: 0.5% v/v Prionex+5 mM ascorbate The pH of each buffer was maintained at pH 7.

Spots were prepared from Whatman® 903 protein saver cards as described in Example 6. Each buffer was treated with either buffer 1-6 and then dried at 35° C. for 1 hour. 200 µM stock of furimazine was prepared in ethanol, and 5 µL of this solution was added to each spot. The spots were then dried at 35° C. for an additional 30 minutes. The spots were then stored at 25° C., in the dark for up to 20 days. At time of testing, a spot corresponding to each condition was placed into a separate well of a standard 96-well plate, and was rehydrated with 100 µL PBS solution, pH 7.0 and 2 ng/mL Nluc in each well for a final concentration of 10 µM furimazine in the solution. RLUs were read and compared to freshly prepared commercial furimazine substrate (Nano-Glo® Live Cell Substrate, Promega cat. #N205). The results are described in FIG. 44.

In all cases, a high level of RLU output was observed over the course of the experiment. Only the condition that was pretreated with water showed some signal loss over three weeks (FIG. 45A). Kinetic data from the first day of testing is shown in FIG. 45B. The presence of Prionex helps stabilize signal once reconstituted, and limit signal decay as compared to conditions that lack Prionex.

Example 27

Effects of ATT on Formulated Furimazine Activity and Stability

Six different protein-loading buffers were prepared in order to determine if the presence of ATT had an effect on furimazine activity and stability while stored on solid paper surfaces. The loading buffers that were prepared and tested are as follows:
1. Water+5 mM ascorbate
2. Water+5 mM ascorbate+5 mM ATT
3. 1% Prionex+5 mM ascorbate
4. 1% Prionex+5 mM ascorbate+5 mM ATT
5. 0.5% Prionex+5 mM ascorbate
6. 0.5% Prionex+5 mM ascorbate+5 mM ATT The pH of each buffer was controlled to pH 7.

Spots were prepared from Whatman® 903 protein saver cards as described in Example 6. Each buffer was treated with either buffer 1-6 and then dried at 35° C. for 1 hour. 200 µM stock of furimazine was prepared in ethanol, and 5 µL of this solution was added to each spot. The spots were then dried at 35° C. for an additional hour. The spots were then stored at 25° C., in the dark for up to 23 days. At time of testing, a spot corresponding to each condition was placed into a separate well of a standard 96-well plate and rehydrated with 100 µL PBS solution, pH 7.0, and 2 ng/mL Nluc in each well for a final concentration of 10 µM furimazine in the solution. RLUs were read and compared to freshly prepared commercial furimazine substrate (Nano-Glo® Live Cell Substrate, Promega cat. #N205). The results are described in FIG. 45.

In all cases, a high RLU output was observed (FIG. 46A). A kinetic trace from spots after 22 days of storage also shows a high and stable signal over the course of the experiment (FIG. 46B). All of the present conditions are favorable for substrate activity and storage stability on solid surfaces under ambient temperature.

Example 28

Formulated Furimazine Lyophilized Directed into Microtiter Plates

Furimazine was prepared and directly lyophilized within a microtiter plate well. Preparation resulted in wells containing lyophilized powdered formulations of 200 µM or 2 mM furimazine in 5% (w/v) pullulan were prepared directly in the wells of a standard 96-well microtiter plate (Costar cat #3912). A representative image of this format is shown in FIG. 47A. Plates were prepared as follows: 2 mM and 200 µM furimazine stocks in ethanol were prepared (solution 1). Separately, a solution of 5% w/v pullulan was prepared in water (solution 2). 45 µL of solution 2 was added to individual wells. 5 µL of solution 1 was then added to each of the wells containing solution 2, and pipetted thoroughly to mix. 5 µL of pure ethanol was added to solution 2 as a negative control. The plates were placed on dry ice to freeze for 1 hour, and then lyophilized overnight.

Plates containing furimazine cake were rehydrated with 100 µL PBS, pH 7.0, and 2 ng/mL Nluc in each well for a final concentration of 10 µM or 100 µM furimazine respectively. RLUs were read and were compared to freshly prepared commercial furimazine substrate (Nano-Glo® Live Cell Substrate, Promega cat. #N205) or fresh Nano-Glo® Live Cell Substrate in the presence of 5% w/v pullulan. Kinetic data is shown in FIG. 47B. This example shows that the lyophilized powder formulation format can be prepared directly on a solid-surface such as a microtiter plate and reconstituted using aqueous buffer such as PBS.

Example 29

Layering Format for Substrate Addition

Figure 48:
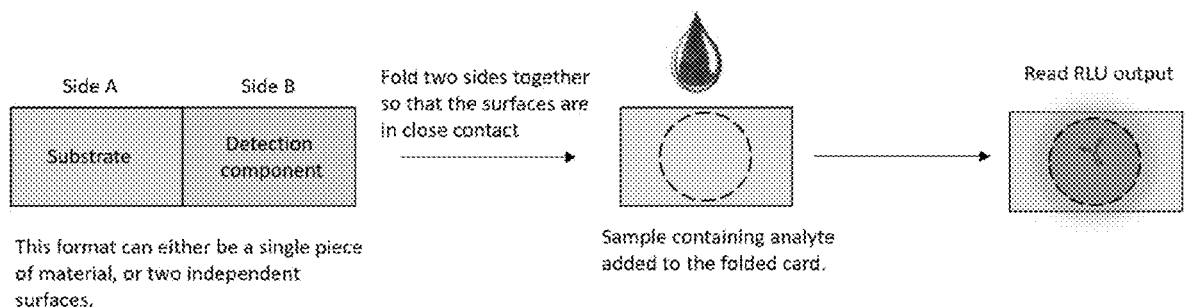
FIG. 48 shows a prophetic drawing of the assembly of an example layering assay format in which furimazine formulations are placed in one layer of a multi-layered device as described in Example 29.

FIG. 48 shows a prophetic example of a two-part layering system that includes separate surface components on individual paper cards, or separately treated components of the same surface, which contain either substrate or detection components, respectively. At time of use, the two sides of the surface are folded together so that each surface is held in close contact with each other. Sample solution containing the analyte of interest is then added to the folded surface material. The presence of the solution will cause the different components to rehydrate and mix within the solid matrix, leading to complementary induced formation of the bioluminescent complex. This process, in combination with the substrate, will produce light that can then be detected and analyzed.

Example 30

Effects of Sodium Ascorbate on Substrate Formulations

One volume of Nano-Glo® Luciferase Assay Substrate (Promega Cat. #N113) was combined with 50 volumes of Nano-Glo® Luciferase Assay Buffer (Promega Cat. #N112) containing sodium ascorbate at concentrations ranging from 0 to 300 mM. The solutions were incubated at 37° C. prior to assay at several time points. Nano-Glo® Luciferase Assay Substrate used according to manufacturer's instructions (stored at −20° C. during the course of the experiment and reconstituted for each time point) was used as a positive control. A cell culture expressing NanoLuc® enzyme was used as a sample for each time point. One volume of reconstituted Nano-Glo® Luciferase Assay Buffer was mixed with one volume of sample. After 3 minutes, the luminescence intensity was measured with a Bio-Tek Synergy® H1 96-well plate reader. For each sample, the luminescence intensity was background subtracted and normalized to the −20° C. control signal.

Figure 49:
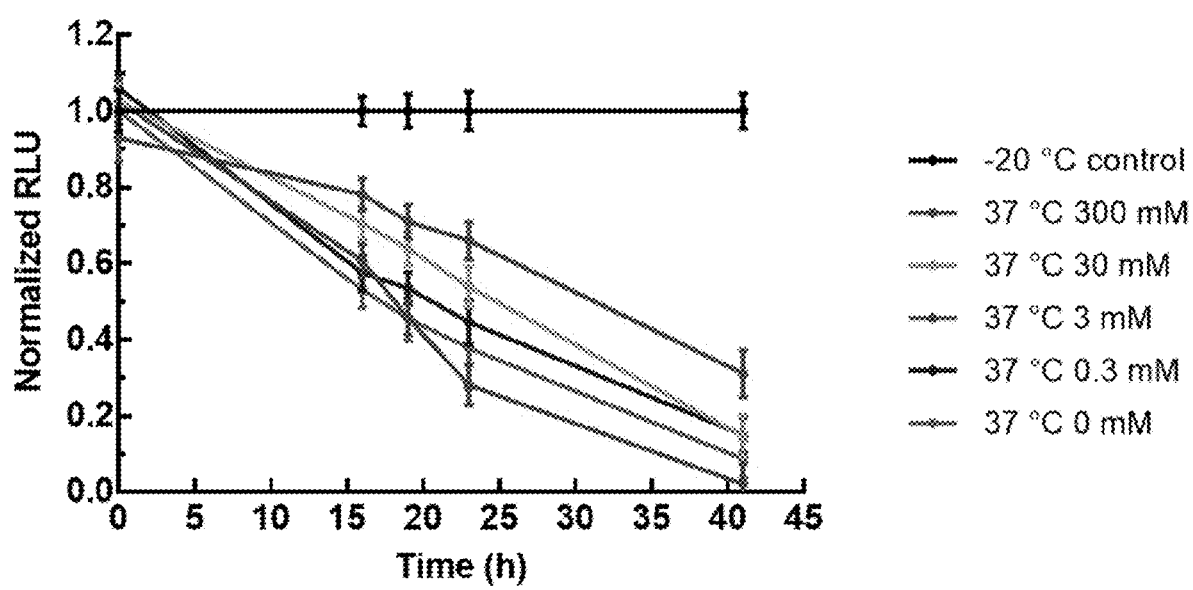
FIG. 49 shows data demonstrating RLU output of Nano-Glo® substrate (Promega Cat #N113) formulations containing sodium ascorbate at 37° C. as described in Example 30.

The addition of sodium ascorbate to Nano-Glo® Luciferase Assay Buffer reduces the loss of reagent activity after reconstitution, as shown in FIG. 49. When the substrate is reconstituted in Nano-Glo® Luciferase Assay Buffer containing 300 mM sodium ascorbate and kept at 37° C. for 23 hours, the luminescence intensity is 66% of the control compared to 38% in the absence of sodium ascorbate. After 41 hours at 37° C., the luminescence intensity is 31% compared to 9%. The stabilization effect diminishes with decreasing quantities of sodium ascorbate. Note that the result from the buffer condition containing 3 mM sodium ascorbate is most likely due to an experimental error.

Example 31

Effects of Hydroxypropyl-β-Cyclodextrin on Substrate Formulations

A 4× furimazine solution was prepared by diluting the stock 1:25 in a buffer containing 200 mM MES pH 6.0, 200 mM hydroxypropyl-β-cyclodextrin (HP-β-CD), and 600 mM sodium ascorbate. The solution was lyophilized for 48 hours using a Virtis Advantage Pro® Lyophilizer. These lyophilized preparations were then stored at elevated temperature (37° C.) for the duration of the experiment. After 24 and 48 hours, the pellet was reconstituted in Nano-Glo® Luciferase Assay Buffer such that the final concentration of components in the solution was 2× furimazine (1:50 dilution from stock), 100 mM MES pH 6.0, 100 mM HP-β-CD, and 300 mM sodium ascorbate. For comparison, Nano-Glo® substrate was prepared in Nano-Glo® Luciferase Assay Buffer and incubated at 37° C. for the duration of the experiment. Nano-Glo® substrate used according to manufacturer's instructions (stored at −20° C. during the course of the experiment and reconstituted for each time point) was used as a positive control. In each case, one volume of reconstituted Nano-Glo® Luciferase Assay Substrate was mixed with one volume of sample. After 3 min, the luminescence intensity was measured with a Bio-Tek Synergy H1 96-well plate reader. A cell culture expressing NanoLuc was used as a sample. For each sample, the luminescence intensity was background subtracted and normalized to the −20° C. control signal.

Figure 50:
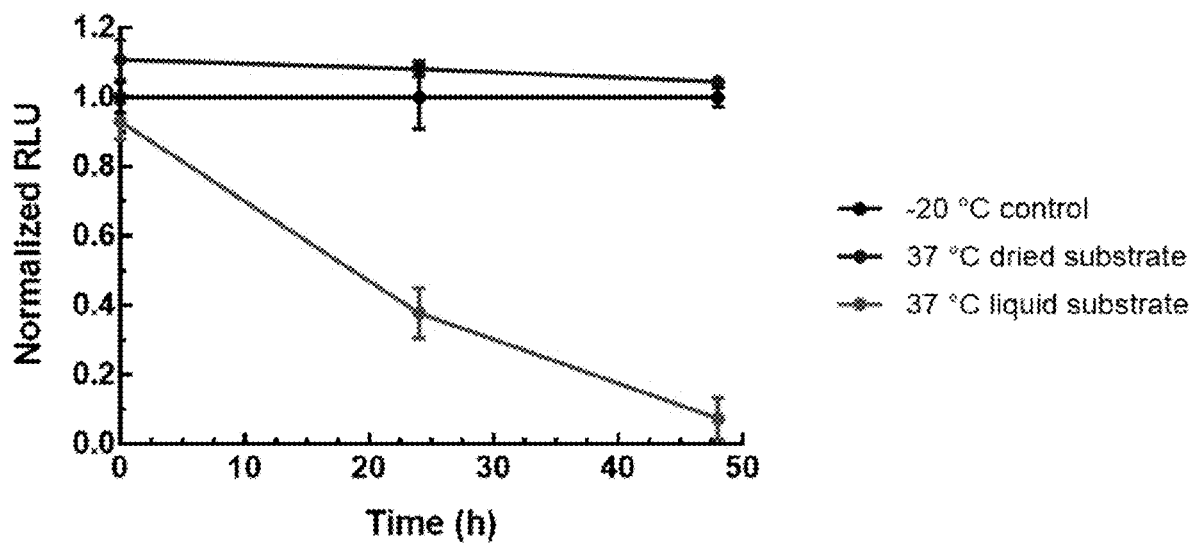
FIG. 50 shows data demonstrating RLU output of Nano-Glo® substrate (Promega cat #N113) formulations containing hydroxypropyl-β-cyclodextrin and lyophilized as described in Example 31.

The addition of HP-β-CD and sodium ascorbate to the buffer prior to lyophilization allowed the pellets to be directly dissolved in Nano-Glo® buffer (without the addition of solvent) and to remain stable over a period of 48 hours at 37° C. as shown in FIG. 50. The non-lyophilized solution of working concentration Nano-Glo® substrate in Nano-Glo® Luciferase Assay Buffer incubated at 37° C. showed a 90% decrease in activity after the same amount of time. Additionally, it's important to note that some signal enhancement was observed when comparing the pellet to the standard kit preparation.

Example 32

Effects of Individual and Combined Buffer Additives to Substrate Formulations

Furimazine was diluted 1:50 into buffers with the following final compositions:
Nano-Glo® buffer
Nano-Glo® buffer+300 mM sodium ascorbate
Nano-Glo® buffer+100 mM hydroxypropyl-β-cyclodextrin (HP-β-CD)
Nano-Glo® buffer+300 mM sodium ascorbate+100 mM HP-β-CD.

One volume of cell culture expressing NanoLuc was added to one volume of each buffer and mixed. After 3 minutes, the luminescence intensity was measured with a standard plate reader. Following the same procedure, the background intensity was measured by mixing one volume of cell culture media with each buffer.

These experimental results suggest that HP-β-CD is the primary causative agent for signal enhancement. As shown in FIG. 51A, HP-β-CD enhances signal by 15 to 20% compared to a solution with Nano-Glo® buffer alone. The background signal when the reporter enzyme is absent (FIG. 51B) showed that the increase in signal is not due to an increase in background signal.

Example 33

Effects of Mixed Polymer Substrate Formulations on Substrate Stability

Preparations of Nano-Glo® substrate (1:50 dilution) were lyophilized in a MES, pH 6.0 solution containing 200 mM HP-β-CD, 600 mM sodium ascorbate, and 10% w/v pullulan. After freeze drying, vials were capped by hand (not under vacuum). Some of the vials were stored in a 37° C. incubator while others were left on the lab bench at room temperature. Prior to each measurement, vials were rehydrated in twice their original volume such that the final concentration of each component was 100 mM HP-β-CD, 300 mM sodium ascorbate, and 5% pullulan. Nano-Glo® substrate used according to manufacturer's instructions (stored at −20° C. during the course of the experiment and reconstituted for each time point) was used as a positive control. In each case, one volume of reconstituted Nano-Glo® Luciferase Assay Substrate was mixed with one volume of sample. After 3 min, the luminescence intensity was measured with a Bio-Tek Synergy H1 96-well plate reader. A cell culture expressing NanoLuc was used as a sample. For each sample, the luminescence intensity was background subtracted and normalized to the −20° C. control signal.

Figure 52:
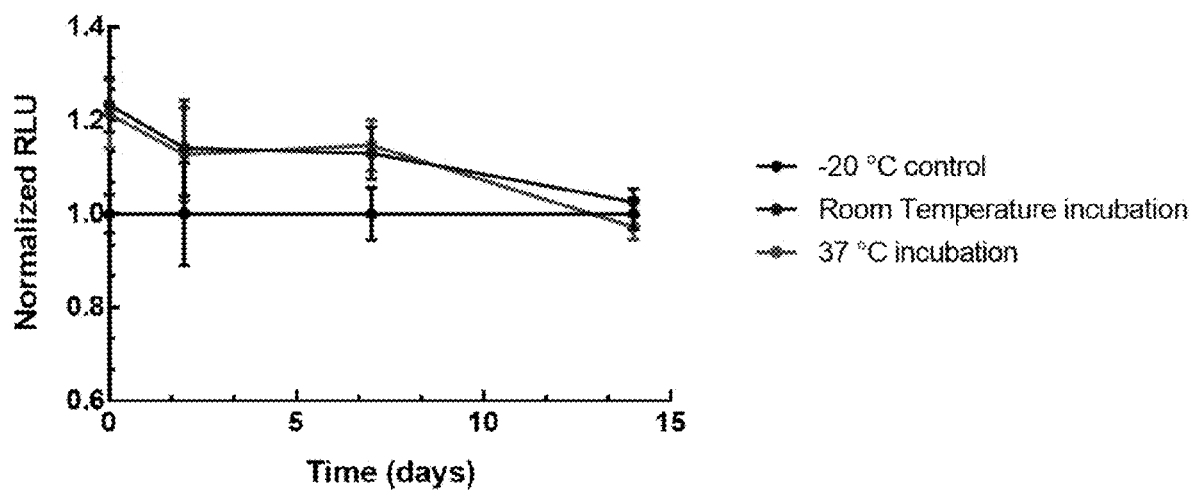
FIG. 52 shows data demonstrating RLU output of Nano-Glo® substrate (Promega cat #N113) formulations containing mixed polymers of pullulan and hydroxypropyl-β-cyclodextrin along with other buffer additives as described in Example 33.

As shown in FIG. 52, the presence of pullulan in the lyophilized preparations allows the substrate to retain its activity over a period of 15 days when stored at room temperature and at 37° C. The addition of pullulan is thought to provide a barrier to oxygen and moisture and, when combined with the additives described previously, provides a stabilizing matrix that has the potential to retain activity of furimazine over weeks to months. When combined with inert gas this storage method shows promise towards attaining incredibly long periods of stability for this substrate.

Example 34

JRW-0238 Formulated with Pluronic® F-127

Figure 53:
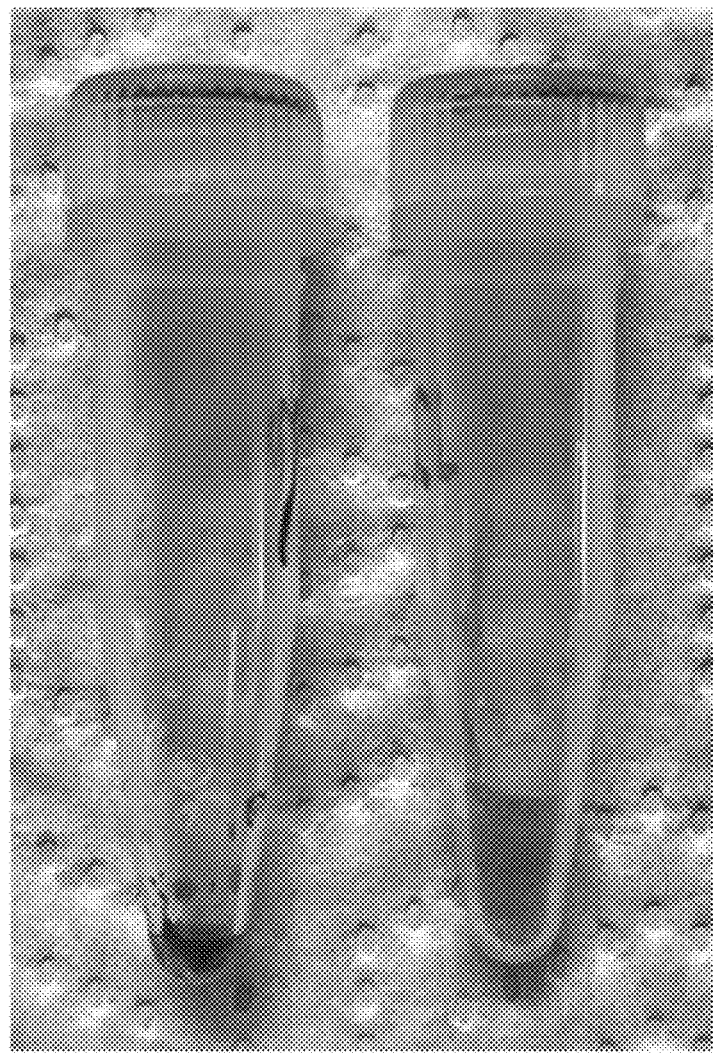
FIG. 53 shows images of representative examples of formulated substrates as described in Example 34.

2.5 mgs of Pluronic® F-127 (Sigma Aldrich) were massed out into 5 mL snap-top Eppendorf tubes. The polymer was heated to 70° C. in a water bath until melted, becoming a clear solution. A 174 mM stock solution of the coelenterazine analog, JRW-0238, was prepared in EtOH. 5 μL of this stock was added to the melted polymer and pipetted to mix. Two separate conditions were prepared: Condition 1—After the addition of the substrate, the substrate/polymer solution was dried under high vacuum for 30 minutes. Condition 2—After addition of substrate, the substrate/polymer solution was further diluted with 45 μL of water, frozen, and lyophilized overnight. Representative examples of the final, dry formulated substrates are shown in FIG. 53.

Figure 54:
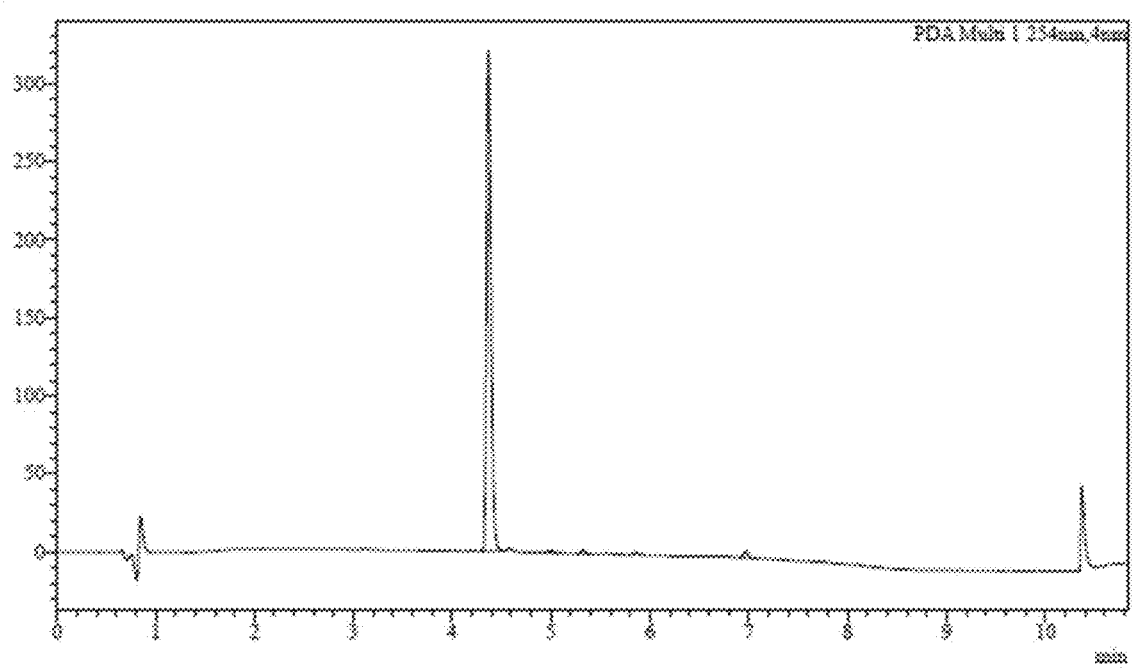
FIG. 54, Panels A-C show representative examples of HPLC analyses of samples of JRW-0238 formulated with Pluronic® F-127 as described in Example 34.

Samples from both conditions 1 and 2 were reconstituted in water, diluted to 100 μM, and analyzed for chemical integrity via analytical HPLC (FIG. 54). Compared to freshly prepared substrate (100 μM JRW-0238 in EtOH, FIG. 54A), neither of the formulated substrate conditions showed any significant chemical degradation (FIG. 54B and FIG. 54C). Peak information is summarized in Table 3.

TABLE 3

| Sample | FIG. | Retention Time (min) | Area Percent |
|---|---|---|---|
| JRW-0238 in EtOH | 54A | 4.357 | 98.429 |
|  |  | 6.977 | 1.571 |
| Condition 1 | 54B | 4.362 | 98.374 |
|  |  | 6.985 | 1.626 |
| Condition 2 | 54C | 4.366 | 97.638 |
|  |  | 4.992 | 0.372 |
|  |  | 5.321 | 0.728 |
|  |  | 6.969 | 1.262 |

The reconstituted samples from both conditions were left at ambient temperature in the dark. After 24 hours, a small amount of precipitate was observed in the sample prepared from condition 1. The solution prepared from condition 2 remained clear over the course of the experiment. This series of experiments show that solid formulations of coelenterazine analogs can be prepared with a synthetic polymer and improve the overall kinetic solubility in aqueous media without the need for organic solvents or stabilizers. The method of preparation, however, may have an effect on thermodynamic solubility. The condition that was lyophilized (condition 2) was still in solution after 24 hours at ambient temperature. This is in contrast to the sample from condition 1, which began to precipitate out of solution within 24 hours of being reconstituted in water.

Example 35

Furimazine Formulated with Pluronic® F-127

This formulation was also prepared for the coelenterazine analog, furimazine. 2.5 mgs of Pluronic® F-127(Sigma Aldrich) were massed out into 1.5 mL, snap-top Eppendorf tubes. The polymer was heated to 70° C. in a water bath until melted. A 10 mM stock solution of furimazine was prepared in EtOH. 5 μL of this stock was then added to the melted polymer and pipetted to mix. Two separate conditions were prepared: Condition 1—After the addition of the substrate, the solution was dried under vacuum for 30 minutes. Condition 2—After addition of substrate, the substrate/polymer solution was further diluted with 45 μL of water, frozen, and then lyophilized overnight.

Figure 55:
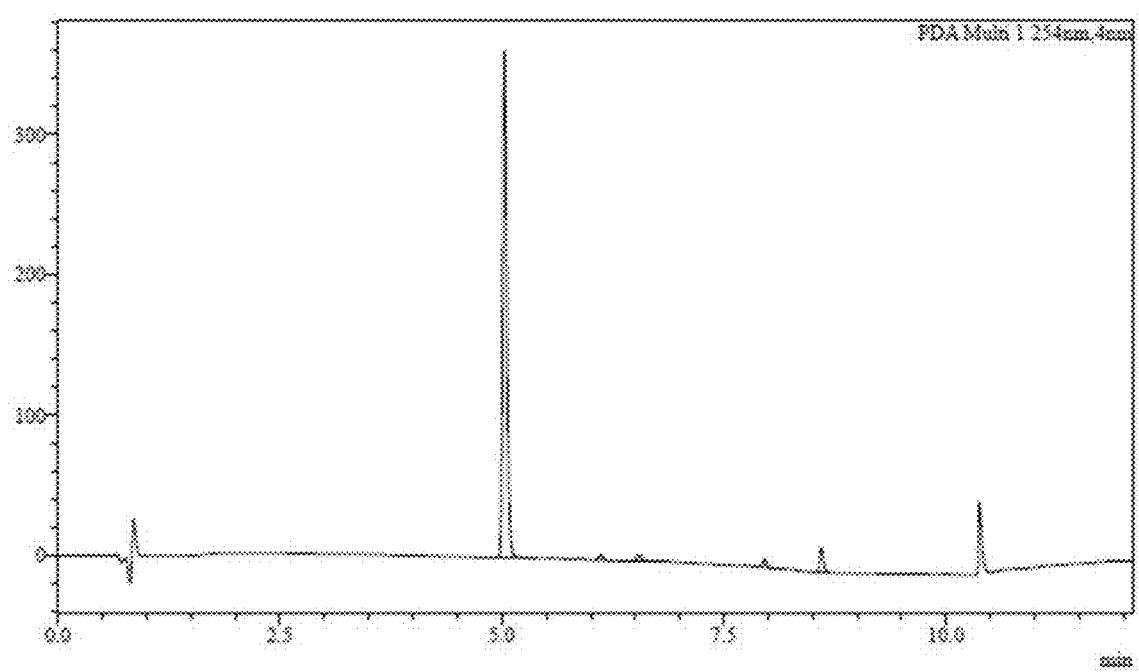
FIG. 55, Panels A-C show representative examples of HPLC analyses of samples of furimazine formulated with Pluronic® F-127 as described in Example 35.

The samples in both condition 1 and 2 were reconstituted in water, diluted to 100 μM, and analyzed for substrate integrity via analytical HPLC (FIG. 55). Compared to freshly prepared furimazine (FIG. 55A), condition 1 showed considerable degradation (FIG. 55B). This may be due to the extensive sonication that was required to reconstitute this sample. In contrast, the reconstituted sample from condition 2 showed no significant degradation (FIG. 55C). Peak information is summarized in Table 4.

TABLE 4

| Sample | FIG. | Retention Time (min) | Area Percent |
|---|---|---|---|
| Furimazine in EtOH | 55A | 5.038 | 96.858 |
|  |  | 6.109 | 0.705 |
|  |  | 6.548 | 1.407 |
|  |  | 7.952 | 1.030 |
| Condition 1 | 55B | 5.028 | 64.807 |
|  |  | 5.888 | 1.717 |
|  |  | 6.104 | 8.287 |
|  |  | 6.268 | 1.881 |
|  |  | 6.541 | 4.522 |
|  |  | 7.672 | 0.635 |
|  |  | 7.768 | 1.828 |
|  |  | 7.949 | 16.323 |
| Condition 2 | 55C | 5.031 | 92.677 |
|  |  | 6.107 | 0.922 |
|  |  | 6.545 | 1.741 |
|  |  | 7.957 | 1.346 |
|  |  | 8.599 | 3.583 |

This series of experiments show that solid formulations of coelenterazine analogs, including furimazine, can be prepared with a synthetic polymer and improve the overall kinetic solubility in aqueous media without the need for organic solvents or stabilizers.

Example 36

Maximum Concentration of Formulated JRW-0238 in Water 25 mgs of Pluronic® F-127 were massed out into a 1.5 mL, snap-top Eppendorf tube. The polymer was heated to 70° C. in a water bath until melted. 3.4 mg of JRW-0238 was dissolved in 50 μL of EtOH and then added to the hot polymer and mixed by pipetting. An additional 50 μL of EtOH was used to wash and aid transfer of the substrate into the polymer solution. The solvent was removed under reduced pressure without heat.

Four vials were prepared in a similar fashion, and all vials contained a ratio of polymer to substrate of 7.3:1 w/w. Different volumes of water were used to make the initial aqueous stocks as described below:

Vial 1: After infusion of the polymer with the substrate, the solution was taken up in 500 μL water. All material went into solution after some sonication. The sample was frozen and lyophilized overnight. The calculated concentration of substrate was determined to be 17.4 mM with 5% w/v polymer.

Vial 2: After infusion of the polymer with the substrate, the solution was taken up in 400 μL water. All material went into solution after some sonication. The sample was frozen and lyophilized overnight. The calculated concentration of substrate in water was determined to be 21.4 mM with 6.25% w/v polymer.

Vial 3: After infusion of the polymer with the substrate, the solution was taken up in 250 μL water. All material went into solution after some sonication. The sample was frozen and lyophilized overnight. The calculated concentration of substrate in water was determined to be 34.4 mM with 10% w/v polymer.

Vial 4: After infusion of the polymer with the substrate, the solution was taken up in 100 µL water. All material went into solution after some sonication. The sample was frozen and lyophilized overnight. The calculated concentration of substrate in water was determined to be 85.4 mM with 25% w/v polymer.

Figure 57:
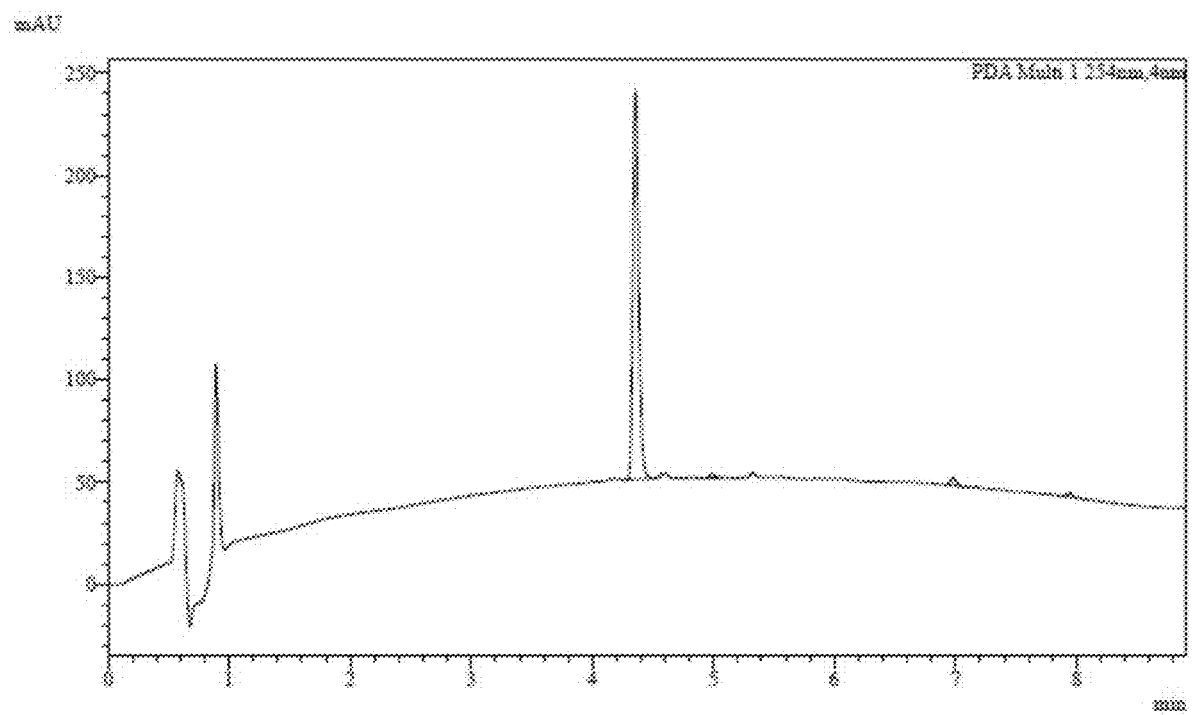
FIG. 57 shows a representative example of an HPLC analysis of samples of JRW-0238 formulated with Pluronic® F-127 as described in Example 36.

After lyophilization, each sample was reconstituted with either 500 µL, 400 µL, 250 µL, or 100 µL water, respectively. All material in each condition went into solution. Representative images of these solutions are shown in FIG. 56. After 24 hours at ambient temperature, the reconstituted stocks were centrifuged, and no precipitation was observed. A representative HPLC trace showing the chemical integrity of the reconstituted substrate after standing in solution for 24 hours is shown in FIG. 57. No significant chemical degradation was observed. Peak information is summarized in Table 5.

TABLE 5

| Retention Time (min) | Area Percent |
| --- | --- |
| 4.354 | 96.398 |
| 4.988 | 0.810 |
| 6.980 | 1.858 |
| 7.944 | 0.935 |

These experiments indicate that high concentrations of the coelenterazine analog, JRW-0238, can be achieved in water without any loss to chemical integrity under ambient conditions by formulating with a polymer in the solid state.

Example 37

Lower Polymer/Substrate Ratio without Loss of Observable Substrate Solubility 23.8, 20.4, 17, 13.6, 10.2, and 6.8 mgs of Pluronic® F-127 were massed out into individual 1.5 mL snap-top, Eppendorf tubes. The polymer was heated to 70° C. in a water bath until melted. 23.7 mg of JRW-0238 was dissolved in 350 µL of EtOH, and 50 µL of this stock was added to each vial containing the hot polymer; mixing well by pipetting. The vials were then placed under high vacuum for 30 minutes to remove all organic solvent. Each vial was diluted with 500 µL of water to a final concentration of 17.4 mM JRW-0238 with either 7×, 6×, 5×, 4×, 3×, or 2× w/w polymer/substrate, respectively. Each tube was frozen and lyophilized overnight.

At the time of testing, 500 µL of water was added to each vial and vortexed until all material was dissolved. After initial reconstitution, all samples were clear except the sample containing 2×w/w polymer relative to substrate (FIG. 58A). This sample alone was observed to be slightly hazy. After 1 hour in solution at room temperature, the reconstituted substrates were still observed to be in solution with the exception of the sample containing 2×w/w polymer relative to substrate (FIG. 58B).

Example 38

Solid Formulation for Use in Whole-Animal Imaging

For whole-animal imaging in the mouse model, stock samples of solid formulated JRW-0238 were prepared as follows: 90 mgs of Pluronic® F-127 were massed out into a glass, screw cap vial. The polymer was then heated to 70° C. in a water bath until melted (becomes a clear solution). 12.5 mg of JRW-0238 was dissolved in 250 µL of EtOH and added to the hot polymer, mixing well with a thin spatula. The solvent was then removed under reduced pressure. This concentrated sample was diluted with 3.646 ml of water to make a master stock of 8.7 mM substrate in water. 480 µL of this aqueous stock was then aliquoted into 1.5 mL screw cap vials, frozen, and lyophilized overnight. A representative image of this formulation is shown in FIG. 59A. At the time of testing, 480 µL of water was added to the vial and vortexed for ~15 seconds until all material was dissolved (FIG. 59B).

Transgenic mouse subjects (average age: 6 months) that were engineered to express the Antares protein construct (see U.S. Pat. No. 9,908,918), a fusion of NanoLuc and cyan-excitable orange-red fluorescent protein (CyOFP), were anesthetized using isoflurane and injected with 480 µL of the reconstituted substrate solution either via intraperitoneal injection (I.P.) or subcutaneous injection (S.C.). Each mouse was then imaged every minute after injection using the Ami Imaging System. FIG. 60A shows a trace of the average RLUs from five animals that were injected I.P. with reconstituted JRW-0238. FIG. 60B representative images of each mouse when light output was measured at its maximum. FIG. 61A shows a trace of the average RLUs from five animals that were injected S.C. with reconstituted JRW-0238. FIG. 61B shows representative images of each mouse subject when light output was measured to be at its maximum. Together, these results indicate that in vivo imaging can be achieved with a coelenterazine analog that was prepared as a dry formulation, reconstituted in water at the time of use, and injected into live animal subjects via I.P. or S.C. injection routes.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Example 39

Preparing Polymer Furimazine Formulation at Larger Scale

The dry furimazine formulation was scaled to larger volumes and demonstrated that these compositions can be prepared under manufacturing conditions. The concentration of furimazine in the cake is 200 uM. The cake can be reconstituted to a stock volume of 10 mL, providing a 2× stock (20 uM) of furimazine. This can then be diluted 1:1 with sample for a final concentration of 10 uM.

In order to prepare the bulk solution, 50 mL of milli-Q purified water was added to 1.25 g pullulan, 35.7 mg ATT, and 44 mg ascorbate and mixed until all solids dissolved. The final solution contains 2.5% w/v pullulan with 5 mM ATT and 5 mM Ascorbate, respectively.

29.4 mL of pullulan solution was measured into a 50 ml plastic vial. 600 µL of furimazine prepared as a 10 mM stock in EtOH was added and mixed well. A small amount of thin, needle-like precipitate was observed in solution. This precipitate is most likely due to the pullulan polymer interacting with the EtOH in solution. This did not impact the success of the preparation or the properties of the final material.

10 mL glass amber vials were used. One mL of the furimazine-pullulan stock solution was aliquoted into 10 mL amber glass vials, and a rubber stopper was partially inserted into the vial.

The lyophilizer used (Virtis Genesis 12EL lyophilizer) has 4 ft² of shelf surface and three shelves in total. The refrigeration system consists of 2 two-stage compressors. Vacuum/pressure control is achieved through a single vacuum pump and a modulating control valve that bleeds nitrogen into the lyophilizer chamber to balance the suction force of the vacuum pump and hold the pressure at the specified set-point. Shelves are compressible via a hydraulic piston. One small tray containing 178×10 vials (comprising a combination of fourteen different formulations) of manually dispensed product was loaded onto a single shelf in the lyophilizer that was at a temperature of +4.7° C. Product then underwent a freezing step with a shelf temperature of −50° C. for 2 hours after which time then condenser step started. During the run, the condenser temperature ran between −5° C. and −87° C. Vacuum pulled down next and ran at the pressure set-points of 75 and 200 mToor. Good control at both of those pressure set-points was shown throughout the run. All steps of the lyophilization recipe/cycle were executed as programmed. Based on the product probe average temperature, sublimation lasted ~7.5 hours and desorption lasted ~16.1 hours. At the end of the run, the vials were back-filled with nitrogen and sealed with fully inserted stoppers at ~600 Torr of pressure (~740 Torr is atmospheric pressure).

After lyophilization, nitrogen gas was administered to each glass vial that contained a lyo-cake with 20× furimazine to fill the vial headspace, caps completely sealed, and vials stored at either 25° C. or 60° C., respectively. At various time points post lyophilization, the formulated furimazine was reconstituted with 10 mls of PBS, pH 7.0, containing 0.01% BSA, and the vials shaken manually and allowed to equilibrate at room temperature for 5 minutes. 50 ul of the formulated furimazine stock solution was added to 50 ul of 1 ng/ml purified NanoLuc® enzyme (Nluc) (Promega cat #E499) in PBS, pH 7, containing 0.01% BSA (final [Nluc]=0.5 ng/ml). The control used was a 10 uM final solution of the NanoGlo® live cell substrate (Promega Cat #N205) sampled fresh from the −20° C. for each time point data collection. Assays were performed in solid, white, nonbinding surface (NBS) plate and analyzed using a kinetic read on a luminometer (GloMax® Discover Multimode Microplate reader—Promega Cat. #GM3000) collecting total luminescence.

Figure 62:
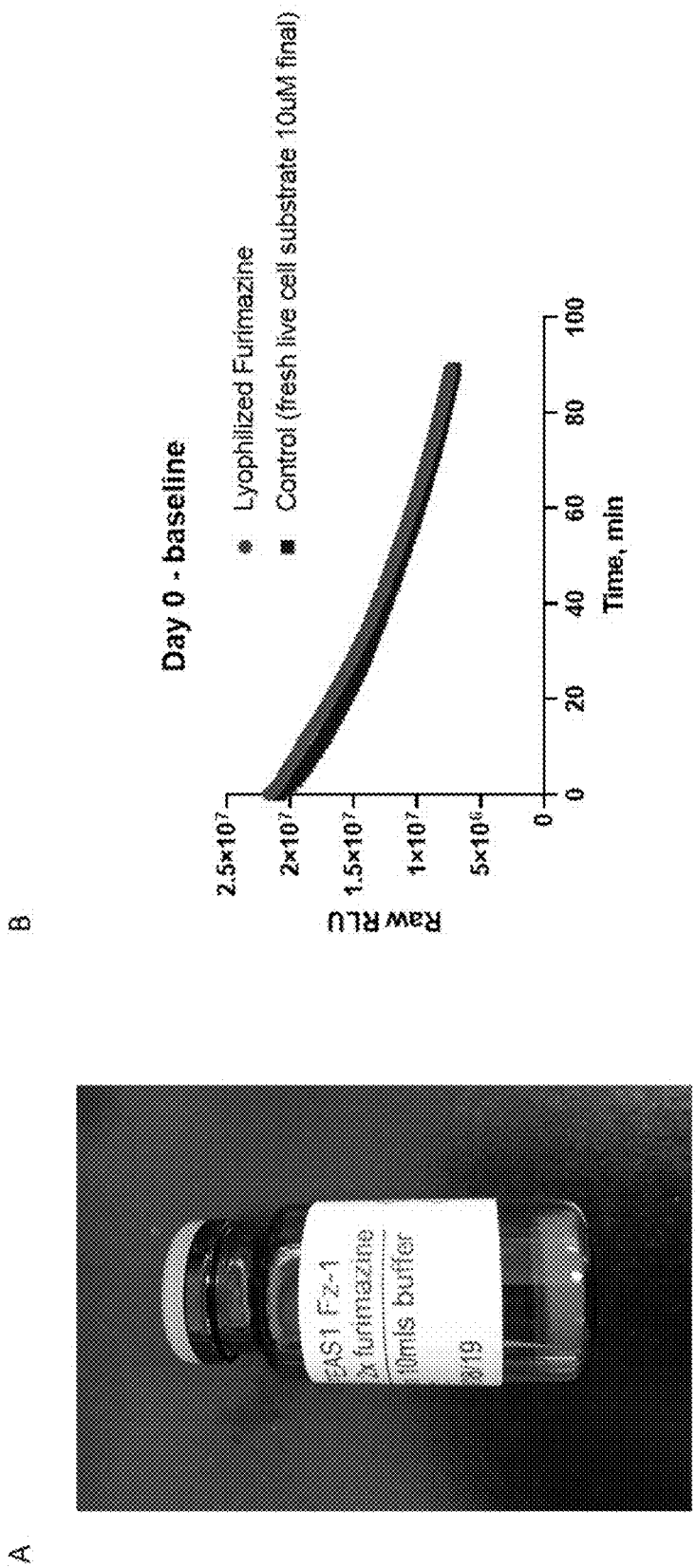
FIGS. 62A-B show images of the formulated furimazine lyophilized cake within an amber glass vial post scale up and manufacturing, and the activity of this substrate relative to freshly prepared NanoGlo® live cell substrate at timepoint day "0" as described in Example 39.
Figure 63:
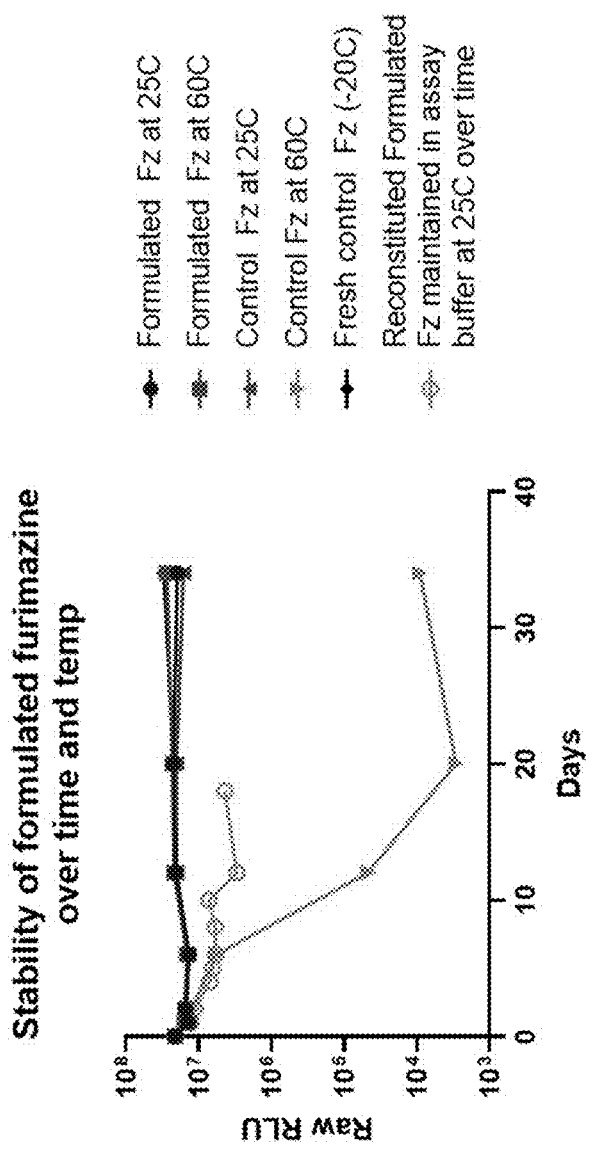
FIG. 63 shows RLU values at various time points following addition of purified NanoLuc® enzyme when compositions according to the present disclosure were incubated at 25° C. or 60° C. and tested for luminescence output in PBS, pH 7.0, containing 0.01% BSA as described in Example 39.

FIG. 62A displays the lyophilized formulated furimazine cakes at timepoint "day 0" showing the vial to contain a uniform cake with even distribution at the bottom of the vial without any obvious flaws in appearance indicating that the formulation and lyophilization protocol were appropriate. FIG. 62 B displays the NanoLuc® activity results expressed as raw RLU using the formulated furimazine after reconstituted with buffer as described above. The formulated furimazine performed as well as the control substrate (NanoGlo® Live Cell Substrate Promega Cat #N205). This is the baseline read to start the accelerated stability studies. A portion of the vials or control substrate were then placed at 60° C. or 25° C. A new vial was reconstituted at various time points and analyzed for activity using purified NanoLuc® enzyme. FIG. 63 shows the raw RLU from formulated samples that were stored at either 25° C. (blue closed circle) or 60° C. (red square), from NanoGlo® live cell substrate that was stored at 25° C. (green triangle) or 60° C. (orange downward triangle), and from freshly prepared control NanoGlo® live cell substrate that was maintained at −20° C. (black diamond) as monitored for 34 days. A vial that was reconstituted at day 0 was maintained in solution, maintained at room temperature, and sampled over 18 days for activity as well (light blue open circles). The data shows that formulated furimazine maintains activity over the time period tested at both temperatures tested and shows improvement over furimazine dissolved in organic solvents. All of the formulated furimazine reconstituted within 5 min after addition of buffer, in stark contrast to the behavior of solid furimazine.

The results in FIGS. 62 and 63 demonstrate that furimazine compositions can be prepared at a larger scale and under stricter quality control conditions including in glass vials and under inert atmosphere. The compositions can be stored at ambient or elevated temperature for extended periods, and reconstituted in neutral buffer with no need for organic solvents or special buffer conditions. Even after reconstitution in aqueous buffer, the composition does not lose any significant performance while being stored in solution and under ambient conditions for up to 24-48 hours, and maintains some activity for up to 18 days.

Example 40

Preparation of Formulated JRW-1744

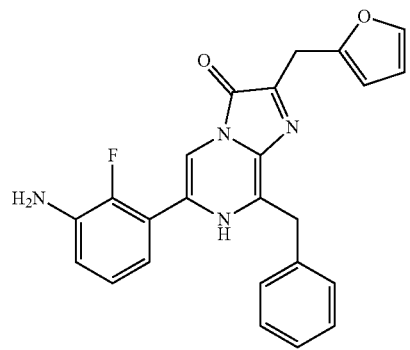

JRW-1744

6-(3-amino-2-fluorophenyl)-8-benzyl-2-(furan-2-ylmethyl)imidazo[1,2-a]pyrazin-3(7H)-one Formulated examples of JRW-1744 were prepared in a similar manner as JRW-0238 in Examples 34 and 38. Stock samples of solid formulated JRW-1744 were prepared as follows: 77 mgs of Pluronic® F-127 (~7.2×w/w) was massed out into a glass, screw cap vial. The polymer was then heated to 80° C. in a water bath until melted (becomes a clear solution). 10.8 mg of JRW-1744 was dissolved in a small amount of EtOH and added to the hot polymer, mixing well with a thin spatula. Additional EtOH (up to 2 mL total) was used to fully transfer and dissolve all the substrate into the polymer solution. The solvent was then removed under reduced pressure. This concentrated sample was then placed under high vacuum for 1 hour to remove residual EtOH, resulting in an orange solid. This solid was diluted in 3.0 mL of water and sonicated to make a master stock of 8.7 mM JRW-1744 in water. 480 µL aliquots of this aqueous stock was then transferred into 1.5 mL screw cap vials, frozen, and lyophilized overnight.

Example 41

Preparation of Formulated JRW-1743

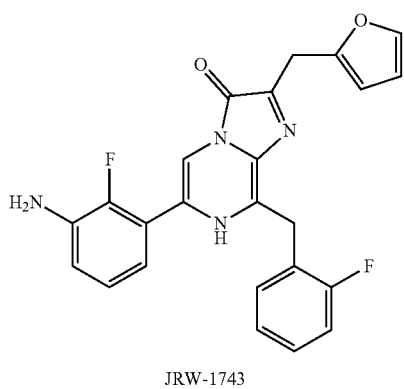 [SMILES: Nc1cccc(-c2cn3c(=O)c(Cc4ccco4)nc-3c(Cc3ccccc3F)[nH]2)c1F]

JRW-1743

6-(3-amino-2-fluorophenyl)-8-(2-fluorobenzyl)-2-(furan-2-ylmethyl)imidazo[1,2-a]pyrazin-3(7H)-one Formulated examples of JRW-1743 were prepared in a similar manner as JRW-0238 in Examples 34 and 38.

Stock samples of formulated JRW-1743 were prepared as follows: 72 mgs (7.2×w/w) of Pluronic® F-127 was massed out and placed in a glass, screw-cap vial. The polymer was then heated in a water bath at 80° C. until it was fully melted (FIG. 64A).

10.0 mgs of solid JRW-1743 was dissolved in a small amount EtOH and transferred to the hot polymer while stirring with a thin spatula. Additional EtOH (up to 2 mL total) was used to aid in the transfer of the substrate into the polymer solution. The solvent was then removed under reduced pressure, concentrating the polymer/substrate mixture into a red-orange gel. This concentrated sample was then placed under high vacuum for 1 hour to remove any residual EtOH.

In order to prepare a master stock of formulated JRW-1743 in Pluronic® F-127, 2.6 mL of water was added to the gel, and the resulting was solution was sonicated until it was completely homogenous (FIG. 64B). The final concentration of JRW-1743 at this volume was calculated to be 8.7 mM. 480 µL aliquots of this aqueous stock was then transferred into 1.5 mL screw cap vials, frozen, and lyophilized overnight, resulting in a lyophilized cake containing JRW-1743 (FIG. 64C).

Figure 65:
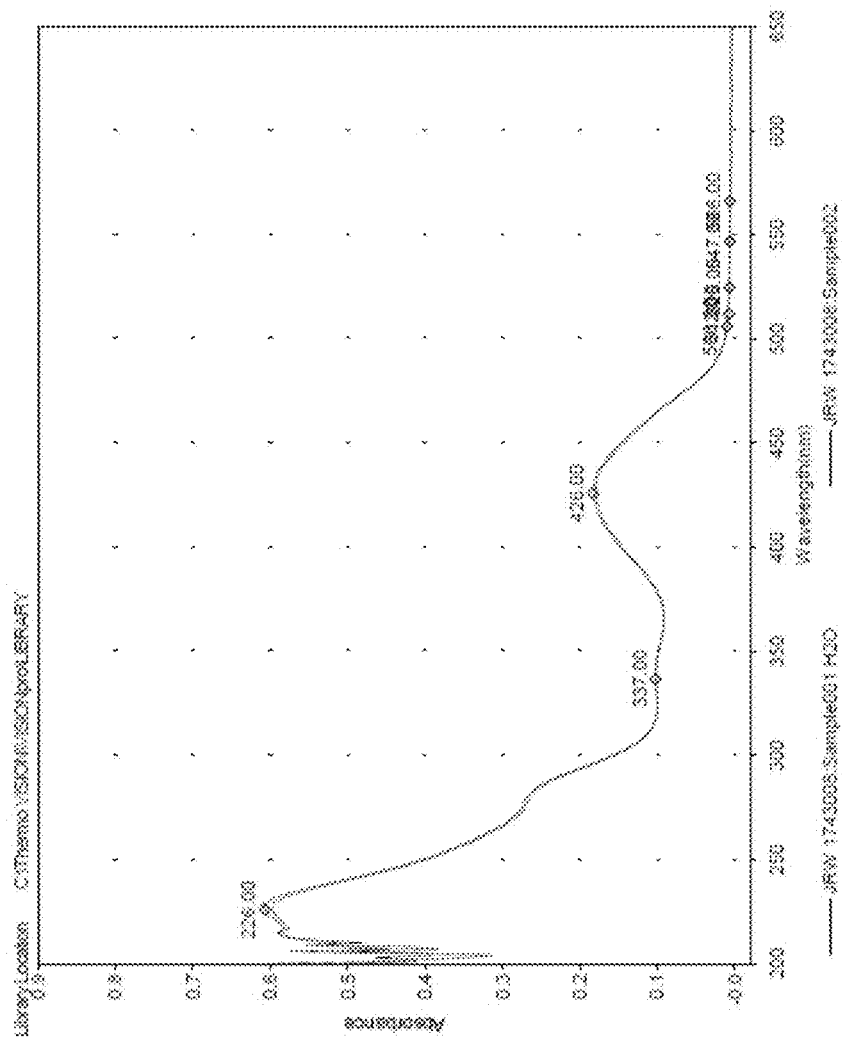
FIG. 65. Representative absorbance trace of JRW-1743 after it was formulated with of Pluronic® F-127 and reconstituted in nano-pure water. Concentration of the substrate in solution was determined by absorbance. The mean concentration of JRM-1743 was experimentally determined to be 8.5 mM in water. The calculated theoretical concentration of dry formulated substrate was 8.7 mM.

One vial containing formulated JRW-1743 was reconstituted in 480 uL of water (FIG. 64C middle and right). Absorbance measurements for substrate concentration in water was performed and indicated that the working concentration of JRW-1743 in this solution was found to be 8.5 mM compared to the theoretical concentration of ~8.7 mM (FIG. 65).

Sequences

SEQ ID NO: 1-Native Mature *Oplophorus luciferase* amino acid sequence
FTLADFVGDWQQTAGYNQDQVLEQGGLSSLFQALGVSVTPIQKVVLSGEN
GLKADIHVIIPYEGLSGFQMGLIEMIFKVVYPVDDHHFKIILHYGTLVID
GVTPNMIDYFGRPYPGIAVFDGKQITVTGTLWNGNKIYDERLINPDGSLL
FRVTINGVTGWRLCENILA SEQ ID NO: 2-Nluc amino acid sequence
MVFTLEDFVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTLV
IDGVTPNMIDYFGRPYEGIAVFDGKKITVTGTLWNGNKIIDERLINPDGS
LLFRVTINGVTGWRLCERILA SEQ ID NO: 3-LgTrip (3546)
MKHHHHHHVFTLDDFVGDWEQTAAYNLDQVLEQGGVSSLLQNLAVSVTP
IMRIVRSGENALKIDIHVIIPYEGLSADQMAQIEEVEKVVYPVDDHHEKV
ILPYGTLVIDGVTPNKLNYEGRPYEGIAVEDGKKITTTGTLWNGNKIIDE
RLITPD

---

The invention claimed is:

1. A composition comprising:
 a compound selected from coelenterazine-h, coelenterazine-h-h, furimazine, JRW-0238, JRW-1743, and JRW-1744; and
 pullulan;
 wherein the composition is in the form of a lyophilized powder or cake.

2. The composition of claim 1, wherein the compound is furimazine.

3. The composition of claim 1, wherein the composition further comprises a buffer, a surfactant, a reducing agent, a salt, a radical scavenger, a chelating agent, a protein, or any combination thereof.

4. The composition of claim 3, wherein the composition further comprises a buffer selected from a phosphate buffer, tricine, and 2-(N-morpholino)ethanesulfonic acid.

5. The composition of claim 3, wherein the composition further comprises a surfactant selected from polysorbate 20, polysorbate 40, and polysorbate 80.

6. The composition of claim 3, wherein the composition comprises a reducing agent selected from thiourea and 6-aza-2-thiothymine.

7. The composition of claim 3, wherein the composition further comprises a salt selected from sodium chloride and sodium phosphate.

8. The composition of claim 3, wherein the composition further comprises a radical scavenger agent selected from ascorbic acid and sodium ascorbate.

9. The composition of claim 3, wherein the composition further comprises a chelating agent, and the chelating agent selected from citric acid and trans-1,2-diaminocyclohexane-tetraacetic acid.

10. The composition of claim 3, wherein the composition further comprises a protein selected from bovine serum albumin, gelatin, and a polypeptide fraction of purified dermal collagen of porcine origin.

11. The composition of claim 1, wherein the compound is furimazine, JRW-0238, JRW-1743, or JRW-1744.

12. A kit comprising the composition of claim 1, wherein the composition is included in one or more containers.

13. The kit of claim 12, wherein the compound is furimazine.

14. The kit of claim 12, wherein the compound is furimazine, JRW-0238, JRW-1743, or JRW-1744.

15. A method of stabilizing a compound selected from coelenterazine-h, coelenterazine-h-h, furimazine, JRW-0238, JRW-1743, and JRW-1744, comprising:
 contacting the compound with an effective amount of pullulan;
 wherein the contacting step comprises:
  dissolving the compound in an organic solvent to form a first solution;
  mixing the first solution with the pullulan to form a mixture; and
  lyophilizing the mixture;
 to form a composition in the form of a lyophilized powder or cake.

16. A method of improving the solubility of a compound selected from coelenterazine-h, coelenterazine-h-h, furimazine, JRW-0238, JRW-1743, and JRW-1744, comprising:
 contacting the compound with an effective amount of pullulan;
 wherein the contacting step comprises:
  dissolving the compound in an organic solvent to form a first solution;
  mixing the first solution with the pullulan to form a mixture; and
  lyophilizing the mixture;
 to form a composition in the form of a lyophilized powder or cake.

17. A method of improving the reconstitution rate of a compound selected from coelenterazine-h, coelenterazine-h-h, furimazine, JRW-0238, JRW-1743, and JRW-1744, comprising:
 contacting the compound with an effective amount of pullulan;
 wherein the contacting step comprises:
  dissolving the compound in an organic solvent to form a first solution;
  mixing the first solution with the pullulan to form a mixture; and
  lyophilizing the mixture;
 to form a composition in the form of a lyophilized powder or cake,
 wherein the reconstitution rate for the compound is improved compared to a compound that has not been contacted with the pullulan.

* * * * *

SEQUENCE LISTING

<160> NUMBER OF SEQ ID NOS: 3

<210> SEQ ID NO 1
<211> LENGTH: 169
<212> TYPE: PRT
<213> ORGANISM: Oplophorus gracilirostris

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
                100                 105                 110

Pro Tyr Pro Gly Ile Ala Val Phe Asp Gly Lys Gln Ile Thr Val Thr
            115                 120                 125

Gly Thr Leu Trp Asn Gly Asn Lys Ile Tyr Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 171
<212> TYPE: PRT
<213> ORGANISM: Artificial sequence
<220> FEATURE:
<223> OTHER INFORMATION: Synthetic

<400> SEQUENCE: 2

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
                20                  25                  30

Phe Gln Asn Leu Gly Val Ser Val Thr Pro Ile Gln Arg Ile Val Leu
            35                  40                  45

Ser Gly Glu Asn Gly Leu Lys Ile Asp Ile His Val Ile Ile Pro Tyr
        50                  55                  60

Glu Gly Leu Ser Gly Asp Gln Met Gly Gln Ile Glu Lys Ile Phe Lys
65                  70                  75                  80

Val Val Tyr Pro Val Asp His His Phe Lys Val Ile Leu His Tyr
                85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 3
<211> LENGTH: 155
<212> TYPE: PRT
<213> ORGANISM: Artificial sequence
<220> FEATURE:
<223> OTHER INFORMATION: Synthetic

<400> SEQUENCE: 3

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp

```
                50                  55                  60
Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
            130                 135                 140

Lys Ile Ile Asp Glu Arg Leu Ile Thr Pro Asp
145                 150                 155
```